(12) United States Patent
Arnaout

(10) Patent No.: US 11,939,369 B2
(45) Date of Patent: Mar. 26, 2024

(54) INTEGRIN ANTAGONISTS

(71) Applicant: The General Hospital Corporation, Boston, MA (US)

(72) Inventor: M. Amin Arnaout, Chestnut Hill, MA (US)

(73) Assignee: The General Hospital Corporation, Boston, MA (US)

( * ) Notice: Subject to any disclaimer, the term of this patent is extended or adjusted under 35 U.S.C. 154(b) by 70 days.

(21) Appl. No.: 17/390,653

(22) Filed: Jul. 30, 2021

(65) Prior Publication Data

US 2022/0153812 A1    May 19, 2022

Related U.S. Application Data

(63) Continuation of application No. 16/575,009, filed on Sep. 18, 2019, now abandoned, which is a continuation of application No. 15/109,602, filed as application No. PCT/US2015/010384 on Jan. 6, 2015, now Pat. No. 10,533,044.

(60) Provisional application No. 61/968,989, filed on Mar. 21, 2014, provisional application No. 61/925,548, filed on Jan. 9, 2014, provisional application No. 61/924,103, filed on Jan. 6, 2014.

(51) Int. Cl.

| C07K 14/78 | (2006.01) |
|---|---|
| A61K 38/00 | (2006.01) |
| C07K 7/06 | (2006.01) |
| C07K 7/08 | (2006.01) |
| C07K 7/64 | (2006.01) |
| C07K 14/47 | (2006.01) |

(52) U.S. Cl.
CPC ............ *C07K 14/78* (2013.01); *C07K 7/06* (2013.01); *C07K 7/08* (2013.01); *C07K 7/64* (2013.01); *C07K 14/47* (2013.01); *A61K 38/00* (2013.01)

(58) Field of Classification Search
CPC . C07K 14/78; C07K 7/06; C07K 7/08; C07K 7/64; C07K 14/47; A61K 38/00
See application file for complete search history.

(56) References Cited

U.S. PATENT DOCUMENTS

| 4,522,811 | A | 6/1985 | Eppstein et al. |
| 5,100,875 | A * | 3/1992 | Marguerie de Rotrou ........... C07K 5/1019 514/14.9 |
| 5,834,228 | A | 11/1998 | Becker et al. |
| 5,856,116 | A | 1/1999 | Wilson et al. |
| 5,939,528 | A | 8/1999 | Clardy et al. |
| 6,468,798 | B1 | 10/2002 | Debs et al. |
| 7,498,410 | B2 * | 3/2009 | Li ................... A61P 9/10 530/350 |
| 8,536,301 | B2 | 9/2013 | Cochran et al. |
| 9,585,899 | B2 | 3/2017 | Faraday |
| 9,587,001 | B2 | 3/2017 | Cochran et al. |
| 10,533,044 | B2 | 1/2020 | Arnaout |
| 2006/0142548 | A1 | 6/2006 | Arnaout et al. |
| 2009/0257952 | A1 | 10/2009 | Cochran et al. |
| 2013/0281602 | A1 | 10/2013 | Saiani et al. |
| 2014/0086835 | A1 | 3/2014 | Liu |
| 2014/0356324 | A1 | 12/2014 | Wei et al. |
| 2022/0356217 | A1 * | 11/2022 | Arnaout .................. A61P 7/02 |

FOREIGN PATENT DOCUMENTS

| CN | 101085809 | 9/2010 |
| WO | WO 1984/003087 | 8/1984 |
| WO | WO 1987/005297 | 9/1987 |
| WO | WO 1989/005150 | 6/1989 |
| WO | WO 1992/007874 | 5/1992 |
| WO | WO 1999/009148 | 2/1999 |
| WO | WO 2012/162418 | 11/2012 |
| WO | WO 2013/185027 | 12/2013 |

OTHER PUBLICATIONS

Adams et al., "PHENIX: a comprehensive Python-based system for macromolecular structure solution," Acta Crystallogr D Biol Crystallogr, Feb. 2010, 66:213-221.

Altschul et al. "Gapped BLAST and PSI-BLAST: a new generation of protein database search programs," Nucleic Acids Res., 1997, 25(17):3389-3402.

Bacon and Anderson, "A fast algorithm for rendering space-filling molecule pictures," J Mol. Graph., 1988, 6(4): 219-220.

Baker and Hubbard, "Hydrogen bonding in globular proteins," Prog. Biophys. Molec. Biol., 1984, 44(2):97-179.

Battye et al., "iMOSFLM: a new graphical interface for diffraction-image processing with MOSFLM," Acta Crystallogr D Biol Crystallogr, 2011, 67: 271-281.

Berliner et al., "Generation and Characterization of Peptide-specific Antibodies That Inhibit Von Willebrand Factor Binding to Glycoprotein IIb-IIIa without Interacting with Other Adhesive Molecules. Selectivity is conferred by Pro1743 and other amino acid residues adjacent to the sequence Arg1744-Gly1745-Asp1746," The Journal of Biological Chemistry, 1988, 263(6):7500-7505.

Brunger et al., "Crystallography & NMR System: A New Software Suite for Macromolecular Structure Determination," Acta Crystallogr., 1998, D54:905-921.

Chen et al., "Molecular Dynamics Simulations of Forced Unbending of Integrin aVb3," PLoS computational biology, Feb. 2011, 7(2): e1001086.

Cheng et al., "Mutation of a conserved asparagine in the I-like domain promotes constitutively active integrins alphaLbeta2 and alphaIIbbeta3," The Journal of Biological Chemistry, Jun. 22, 2007, 282(25): 18225-18232.

Chung et al., "A practical synthesis of fibrinogen receptor antagonist MK-383. selective functionalization of (S)-tyrosine," Tetrahedron, Jun. 1993, 49(26): 5767-5776.

Cox et al., "Integrins as therapeutic targets: lessons and opportunities," Nature Reviews Drug Discovery, 2010, 9(10):804-20.

(Continued)

*Primary Examiner* — Marcela M Cordero Garcia
(74) *Attorney, Agent, or Firm* — Fish & Richardson P.C.

(57) ABSTRACT

Provided herein are integrin antagonists and methods of using the same. For example, one or more of the compounds or polypeptides provided herein can be used in the treatment of disorders such as heart attacks, stroke, and cancer metastasis.

12 Claims, 16 Drawing Sheets

Specification includes a Sequence Listing.

(56) References Cited

OTHER PUBLICATIONS

Emsley and Cowtan, Acta Crystallogr D Biol Crystallogr, 2004, D60: 2126-2132.
Gerber et al., "Integrin Modulating Therapies Prevent Fibrosis and Autoimmunity in Genetic Mouse Models of Scleroderma," Nature, Nov. 7, 2013, 503:126-130.
Greenberg et al., "Covalent Immobilization of Recombinant Human alpha-v-beta-3 Integrin on a Solid Support with Retention of Functionality," Analytical Biochemistry, 1999, 266(1):153-164.
Guex and Peitsch, SWISS-MODEL and the Swiss-Pdb Viewer: An environment for comparative protein modeling, Electrophoresis, 1997, 18: 2714-2723.
Hershkoviz et al., "Nonpeptidic analogues of the Arg-Gly-Asp (RGD) sequence specifically inhibit the adhesion of human tenon's capsule fibroblasts to fibronectin," Investigative Ophthalmology & Visual Science, Apr. 1994, 35(5): 2585-2591.
International Preliminary Report on Patentability in International Application No. PCT/US2015/010384, dated Jul. 12, 2016, 10 pages.
International Search Report and Written Opinion dated Aug. 5, 2015 in international application No. PCT/US2015/010384, 18 pgs.
Jones et al., "Molecular recognition of receptor sites using a genetic algorithm with a description of desolvation," J. Mot. Biol., 1995, 245(1): 43-53.
Juan et al., "Proteomics analysis of a novel compound: Cyclic RGD in breast carcinoma cell line MCF-7," Proteomics, Apr. 2006, 6(10):2991-3000.
Kamber et al. "The Synthesis of Cystine Peptides by Iodine Oxidation of S-Trityl-cysteine and S-Acetamidomethyl-cysteine Peptides," Helvetica Chimica Acta, Jun. 6, 1980, 63(4): 899-915.
Kimura et al, "Engineered Knottin Peptides: A New Class of Agents for Imaging Integrin Expression in Living Subjects," Cancer Res, 2009, 69(6): 2435-42.
Kraulis, "MOLSCRIPT: a program to produce both detailed and schematic plots of protein structures," J Appl. Crystallogr., 1991, 24: 946-950.
Krautler et al., "A fast SHAKE algorithm to solve distance constraint equations for small molecules in molecular dynamics simulations," Journal of Computational Chemistry, Apr. 15, 2001, 22(5): 501-508.
Leahy et al., "2.0 A crystal structure of a four-domain segment of human fibronectin encompassing the RGD loop and synergy region," Cell, Jan. 12, 1996, 84(1): 155-164.
Mahalingam et al., "Atomic basis for the species-specific inhibition of αV integrins by monoclonal antibody 17E6 is revealed by the crystal structure of αVβ3 ectodomain-17E6 Fab complex," J Biol Chem., May 16, 2014, 289(20):13801-9.
Maile et al., "A monoclonal antibody against alpha Vbeta3 integrin inhibits development of atherosclerotic lesions in diabetic pigs," Sci Transl Med, Feb. 10, 2010, 2(18): 18ra11.
McCoy et al., "Phaser crystallographic software," Journal of Applied Crystallography, 2007, 40: 658-674.
Mehrbod and Mofrad, "Localized Lipid Packing of Transmembrane Domains Impedes Integrin Clustering," PLoS Computational Biology, Mar. 2013, 9(3): e1002948.
Mehrbod et al., "On the Activation of Integrin αIIbβ3: Outside-in and Inside-out Pathways," Biophysical Journal, Sep. 17, 2013, 105(6): 1304-1315.
Mehta et al., "Transmembrane-truncated alphavbeta3 integrin retains high affinity for ligand binding: evidence for an 'inside-out' suppressor? ," Biochem J., Mar. 1, 1998, 330 (Pt 2): 861-869.

Miao et al., "An Engineered Knottin Peptide Labeled with 18F for PET Imaging of Integrin Expression," Bioconjugate Chemistry, 2009, 20(12):2342-2347.
Mitjans et al., "An anti-alpha v-integrin antibody that blocks integrin function inhibits the development of a human melanoma in nude mice," J Cell Sci,, Aug. 1995, 108(Pt 8):2825-2838.
Miyashita et al., "Structure-activity relationships of RGD mimetics as fibrinogen-receptor antagonists," Bioscience Biotechnology Biochem., Oct. 1999, 63(10): 1684-1690.
Moore et al, "Engineered knottin peptide enables noninvasive optical imaging of intracranial medulloblastoma," Sep. 3, 2013, PNAS, 110(36): 14598-603.
Nagae et al., "Crystal structure of α5β1 integrin ectodomain: Atomic details of the fibronectin receptor," The Journal of Cell Biology, Mar. 26, 2012, 197(1): 131-140.
Otwinowski and Minor, "[20] Processing of X-ray diffraction data collected in oscillation mode," Methods Enzymol, 1997, 276: 307-326.
Petterson et al., "UCSF Chimera—a visualization system for exploratory research and analysis," J Comput Chem, Oct. 2004, 25(13): 1605-1612.
Phillips et al., "Scalable Molecular Dynamics with NAMD," Journal of Computational Chemistry, Dec. 2005, 26(16): 1781-1802.
Pollina, "Design and synthesis of RGD mimetics as potent inhibitors of platelet aggregation," Journal of Undergraduate Science, 1996, 3: 119-126.
Richards et al., "Engineered fibronectin type III domain with a RGDWXE sequence binds with enhanced affinity and specificity to human alphavbeta3 integrin," Journal of Molecular Biology, Mar. 7, 2003, 326(5): 1475-1488.
Rui et al., "The α-subunit regulates stability of the metal ion at the ligand-associated metal ion-binding site in β3 integrins," J Biol Chem, Aug. 15, 2014, 289(33):23256-63.
Sato et al., "An N-glycosylation site on the beta-propeller domain of the integrin alpha5 subunit plays key roles in both its function and site-specific modification by beta1,4-N-acetylglucosaminyltransferase III," The Journal of Biological Chemistry, May 1, 2009, 284(18): 11873-11881.
Scarborough, "Development of eptifibatide," American Heart Journal, Dec. 1999, 138(6 Pt 1): 1093-1104.
Silverman et al., "Engineered Cystine-Knot Peptides That Bind αvβ3 Integrin With Antibody-Like Affinities," J. Mol. Biol., Jan. 30, 2009, 385(4): 1064-1075.
Takahashi et al., Novel diphenylmethyl-derived amide protecting group for efficient liquid-phase peptide synthesis: AJIPHASE, Organic Letters, Sep. 7, 2012, 14(17): 4514-4517.
Van Agthoven et al, "Structural basis for pure antagonism of integrin αVβ3 by a high-affinity form of fibronectin," Nature Struc Mol. Biol, Apr. 2014, 21( 4): 383-8.
Viertler et al., Activity based subcellular resolution imaging of lipases, Bioorg Med Chem., Jan. 15, 2012, 20(2): 628-632.
Xiao et al., "Structural basis for allostery in integrins and binding to fibrinogen-mimetic therapeutics," Nature, Nov. 4, 2004, 432(7013): 59-67.
Xiong et al., "New insights into the structural basis of integrin activation," Blood, Aug. 2003, 102(4):1155-1159.
Xiong et al., "Crystal structure of the complete integrin αVβ3 ectodomain plus an α/β transmembrane fragment," The Journal of Cell Biology, Aug. 24, 2009, 186(4): 589-600.
Zhou et al., "Stereospecific halogenation of P(O)—H bonds with copper(II) chloride affording optically active Z1Z2P(O)Cl," The Journal of Organic Chemistry, Nov. 19, 2010, 75(22):7924-7.

\* cited by examiner

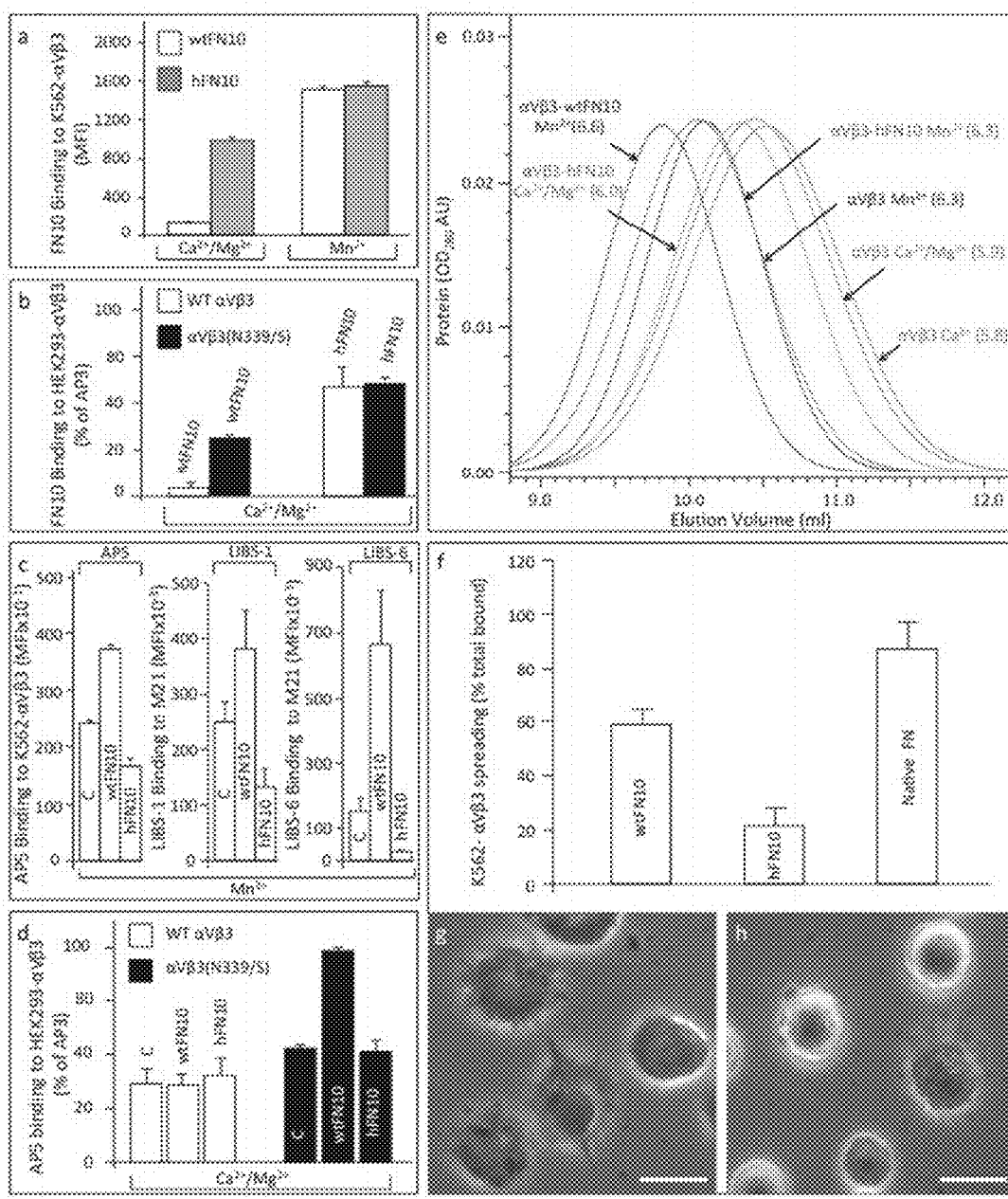
FIGs. 1A-H

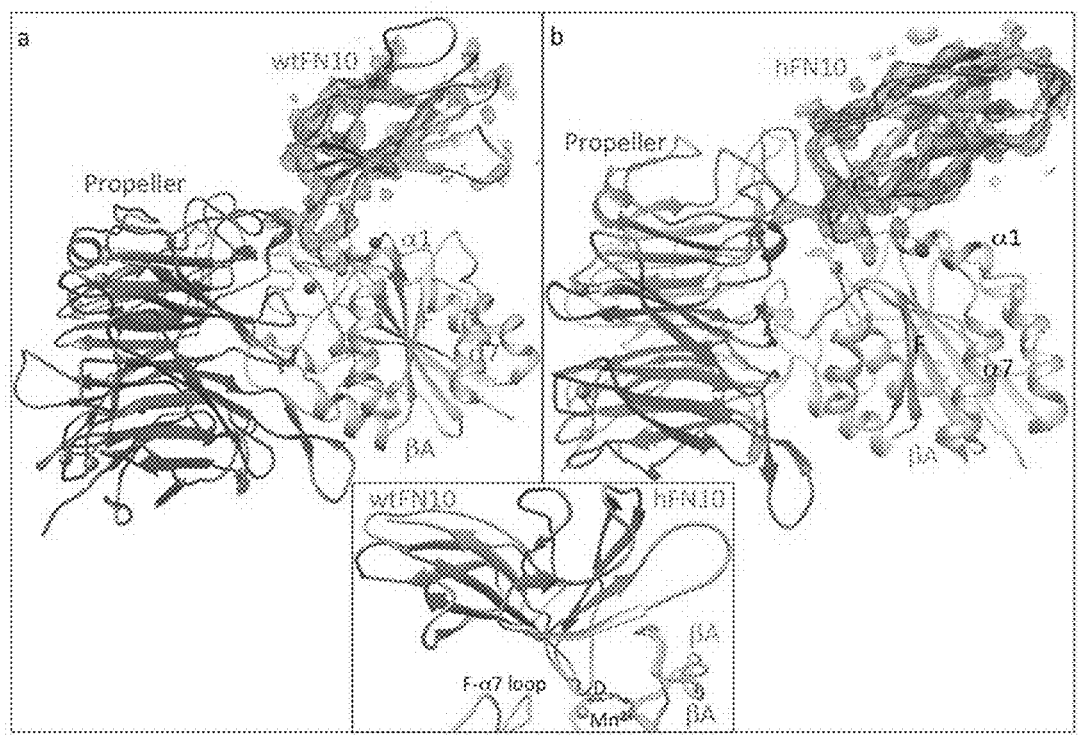
FIGs. 2A-B

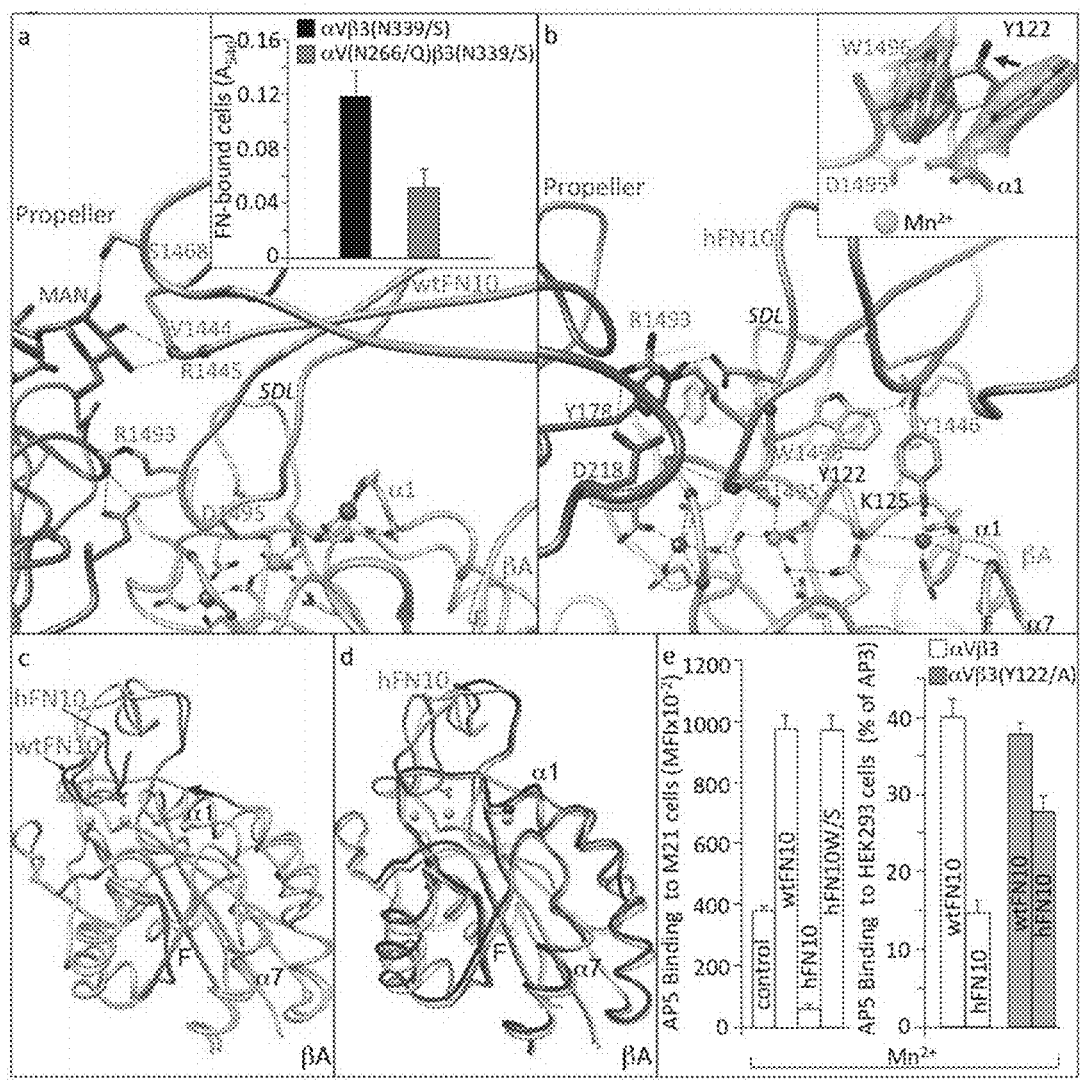
FIGs. 3A-E

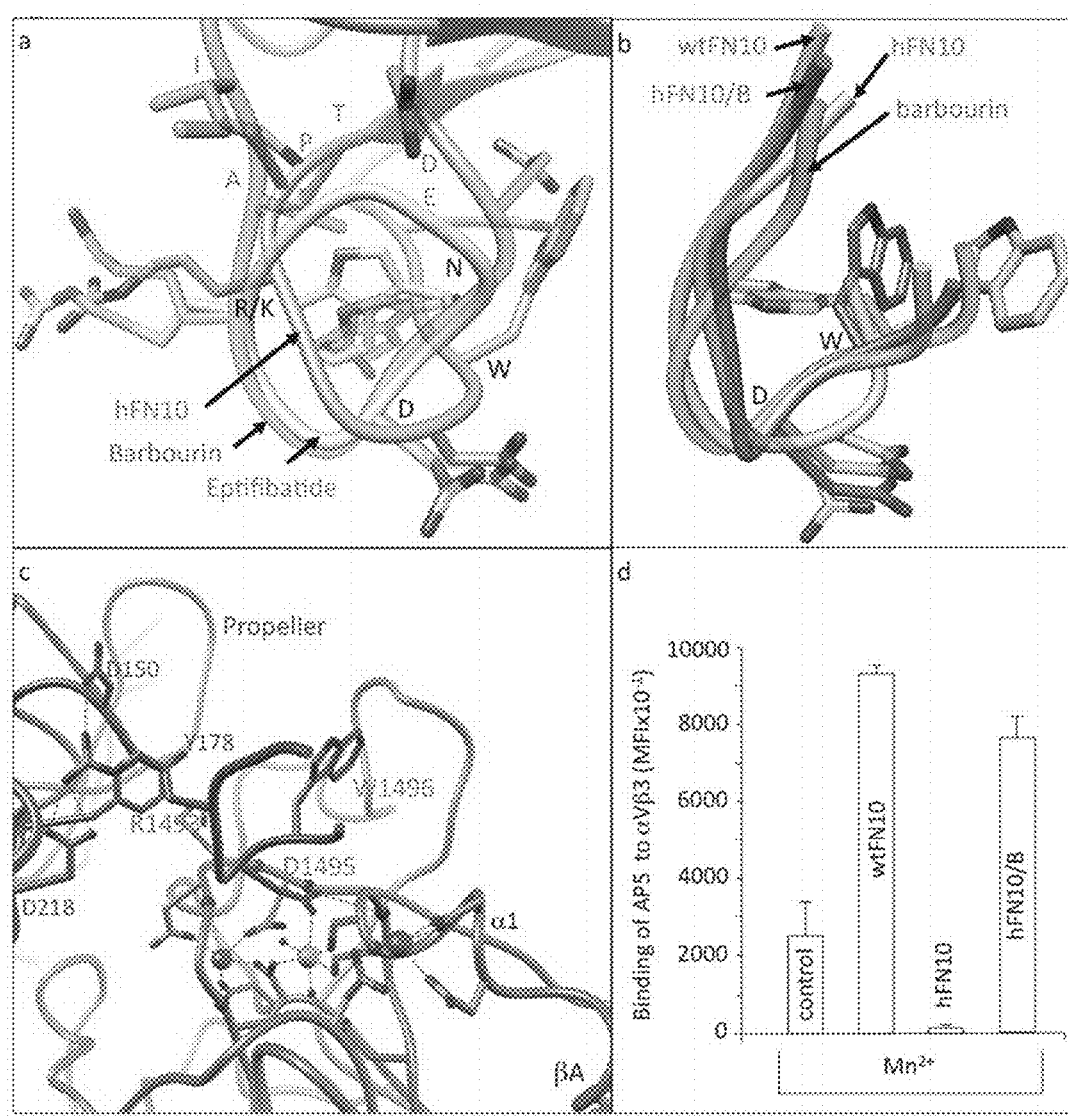
FIGs. 4A-D

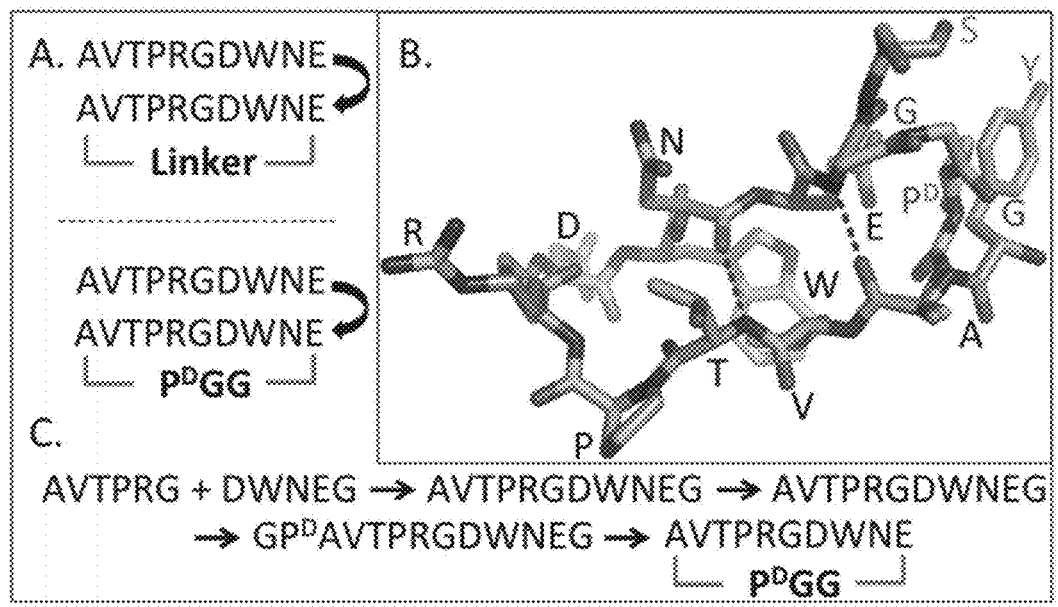
FIGs. 5A-C

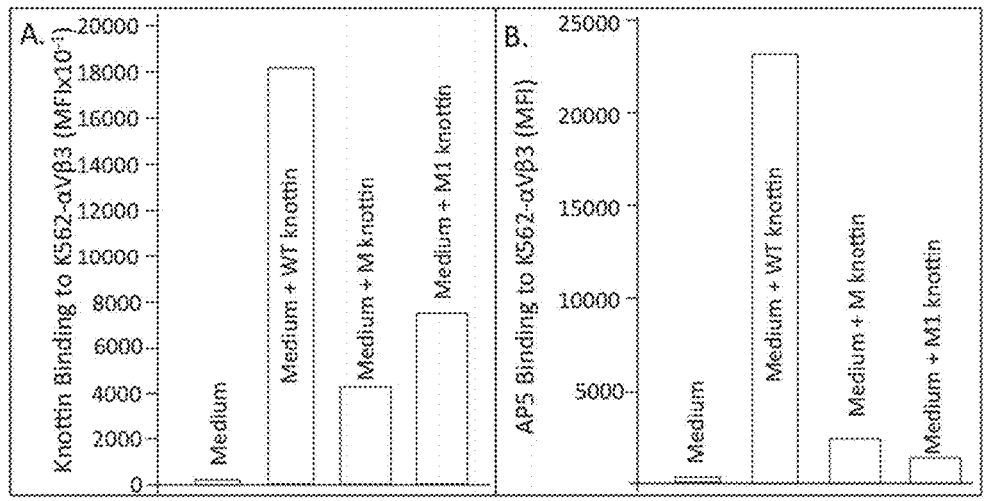
FIGs. 6A-B
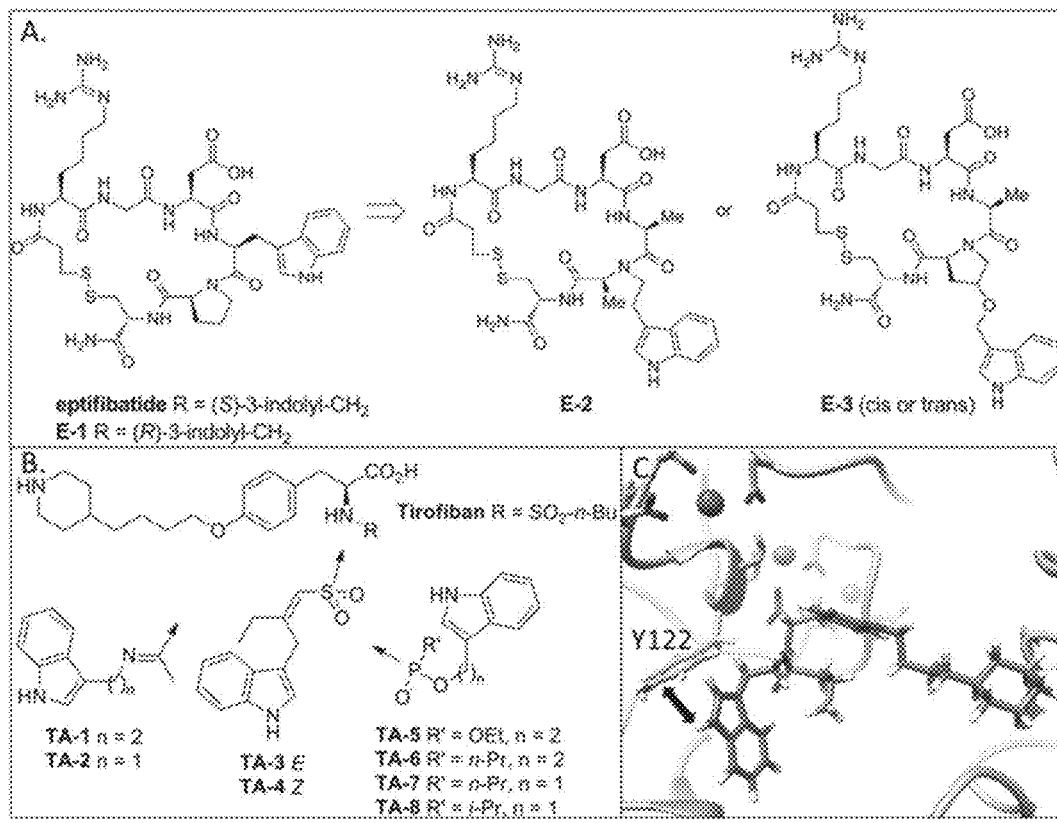
FIGs. 7A-C

```
beta3   1   YPVDLYYILMDLSYSMKDDLWSIQNLGTKLATQMRKLTSNLRIGFGSAFVDKPVSPYMYISPEALENPC--YDMKTTCLPM    78
beta1   1   YPIDLYYILMDLSYSMKDDIENVKSIGTDLMNEMRKITSDFRIGFGSFVEKTVMPYISTTP-AKLRNPCT--S-EQNCTTP    76
beta2   1   YPIDLYYILMDLSYSMLDDLRNVKKLGGDILRALNEITESGRIGFGSFVDKTVLFFVNTHP-DKLRNPCP---NKEKECQPP   77
beta7   1   YPVDLYYILMDLSYSMKDDLERVRQLGHALLVRLQEVTHSVRIGFGSFVDKTVLPFVSTVP-SKLRHPCP---TRLERCQSP   77
beta8   1   YPVDLYYIVDVSASMHNNIEKLNSVGNDLSRKMAFFSRDFRLGFGSYVDKTVSPFYISHP-ERIHNQCS---DYNLDCMPP   77
beta6   1   YPVDLYYILMDLSASMDDDLNTIKELGSRLSKEMSKLTSNFRLGFGSFVEKPVSPFVKTTP-EEIANPCS---SIPYFCLPT   77
beta5   1   YPVDLYYILMDLSLSMKDDLDNIRSLGTKLAFEMRKLTSNFRLGFGSFVDKDISPFSYTAP-RYQTNPCIgyKLFPNCVPS   79
beta4   1   -PVDLYILMDFSNSMSDDLDNLKKMGQNLARVLSQLTSDYTIGFGKFVDKVSVPQTDMKP-EKLKEPWP------NSDPP   72
                *             *                *       * ***          *        *          * beta3   79  FGYKHVLTLHDQVTRFNEEVKRQSVSRNRDAPEGGFDAIMQATVCDEKIGWRNDASHLLVFTT---THIALDGR--LAGI   153
beta1   77  FSYKNVLSLFTNKGEVFNELVGKVFNELVGKQRISGNLDSPEGGFDAIMQAVCGSLIGWRN-VTRLLVFSTDAGFHFAGDGK--LGGI   153
beta2   78  FAFRHVLKLTNNSNQFQTEVGKQLISGNLDAPEGGLDAMMQVAACPEEIGWRN-VTRLLVFATDDGFHFAGDGK--LGAI   154
beta7   78  FSFHHVLSLFTGDAQAFEREVGRQSVSGNLDSPEGGFDAILQAALCQEQIGWRN-VSRLLVFTSDDTFHTAGDGK--LGGI   154
beta8   78  HGYIHVLSLTENITEFEKAVHRQKISGNIDTPEGGFDAMLQAAVCESHIGWRKEAKRLLLVMFDQTSHLALDSK--LAGI   155
beta6   78  FGFKHILPLTMDAERFNEIVKNQKISANIDTPEGGFDAIMQAAVCKEKIGWRNDSLHLLVFVSDADSHFGMDSK--LAGI   155
beta5   80  FGFRHLLPLTDRVDSFNEEVRKQRVSRNRDAPEGGFDAVLQAAVCKEKIGWRKDALHLLVFTTDDVPHIALDGK--LGGL   157
beta4   73  FSFKNVISLTEDVDEFRNKLQGERISGNLDAPEGGFDAILQTAVCTRDIGWRPDSTHLLVFSTESAFHYEADGAnvLAGI   152
                *               *                 **                  *                      * beta3   154 VQPNDGQCHVGS-DNHYSASTTMDYPSLGLMTEKLSQRNINLIFAVTENVVNLYQNYSELIPGTTVGVLSMDSSNVLQLI   232
beta1   154 VLPNDGQCHLEN-N-MYTMSHYYDYPSIAHLVQKLSENNIQTIFAVTEEFQPVYKELEKNLIPKSAVGTLSANSSNVIQLI   231
beta2   155 LTPNDGRCHLED-N-LYKRSNEFDYPSVGQLAHKLAENNIQPIFAVTSRMVKTYEKLTELIPKSAVGELSEDSSNVVHLI   232
beta7   155 FMPSDGHCHLDS-NGLYSRSTEEFDYPSVGQVAQALSAANIQPIFAVTSAALPVYQELSKLIPKSAVGELSEDSSNVVQLI   233
beta8   156 VVPNDGNCHLKN-N-VYVKSTTMEHPSLGQLSEKLIDNNINVIFAVQGKQFHWYKDLLPLLPGTIAGEIESKAANLNNLV   233
beta6   156 VIPNDGLCHLDSKN-EYSMSTVLEYPTIGQLIDKLVQNNVLLIFAVTQEQVHLYENYAKLIPGATVGLLQKDSGNLIQLI   234
beta5   158 VQPHDGQCHLNE-ANEYTASNQMDYPSLALLIGEKLAENNINLIFAVTKNHYMLYKN-----------   212
beta4   153 MSRNDERCHLDT-FGTYTQYRTQDYPSVPTLVRLLAKHNIIPIFAVTNYSYYEKLHTYFPVSSLGVLQEDSSNIVELL   231
                *                         *                                  * beta3   233 VDAYGKIf    240
beta1   232 IDAYNSL-    238
beta2   233 KNAYNKL-    239
beta7   234 MDAYNSL-    240
beta8   234 VEAYQKL-    240
beta6   235 ISAYEELf    242
beta5       --------
beta4   232 EEAFNRIf    239
```

INTEGRIN ANTAGONISTS

CLAIM OF PRIORITY

This application is a continuation of U.S. patent application Ser. No. 16/575,009, filed Sep. 18, 2019, which is a continuation of U.S. patent application Ser. No. 15/109,602, filed Jul. 1, 2016, now U.S. Pat. No. 10,533,044, which claims priority under 35 U.S.C. § 371 to PCT/US2015/010384, filed Jan. 6, 2015, which claims the benefit of U.S. Provisional Patent Application Ser. No. 61/968,989 filed on Mar. 21, 2014; Patent Application No. 61/925,548, filed on Jan. 9, 2014; and Patent Application No. 61/924,103, filed on Jan. 6, 2014. The entire contents of the foregoing are hereby incorporated by reference.

FEDERALLY SPONSORED RESEARCH OR DEVELOPMENT

This invention was made with Government support under Grant Nos. DK088327 and DK096334 awarded by the National Institutes of Health. The Government has certain rights in the invention.

SEQUENCE LISTING

The instant application contains a Sequence Listing which has been submitted electronically in ASCII format and is hereby incorporated by reference in its entirety. Said ASCII copy, created on Jul. 29, 2021, is named "Sequence Listing.txt" and is 87,549 bytes in size.

TECHNICAL FIELD

This disclosure relates to integrin antagonists and methods of using the same. For example, one or more of the compounds or polypeptides provided herein can be used in the treatment of disorders such as heart attacks, stroke, and cancer metastasis.

BACKGROUND

Integrins are α/β heterodimeric cell adhesion receptors of metazoa, consisting of a bilobular head and two legs or tails that both span the plasma membrane. Integrins are unusual receptors, as they often exist on the cell surface in an inactive state (e.g., unable to engage a physiologic ligand). This is an important feature of integrin biology; for example, it allows patrolling blood platelets and immune cells to circulate with minimal aggregation or interaction with vessel walls. Physiological stimuli (e.g., chemokines), acting through the short integrin cytoplasmic tails, induce allosteric changes in the ectodomain required for extracellular physiologic ligand binding (i.e. "inside-out" signaling). Binding of extracellular ligands can induce "outside-in" signaling by initiating additional structural rearrangements, detectable in the isolated ectodomain using biophysical assays, and in integrins on the cell surface by their expression of novel epitopes (Ligand-induced binding sites, LIBS) including the epitopes of monoclonal antibodies (mAbs) AP5, LIBS-1 and LIBS-6. These ligand-induced structural rearrangements can trigger cell spreading, for example via connections established between integrin cytoplasmic tails and actin. Disruption of these regulatory processes can influence the pathogenesis of many diseases.

SUMMARY

Despite the clinical efficacy of cyclic RGD-like molecules in preventing thrombosis, parenteral ligand-mimetic antagonists of platelet integrin αIIbβ3, such as the cyclic peptide eptifibatide, have been found to induce severe thrombocytopenia in some 2% of patients, a major life-threatening complication given the widespread use of such drugs. In addition, during oral therapy of acute coronary syndromes, such drugs paradoxically induced thrombosis and mortality, leading to the failure of large clinical trials. Crystal structures of complete or partial integrin ectodomains complexed with small RGD-based peptidomimetics indicate that for the RGD motif to bind the integrin head, the Arg contacts the Propeller domain of the α-subunit, and Asp binds the βA domain of the β-subunit at a metal-ion-dependent-adhesion-site (MIDAS) via $Mg^{2+}$ (or $Mn^{2+}$). Two regulatory $Ca^{2+}$ cations at the ligand-associated metal binding site (LIMBS or SymBS) and at adjacent to MIDAS (ADMIDAS), flank the MIDAS metal ion. Binding of ligand-mimetic compounds to integrins is thought to be mechanically coupled to the inward movement of the N-terminal al helix of the βA domain towards MIDAS. This forces reorganization of βA's C-terminal F-strand/α7 loop, a one-turn displacement of helix α7, Hybrid domain swing-out, and other conformational changes that lead to outside-in signaling. These receptor changes may persist even after dissociation of ligand-mimetics, contributing to immune thrombocytopenia, and enhancing physiological ligand binding to the integrin, which may have contributed to increased mortality in patients treated with orally active RGD-like compounds targeting platelet αIIbβ3. RGD-bearing αVβ3 antagonists (e.g., cyclic pentapeptide cilengitide) paradoxically stimulated model tumor growth and angiogenesis, suggesting that they can exert similar effects.

Provided herein is a polypeptide comprising the amino acid sequence:

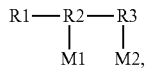

wherein
R1 is selected from the group consisting of: RGD, LDV, IDA, REDV (SEQ ID NO: 45), KGD, NGR, DGR, KQAGD (SEQ ID NO: 42), DALR (SEQ ID NO: 46), DLR, RLD, [L/I]ET, LRE, and TDE;
R2 and R3 are each independently an amino acid in L or D form;
M1 and M2 are each independently absent or a side chain comprising at least one of: a branched C1-C6 alkyl, a heteroaryl, or an aryl, wherein the alkyl, heteroaryl, or aryl is optionally substituted with 1-3 groups consisting of: halo, C1-C6 alkyl, C2-C6 alkenyl, C2-C6 alkynyl, heteroaryl, aryl, heterocyclyl, and carbocyclyl;
wherein M1 and M2 are not both absent, and at least one of the bonds designated
between M1 and R2, and M2 and R3, when present, is freely rotating.

In some embodiments, R1 is selected from the group consisting of: RGD, LDV, KGD, KQAGD (SEQ ID NO: 42), IDA, L/IET, RLD, LRE, and TDE. In some embodiments, R1 is selected from the group consisting of: RGD, LDV, KGD, KQAGD (SEQ ID NO: 42), IDA, and L/IET. In some embodiments, R1 is selected from the group consisting of: RGD, LDV, and KGD.

In some embodiments, R2 is selected from the group consisting of W, F, S, A, N, pG, pP, and (4S)-4-hydroxy-L-proline and derivatives thereof or unnatural derivatives thereof, in L or D form; and R3 is selected from the group consisting of V, I, F, (4S)-4-hydroxy-L-proline, pP, pG and derivatives thereof or unnatural derivatives thereof, in L or D form.

Also provided herein is a polypeptide comprising the amino acid sequence:

R*-G-D-X1-X2-X3 (SEQ ID NO: 40),
wherein
R* is R or unnatural derivatives thereof, in L or D form;
X1 is any amino acid or unnatural derivatives thereof, in L or D form, with the proviso that X1 is not P;
X2 is any amino acid or unnatural derivatives thereof, in L or D form, with the proviso that X2 is not P, pP, or pG;
X3 is any amino acid, in L or D form;
and wherein the polypeptide has a length of 6 to 100 amino acids, provided that the polypeptide does not comprise the sequence:

SDVPRDLEVVAATPTSLLISWDAPAVTVRYYRITYGETGGNSPVQEFTVPGSKSTA
TISGLKPGVDYTITVYAVTGRGDSPASSKPISINYRT;

GCPRPRGDNPPLTCSQDSDCLAGCVCGPNGFCG;

GCPQGRGDWAPTSCKQDSDCLAGCVCGPNGFCG;

GCPQGRGDWAPTSCSQDSDCLAGCVCGPNGFCG and

RGDWPC,
└Linker┘ wherein the linker is the moiety

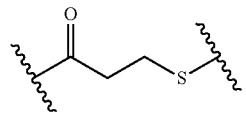 [SMILES: *SCCC(*)=O]

connecting the N-terminal end of Arg and the thiol side chain of Cys.

In some embodiments, X1 is selected from the group consisting of W, F, S, A, N, pG, and unnatural derivatives thereof, in L or D form. In some embodiments, X2 is selected from the group consisting of V, I, N, F, (4S)-4-hydroxy-L-proline, pP, pG, and unnatural derivatives thereof, in L or D form. In some embodiments, X1 is W or unnatural derivatives thereof, in L or D form; and X2 is N, in L or D form.

In some embodiments, X3 is P, in L or D form. For example, X3 is L-proline.

In some embodiments, the polypeptide has a length of 6 to 40 amino acids.

In some embodiments, a polypeptide of SEQ ID NO: 40 has at least 75% sequence identity to a polypeptide selected from the group consisting of:

(SEQ ID NO: 9)
SDVPRDLEVVAATPTSLLISWDAPAVTVRYYRI

TYGETGGNSPVQEFTVPGSKSTATISGLKPGVD

YTITVYAVTPRGDWNEGSKPISINY;

-continued
(SEQ ID NO: 10)
SDVPRDLEVVAATPTSLLISWDAPAVTVRYYRI

TYGETGGNSPVQEFTVPGSKSTATISGLKPGVD

YTITVYAVTPKGDWNEGSKPISINY;

(SEQ ID NO: 11)
VPRDLEVVAATPTSLLISWDAPAVTVRYYRIT

YGETGGNSPVQEFTVPGSKSTATISGLKPGVD

YTITVYAVTPKGDWNEGSKPISINY;

(SEQ ID NO: 12)
VPRDLEVVAATPTSLLISWDAPAVTVRYYRIT

YGETGGNSPVQEFTVPGSKSTATISGLKPGVD

YTITVYAVTPKGDWNEGGPISINY;

(SEQ ID NO: 20)

(SEQ ID NO: 47)

(SEQ ID NO: 41)

(SEQ ID NO 48)

(SEQ ID NO: 26)

-continued
(SEQ ID NO: 13)
VPRDLEVVAATPTSLLISWDAPAVTVRYYRIT

YGETGGNSPVQEFTVPGSKSTATISGLKPGVD

YTITVYAVTPRGDWNEGSKPISINY;

(SEQ ID NO: 14)
VPRDLEVVAATPTSLLISWDAPAVTVRYYRIT

YGETGGNSPVQEFTVPGSKSTATISGLKPGVD

YTITVYAVTPRGDWNEGGPISINY;

(SEQ ID NO: 29)
SDVPRDLEVVAATPTSLLISWDAPAVTVRYYR

ITYGETGGNSPVQEFTVPGSKSTATISGLKPG

VDYTITVYAVTPRGDWNEGSKPISINY (SEQ ID NO: 30)
SDVPRDLEVVAATPTSLLISWDAPAVTVRYYR

ITYGETGGNSPVQEFTVPGSKSTATISGLKPG

VDYTITVYAVTGPGRGDWNEGSKPISINY (SEQ ID NO: 31)
SDVPRDLEVVAATPTSLLISWDAPAVTVRYYR

ITYGETGGNSPVQEFTVPGSKSTATISGLKPG

VDYTITVYAVTPARGDWNEGSKPISINY

-continued

```
                                       (SEQ ID NO: 32)
SDVPRDLEVVAATPTSLLISWDAPAVTVRYYR

ITYGETGGNSPVQEFTVPGSKSTATISGLKPG

VDYTITVYAVTP(HRG)GDWNEGSKPISINY.
```

In some embodiments, the polypeptide further comprises a tag. For example, the polypeptide can further include an affinity tag such as one or more histidine amino acids.

In some embodiments, the polypeptides of SEQ ID NO: 40 is selected from the group consisting of:

```
                                        (SEQ ID NO: 9)
SDVPRDLEVVAATPTSLLISWDAPAVTV

RYYRITYGETGGNSPVQEFTVPGSKSTA

TISGLKPGVDYTITVYAVTPRGDWNEGS

KPISINY;

(SEQ ID NO: 10)
SDVPRDLEVVAATPTSLLISWDAPAVTV

RYYRITYGETGGNSPVQEFTVPGSKSTA

TISGLKPGVDYTITVYAVTPKGDWNEGS

KPISINY;

(SEQ ID NO: 11)
VPRDLEVVAATPTSLLISWDAPAVTVRY

YRITYGETGGNSPVQEFTVPGSKSTATI

SGLKPGVDYTITVYAVTPKGDWNEGSKP

ISINY;

(SEQ ID NO: 49)
VPRDLEVVAATPTSLLISWDAPAVTVRY

YRITYGETGGNSPVQEFTVPGSKSTATI

SGLKPGVDYTITVYAVTPKGDWNEG--P

ISINY;

(SEQ ID NO: 13)
VPRDLEVVAATPTSLLISWDAPAVTVRY

YRITYGETGGNSPVQEFTVPGSKSTATI

SGLKPGVDYTITVYAVTPRGDWNEGSKP

ISINY;

(SEQ ID NO: 14)
VPRDLEVVAATPTSLLISWDAPAVTVRY

YRITYGETGGNSPVQEFTVPGSKSTATI

SGLKPGVDYTITVYAVTPRGDWNEGGPI

SINY;

(SEQ ID NO: 29)
SDVPRDLEVVAATPTSLLISWDAPAVT

VRYYRITYGETGGNSPVQEFTVPGSKS

TATISGLKPGVDYTITVYAVTPGRGDW

NEGSKPISINY
```

```
                                       (SEQ ID NO: 30)
SDVPRDLEVVAATPTSLLISWDAPAVT

VRYYRITYGETGGNSPVQEFTVPGSKS

TATISGLKPGVDYTITVYAVTGPGRGD

WNEGSKPISINY (SEQ ID NO: 31)
SDVPRDLEVVAATPTSLLISWDAPAVT

VRYYRITYGETGGNSPVQEFTVPGSKS

TATISGLKPGVDYTITVYAVTPARGDW

NEGSKPISINY (SEQ ID NO: 32)
SDVPRDLEVVAATPTSLLISWDAPAVT

VRYYRITYGETGGNSPVQEFTVPGSKS

TATISGLKPGVDYTITVYAVTP(HRG)

GDWNEGSKPISINY.
```

In some embodiments, a polypeptide of SEQ ID NO: 40 has at least 75% sequence identity to a sequence selected from the group consisting of:

```
                                        (SEQ ID NO: 3)
G-C-P-R-P-R-G-D-W-N-E-G-T-C-S-Q-D-

S-D-C-L-A-G-C-V-C-G-P-N-G-F-C-G;

(SEQ ID NO: 50)
G-C-P-R-P-R-G-D-W-N-E-G-S-C-S-Q-D-

S-D-C-L-A-G-C-V-C-G-P-N-G-F-C-G;

(SEQ ID NO: 4)
G-C-P-R-P-R-G-D-W-N-P-L-T-C-S-Q-D-

S-D-C-L-A-G-C-V-C-G-P-N-G-F-C-G;

(SEQ ID NO: 5)
G-C-A-V-T-P-R-G-D-W-N-E-G-S-L-P-C-

S-Q-D-S-D-C-L-A-G-C-V-C-G-P-N-G-F-

C-G;

(SEQ ID NO: 6)
G-C-V-R-L-H-E-S-C-L-G-Q-Q-V-P-C-C-

D-P-A-A-T-C-Y-C-Y-G-R-G-D-W-N-E-G-

C-Y-C-R;

(SEQ ID NO: 7)
G-C-V-R-L-H-E-S-C-L-G-Q-Q-V-P-C-C-

D-P-A-A-T-C-Y-C-Y-G-R-G-D-W-N-L-R-

C-Y-C-R;

(SEQ ID NO: 8)
G-C-V-R-L-H-E-S-C-L-G-Q-Q-V-P-C-C-

D-P-A-A-T-C-Y-C-A-V-T-P-R-G-D-W-N-

E-G-S-K-P-C-Y-C-R;
```

```
                                               (SEQ ID NO: 21)
G-C-A-V-T-P-R-G-D-W-N-E-G-S-K-P-I-
S-C-S-Q-D-S-D-C-L-A-G-C-V-C-G-P-N-
G-F-C-G;
                                               (SEQ ID NO: 22)
G-C-P-R-I-L-M-R-C-S-Q-D-S-D-C-L-A-
G-C-V-C-G-P-K-S-G-E-N-W-D-G-R-P-T-
V-A-G-F-C-G;
                                               (SEQ ID NO: 23)
G-C-P-R-G-D-W-N-E-G-S-K-P-L-S-C-S-
Q-D-S-D-C-L-A-G-C-V-C-G-P-N-G-F-C-
G;
                                               (SEQ ID NO: 24)
G-C-A-V-T-P-R-G-D-W-N-E-G-S-K-P-G-
C-K-Q-D-S-D-C-L-A-G-C-V-C-G-P-N-G-
F-C-G;
                                               (SEQ ID NO: 25)
G-C-P-R-I-L-M-R-C-K-Q-D-S-D-C-L-A-
G-C-V-C-G-P-K-S-G-E-N-W-D-G-R-P-T-
V-G-F-C-G;
                                               (SEQ ID NO. 33)
GCPRPRGDNXPLTCSQDSDCLAGCVCGPNGFCG
                                               (SEQ ID NO. 34)
GCPRPRGDN(PP)PLTCSQDSDCLAGCVCGPNGFCG
                                               (SEQ ID NO. 35)
GCPRPRGDN(XP)PLTCSQDSDCLAGCVCGPNGFCG
                                               (SEQ ID NO. 36)
GCPRPRGDN(PG)PLTCSQDSDCLAGCVCGPNGFCG;
                                               (SEQ ID NO. 37)
GCPQGRGDWXPTSCSQDSDCLAGCVCGPNGFCG
                                               (SEQ ID NO. 38)
GCPQGRGDW(PP)PTSCSQDSDCLAGCVCGPNGFCG;
and
                                               (SEQ ID NO. 39)
GCPQGRGDW(PG)PTSCSQDSDCLAGCVCGPNGFCG,
``` wherein X can be any amino acid or unnatural derivative thereof, in L or D form, with the proviso that X is not P.

For example, the polypeptide is selected from the group consisting of:

```
                                               (SEQ ID NO: 3)
G-C-P-R-P-R-G-D-W-N-E-G-T-C-S-Q-D-S-D-C-L-A-G-C-V-
C-G-P-N-G-F-C-G;
                                               (SEQ ID NO: 50)
G-C-P-R-P-R-G-D-W-N-E-G-S-C-S-Q-D-S-D-C-L-A-G-C-V-
C-G-P-N-G-F-C-G;
                                               (SEQ ID NO: 4)
G-C-P-R-P-R-G-D-W-N-P-L-T-C-S-Q-D-S-D-C-L-A-G-C-V-
C-G-P-N-G-F-C-G;
                                               (SEQ ID NO: 5)
G-C-A-V-T-P-R-G-D-W-N-E-G-S-L-P-C-S-Q-D-S-D-C-L-A-
G-C-V-C-G-P-N-G-F-C-G;
                                               (SEQ ID NO: 6)
G-C-V-R-L-H-E-S-C-L-G-Q-Q-V-P-C-C-D-P-A-A-T-C-Y-C-
Y-G-R-G-D-W-N-E-G-C-Y-C-R;
                                               (SEQ ID NO: 7)
G-C-V-R-L-H-E-S-C-L-G-Q-Q-V-P-C-C-D-P-A-A-T-C-Y-C-
Y-G-R-G-D-W-N-L-R-C-Y-C-R;
                                               (SEQ ID NO: 8)
G-C-V-R-L-H-E-S-C-L-G-Q-Q-V-P-C-C-D-P-A-A-T-C-Y-C-
A-V-T-P-R-G-D-W-N-E-G-S-K-P-C-Y-C-R;
                                               (SEQ ID NO: 21)
G-C-A-V-T-P-R-G-D-W-N-E-G-S-K-P-I-S-C-S-Q-D-S-D-C-
L-A-G-C-V-C-G-P-N-G-F-C-G;
                                               (SEQ ID NO: 22)
G-C-P-R-I-L-M-R-C-S-Q-D-S-D-C-L-A-G-C-V-C-G-P-K-S-
G-E-N-W-D-G-R-P-T-V-A-G-F-C-G;
                                               (SEQ ID NO: 23)
G-C-P-R-G-D-W-N-E-G-S-K-P-L-S-C-S-Q-D-S-D-C-L-A-G-
C-V-C-G-P-N-G-F-C-G;
                                               (SEQ ID NO: 24)
G-C-A-V-T-P-R-G-D-W-N-E-G-S-K-P-G-C-K-Q-D-S-D-C-L-
A-G-C-V-C-G-P-N-G-F-C-G;
                                               (SEQ ID NO: 25)
G-C-P-R-I-L-M-R-C-K-Q-D-S-D-C-L-A-G-C-V-C-G-P-K-S-
G-E-N-W-D-G-R-P-T-V-G-F-C-G;
                                               (SEQ ID NO. 33)
GCPRPRGDNXPLTCSQDSDCLAGCVCGPNGFCG
                                               (SEQ ID NO. 34)
GCPRPRGDN(PP)PLTCSQDSDCLAGCVCGPNGFCG
                                               (SEQ ID NO. 35)
GCPRPRGDN(XP)PLTCSQDSDCLAGCVCGPNGFCG
                                               (SEQ ID NO. 36)
GCPRPRGDN(PG)PLTCSQDSDCLAGCVCGPNGFCG;
                                               (SEQ ID NO. 37)
GCPQGRGDWXPTSCSQDSDCLAGCVCGPNGFCG
                                               (SEQ ID NO. 38)
GCPQGRGDW(PP)PTSCSQDSDCLAGCVCGPNGFCG;
and
                                               (SEQ ID NO. 39)
GCPQGRGDW(PG)PTSCSQDSDCLAGCVCGPNGFCG,
``` wherein X can be any amino acid or unnatural derivative thereof, in L or D form, with the proviso that X is not P.

In some embodiments, a polypeptide of SEQ ID NO: 40, the polypeptide comprises a cyclic polypeptide.

For example, a polypeptide of SEQ ID NO: 40 can have at least 75% sequence identity to the sequence:

AVTPRGDWNE (SEQ ID NO: 1)
|_Linker_| wherein the linker comprises two or more amino acids.

In some embodiments, the linker has a length of 2-13 amino acids. For example, the linker can have a length of 2-10 amino acids or 2-6 amino acids. In some embodiments, the linker is a tripeptide. For example, the linker can be selected from the group consisting of: $P^D$-G-G; G-$P^D$-G; and G-G-$P^D$. In some embodiments, the linker is $P^D$GG. In some embodiments, the polypeptide has the sequence:

A-V-T-P-R-G-D-W-N-E. (SEQ ID NO: 2)
|_____$P^D$-G-G_____|

In some embodiments, a polypeptide of SEQ ID NO: 40 has at least 75% sequence identity to the sequence:

PRPRGDN (SEQ ID NO: 27)
|_Linker_| wherein the linker comprises two or more amino acids. In some embodiments, the linker has a length of 2-9 amino acids or about 2-6 amino acids.

In some embodiments, a polypeptide of SEQ ID NO: 40 has at least 75% sequence identity to the sequence:

PRGDNXP (SEQ ID NO: 43)
|_Linker_| wherein the linker comprises two or more amino acids; and X is any amino acid or unnatural derivative thereof, in L or D form, preferably W, F, S, A, N, pG, pP, (4S)-4-hydroxy-L-proline and derivatives thereof or unnatural derivatives thereof, in L or D form. In some embodiments, the linker has a length of 2-9 amino acids or about 2-6 amino acids.

In some embodiments, a polypeptide of SEQ ID NO: 40 has at least 75% sequence identity to the sequence:

PQGRGDW (SEQ ID NO: 28)
|_Linker_| wherein the linker comprises two or more amino acids. In some embodiments, the linker has a length of 2-9 amino acids or about 2-6 amino acids.

In some embodiments, a polypeptide of SEQ ID NO: 40 has at least 75% sequence identity to the sequence:

PGRGDWXP (SEQ ID NO: 44)
|_Linker_| wherein the linker comprises two or more amino acids; and X is any amino acid or unnatural derivative thereof, in L or D form, preferably V, I, F, (4S)-4-hydroxy-L-proline, pP, pG and derivatives or unnatural derivatives thereof, in L or D form. In some embodiments, the linker has a length of 2-9 amino acids or about 2-6 amino acids.

In some embodiments, a polypeptide of SEQ ID NO: 40 is a compound of Formula (I):

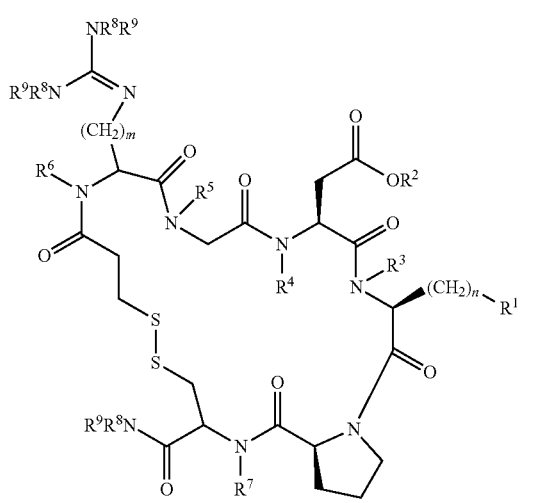

(I)

or a pharmaceutically acceptable salt thereof, wherein:

$R^1$ is selected from the group consisting of a 3-12 membered heterocyclyl and a 5-12 membered heteroaryl;

each of $R^2$, $R^3$, $R^4$, $R^5$, $R^6$, $R^7$, $R^8$, and $R^9$ is independently selected from H and $(C_1-C_6)$alkyl;

m is an integer from 1 to 10; and n is an integer from 1 to 6.

In some embodiments, $R^1$ is an electron-rich heterocyclyl or heteroaryl. In some embodiments, $R^1$ is an electron-poor heterocyclyl or heteroaryl. In some embodiments, $R^1$ is selected from the group consisting of indolyl, pyridyl, thiophenyl, and pyrrolyl. For example, $R^1$ is indolyl.

In some embodiments, n is 1. In some embodiments, $R^2$, $R^3$, $R^4$, $R^5$, $R^6$, $R^7$, $R^8$, and $R^9$ are H. In some embodiments, m is 4.

A non-limiting example of a compound of Formula (I) is:

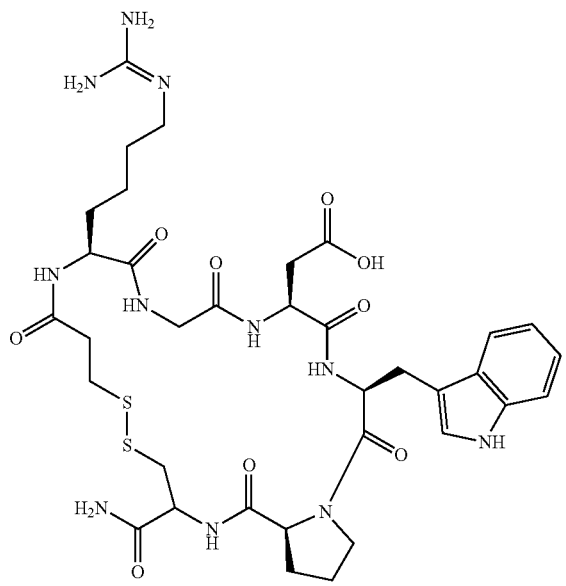 [SMILES: NC(=O)C1CSSCCC(=O)N[C@@H](CCCCN=C(N)N)C(=O)NCC(=O)N[C@@H](CC(=O)O)C(=O)N[C@@H](Cc2c[nH]c3ccccc23)C(=O)N2CCC[C@H]2C(=O)N1]

or a pharmaceutically acceptable salt thereof.

In some embodiments, a polypeptide of SEQ ID NO: 40 is a compound of Formula (II):

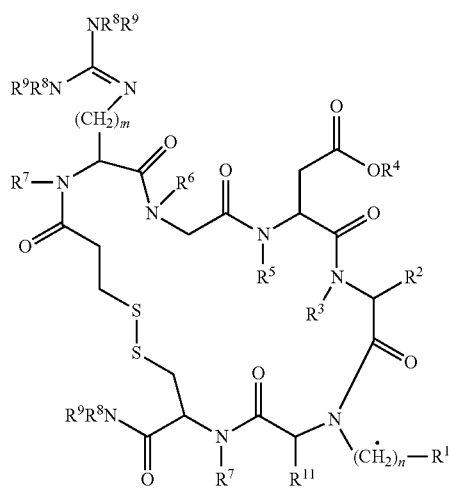

or a pharmaceutically acceptable salt thereof,
wherein:
$R^1$ is selected from the group consisting of a 3-12 membered heterocyclyl and a 5-12 membered heteroaryl;
each of $R^2$, $R^3$, $R^4$, $R^5$, $R^6$, $R^7$, $R^8$, $R^9$, $R^{10}$, and $R^{11}$ is independently selected from H and $(C_1\text{-}C_6)$alkyl;
m is an integer from 1 to 10; and
n is an integer from 1 to 6.

In some embodiments, $R^1$ is an electron-rich heterocyclyl or heteroaryl. In some embodiments, $R^1$ is an electron-poor heterocyclyl or heteroaryl. In some embodiments, $R^1$ is selected from the group consisting of indolyl, pyridyl, thiophenyl, and pyrrolyl. For example, $R^1$ is indolyl.

In some embodiments, n is 2. In some embodiments, $R^3$, $R^4$, $R^5$, $R^6$, $R^7$, $R^8$, $R^9$, and $R^{10}$ are H. In some embodiments, $R^2$ and $R^{11}$ are $CH_3$. In some embodiments, m is 4.

Non-limiting examples of a compound of Formula (II) include:

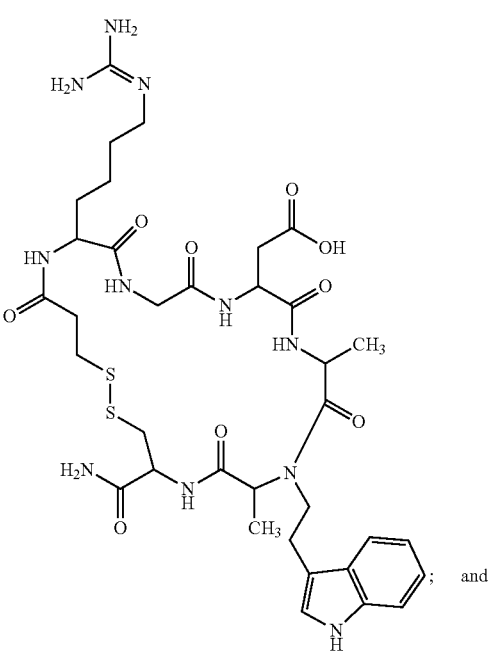

; and

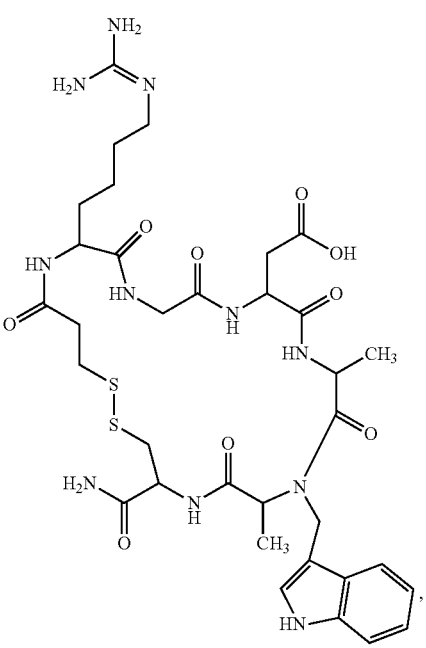

, or a pharmaceutically acceptable salt thereof. In some embodiments, the compound of Formula (II) is selected from the group consisting of:

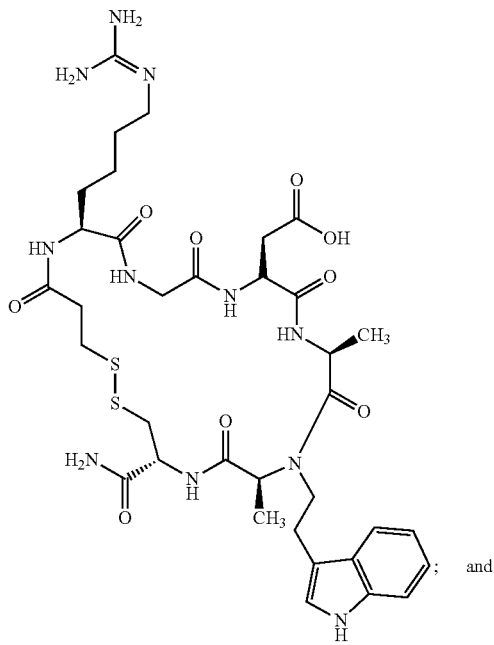

and

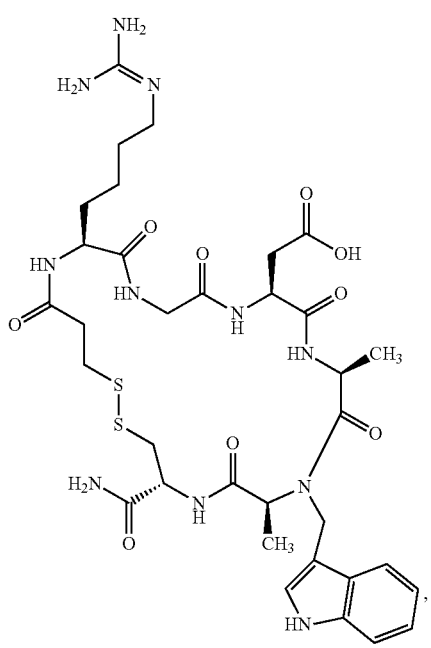

or a pharmaceutically acceptable salt thereof.

In some embodiments, a polypeptide of SEQ ID NO: 40 is a compound of Formula (III):

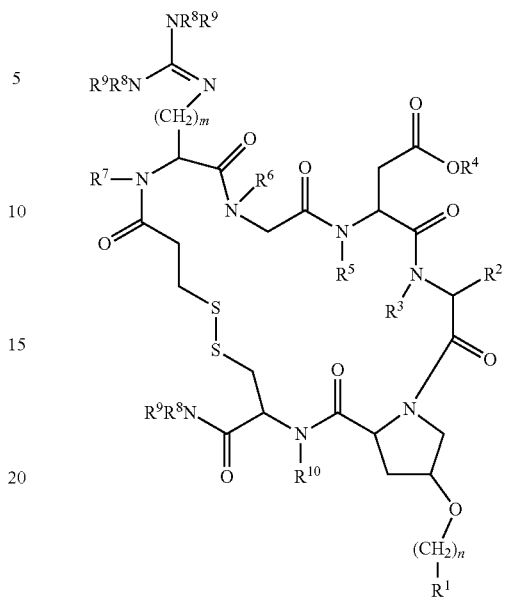

(III)

or a pharmaceutically acceptable salt thereof,
wherein:
$R^1$ is selected from the group consisting of a 3-12 membered heterocyclyl and a 5-12 membered heteroaryl;
each of $R^2$, $R^3$, $R^4$, $R^5$, $R^6$, $R^7$, $R^1$, $R^9$, and $R^{10}$ is independently selected from H and $(C_1\text{-}C_6)$alkyl;
m is an integer from 1 to 10; and
n is an integer from 0 to 6.

In some embodiments, $R^1$ is an electron-rich heterocyclyl or heteroaryl. In some embodiments, $R^1$ is an electron-poor heterocyclyl or heteroaryl. In some embodiments, $R^1$ is selected from the group consisting of indolyl, pyridyl, thiophenyl, and pyrrolyl. For example, $R^1$ is indolyl.

In some embodiments, n is 1. In some embodiments, $R^3$, $R^4$, $R^5$, $R^6$, $R^7$, $R^8$, $R^9$, $R^{10}$ are H. In some embodiments, $R^2$ is $CH_3$. In some embodiments, m is 4.

A non-limiting example of a compound of Formula (III) includes:

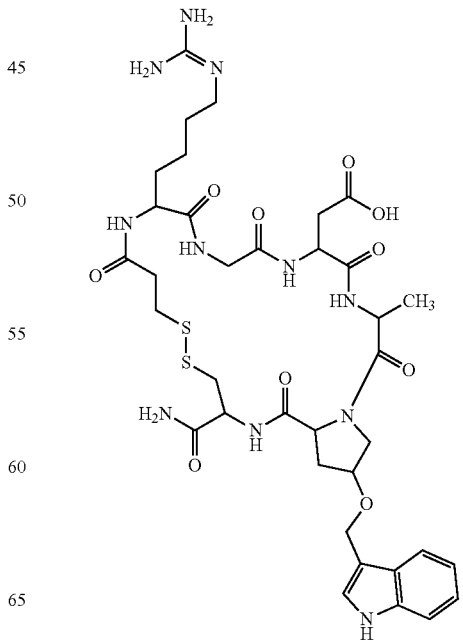

or a pharmaceutically acceptable salt thereof. For example, the compound of Formula (III) can be:

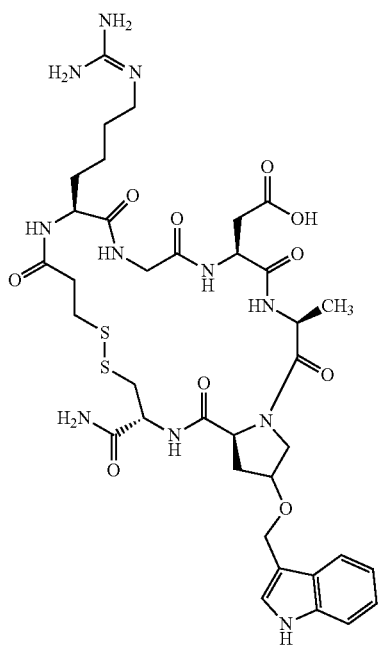

or a pharmaceutically acceptable salt thereof.

In some embodiments, a polypeptide of SEQ ID NO: 40 is a compound of Formula (V):

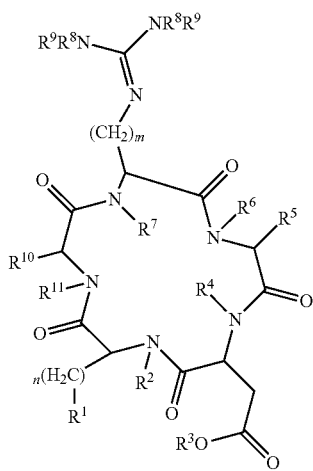

or a pharmaceutically acceptable salt thereof, wherein:

$R^1$ is selected from the group consisting of a 3-12 membered heterocyclyl and a 5-12 membered heteroaryl;

each of $R^2$, $R^3$, $R^4$, $R^5$, $R^6$, $R^7$, $R^8$, $R^9$, $R^{10}$, and $R^{11}$ is independently selected from H and ($C_1$-$C_6$)alkyl;

m is an integer from 1 to 10; and n is an integer from 0 to 6.

In some embodiments, $R^1$ is an electron-rich heterocyclyl or heteroaryl. In some embodiments, $R^1$ is an electron-poor heterocyclyl or heteroaryl. In some embodiments, $R^1$ is selected from the group consisting of indolyl, pyridyl, thiophenyl, and pyrrolyl. For example, $R^1$ is indolyl.

In some embodiments, n is 1. In some embodiments, $R^2$, $R^3$, $R^4$, $R^5$, $R^6$, $R^7$, $R^8$, and $R^9$ are H. In some embodiments, m is 3. In some embodiments, $R^{10}$ is $CH(CH_3)_2$. In some embodiments, $R^{11}$ is $CH_3$.

A non-limiting example of a compound of Formula (V) is:

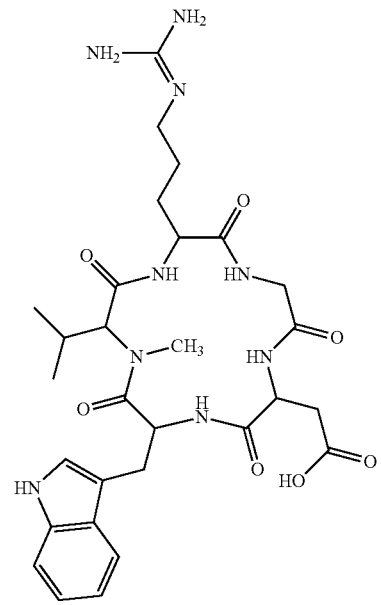 [SMILES: CC(C)C1C(=O)NC(CCCN=C(N)N)C(=O)NCC(=O)NC(CC(=O)O)C(=O)NC(Cc2c[nH]c3ccccc23)C(=O)N1C]

or a pharmaceutically acceptable salt thereof. For example, a compound of Formula (V) can be:

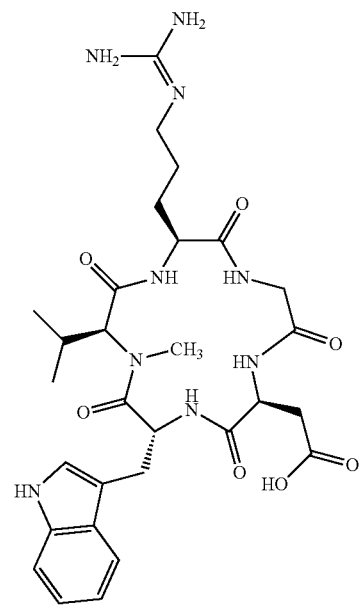 [SMILES: CC(C)[C@H]1C(=O)N[C@@H](CCCN=C(N)N)C(=O)NCC(=O)N[C@@H](CC(=O)O)C(=O)N[C@H](Cc2c[nH]c3ccccc23)C(=O)N1C]

or a pharmaceutically acceptable salt thereof.

In some embodiments, a polypeptide of SEQ ID NO: 40 is a compound of Formula (VI):

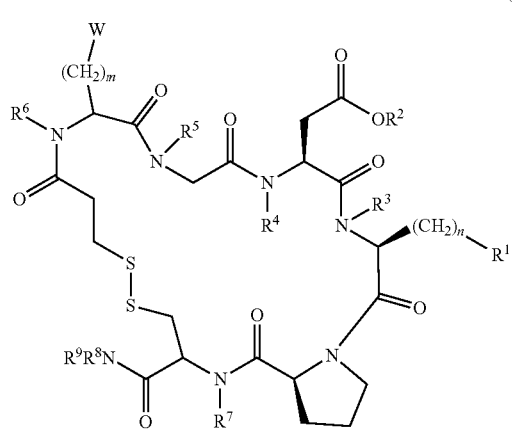

(VI)

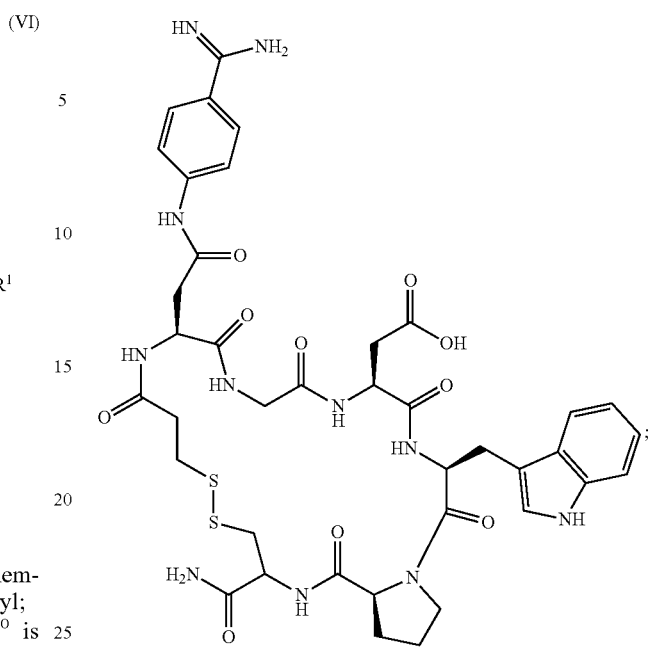

or a pharmaceutically acceptable salt thereof,
wherein:
$R^1$ is selected from the group consisting of a 3-12 membered heterocyclyl and a 5-12 membered heteroaryl;
each of $R^2$, $R^3$, $R^4$, $R^5$, $R^6$, $R^7$, $R^8$, $R^9$ and $R^{10}$ is independently selected from H and ($C_1$-$C_6$)alkyl;
W is selected from the group consisting of:

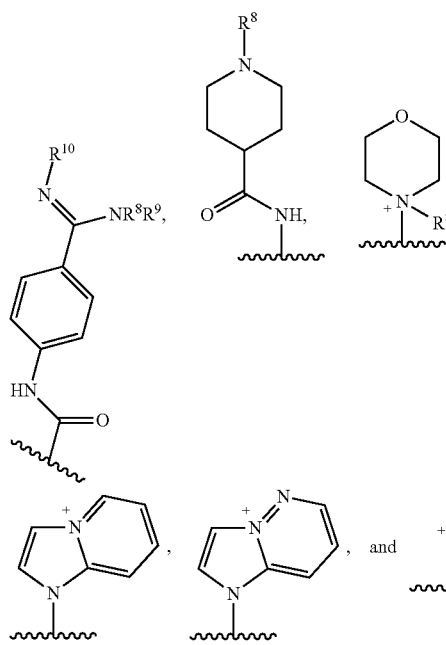

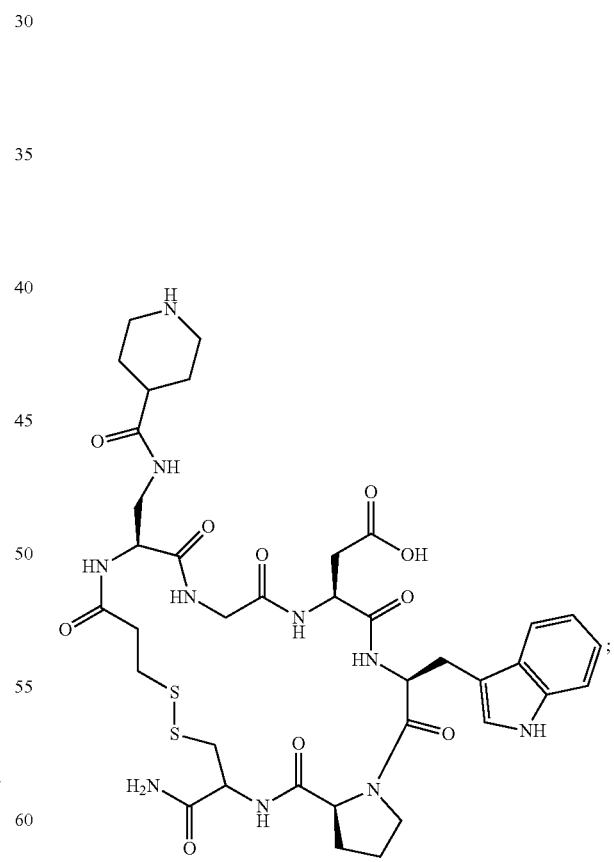

m is an integer from 1 to 10; and
n is an integer from 1 to 6.

In some embodiments, $R^1$ is an electron-rich heterocyclyl or heteroaryl. In some embodiments, R1 is an electron-poor heterocyclyl or heteroaryl. In some embodiments, R1 is selected from the group consisting of indolyl, pyridyl, thiophenyl, and pyrrolyl. For example, R1 is indolyl.

In some embodiments, n is 1. In some embodiments, $R^2$, $R^3$, $R^4$, $R^5$, $R^6$, $R^7$, $R^8$, $R^9$ and $R^{10}$ are H. In some embodiments, m is 4.

Non-limiting examples of a compound of Formula (VI) include:

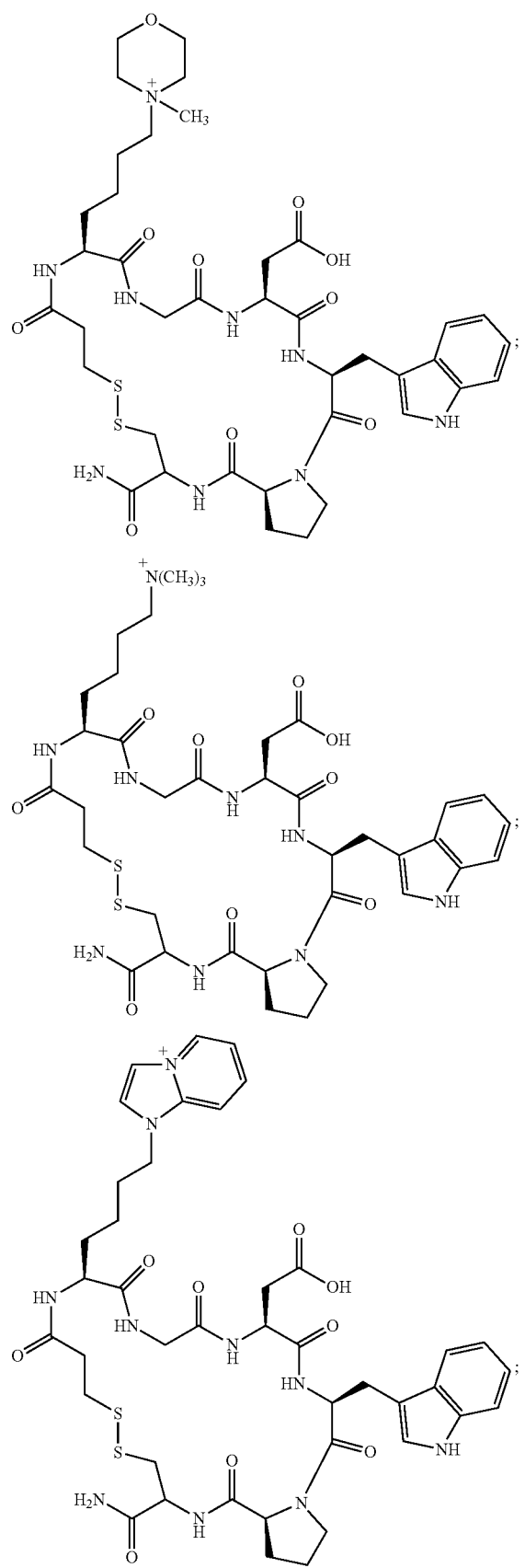

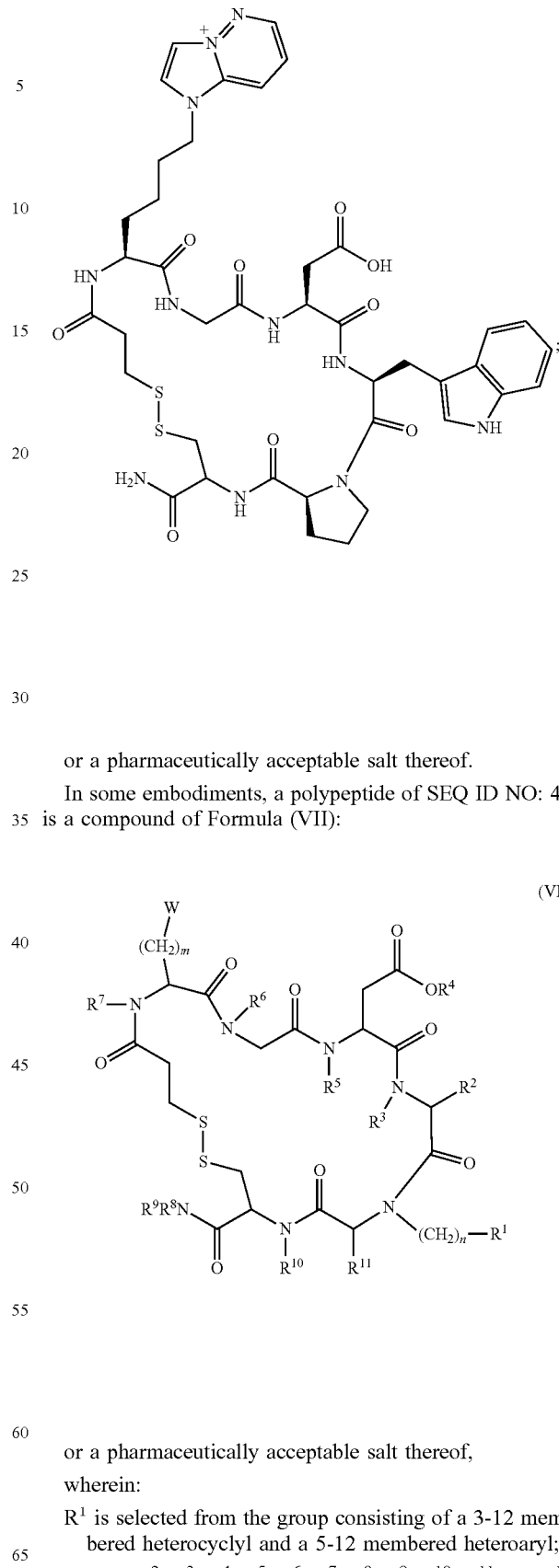

or a pharmaceutically acceptable salt thereof.

In some embodiments, a polypeptide of SEQ ID NO: 40 is a compound of Formula (VII):

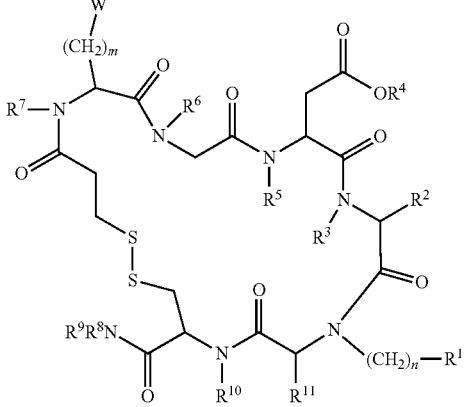

(VII)

or a pharmaceutically acceptable salt thereof,
wherein:
$R^1$ is selected from the group consisting of a 3-12 membered heterocyclyl and a 5-12 membered heteroaryl;
each of $R^2$, $R^3$, $R^4$, $R^5$, $R^6$, $R^7$, $R^8$, $R^9$, $R^{10}$, $R^{11}$ and $R^{12}$ is independently selected from H and ($C_1$-$C_6$)alkyl;

W is selected from the group consisting of:

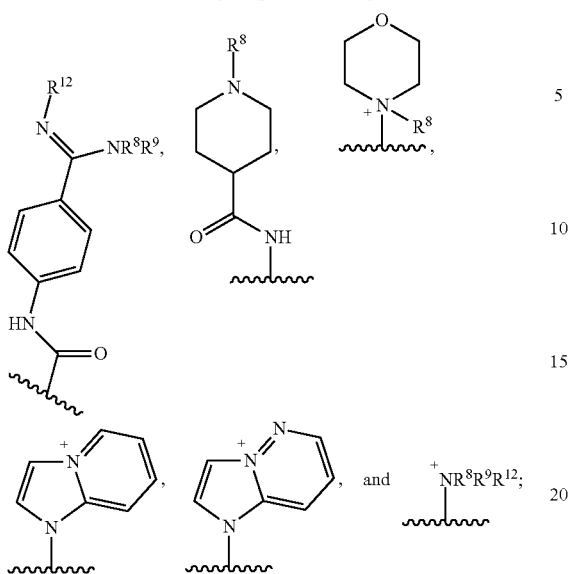

m is an integer from 1 to 10; and
n is an integer from 1 to 6.

In some embodiments, R1 is an electron-rich heterocyclyl or heteroaryl. In some embodiments, R1 is an electron-poor heterocyclyl or heteroaryl. In some embodiments, R1 is selected from the group consisting of indolyl, pyridyl, thiophenyl, and pyrrolyl. For example, R1 is indolyl.

In some embodiments, n is 2. In some embodiments, $R^3$, $R^4$, $R^5$, $R^6$, $R^7$, $R^8$, $R^9$, $R^{10}$, $R^{11}$, and $R^{12}$ are H. In some embodiments, $R^2$ and $R^{11}$ are $CH_3$. In some embodiments, m is 4.

Non-limiting examples of a compound of Formula (VII) include:

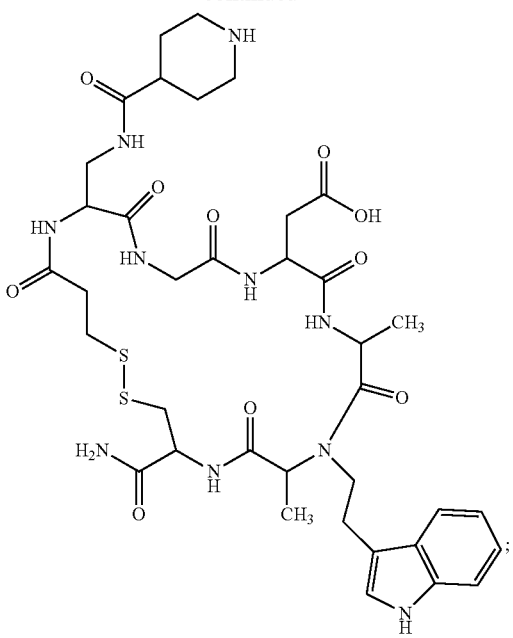

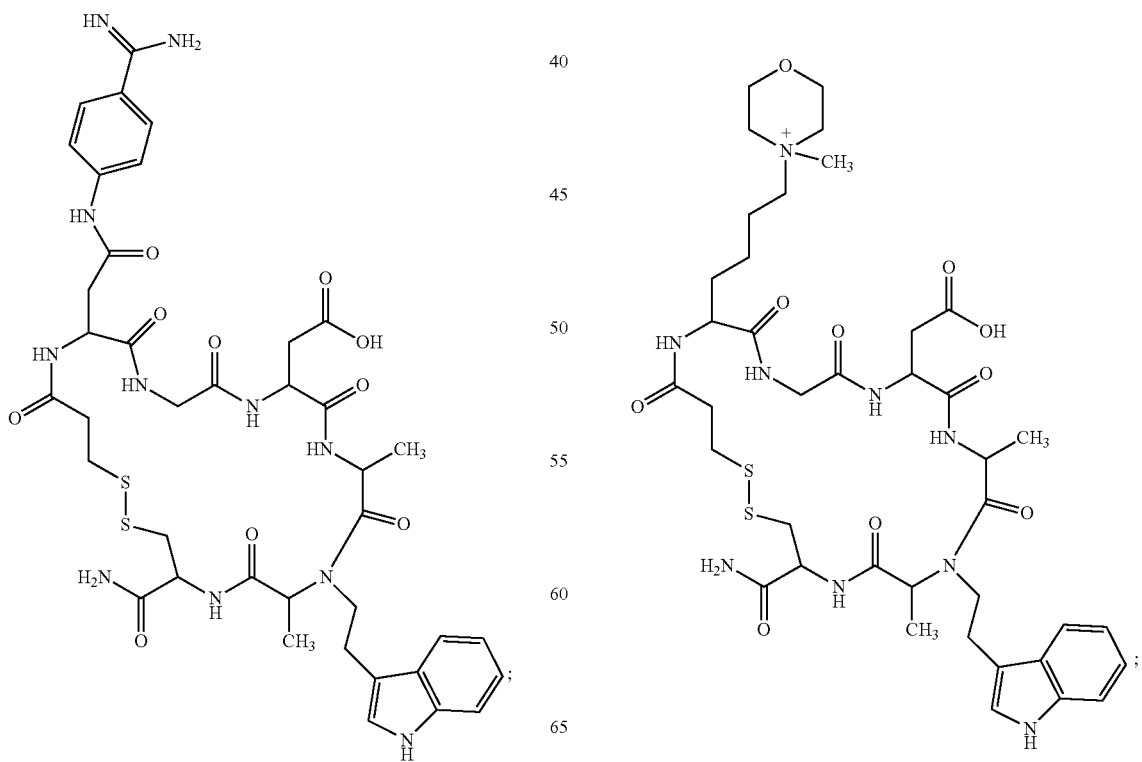

23
-continued
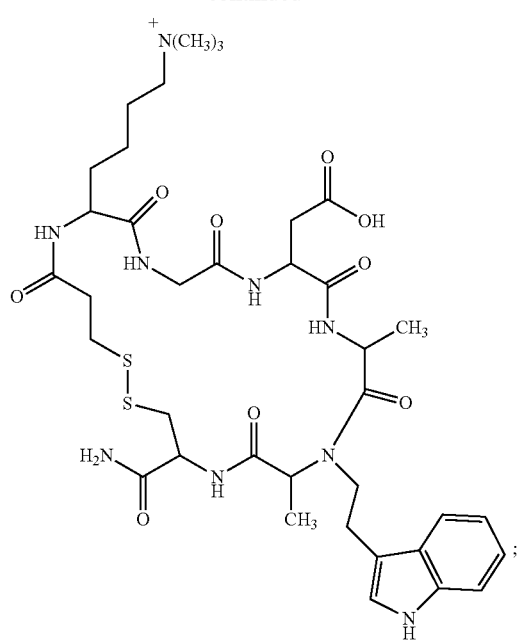
;
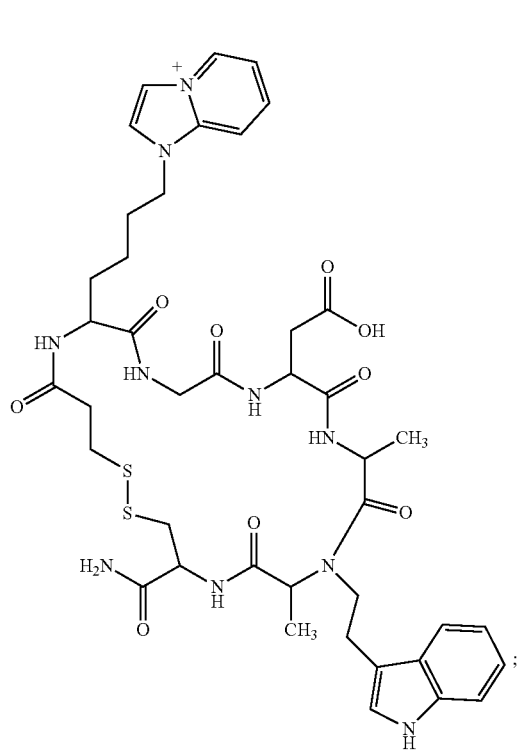
;
24
-continued
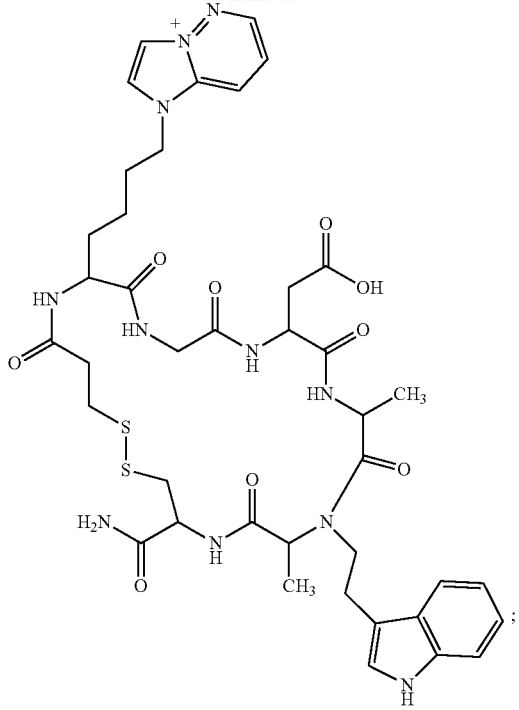
;
or a pharmaceutically acceptable salt thereof. For example, the compound of Formula (VII) can be:
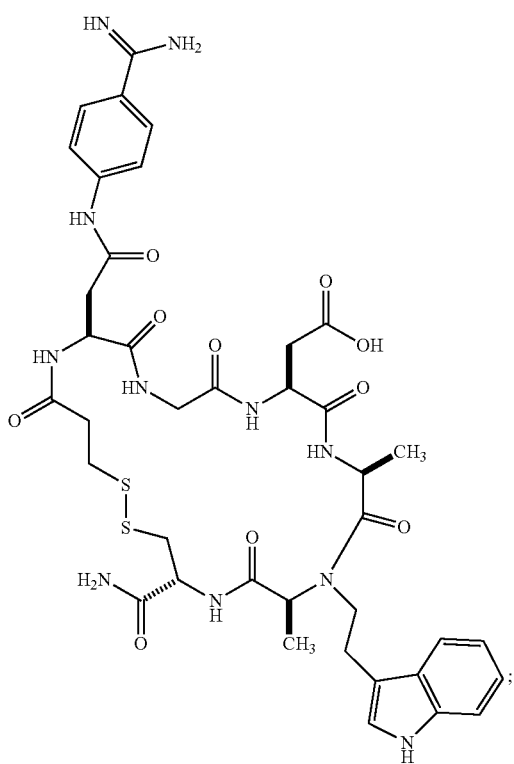
;

25
-continued
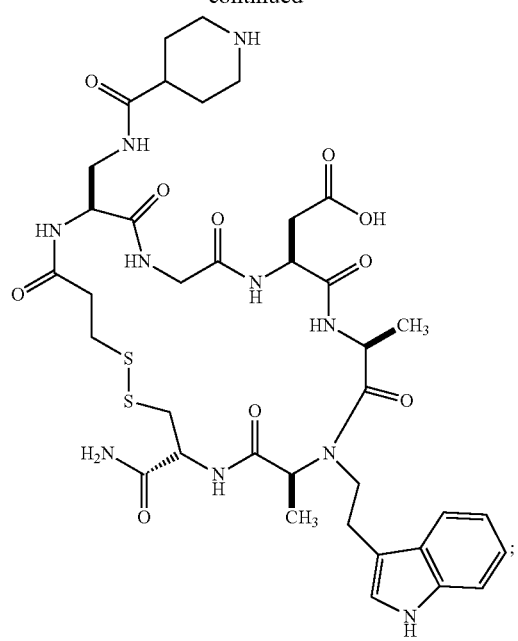
26
-continued
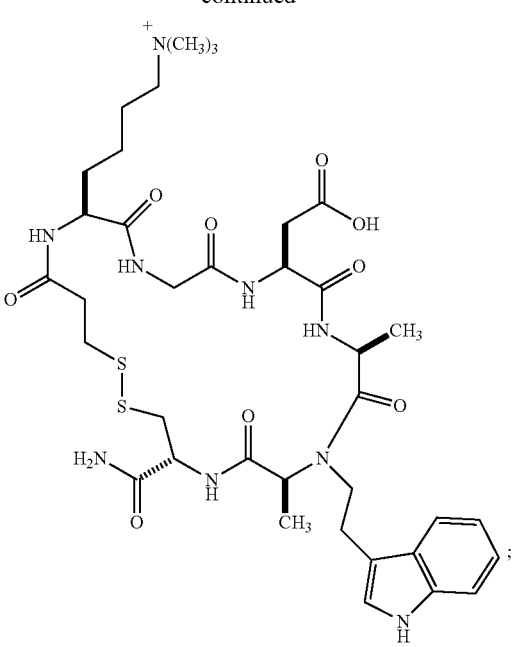
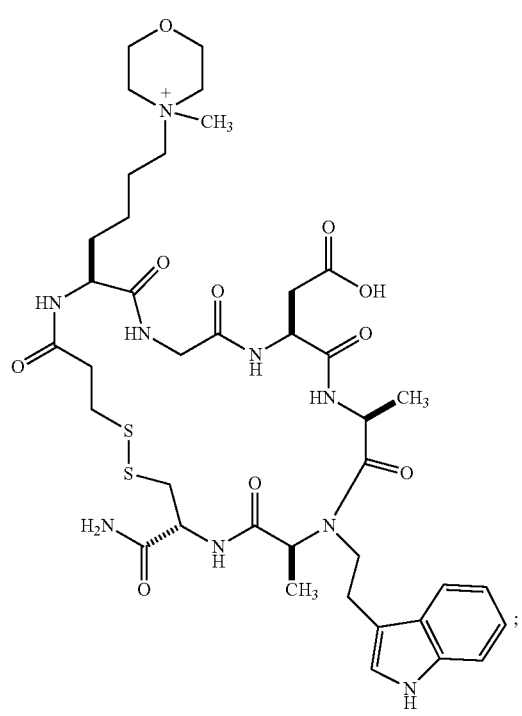
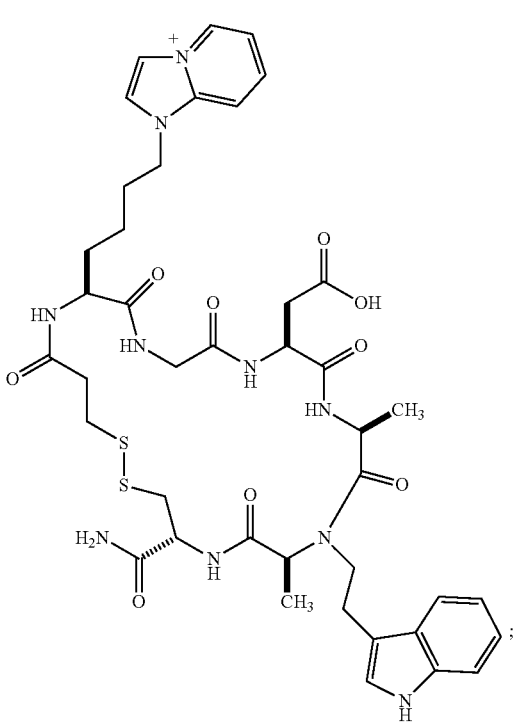

-continued

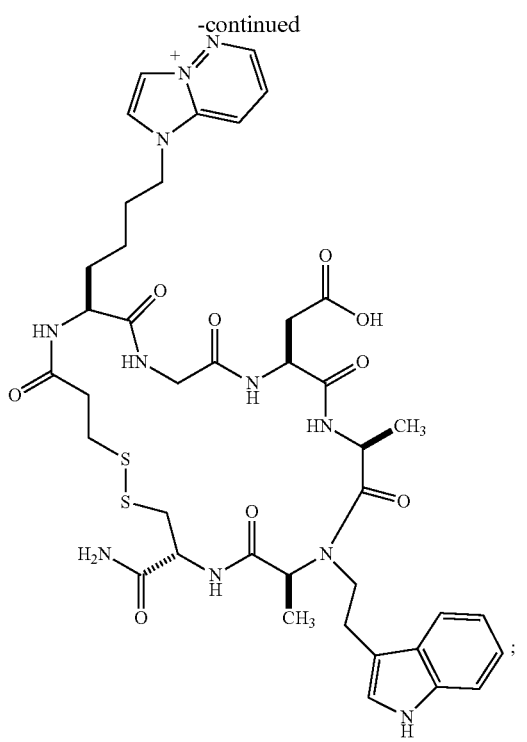

or a pharmaceutically acceptable salt thereof.

In some embodiments, a polypeptide of SEQ ID NO: 40 is a compound of Formula (VIII):

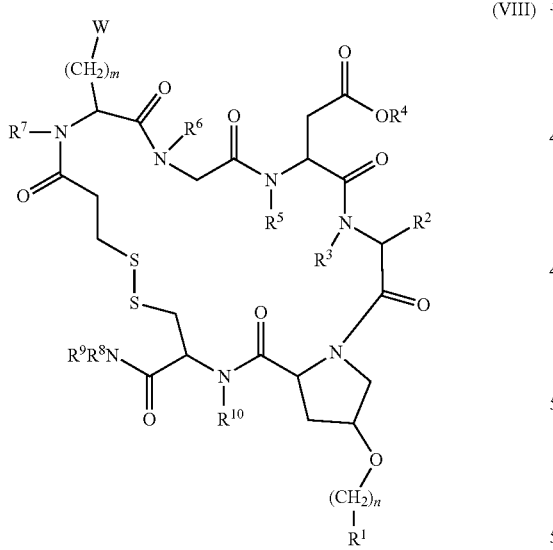

(VIII)

or a pharmaceutically acceptable salt thereof,
wherein:
$R^1$ is selected from the group consisting of a 3-12 membered heterocyclyl and a 5-12 membered heteroaryl;
each of $R^2$, $R^3$, $R^4$, $R^5$, $R^6$, $R^7$, $R^8$, $R^9$, $R^{10}$ and $R^{11}$ is independently selected from H and $(C_1$-$C_6)$alkyl;

W is selected from the group consisting of:

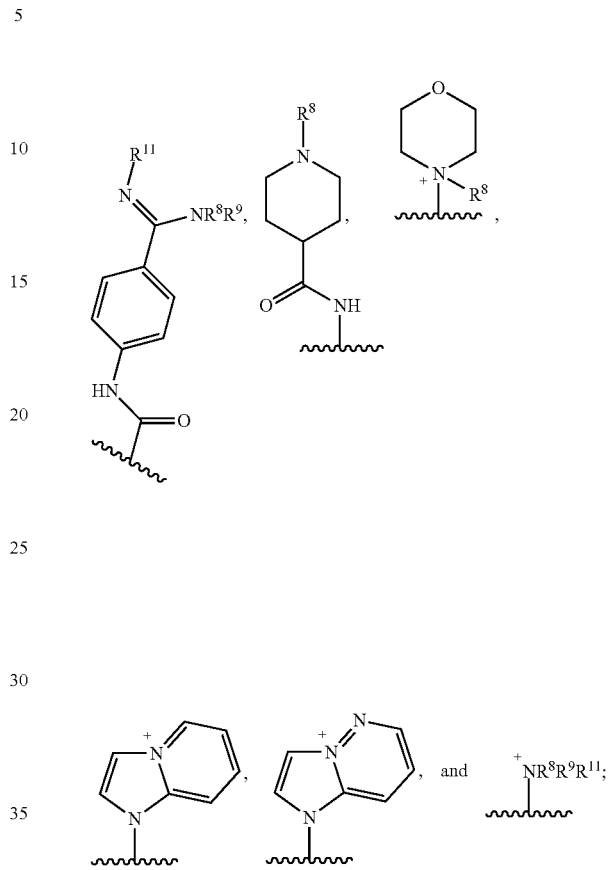

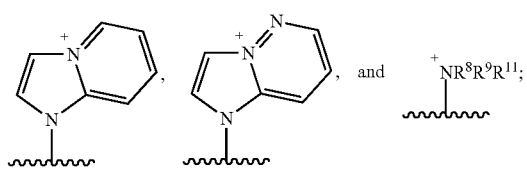

m is an integer from 1 to 10; and
n is an integer from 0 to 6.

In some embodiments, R1 is an electron-rich heterocyclyl or heteroaryl. In some embodiments, R1 is an electron-poor heterocyclyl or heteroaryl. In some embodiments, R1 is selected from the group consisting of indolyl, pyridyl, thiophenyl, and pyrrolyl. For example, R1 is indolyl.

In some embodiments, n is 1. In some embodiments, $R^3$, $R^4$, $R^5$, $R^6$, $R^7$, $R^8$, $R^9$, $R^{10}$ and $R^{11}$ are H. In some embodiments, $R^2$ is $CH_3$. In some embodiments, m is 4.

Non-limiting examples of a compound of Formula (VIII) include:

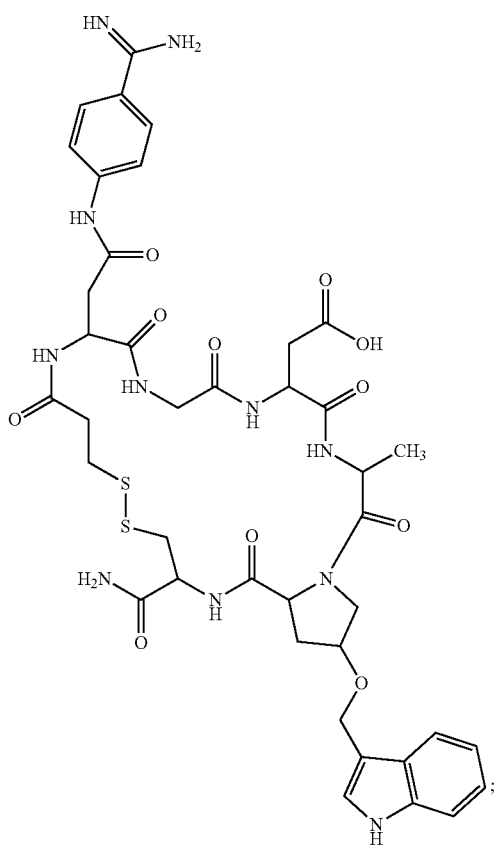
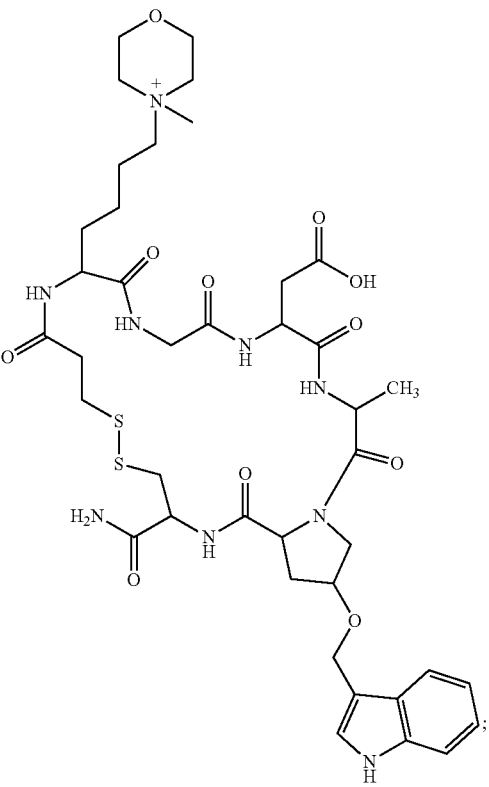
-continued
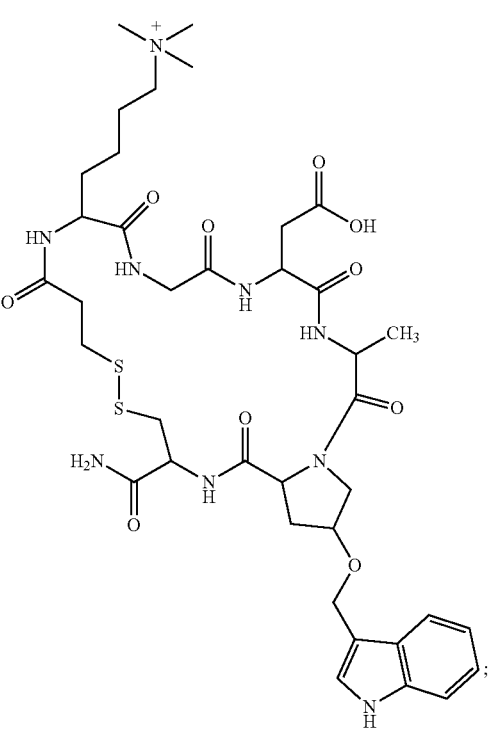

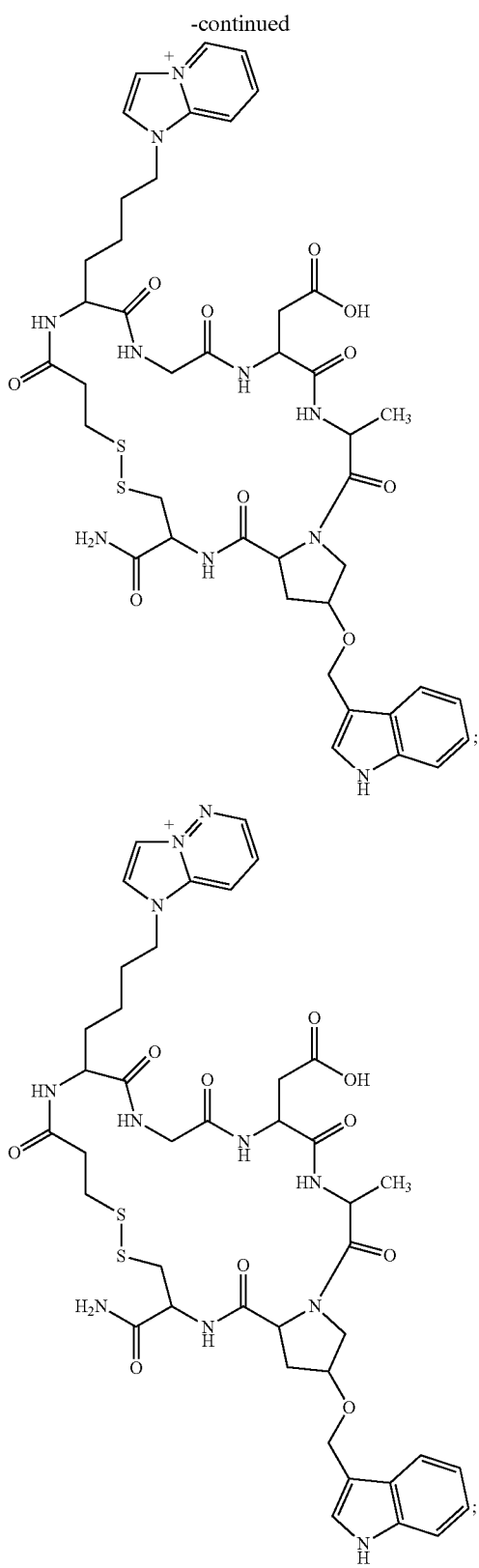
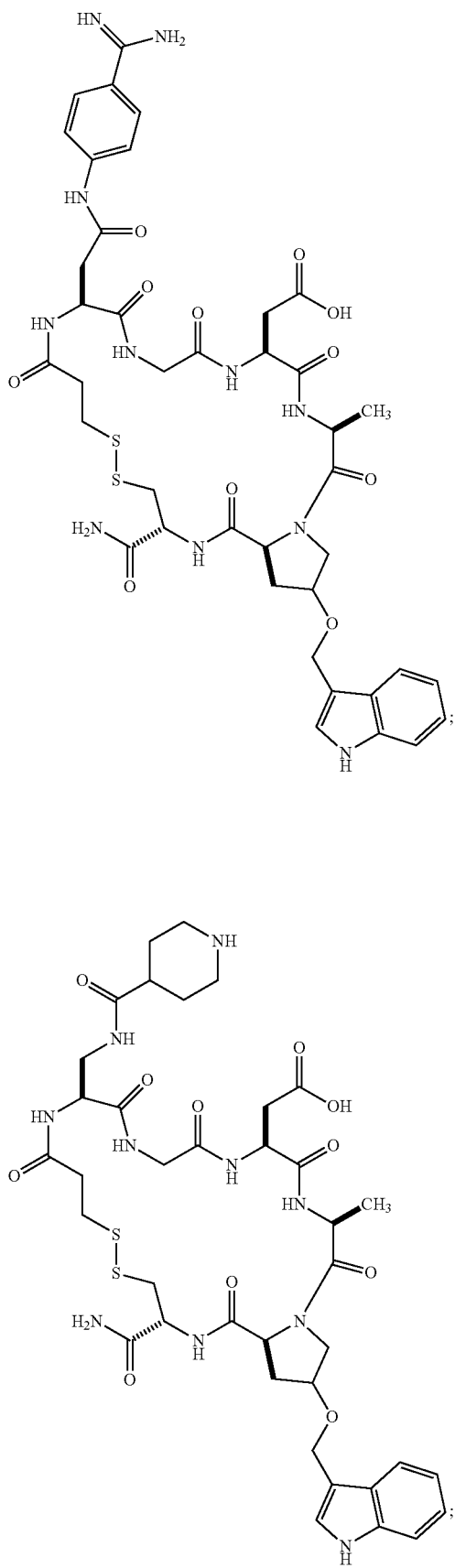
or a pharmaceutically acceptable salt thereof. For example, a compound of Formula (VIII) is:

33
-continued
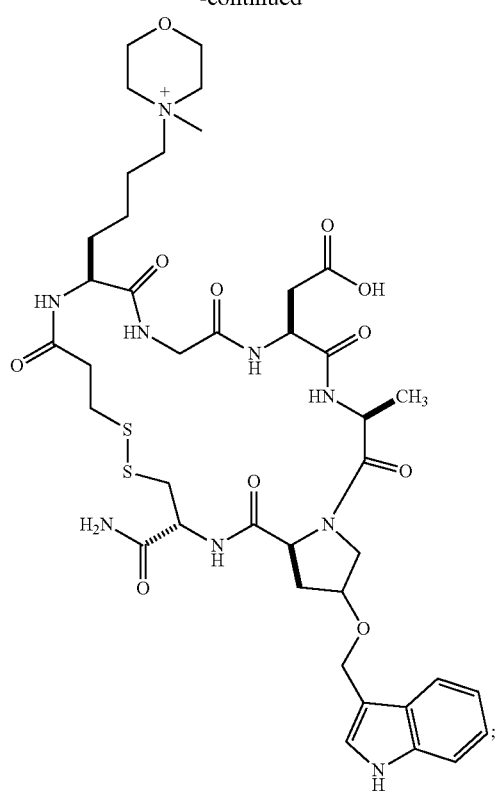
34
-continued
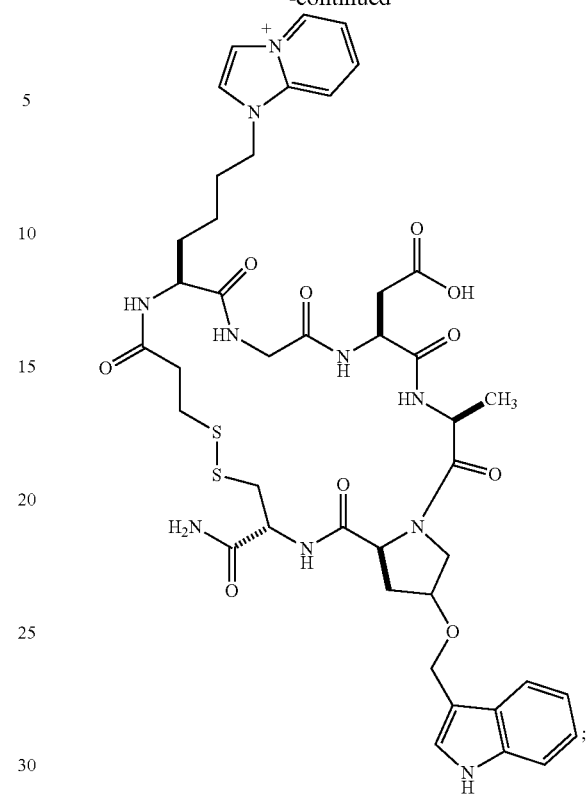
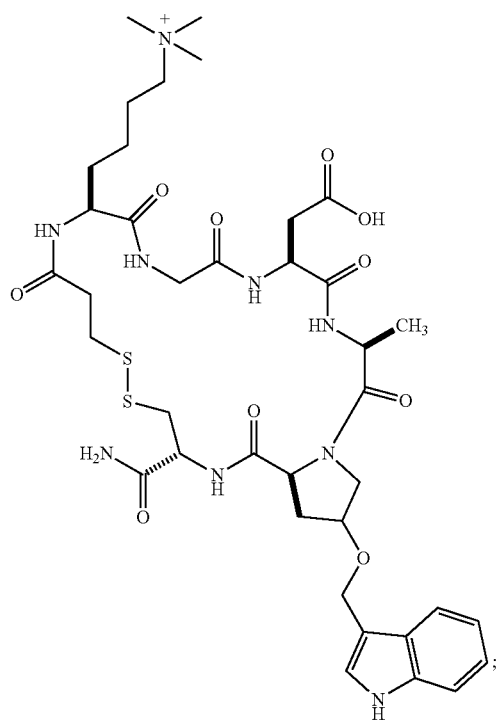
or a pharmaceutically acceptable salt thereof.
In some embodiments, a polypeptide of SEQ ID NO: 40 is a compound of Formula (IX):

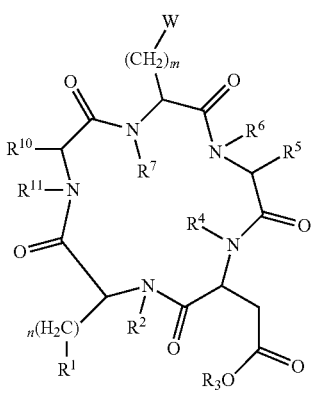

or a pharmaceutically acceptable salt thereof,
wherein:

R¹ is selected from the group consisting of a 3-12 membered heterocyclyl and a 5-12 membered heteroaryl;

W is selected from the group consisting of:

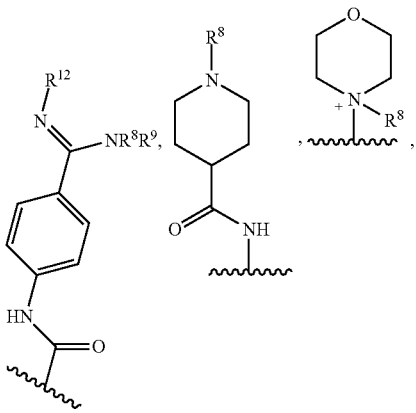

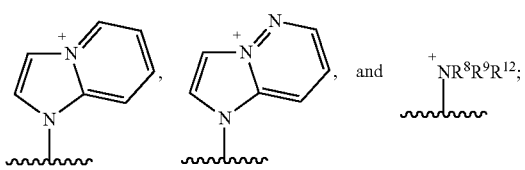

each of $R^2$, $R^3$, $R^5$, $R^6$, $R^7$, $R^8$, $R^9$, $R^{10}$, $R^{11}$, and $R^{12}$ is independently selected from H and $(C_1\text{-}C_6)$alkyl;

m is an integer from 1 to 10; and n is an integer from 0 to 6.

In some embodiments, R1 is an electron-rich heterocyclyl or heteroaryl. In some embodiments, R1 is an electron-poor heterocyclyl or heteroaryl. In some embodiments, R1 is selected from the group consisting of indolyl, pyridyl, thiophenyl, and pyrrolyl. For example, R1 is indolyl.

In some embodiments, n is 1. In some embodiments, $R^2$, $R^3$, $R^4$, $R^5$, $R^6$, $R^7$, $R^8$, and $R^9$ are H. In some embodiments, m is 3. In some embodiments, $R^{10}$ is $CH(CH_3)_2$. In some embodiments, $R^{11}$ is $CH_3$.

Non-limiting examples of a compound of Formula (IX) include:

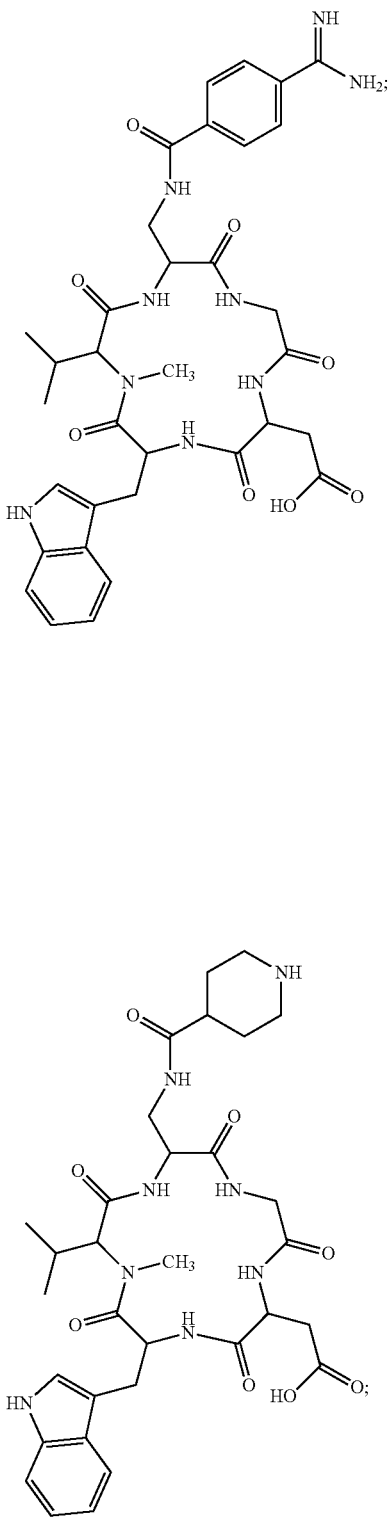

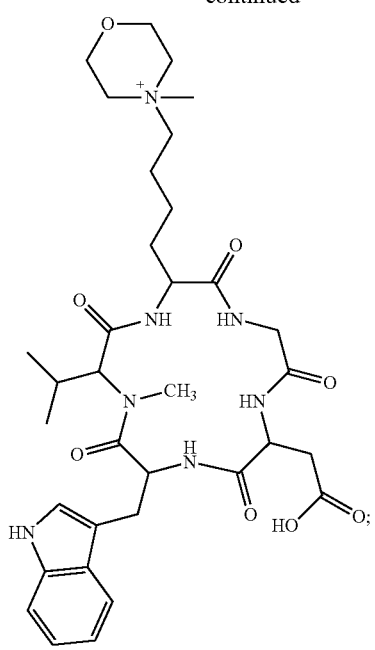
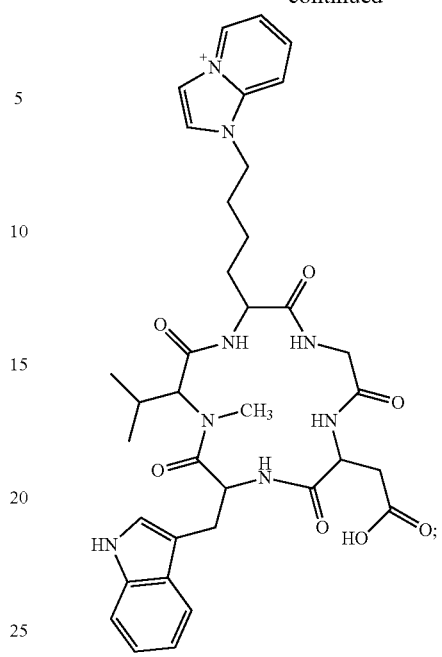
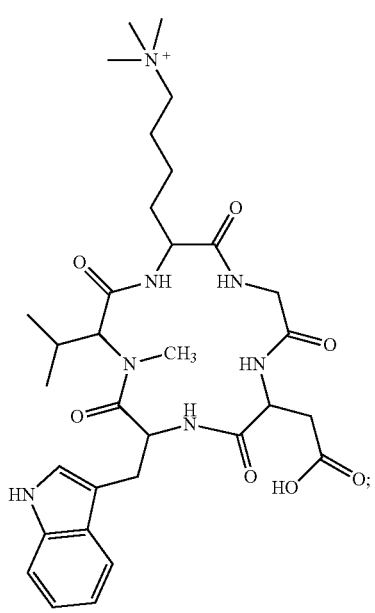
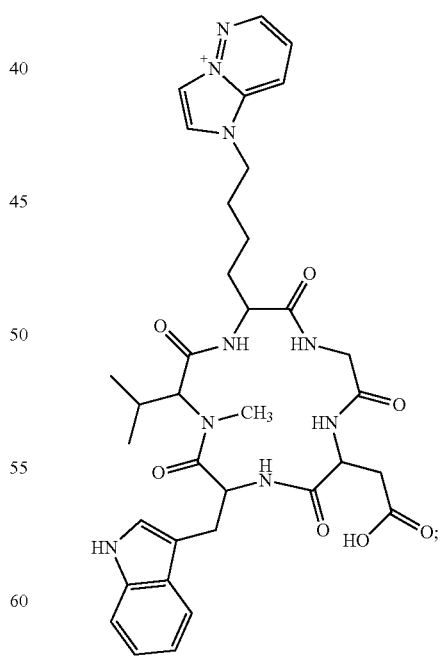
or a pharmaceutically acceptable salt thereof. For example, a compound of Formula (IX) can include:

39
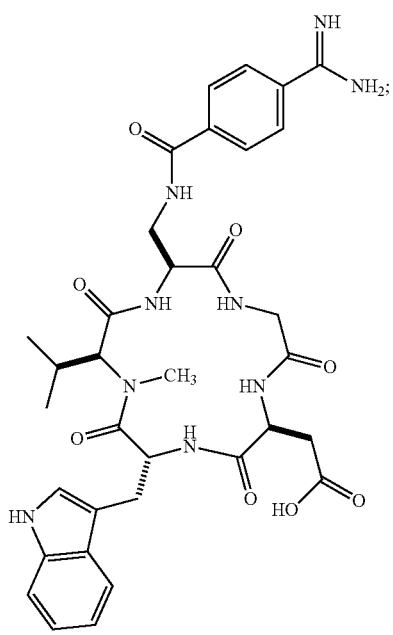
40
-continued
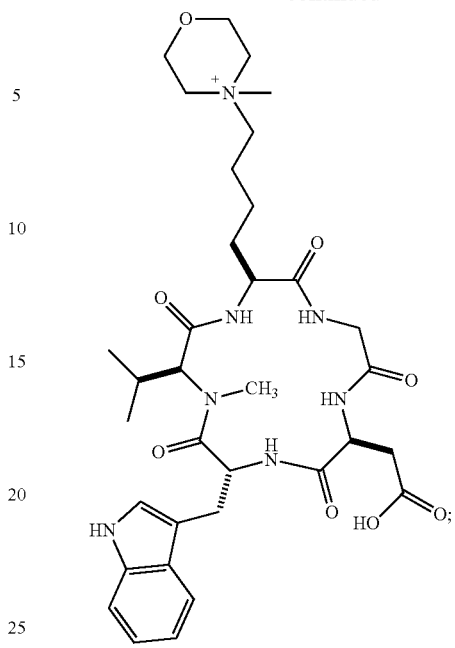
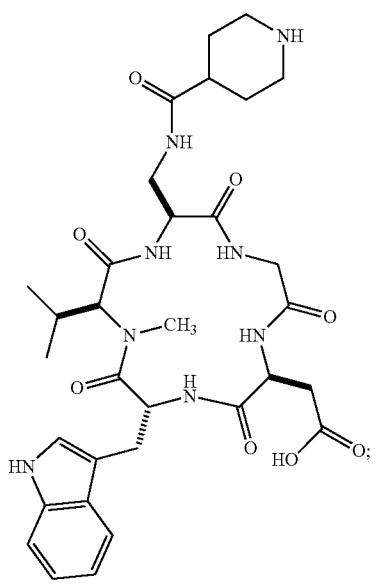
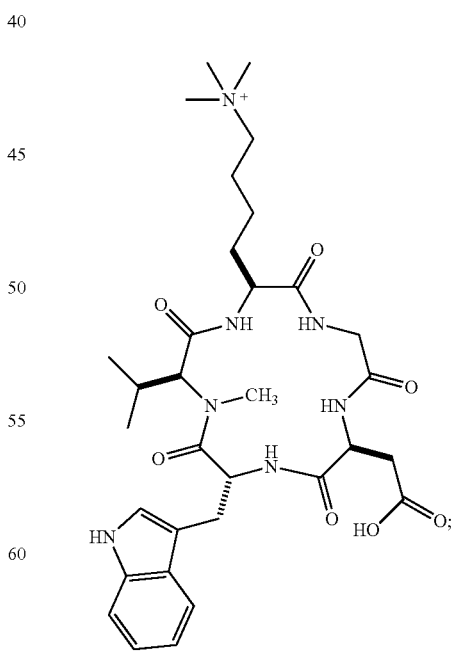

-continued
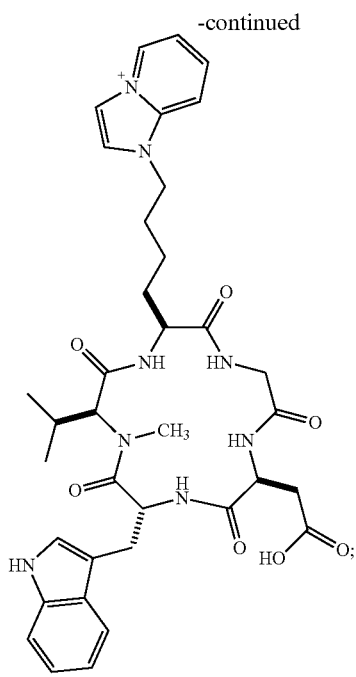
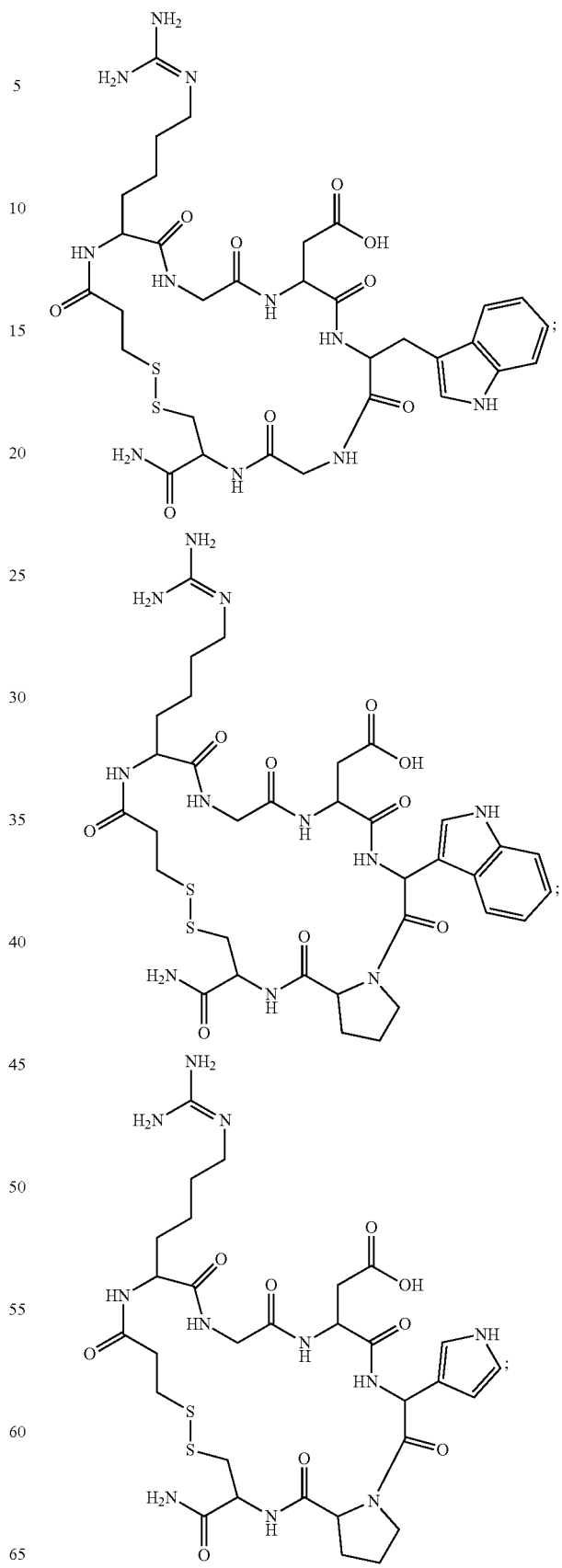
or a pharmaceutically acceptable salt thereof.
In some embodiments, a polypeptide of SEQ ID NO: 40 is a compound selected from the group consisting of:

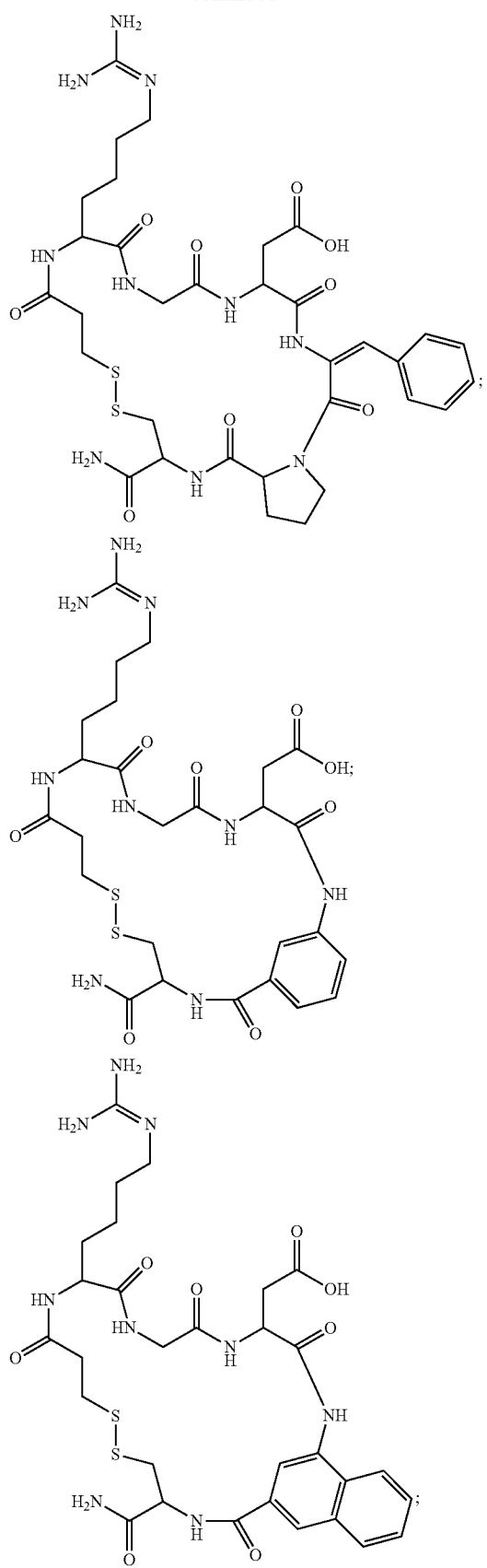
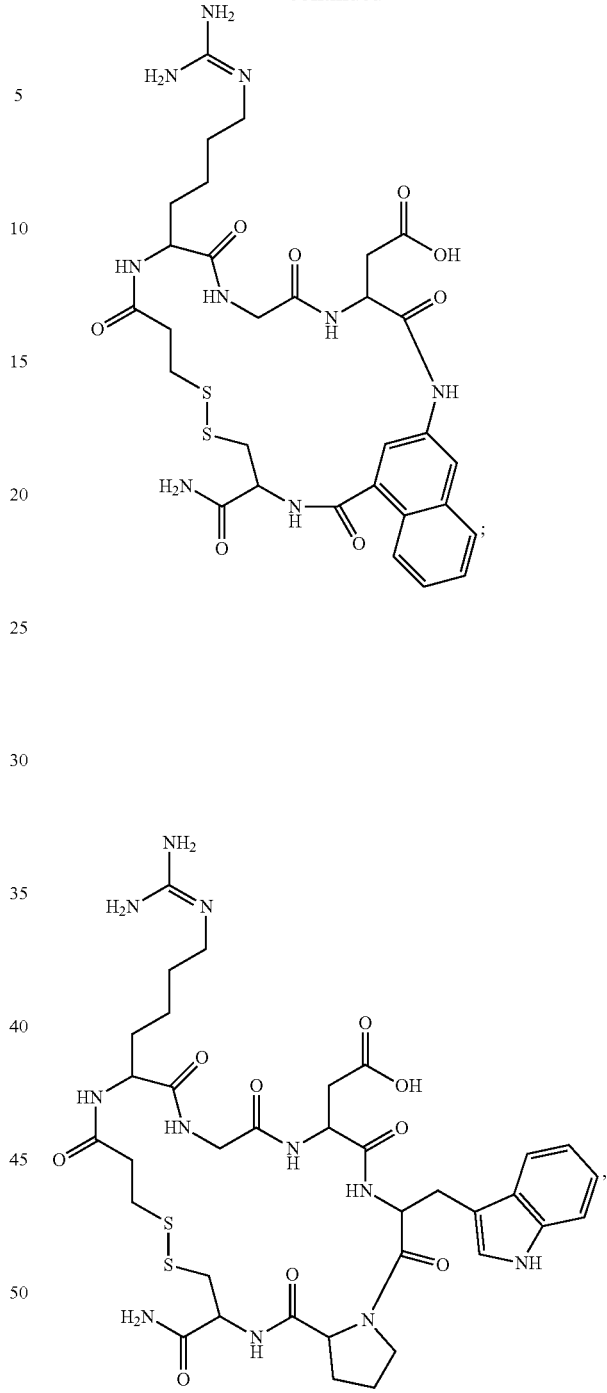
or a pharmaceutically acceptable salt thereof. For example, the compound can be selected from the group consisting of:

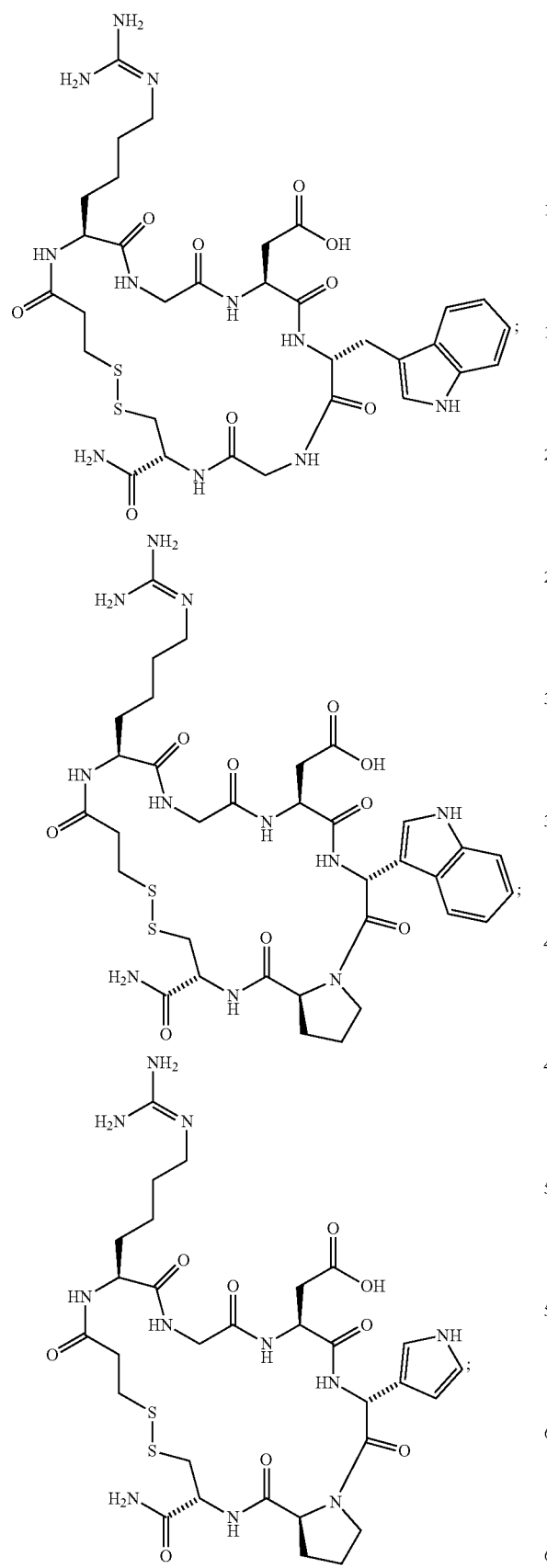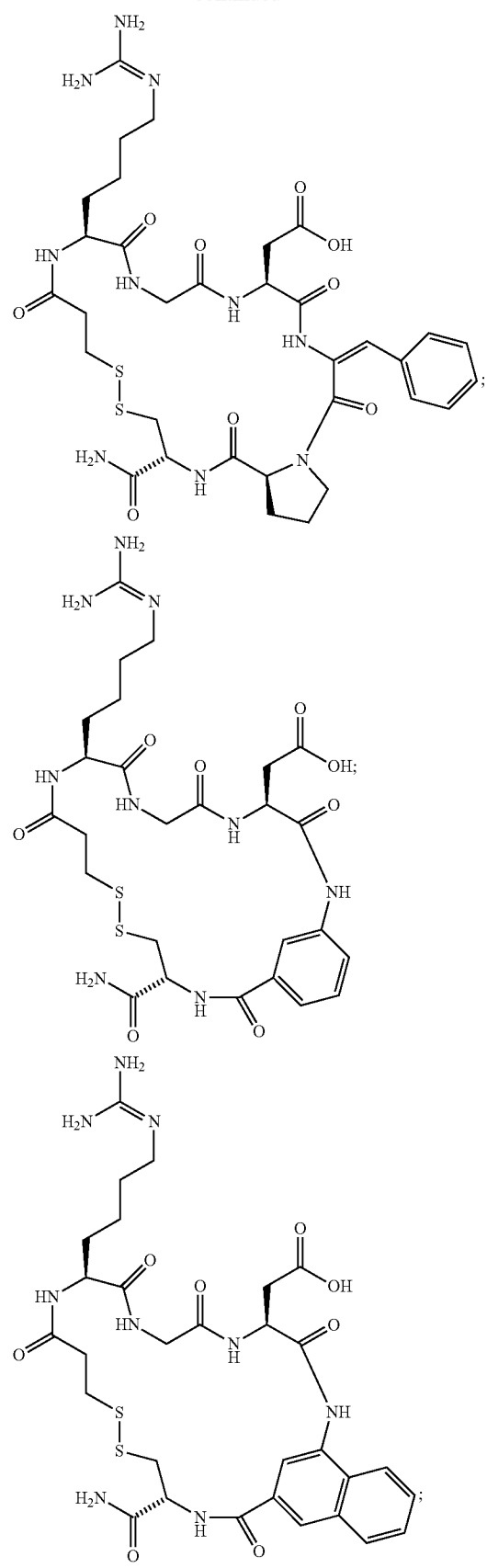

-continued

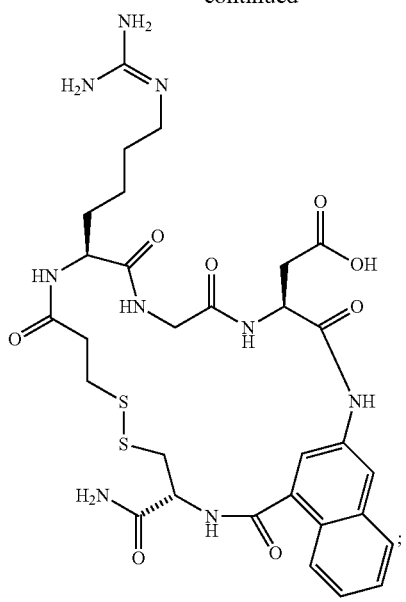

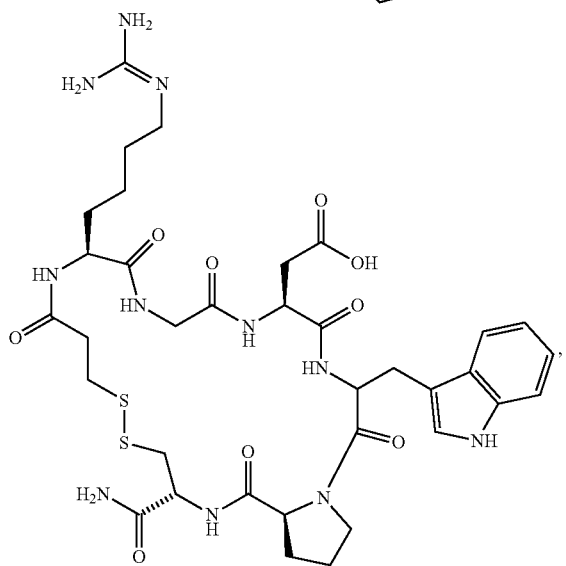

or a pharmaceutically acceptable salt thereof.

Further provided herein is a compound of Formula (IV):

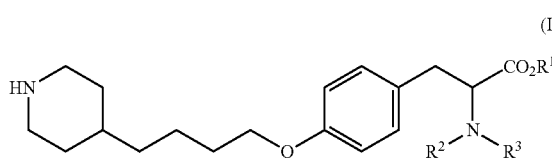

(IV)

or a pharmaceutically acceptable salt thereof,
wherein:
$R^1$ and $R^2$ are independently selected from H and $(C_1-C_6)$alkyl;

$R^3$ is selected from the group consisting of:

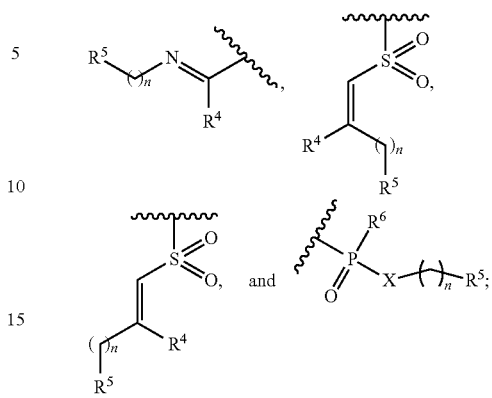

$R^4$ is selected from H and $(C_1-C_6)$alkyl;
$R^5$ is selected from the group consisting of a 3-12 membered heterocyclyl and a 5-12 membered heteroaryl;
$R^6$ is selected from H, $(C_1-C_6)$alkyl, OH, and $O(C_1-C_6)$alkyl;
X is O or $CH_2$; and
n is an integer from 0 to 6.

In some embodiments, $R^4$ is a $(C_1-C_6)$alkyl.
In some embodiments, R5 is an electron-rich heterocyclyl or heteroaryl. In some embodiments, R5 is an electron-poor heterocyclyl or heteroaryl. In some embodiments, R5 is selected from the group consisting of indolyl, pyridyl, thiophenyl, and pyrrolyl. For example, R5 is indolyl.

In some embodiments, n is an integer from 1 to 2. In some embodiments, $R^6$ is $O(C_1-C_6)$alkyl or $(C_1-C_6)$alkyl.

In some embodiments, $R^3$ is:

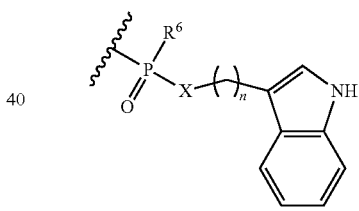

$R^6$ is selected from H, $(C_1-C_6)$alkyl, OH, and $O(C_1-C_6)$alkyl;
X is O or $CH_2$; and
n is an integer from 0 to 6.

In some embodiments, X is O. In some embodiments, X is $CH_2$.
In some embodiments, n is 1 or 2.
Non-limiting examples of a compound of Formula (IV) include:

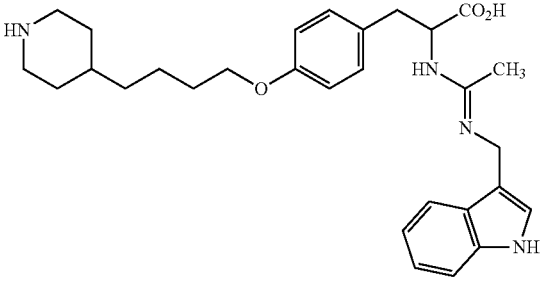

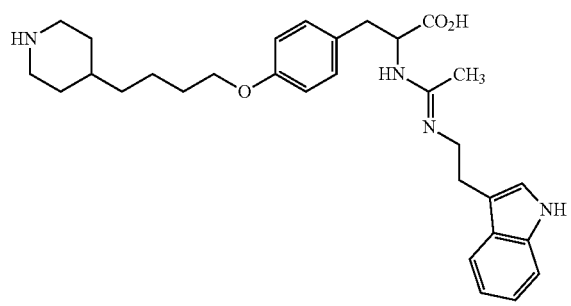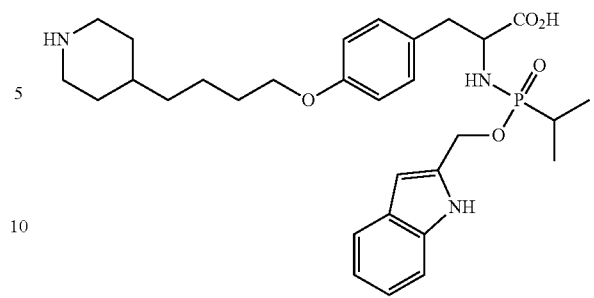
or a pharmaceutically acceptable salt thereof. For example, a compound of Formula (IV) ca be selected from the group consisting of:

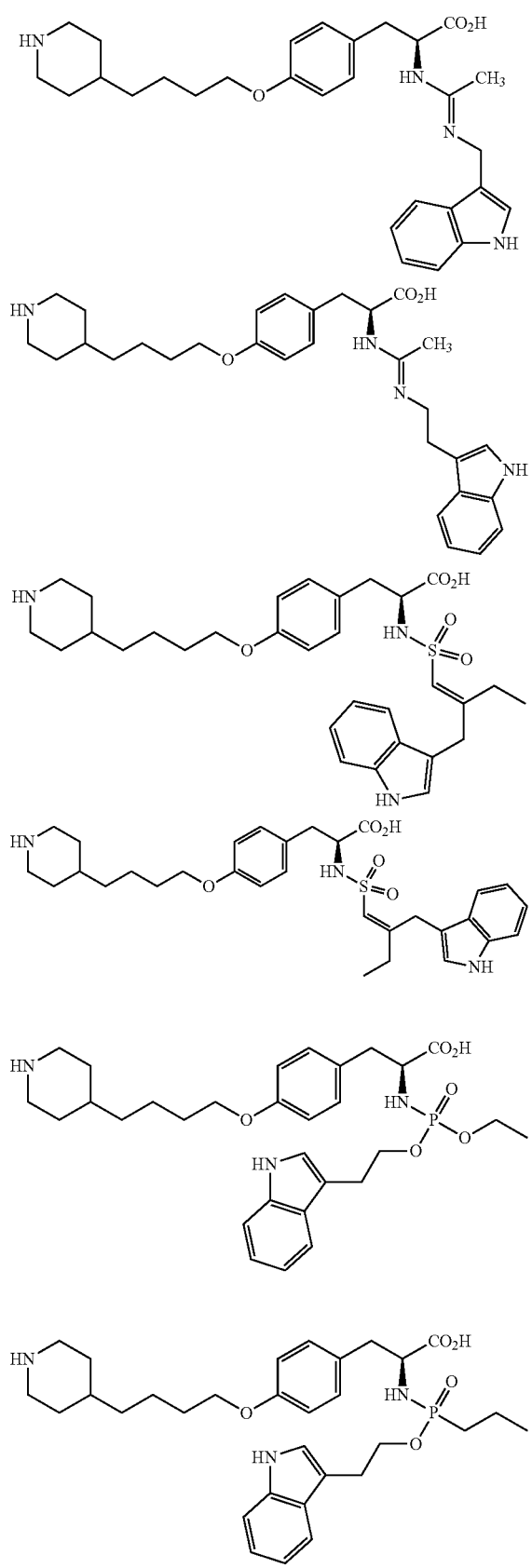
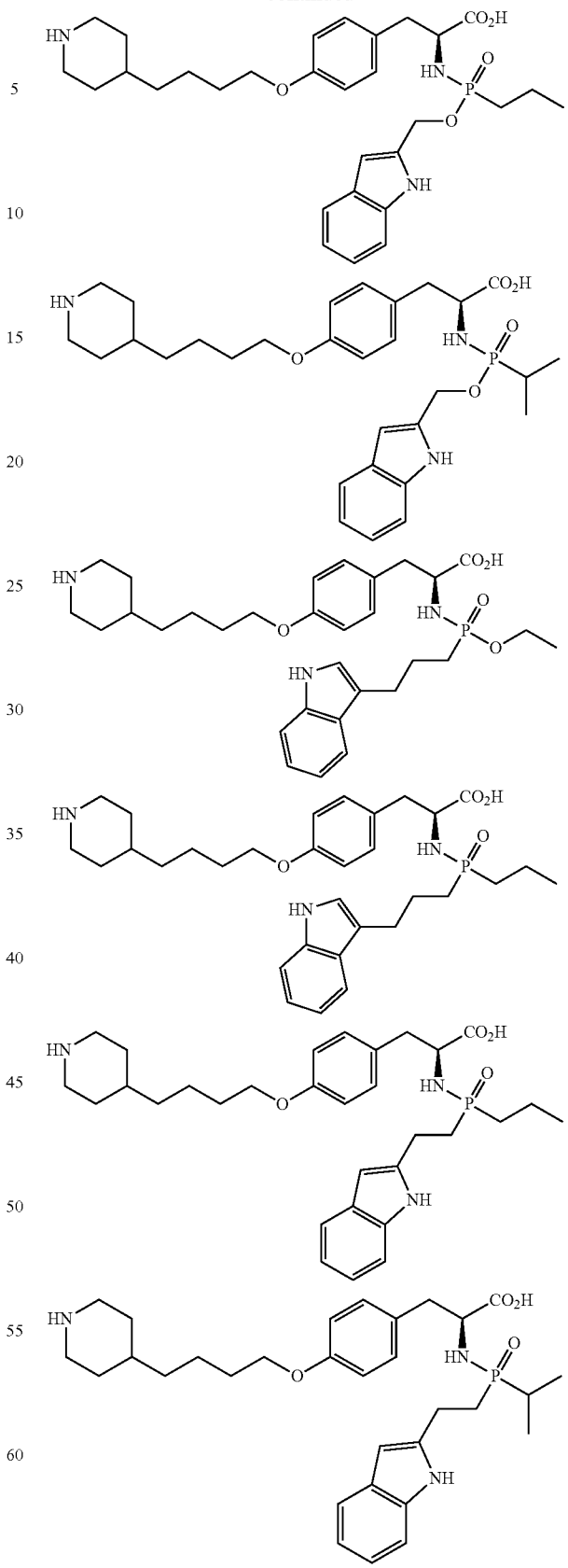
or a pharmaceutically acceptable salt thereof.

Also provided herein is a pure ligand-mimetic integrin antagonist, wherein the antagonist comprises the sequence RGD and this sequence stabilizes the α1 helix of the βA domain in the inactive state of the integrin, thus inhibiting integrin activation. For example, the pure integrin antagonist is a compound or polypeptide provided herein, or a pharmaceutically acceptable salt thereof.

The compounds provided herein can be included in a pharmaceutical composition comprising a pharmaceutically acceptable carrier and at least one compound or polypeptide provided herein.

Further provided herein is a method of treating one or more disorders selected from the group consisting of thrombosis, unstable angina, first or recurrent myocardial infarction, ischemic sudden death, diastolic dysfunction, transient ischemic attack, stroke, atherosclerosis, venous thrombosis, deep vein thrombosis, thrombophlebitis, arterial embolism, coronary and cerebral arterial thrombosis, myocardial infarction, cerebral embolisms, kidney embolisms, pulmonary embolisms, fibrosis, renal fibrosis, delayed graft function, diabetes, tumor angiogenesis, melanoma, cancer metastasis, diabetic nephropathy, diabetic retinopathy, neovascular glaucoma, restenosis, osteoporosis, multiple sclerosis, asthma, ulcerative colitis, side burns, random flaps, and macular degeneration, wherein the method comprises administering to a patient in need thereof a therapeutically effective amount of at least one compound or polypeptide provided herein, a pharmaceutically acceptable salt thereof, or a pharmaceutical composition of comprising one or more of the same.

A compound or polypeptide provided herein for use in treating a disorder selected from the group consisting of thrombosis, unstable angina, first or recurrent myocardial infarction, ischemic sudden death, diastolic dysfunction, transient ischemic attack, stroke, atherosclerosis, venous thrombosis, deep vein thrombosis, thrombophlebitis, arterial embolism, coronary and cerebral arterial thrombosis, myocardial infarction, cerebral embolisms, kidney embolisms, pulmonary embolisms, fibrosis, renal fibrosis, delayed graft function, diabetes, tumor angiogenesis, melanoma, cancer metastasis, diabetic nephropathy, diabetic retinopathy, neovascular glaucoma, restenosis, osteoporosis, multiple sclerosis, asthma, ulcerative colitis, side burns, random flaps, and macular degeneration.

Use of a compound or polypeptide provided herein in the manufacture of a medicament for treating a disorder selected from the group consisting of thrombosis, unstable angina, first or recurrent myocardial infarction, ischemic sudden death, diastolic dysfunction, transient ischemic attack, stroke, atherosclerosis, venous thrombosis, deep vein thrombosis, thrombophlebitis, arterial embolism, coronary and cerebral arterial thrombosis, myocardial infarction, cerebral embolisms, kidney embolisms, pulmonary embolisms, fibrosis, renal fibrosis, delayed graft function, diabetes, tumor angiogenesis, melanoma, cancer metastasis, diabetic nephropathy, diabetic retinopathy, neovascular glaucoma, restenosis, osteoporosis, multiple sclerosis, asthma, ulcerative colitis, side burns, random flaps, and macular degeneration.

This disclosure also provides a method of inhibiting integrin binding and activation on a cell, comprising contacting the cell with a therapeutically effective amount of a compound or polypeptide provided herein, a pharmaceutically acceptable salt thereof, or a pharmaceutical composition including one or more of the same. In some embodiments, the contacting is in vitro.

Further provided herein is a crystal comprising αVβ3 ectodomain complexed with inhibitor hFN10, having space group $P3_221$. In some embodiments, the crystal has the following cell dimensions:

| | |
|---|---|
| a (Å) | 129.8 |
| b (Å) | 129.8 |
| c (Å) | 307.6 |

Also provided herein is a crystal comprising αVβ3 ectodomain complexed with inhibitor knottin 2.5F, having space group $P3_221$. In some embodiments, the crystal has the following cell dimensions:

| | |
|---|---|
| a (Å) | 129.8 |
| b (Å) | 129.8 |
| c (Å) | 305.2 |

Further provided herein is a crystal comprising αVβ3 ectodomain complexed with inhibitor knottin 2.5D, having space group $P3_221$. In some embodiments, the crystal has the following cell dimensions:

| | |
|---|---|
| a (Å) | 129.8 |
| b (Å) | 129.8 |
| c (Å) | 305.9 |

In one aspect, the invention features a crystallized integrin ectodomain/inhibitor complex that includes an integrin ectodomain and an inhibitor described herein. In some embodiments, a ligand-binding betaA domain (βA) as shown in FIG. 8 is used. As used herein, "integrin ectodomain" is a heterodimer comprising or consisting of an alpha chain and a beta chain, e.g., as shown in Example 1. In some embodiments, the integrin ectodomain is from one of the following integrins:

beta3 integrins: αIIbβ3 and αVβ3 beta1 integrins: α1β1, α2β1, α3β1, α4β1, α5β1, α6β1, α7β1, α8β1, α9β1, α10β1, α11β1, αVβ1 beta2 integrins: αLβ2 (LFA-1, CD11a/CD18), αMβ2 (CD11b/CD18), αXβ2 (p150.95, CD11c/CD18) and αDβ2 (CD11d/CD18) beta7 integrins: α4β7 and αEβ7.

In another aspect, the invention features a composition that includes a crystal. The crystal includes an integrin ectodomain (e.g., αVβ3) and an inhibitor described herein, e.g., hFN10.

In another aspect, the invention features a method that includes using a three-dimensional model of a complex that includes an integrin ectodomain. In some embodiments, the complex includes a fragment of the integrin ectodomain as defined by structural coordinates of amino acids sufficient to define a binding pocket. In some embodiments, the integrin ectodomain is from αVβ3, and the structural coordinates are as shown in Table 2, 6 or 7, or a homolog thereof that has a root mean square deviation of not more than 1.5 Angstroms from the backbone atoms of the amino acids as shown in Table 2, 6, or 7. The integrin ectodomain can be free (unbound) or bound to an inhibitor, e.g., hFN10. The three-dimensional model can be used to select or design an inhibitor that binds the integrin ectodomain, with specific binding features as described herein, e.g., an attractive interaction with the residue corresponding to Tyr122 in the βA of αVβ3 (e.g., covalent or noncovalent, e.g., attractive, noncovalent interaction between aromatic rings (e.g., π-π interaction); an interaction between the aromatic ring of Tyr122 and a cation (e.g., a metal or charged side chain, e.g., cation π interaction), or an interaction between the aromatic ring and exposed adjacent methylene groups (e.g., X-H-π)); a hydrogen bond interaction with Tyr122 in the βA; a salt bridge interaction with Lys125 in the βA; and/or an interaction with the $Mn^{2+}$ at ADMIDAS through a water molecule. In some embodiments, employing the three-dimensional structural model to design or select a potential inhibitor includes providing a three-dimensional model of the potential inhibitor, employing computational means to perform a fitting operation between the model of the potential inhibitor and the model of the integrin (e.g., αVβ3) ectodomain binding site to provide an energy minimized configuration of the potential inhibitor in the binding site, and evaluating the results of the fitting operation to design or select a potential inhibitor that has the specified interactions with the integrin ectodomain.

As used herein, a "hydrogen bond" is an interaction between a proton acceptor and a proton donor that forms when the proton-acceptor distance is less than 2.5 Angstroms and the angle defined by the donor-hydrogen-acceptor atoms lies between 90 and 180 degrees (see, e.g., Baker and Hubbard, Prog. Biophys. Molec. Biol. 44:97-179 (1984)).

In a further aspect, the invention features methods that include using a three-dimensional model of an integrin ectodomain to select or design an inhibitor that binds the integrin ectodomain. In some embodiments, the integrin ectodomain is from one of the following integrins:

beta3 integrins: αIIbβ3 and αVβ3
beta1 integrins: α1β1, α2β1, α3β1, α4β1, α5β1, α6β1, α7β1, α8β1 α9β1, α10β1, α11β1, αVβ1
beta2 integrins: αLβ2 (LFA-1, CD11a/CD18), αMβ2 (CD11b/CD18), αXβ2 (p150.95, CD11c/CD18) and αDβ2 (CD11d/CD18)
beta7 integrins: α4β7 and αEβ7.

In another aspect, the invention features methods that include selecting an inhibitor by performing rational drug design with a three-dimensional structure of a crystalline complex of an integrin ectodomain with an inhibitor described herein, e.g., hFN10. In some embodiments, the integrin ectodomain is from one of the following integrins:

beta3 integrins: αIIbβ3 and αVβ3
beta1 integrins: α1β1, α2β1, α3β1, α4β1, α5β1, α6β1, α7β1, α8β1 α9β1, α10β1, α11β1, αVβ1
beta2 integrins: αLβ2 (LFA-1, CD11a/CD18), αMβ2 (CD11b/CD18), αXβ2 (p150.95, CD11c/CD18) and αDβ2 (CD11d/CD18)
beta7 integrins: α4β7 and αEβ7.

In some embodiments, the potential inhibitors identified, designed or selected by a method described herein have at least an interaction, e.g., one or more of:

an attractive interaction with Tyr122 in the βA (e.g., covalent or noncovalent, e.g., attractive, noncovalent interaction between aromatic rings (e.g., π-π interaction); an interaction between the aromatic ring of Tyr122 and a cation (e.g., a metal or charged side chain, e.g., cation n interaction), or an interaction between the aromatic ring and exposed adjacent methylene groups (e.g., X-H-π));
a hydrogen bond interaction with Tyr122 in the βA;
a salt bridge interaction with Lys125 in the βA; and/or
an interaction with the Mn2+ at ADMIDAS through a water molecule.

Thus in some embodiments the potential inhibitors identified, designed or selected by a method described herein have, e.g., an interaction that mimics the edge-to-face interaction of the mutant Trp1496 in hFN10 with Tyr122 in the al helix of βA (see, e.g., FIG. 3b), and/or the hydrogen bond between Tyr122 and Glu1462 of hFN10, and/or forms a salt bridge with Lys125 of βA, and/or coordinates the Mn2+ at ADMIDAS through a water molecule.

In another aspect, the invention provides methods for identifying a potential inhibitor of an integrin. The methods include generating a two- or three-dimensional structural model of a known integrin inhibitor; and employing the two- or three-dimensional structural model to design or select a potential inhibitor, wherein the potential inhibitor has (or is designed to have) at least an interaction, e.g., one or more of:

an attractive interaction with a residue corresponding to Tyr122 in the βA of αVβ3 (e.g., covalent or noncovalent, e.g., attractive, noncovalent interaction between aromatic rings (e.g., π-π interaction); an interaction between the aromatic ring of Tyr122 and a cation (e.g., a metal or charged side chain, e.g., cation it interaction), or an interaction between the aromatic ring and exposed adjacent methylene groups (e.g., X-H-π));
a hydrogen bond interaction with a residue corresponding to Tyr122 in the βA of αVβ3;
a salt bridge interaction with a residue corresponding to Lys125 in the βA of αVβ3; and/or
an interaction with a $Mn^{2+}$ ion at ADMIDAS through a water molecule. In some embodiments, the known integrin inhibitor is selected from the group consisting of tirofiban, orbofiban, xemilofiban, sibrafiban, UR-3216, BMS-587101, BMS-688521, BIRT-377, and BIRT-2584.

In some embodiments, the designed inhibitor is then synthesized or otherwise obtained, and contacted with an integrin (e.g., αVβ3) ectodomain or full-length integrin, and the ability of the inhibitor to bind and/or inhibit the integrin ectodomain or full-length integrin is detected.

In yet another aspect, the invention features a method that includes contacting an integrin (full or ectodomain) with an inhibitor to form a composition and crystallizing the composition to form a crystalline complex where the inhibitor is bound to the integrin ectodomain. The crystalline complex can diffract X-rays to a resolution of at least about 3.5 Å, e.g., 2 Å. The inhibitor is an inhibitor described herein, e.g., hFN10.

In another aspect, the invention features a software system that includes instructions for causing a computer system to accept information relating to the structure of an integrin ectodomain bound to an inhibitor, accept information relating to a candidate inhibitor, and determine binding characteristics of the candidate inhibitor to the integrin ectodomain. Determination of the binding characteristics is based on the information relating to the structure of the integrin ectodomain bound to the inhibitor and the information relating to the candidate inhibitor. The inhibitor is an inhibitor described herein, e.g., hFN10.

In another aspect, the invention features a computer program on a computer readable medium on which is stored a plurality of instructions. When the instructions are executed by one or more processors, the processors accept information relating to the structure of a complex that includes an integrin ectodomain bound to an inhibitor. The processors further accept information relating to a candidate inhibitor and determine binding characteristics of the candidate inhibitor to the integrin ectodomain. Determination of the binding characteristics is based on the information related to the structure of the integrin ectodomain and the information related to the candidate inhibitor.

In a further aspect, the invention features a method that includes accepting information relating to the structure of a complex including an integrin ectodomain bound to an inhibitor and modeling the binding characteristics of the integrin ectodomain with a candidate inhibitor. Such a method is implemented by a software system.

In another aspect, the invention features a computer program on a computer readable medium on which is stored a plurality of instructions. When the instructions are executed by one or more processors, the processors accept information relating to a structure of a complex that includes an integrin ectodomain bound to an inhibitor. The processors further model the binding characteristics of the integrin ectodomain with a candidate inhibitor.

In an additional aspect, the invention features a software system that includes instructions for causing a computer system to accept information relating to a structure of a complex that includes an αVβ3 ectodomain bound to an inhibitor. The instructions also cause a computer system to model the binding characteristics of the αVβ3 ectodomain with a candidate inhibitor.

In another aspect, the invention features a method of modulating integrin activity in a subject. The method includes using rational drug design to select an inhibitor that is capable of modulating integrin activity, and administering a therapeutically effective amount of the inhibitor to the subject.

In another aspect, the invention features a method of treating a subject having a condition associated with αVβ3 ectodomain activity. The method includes using rational drug design to select an inhibitor that is capable of affecting αVβ3 ectodomain activity and administering a therapeutically effective amount of the inhibitor to a subject in need of such an inhibitor.

In another aspect, the invention features a method of prophylactically treating a subject susceptible to a condition associated with integrin activity. The method includes determining that the subject is susceptible to the condition associated with the activity, using rational drug design to select an inhibitor that is capable of reducing integrin activity, and administering a therapeutically effective amount of the inhibitor to the subject.

The following abbreviations are used throughout the application:

| Amino Acid | Singe Letter Abbreviation | Three Letter Abbreviation |
|---|---|---|
| Alanine | A | Ala |
| Threonine | T | Thr |
| Valine | V | Val |
| Cysteine | C | Cys |
| Leucine | L | Leu |
| Tyrosine | Y | Tyr |
| Isoleucine | I | Ile |
| Asparagine | N | Asn |
| Proline | P | Pro |
| Glutamine | Q | Gln |
| Phenylalanine | F | Phe |
| Aspartic Acid | D | Asp |
| Tryptophan | W | Trp |
| Glutamic Acid | E | Glu |
| Methionine | M | Met |
| Lysine | K | Lys |
| Glycine | G | Gly |
| Arginine | R | Arg |
| Serine | S | Ser |
| Histidine | H | His |

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

REFERENCE TO TABLES SUBMITTED AS TEXT FILES

This application incorporates Tables 2-7 submitted in .txt format on a compact disc in PCT/US2015/010384, on Jan. 6, 2015. The entire content of this files is hereby incorporated by reference in the present application.

DESCRIPTION OF DRAWINGS

FIGS. 1A-H. Binding properties of hFN10 and wtFN10 and effects on αVβ3-mediated cell spreading. Binding of fluoresceinated wtFN10 and hFN10 (a, b) or LIBS mAbs (alone or in presence of wtFN10 and hFN10) (c, d) to αVβ3+ cells (a-d). In (c), mAb-binding was assessed using K562-αVβ3 and M21 cells. MFI, mean fluorescence intensity. Histograms represent mean+SD, n=3 independent experiments. (e) Hydrodynamic analyses of unliganded αVβ3 and αVβ3-FN10 complexes in presence of $Ca^{2+}$, $Ca^{2+}/Mg^{2+}$ or $Mn^{2+}$. Stokes radii (in nm) are shown in parentheses. AU: absorbance unit. (f-h) $Mn^{2+}$-induced spreading of K562-αVβ3 on wtFN10, hFN10 (mean+SD, n=3), or on full-length FN (mean+SD, n=2)(f). Spreading under all conditions was eliminated by mAb LM609 against αVβ3. (g,h) Representative phase contrast images of cell spreading on wtFN10 (g) and hFN10 (h). Bar=20 μM.

FIGS. 2A-B. Structures of αVβ3 bound to FN10. Ribbon diagrams of αVβ3 head bound to wtFN10 (a) or hFN10 (b). Fo-Fc omit maps for wtFN10 and hFN10 domains are shown contoured at 3.0 σ. In contrast to that of hFN10, Fo-Fc omit map of wtFN10 is weak and discontinuous in segments farthest from the integrin. $Mn^{2+}$ ions at LIMBS (gray in original), MIDAS (cyan in original) and ADMIDAS (magenta in original) are shown as spheres (also in FIGS. 3a-b, 4c). Inset, orientation of bound FN10 relative to the superimposed βA domains (chain colors in original as in a, b). $Mn^{2+}$ at MIDAS and the ligand Asp (D) are shown.

FIGS. 3A-E. αVβ3-FN10 interfaces, conformational changes and structure validation. (a, b) Ribbon diagrams showing key electrostatic and H-bond interactions and metal ion coordinations, which differ in the two structures. Chain colors in original are as in FIG. 2. Hydrogen bonds and salt bridges are represented by red dotted lines (also in FIG. 4c). SDL, specificity-determining loop. Inset in (a), adhesion (mean+SD, n=3) of HEK 293 cells expressing αVβ3(N339/S) or αV(N266/Q)β3(N339/S) to immobilized full-length FN in presence of $Ca^{2+}/Mg^{2+}$. A540: absorbance at 540 nm. Inset in b, enlarged view of sigma-weighted 2Fo-Fc map contoured at 1.0σ of W1496 and Y122 side-chains in the αVβ3-hFN10 complex. Inward movement (arrow) of Y122 in wtFN10-bound βA (in light green in original) would clash with W1496 side chain. (c, d) γA domain from αVβ3-hFN10 superimposed on that of αVβ3-wtFN10 (c), and on unliganded αVβ3 ectodomain (pdb id 3ije) (d). Arrow in (c)

Figure 9A:
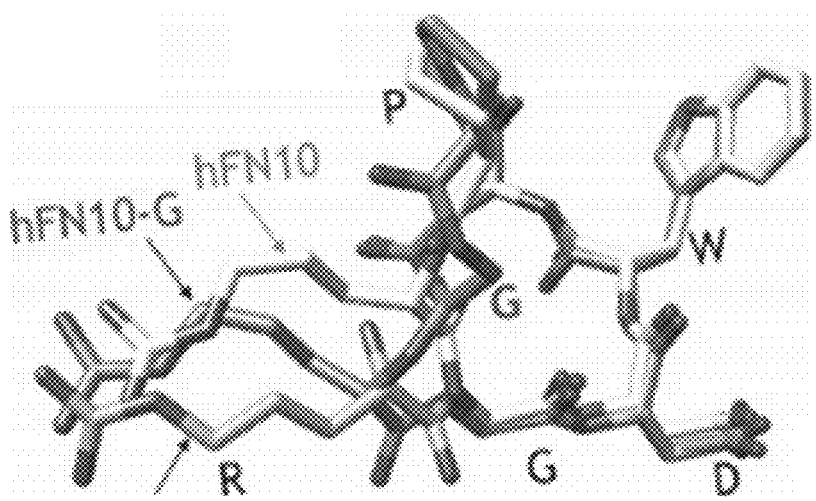

indicates direction of wtFN10-induced inward movement of α1 helix (and ADMIDAS ion) towards MIDAS. The major tertiary change observed in the F-α7 loop of wtFN10-bound βA (c) is not translated into a one-turn displacement of α7, possibly the result of crystal contacts when the complete ectodomain is used. Spheres representing the three metal ions bear the color of respective βA in original. Except for ligand-occupancy and resulting changes in SDL loop, structures of unliganded and hFN10-bound αA are identical (d) (LIMBS and MIDAS are not occupied by metal in unliganded βA). (e) Left panel, binding of fluoresceinated AP5 to M21 cells (αVβ3+) in absence (control) or presence of unlabeled wtFN10, hFN10 or hFN10W/S. Right panel, binding of fluoresceinated AP5 to HEK 293 expressing αVβ3 (white bars) or αVβ3(Y122/A) (gray bars) in presence of unlabeled wt- or hFN10. Histograms represent mean+SD, n=3.

FIGS. 4A-D. RGD-containing loop structures in wild-type and modified FN10. (a) Superimposed R/KGD-containing loops of hFN10, eptifibatide (pdb id 2vdn) and barbourin (pdb id 1q7j, model 2). Residues R/KGDWN (SEQ ID NO: 51) common to hFN10 and barbourin are labeled in black and the three flanking residues are in respective loop color in original. (b) Superimposed structures of RGD-containing loops of αVβ3-hFN10, αVβ3-wtFN10, barbourin and αVβ3-hFN10/B. (c) Ionic interactions at the αVβ3-hFN10/B interface involving the RGD-containing loop (in dark cyan in original). Coordination of the metal ions at MIDAS, ADMIDAS and LIMBS is the same as in αVβ3-wtFN10 (FIG. 3a). (d) Binding (mean+ SD, n=3) of fluoresceinated AP5 mAb to M21 cells in absence (control) or presence of wtFN10, hFN10 and hFN10/B.

FIGS. 5A-C. Design, synthetic scheme and structure model of a cyclic polypeptide. (A) Design using a linker to connect the terminal amino acids of AVTPRGDWNE (SEQ ID NO: 1). Also shown is a cyclic peptide with a tripeptide linker D-proline-glycine-glycine (PDGG) (SEQ ID NO: 2). (B) Energy minimized c-13mer (green in original) overlaid on the loop structure of hFN10 (pink in original). The two intermolecular H-bonds (each 2.8 Å) are preserved. (C) An exemplary synthetic scheme for the illustrative cyclic peptide (SEQ ID NOS 57, 56, 74, 74, 75, and 2, respectively, in order of appearance).

FIGS. 6A-B. Effect of WT and modified knottins on αVβ3 binding and AP5 expression. Histograms from an experiment showing binding of media alone or knottin-containing media to K562-αVβ3 (A) or binding of labeled AP5 to K562-αVβ3 preincubated with media alone or with knottin-containing media (B).

FIGS. 7A-C. Designed Eptifibatide and Tirofiban derivatives. (A) Structure of designed Eptifibatide derivatives to position indole (or similar heterocycle) proximal to Y122 to introduce n-n interaction. E-1 inverts the tryptophan residue. E-2 and E-3 are modifications to the proline residue that incorporate the indole. (B) Structure of designed Tirofiban derivatives. Arrows indicate attachment points of the R groups. (C) TA-6 (green in original) docked to the αVβ3-hFN10 structure. Y122 is proximal to the indole ring on TA-6 (black arrow). The H-bonding network remains intact.

FIG. 8. Alignment of the ligand-binding betaA domain (βA) in all eight human beta subunits (SEQ ID NOS 76-83, respectively, in order of appearance).

Figure 9B:
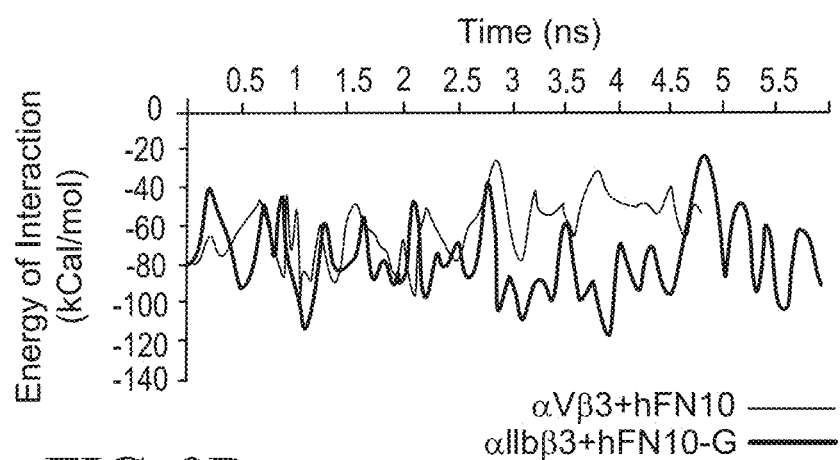
Figure 9C:
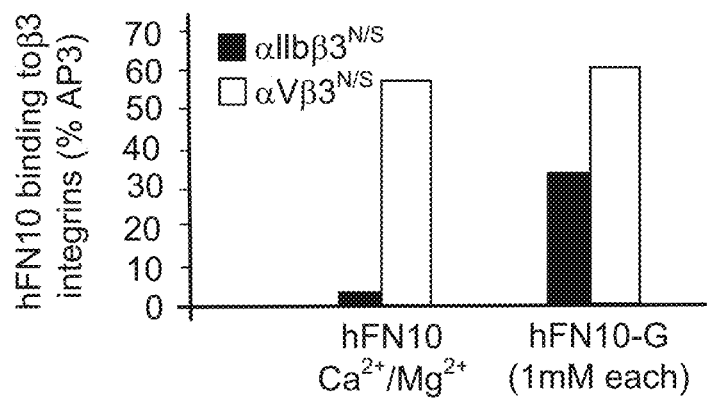

FIGS. 9A-C. Predicted shape of the RGD loop in hFN10-G and its binding profile. (A) Superposed RGD-containing loops of hFN10 (gray in original), hFN10-G (pink in original) onto the RGD loop of frog γC (green in original). Sphere represents the metal ion at MIDAS. (B) Energy of interaction between hFN10's PRGDWN (SEQ ID NO: 52) and hFN10-G's PGRGDWN (SEQ ID NO: 53) loops with αVβ3 and αIIbβ3, respectively. The head domain of αIIbβ3 with the mhFN10 was simulated for ~5 ns and their interactions compared to those of the head domain of αVβ3 with hFN10, simulated for ~6 ns. (C) A representative experiment showing binding of soluble hFN10 or hFN10-G to αVβ3$^{N/S}$ and αIIbβ3$^{N/S}$ (mutationally activated via an N339/S change in βA domain (Van Agthoven et al, *Nature Struc Mol Biol,* 2014, April; 21 (4): 383-8).

Figure 10:
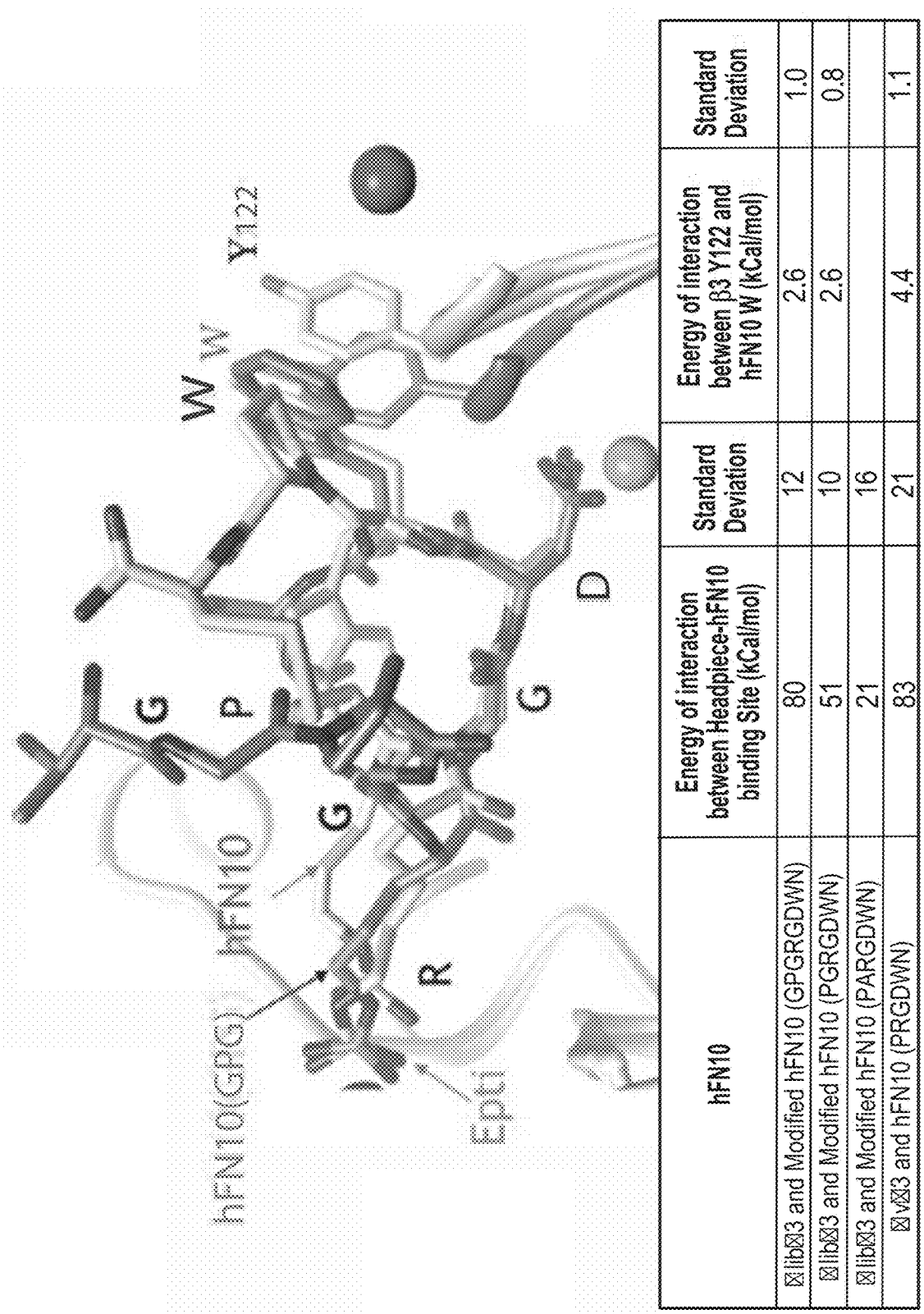

FIG. 10. Generating and modeling hFN10-GPG. RGD-containing loop of hFN10 (gray in original), eptifibatide (green in original) and modeled hFN10-GPG (pink in original), generated after superposing the β3 subunits from each integrin-ligand complex. The two inserted glycines in hFN10-GPG are in bold. For clarity, only structures of RGDW (SEQ ID NO: 54) of eptifibatide and hFN10s are shown. Note the inward movement of Tyr122 in eptifibatide/αIIbβ3 complex but not in hFN10/αVβ3 complex. Spheres represent the metal ion at MIDAS (cyan in original) and ADMIDAS (magenta in original). The table shows calculated energies of interaction. Figure discloses SEQ ID NOS 84, 53, 85, and 52, respectively, in order of appearance.

Figure 11:
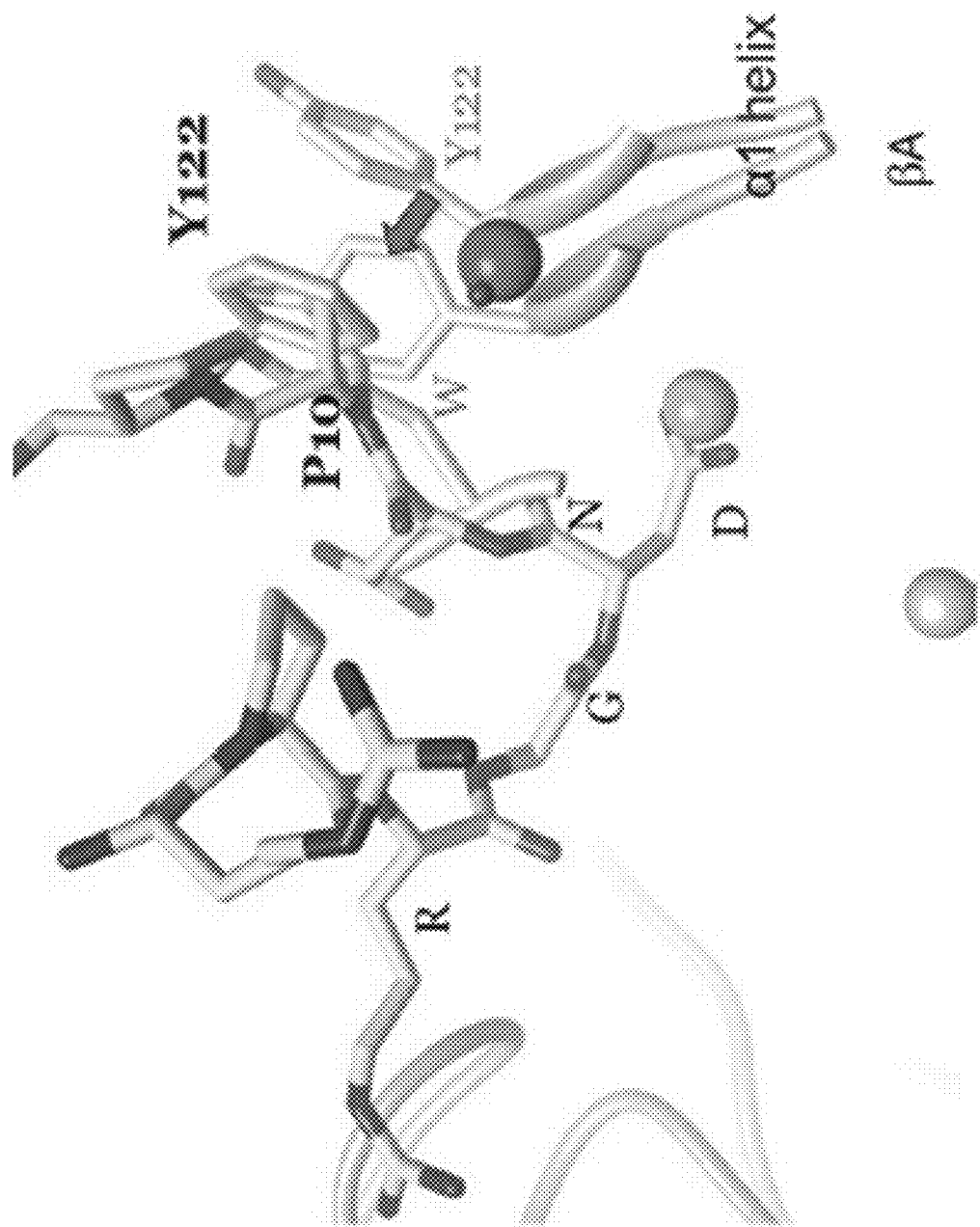

FIG. 11. Crystal structure of αVβ3/knottin2.5F complex. RGD-containing loop residues of knottin 2.5F (carbons in yellow, oxygens in red and nitrogens in blue in original) in the complex. Only the α1 helix residues Tyr122 of the βA domain is shown (in brown in original). The structure was superposed onto that of αVβ3/hFN10 complex (in gray in original) aligning the structures of the βA domains of each. Note the inward movement of Tyr122 in αVβ3/knottin 2.5F complex but not in hFN10/αVβ3 complex. Spheres represent the metal ion at MIDAS (cyan in original) and LIMBS (gray in original).

FIGS. 12A-D. Wild type and modified Knottin 2.5F in structures of αVβ3/knottin 2.5F complex. (A) P10 residue faces integrin Y122 in wild-type knottin 2.5F complexed with integrin αVβ3. It is replaced with Trp, phenylproline (pP) or phenylglycine (pG) in models B, C and D, respectively. The βA domains in all complexes are superposed on the bA from αVβ3/hFN10 complex, of which only a portion of the α1 helix and Ty122 are shown. The sidechains of the new residues replacing P10 now contacts Tyr122 in the inactive state.

Figure 13:
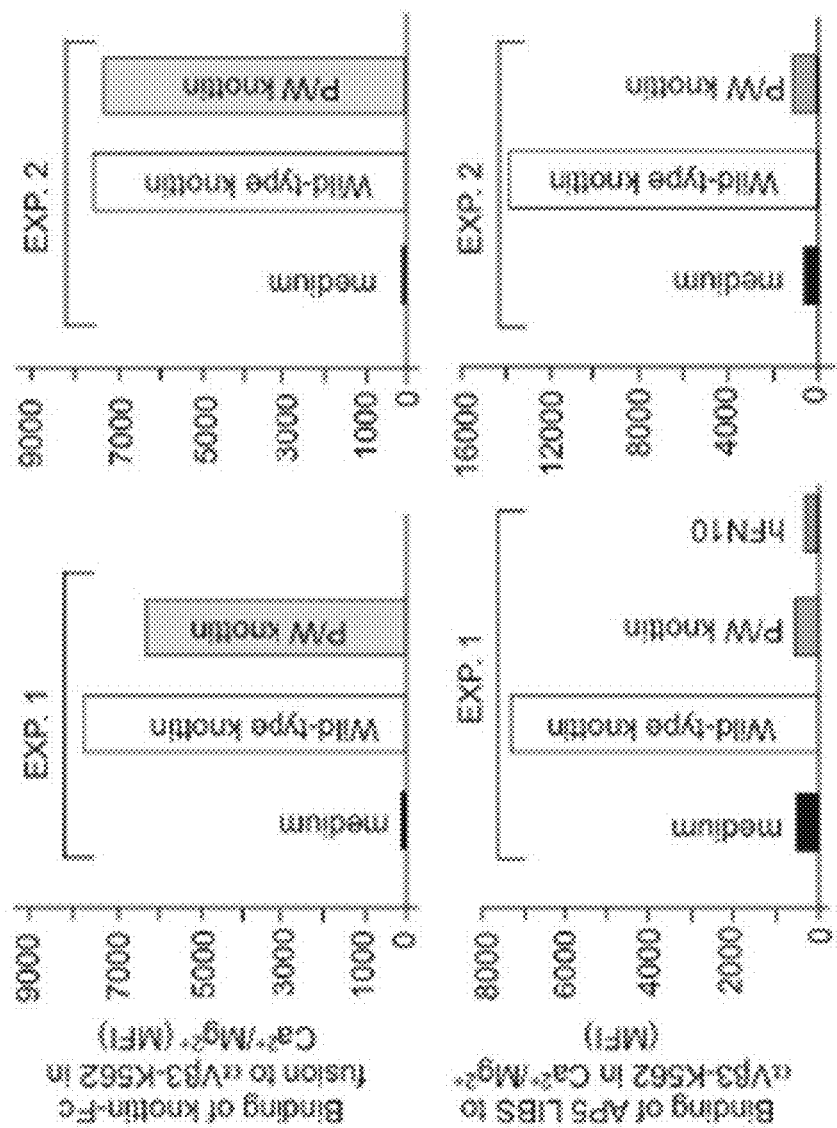

FIG. 13. Binding of wild type and P/W knottin 2.5F-Fc to K562 cells stably expressing αVβ33. Histograms are from two separate experiments. Binding was done in presence of the physiologic cations Ca$^{2+}$ and Mg$^{2+}$ (1 mM each). Suppression of AP5 binding by hFN10 is shown for comparison. Wild-type knottin 2.5F induced integrin activation as reported by binding of mAb AP5.

Figure 14:
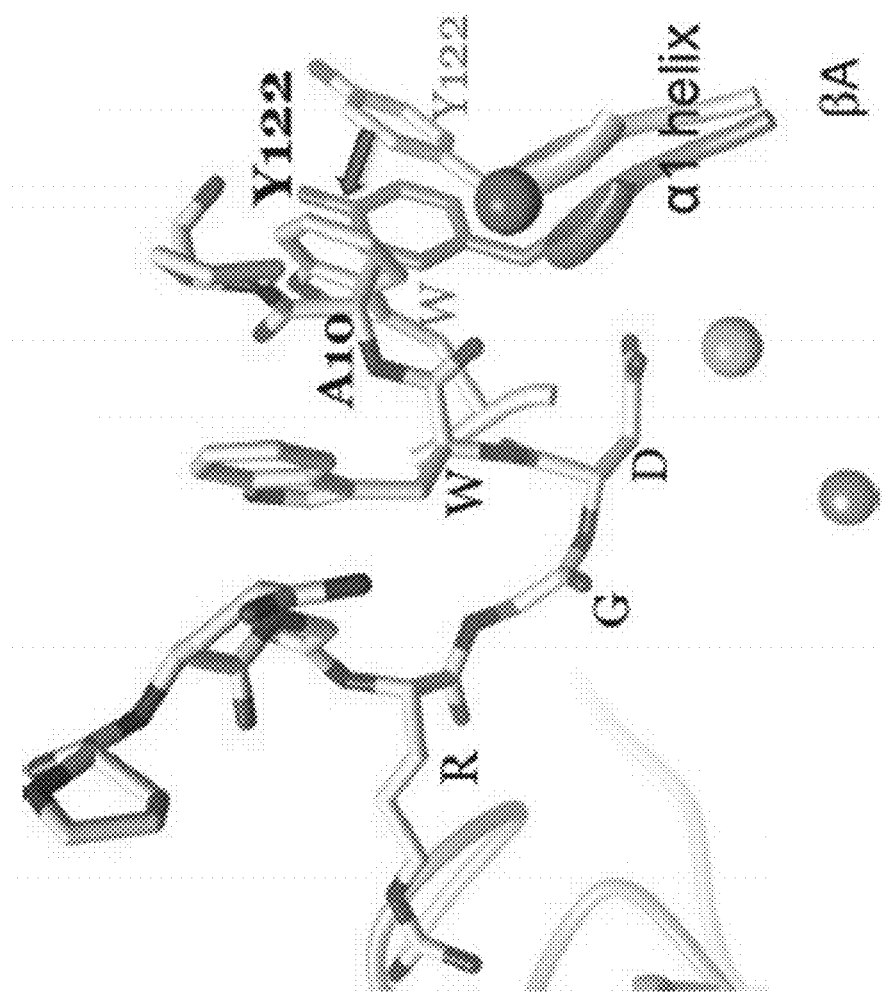

FIG. 14. Crystal structure of αVβ3/knottin 2.5D complex. RGD-containing loop residues of knottin 2.5D (carbons in yellow, oxygens in red and nitrogens in blue in original) in the complex. Only the α1 helix residues Tyr122 of the βA domain is shown (in green in original). The structure was superposed onto that of αVβ3/hFN10 complex (in gray in original) aligning the structures of the βA domains of each. Spheres represent the metal ion at MIDAS (cyan in original) and LIMBS (gray in original).

Figure 15:
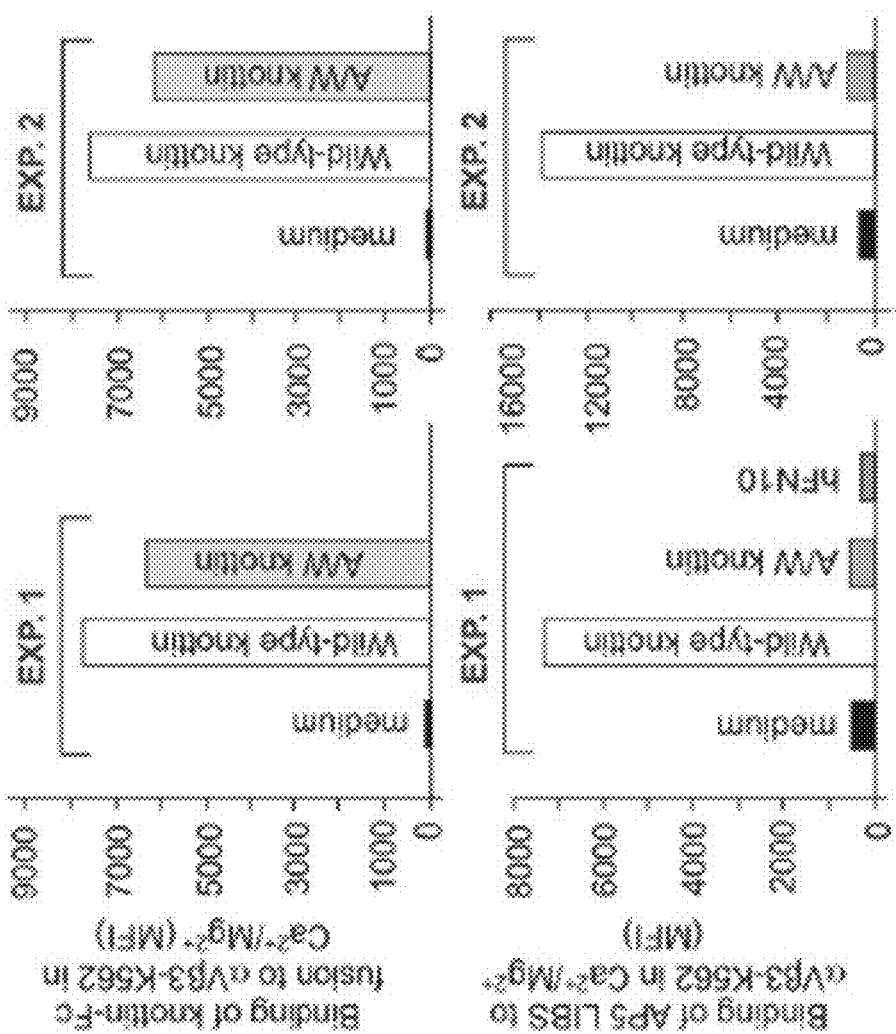

FIG. 15. Binding of wild type and A/W knottin 2.5D-Fc to K562 cells stably expressing αVβ3. Histograms are from two separate experiments. Binding was done in presence of the physiologic cations Ca$^{2+}$ and Mg$^{2+}$ (1 mM each). Suppression of AP5 binding by hFN10 is shown for comparison.

Wild-type knottin 2.5D induced integrin activation as reported by binding of mAb AP5.

FIGS. 16A-D. Properties and crystal structure of R-epit-D-αVβ3 complex. (A) Inhibition of Alex488-fibrinogen binding to αVβ3$^N$/S by increasing concentrations of R-epti-D. (B, C) Binding of AP5 to αVβ3$^N$/s (B) or Mn$^{2+}$-activated αVβ3 in presence of wtFN10, hFN10 or R-epti-D, carried out in physiologic Ca$^{2+}$/Mg$^{2+}$ (B) or in 1 mM Mn$^{2+}$ (C). One experiment was done under each condition. (D) RGD-containing loop of hFN10 (gray in original), eptifibatide (gold in original) and R-epti-D (blue in original), generated after superposing the β33 subunits from each integrin-ligand complex. Common residues are in black. For clarity, only structures of RGDW (SEQ ID NO: 54) of eptifibatide and hFN10 are shown. Note the change in orientation of D-Trp in R-epti-D vs. L-Trp in eptifibatide, and intermediate positioning of Tyr122 (in R-epti-D-αVβ33 complex) between the fully active (in eptifibatide-integrin complex) and fully inhibited states (hFN10-αVβ3). Spheres represent the metal ion at MIDAS.

DETAILED DESCRIPTION

Integrin activity has been linked to numerous human diseases including heart attacks, stroke and cancer. Integrin ligand-mimetic antagonists based on the Arg-Gly-Asp (RGD) motif, however, act as partial agonists, inducing conformational changes in the integrin that can trigger potentially fatal immune reactions and paradoxical cell adhesion in treated patients. Using the first x-ray structures of an integrin, αVβ3, complexed to macromolecular ligands, the 10th type-III RGD-domain of wild-type fibronectin (wtFN10) and a mutant high affinity form of FN10 (hFN10), it was determined that the latter compound acted unexpectedly as a pure antagonist. Comparison of the two structures revealed a central π-π interaction of the tryptophan 1496 side-chain in the mutated RGD-containing loop of hFN10 with the side-chain of tyrosine 122 in the β3-subunit. This new interaction is believed to have sterically blocked the conformational changes triggered by wtFN10, and trapped hFN10-bound αVβ3 in an inactive conformation. Removing the Trp1496 side-chain, reorienting it away from the tyrosine 122 side-chain, or mutating Tyr122 converted hFN10 into a partial agonist. Structures of ligand-occupied active and inactive αVβ3 offer unique mechanistic insights and a basis for the design of the integrin antagonists provided herein.

Definitions

Unless defined otherwise, all technical and scientific terms used herein have the same meaning as is commonly understood by one of ordinary skill in the art to which this disclosure belongs. All patents, applications, published applications, and other publications are incorporated by reference in their entirety. In the event that there is a plurality of definitions for a term herein, those in this section prevail unless stated otherwise.

Wherever the phrase "for example," "such as," and the like are used herein, the phrase "and without limitation" is understood to follow unless explicitly stated otherwise. As used herein, "about" is meant to account for variations due to experimental error. All measurements reported herein are understood to be modified by the term "about", whether or not the term is explicitly used, unless explicitly stated otherwise. As used herein, the singular forms "a," "an," and "the" include plural referents unless the context clearly dictates otherwise.

The term "alkyl" includes saturated aliphatic groups, including straight-chain alkyl groups (e.g., methyl, ethyl, propyl, butyl, pentyl, hexyl, heptyl, octyl, nonyl, and decyl) and branched-chain alkyl groups (isopropyl, tert-butyl, and isobutyl). In certain embodiments, a straight chain or branched chain alkyl has 6 or fewer carbon atoms in its backbone (e.g., $C_{1-6}$ for straight chain, $C_{3-6}$ for branched chain). The term $C_{1-6}$ includes alkyl groups containing 1 to 6 carbon atoms.

Moreover, the term "alkyl" includes both "unsubstituted alkyls" and "substituted alkyls," the latter of which refers to alkyl moieties having substituents replacing a hydrogen on one or more carbons of the hydrocarbon backbone. Such substituents can include, for example, alkyl, alkenyl, alkynyl, halogen, hydroxyl, carboxylate, alkoxyl, amino (including alkyl amino, dialkylamino, arylamino, diarylamino, and alkylarylamino), nitro, trichloromethyl, trifluoromethyl, or an aryl moiety.

In general, the term "aryl" includes groups, including 5- and 6-membered single-ring aromatic groups (e.g., phenyl), alkyl substituted aryl groups, and aryl substituted alkyl groups. Furthermore, the term "aryl" includes polycyclic aryl groups, e.g., tricyclic, bicyclic, such as naphthalene. An aryl group may be substituted at one or more ring positions with substituents.

As used herein, "heterocyclyl" means a cyclic ring system comprising at least one heteroatom in the ring system backbone. Heterocyclyls may include multiple fused rings. Heterocyclyls may have any degree of saturation provided that at least one ring in the ring system is not aromatic. Heterocyclyls can be attached to other groups via any available valence, for example, an available carbon or nitrogen. In some embodiments, heterocyclyls have 5-7 members in the ring. Examples of heterocyclyls include azirinyl, aziridinyl, azetidinyl, oxetanyl, thietanyl, 1,4,2-dithiazolyl, 1,3-benzodioxolyl, dihydroisoindolyl, dihydroisoquinolinyl, dihydrocinnolinyl, dihydrobenzodioxinyl, dihydro[1,3]oxazolo[4,5-b]pyridinyl, benzothiazolyl, dihydroindolyl, dihydropyridinyl, 1,3-dioxanyl, 1,4-dioxanyl, 1,3-dioxolanyl, isoindolinyl, morpholinyl, thiomorpholinyl, piperazinyl, pyranyl, pyrrolidinyl, tetrahydrofuryl, tetrahydropyridinyl, oxazinyl, thiazinyl, thiinyl, thiazolidinyl, isothiazolidinyl, oxazolidinyl, isoxazolidinyl, piperidinyl, pyrazolidinyl imidazolidinyl, and thiomorpholinyl.

As used herein, the term "heteroaryl" means a mono-, bi-, tri- or polycyclic group having 5 to 14 ring atoms, for example 5, 6, 9, or 10 ring atoms; having 6, 10, or 14 pi electrons shared in a cyclic array; wherein at least one ring in the system is aromatic; and at least one ring in the system contains one or more heteroatoms. Heteroaryl groups can either be unsubstituted or substituted with one or more substituents. Examples of heteroaryls include thienyl, pyridinyl, furyl, oxazolyl, oxadiazolyl, pyrrolyl, imidazolyl, triazolyl, thiodiazolyl, pyrazolyl, isoxazolyl, thiadiazolyl, pyranyl, pyrazinyl, pyrimidinyl, pyridazinyl, triazinyl, thiazolyl benzothienyl, benzoxadiazolyl, benzofuranyl, benzimidazolyl, benzotriazolyl, cinnolinyl, indazolyl, indolyl, isoquinolinyl, isothiazolyl, naphthyridinyl, purinyl, thienopyridinyl, pyrido[2,3-d]pyrimidinyl, pyrrolo[2,3-b]pyridinyl, quinazolinyl, quinolinyl, thieno[2,3-c]pyridinyl, pyrazolo[3,4-b]pyridinyl, pyrazolo[3,4-c]pyridinyl, pyrazolo[4,3-c]pyridine, pyrazolo[4,3-b]pyridinyl, tetrazolyl, chromane, 2,3-dihydrobenzo[b][1,4]dioxine, benzo[d][1,3]dioxole, 2,3-dihydrobenzofuran, and 2,3-dihydrobenzo[b][1,4]oxathiine.

As used herein, chemical structures which contain one or more stereocenters depicted with bold and dashed bonds are meant to indicate absolute stereochemistry of the stereocenter(s) present in the chemical structure. As used herein, bonds symbolized by a simple line do not indicate a stereopreference. Unless otherwise indicated to the contrary, chemical structures, which include one or more stereocenters, illustrated herein without indicating absolute or relative stereochemistry encompass all possible steroisomeric forms of the compound (e.g., diastereomers, enantiomers) and mixtures thereof. Structures with a single bold or dashed line, and at least one additional simple line, encompass a single enantiomeric series of all possible diastereomers.

The term "pharmaceutically acceptable salt" refers to salts that retain the biological effectiveness and properties of the compounds provided herein and, which are not biologically or otherwise undesirable. In many cases, the compounds provided herein are capable of forming acid and/or base salts by virtue of the presence of amino and/or carboxyl groups or groups similar thereto. Pharmaceutically acceptable acid addition salts can be formed with inorganic acids and organic acids. Inorganic acids from which salts can be derived include, for example, hydrochloric acid, hydrobromic acid, sulfuric acid, nitric acid, phosphoric acid, and the like. Organic acids from which salts can be derived include, for example, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Pharmaceutically acceptable base addition salts can be formed with inorganic and organic bases. Inorganic bases from which salts can be derived include, for example, sodium, potassium, lithium, ammonium, calcium, magnesium, iron, zinc, copper, manganese, aluminum, and the like; particularly preferred are the ammonium, potassium, sodium, calcium, and magnesium salts. Organic bases from which salts can be derived include, for example, primary, secondary, and tertiary amines, substituted amines including naturally occurring substituted amines, cyclic amines, basic ion exchange resins, and the like, specifically such as isopropylamine, trimethylamine, diethylamine, triethylamine, tripropylamine, and ethanolamine. Many such salts are known in the art, for example, as described in WO 87/05297.

As used herein, "purified" polypeptide refers to a polypeptide that has been removed from its natural environment, i.e., it has been separated from cellular components that naturally accompany it. Typically, a polypeptide is isolated when it is at least 60% (e.g., 70%, 80%, 90%, 95%, or 99%), by weight, free from proteins and molecules that are naturally associated with it.

Also provided are isolated or purified polypeptide sequences that have at least 75% sequence identity (e.g., at least 80%, at least 85%, at least 90%, at least 95%, or at least 99% sequence identity) to one of the specific polypeptide sequences disclosed herein. In some embodiments, the polypeptide has 100% sequence identity to one of the specific polypeptide sequences provided herein. In calculating percent sequence identity, two sequences are aligned and the number of identical matches of amino acid residues between the two sequences is determined. The number of identical matches is divided by the length of the aligned region (i.e. the number of aligned amino acid residues) and multiplied by 100 to arrive at a percent sequence identity value. It will be appreciated that the length of the aligned region can be a portion of one or both sequences up to the full-length size of the shortest sequence. It will be appreciated that a single sequence can align differently with other sequences and hence, can have different percent sequence identity values over each aligned region. It is noted that the percent identity value is usually rounded to the nearest integer. For example, 78.1%, 78.2%, 78.3%, and 78.4% are rounded down to 78%, while 78.5%, 78.6%, 78.7%, 78.8%, and 78.9% are rounded up to 79%. It is also noted that the length of the aligned region is always an integer.

The alignment of two or more sequences to determine percent sequence identity is performed using the algorithm described by Altschul et al. (1997, Nucleic Acids Res., 25:3389-3402) as incorporated into BLAST (basic local alignment search tool) programs, available at ncbi.nlm.nih.gov on the World Wide Web). BLAST searches can be performed to determine percent sequence identity between a sequence having the activity described herein (i.e., inhibition of integrin activity) and any other sequence or portion thereof aligned using the Altschul et al. algorithm. BLASTP is the program used to align and compare the identity between amino acid sequences. When utilizing a BLAST program to calculate the percent identity between a sequence provided herein and another sequence, the default parameters of the program are used.

As used herein, "patient" (as in the subject of the treatment) means both mammals and non-mammals. Mammals include, for example, humans; non-human primates, e.g. apes and monkeys; cattle; horses; sheep; rats; mice; pigs; and goats. Non-mammals include, for example, fish and birds.

The term "contacting" means bringing at least two moieties together, whether in an in vitro system or an in vivo system.

Integrin Ectodomain/Inhibitor Complex Crystal Structures and Rational Drug Design Provided herein are three-dimensional structures of an integrin ectodomain/inhibitor complex, at 3-3.1 Angstrom, or 2.5 Angstrom, resolution or better. Although the structures are exemplified herein by the αVβ3 ectodomain, ectodomains from other integrins can also be used, e.g., as shown in FIG. 8, preferably those that have a conserved Tyr that corresponds to Tyr122 in β3. The alpha domain can be any alpha domain, e.g., as shown in the following table:

| Integrin | GenBank Acc. No. | |
|---|---|---|
| | mRNA | Protein |
| alpha V | NM_002210.4 | NP_002201.1 (isoform 1) |
| | NM_001144999.2 | NP_001138471.1 (isoform 2) |
| | NM_001145000.2 | NP_001138472.1 (isoform 3) |
| alpha 1 | NM_181501.1 | NP_852478.1 |
| alpha 2 | NM_002203.3 | NP_002194.2 |
| alpha 2b | NM_000419.3 | NP_000410.2 |
| alpha 3 | NM_002204.2 | NP_002195.1 (isoform a) |
| | NM_005501.2 | NP_005492.1 (isoform b) |
| alpha 4 | NM_000885.4 | NP_000876.3 |
| alpha 5 | NM_002205.2 | NP_002196.2 |
| alpha 6 | NM_001079818.1 | NP_001073286.1 (isoform a) |
| | NM_000210.2 | NP_000201.2 (isoform b) |
| alpha 7 | NM_001144996.1 | NP_001138468.1 (isoform 1) |
| | NM_002206.2 | NP_002197.2 (isoform 2) |
| | NM_001144997.1 | NP_001138469.1 (isoform 3) |
| alpha 8 | NM_003638.2 | NP_003629.2 (isoform 1) |
| | NM_001291494.1 | NP_001278423.1 (isoform 2) |

-continued

| Integrin | GenBank Acc. No. | |
|---|---|---|
| | mRNA | Protein |
| alpha 9 | NM_002207.2 | NP_002198.2 |
| alpha 10 | NM_003637.4 | NP_003628.2 (isoform 1) |
| | NM_001303040.1 | NP_001289969.1 (isoform 2) |
| | NM_001303041.1 | NP_001289970.1 (isoform 1) |
| alpha 11 | NM_001004439.1 | NP_001004439.1 |
| alpha L | NM_002209.2 | NP_002200.2 (isoform a) |
| | NM_001114380.1 | NP_001107852.1 (isoform b) |
| alpha M | NM_001145808.1 | NP_001139280.1 (isoform 1) |
| | NM_000632.3 | NP_000623.2 (isoform2) |
| alpha X | NM_001286375.1 | NP_001273304.1 (isoform 1) |
| | NM_000887.4 | NP_000878.2 (isoform 2) |

Alpha and beta domain sequences with 80%, 85%, 90%, 95%, 97%, or 99% or more identity to these sequences can also be used.

In some embodiments, the three-dimensional structure of the αVβ3 ectodomain/inhibitor complex described herein is defined by a set of structural coordinates as set forth in Table 2, Table 6, or Table 7. The term "structural coordinates" refers to Cartesian coordinates derived from mathematical equations related to the patterns obtained on diffraction of a monochromatic beam of X-rays by the atoms (scattering centers) of an αVβ3 ectodomain/inhibitor complex in crystal form. The diffraction data are used to calculate an electron density map of the repeating unit of the crystal. The electron density maps are then used to establish the positions of the individual atoms of the αVβ33 ectodomain/inhibitor complex.

Slight variations in structural coordinates can be generated by mathematically manipulating the integrin/ligand structural coordinates. For example, the structural coordinates disclosed herein could be manipulated by crystallographic permutation, fractionalization, addition or subtraction of the entire set, inversion, or any combination of the above. Alternatively, modifications in the crystal structure due to mutations, additions, substitutions, and/or deletions of amino acids, or other changes in any of the components that make up the crystal, could also yield variations in structural coordinates. Such slight variations in the individual coordinates will have little effect on the overall configuration. If such variations are within an acceptable standard error as compared to the original coordinates, the resulting three-dimensional shape is considered to be structurally equivalent. In some embodiments, the structure has unit cell parameters as disclosed herein with a variability of at most 5% in all cell parameters.

An agent that interacts with an integrin ectodomain can be identified or designed by a method that includes using a representation of the integrin ectodomain or a fragment thereof, or a complex of the integrin ectodomain bound to an inhibitor, e.g., hFN10, or a fragment of one of these complexes, and using the representation to select or design an inhibitor that binds the integrin ectodomain, with specific binding features as described herein, e.g., an attractive interaction with the residue corresponding to Tyr122 in the βA of αVβ3 (e.g., covalent or noncovalent, e.g., attractive, noncovalent interaction between aromatic rings (e.g., π-π interaction); an interaction between the aromatic ring of Tyr122 and a cation (e.g., a metal or charged side chain, e.g., cation π interaction), or an interaction between the aromatic ring and exposed adjacent methylene groups (e.g., X-H-π)); a hydrogen bond interaction with Tyr122 in the βA; a salt bridge interaction with Lys125 in the βA; and/or an interaction with the $Mn^{2+}$ at ADMIDAS through a water molecule.

Various software programs allow for the graphical representation of a set of structural coordinates to obtain a representation of a complex of the αVβ3 ectodomain bound to an inhibitor, e.g., hFN10, or a fragment of one of these complexes. In general, such a representation should accurately reflect (relatively and/or absolutely) structural coordinates, or information derived from structural coordinates, such as distances or angles between features. In some embodiments, the representation is a two-dimensional figure, such as a stereoscopic two-dimensional figure. In certain embodiments, the representation is an interactive two-dimensional display, such as an interactive stereoscopic two-dimensional display. An interactive two-dimensional display can be, for example, a computer display that can be rotated to show different faces of a polypeptide, a fragment of a polypeptide, a complex and/or a fragment of a complex. In some embodiments, the representation is a three-dimensional representation. As an example, a three-dimensional model can be a physical model of a molecular structure (e.g., a ball-and-stick model). As another example, a three dimensional representation can be a graphical representation of a molecular structure (e.g., a drawing or a figure presented on a computer display). A two-dimensional graphical representation (e.g., a drawing) can correspond to a three-dimensional representation when the two-dimensional representation reflects three-dimensional information, for example, through the use of perspective, shading, or the obstruction of features more distant from the viewer by features closer to the viewer. In some embodiments, a representation can be modeled at more than one level. As an example, when the three-dimensional representation includes a polypeptide, such as a complex of the αVβ3 ectodomain bound to an inhibitor, e.g., hFN10, the polypeptide can be represented at one or more different levels of structure, such as primary (amino acid sequence), secondary (e.g., α-helices and β-sheets), tertiary (overall fold), and quaternary (oligomerization state) structure. A representation can include different levels of detail. For example, the representation can include the relative locations of secondary structural features of a protein without specifying the positions of atoms. A more detailed representation could, for example, include the positions of atoms.

In some embodiments, a representation can include information in addition to the structural coordinates of the atoms in a complex of the αVβ3 ectodomain bound to an inhibitor, e.g., hFN10 or knottin or a fragment or variant thereof. For example, a representation can provide information regarding the shape of a solvent accessible surface, the van der Waals radii of the atoms of the model, and the van der Waals radius of a solvent (e.g., water). Other features that can be derived from a representation include, for example, electrostatic potential, the location of voids or pockets within a macromolecular structure, and the location of hydrogen bonds and salt bridges.

In some embodiments, the representation can be of an analog polypeptide, polypeptide fragment, complex or fragment of a complex. A candidate agent that interacts with the representation can be designed or identified by performing computer fitting analysis of the candidate agent with the representation. In general, an agent is a molecule. Examples of agents include polypeptides, nucleic acids (including DNA or RNA), steroids and non-steroidal organic compounds. An agent that interacts with a polypeptide (e.g., an ERalpha polypeptide) can interact transiently or stably with the polypeptide. The interaction can be mediated by any of the forces noted herein, including, for example, hydrogen bonding, electrostatic forces, hydrophobic interactions, and van der Waals interactions.

As noted above, X-ray crystallography can be used to obtain structural coordinates of a complex of αVβ3 ectodomain bound to an inhibitor, e.g., hFN10 or knottin or a fragment or variant thereof. However, such structural coordinates can be obtained using other techniques including NMR techniques. Additional structural information can be obtained from spectral techniques (e.g., optical rotary dispersion (ORD), circular dichroism (CD)), homology modeling, and computational methods (e.g., computational methods that can include data from molecular mechanics, computational methods that include data from dynamics assays).

In some embodiments, the X-ray diffraction data can be used to construct an electron density map of a complex of αVβ3 ectodomain bound to an inhibitor, e.g., hFN10 or a fragment thereof, and the electron density map can be used to derive a representation (e.g., a two dimensional representation, a three dimensional representation) of αVβ3 ectodomain bound to an inhibitor, e.g., hFN10 or knottin or a fragment or variant thereof, or a fragment thereof. Creation of an electron density map typically involves using information regarding the phase of the X-ray scatter. Phase information can be extracted, for example, either from the diffraction data or from supplementing diffraction experiments to complete the construction of the electron density map. Methods for calculating phase from X-ray diffraction data include, for example, multiwavelength anomalous dispersion (MAD), multiple isomorphous replacement (MIR), multiple isomorphous replacement with anomalous scattering (MIRAS), single isomorphous replacement with anomalous scattering (SIRAS), reciprocal space solvent flattening, molecular replacement, or any combination thereof. Upon determination of the phase, an electron density map can be constructed. The electron density map can be used to derive a representation of the complex or a fragment thereof by aligning a three-dimensional model of a previously known polypeptide or a previously known complex (e.g., a complex containing a polypeptide bound to a ligand) with the electron density map. For example, the electron density map corresponding to an αVβ3 ectodomain/inhibitor complex can be aligned with the electron density map corresponding to an unliganded αVβ3 ectodomain, or αVβ3 ectodomain complexed to another compound, such as an agonist or partial agonist (e.g., wtFN10 or wtknottin or a fragment or variant thereof).

The alignment process results in a comparative model that shows the degree to which the calculated electron density map varies from the model of the previously known polypeptide or the previously known complex. The comparative model is then refined over one or more cycles (e.g., two cycles, three cycles, four cycles, five cycles, six cycles, seven cycles, eight cycles, nine cycles, 10 cycles) to generate a better fit with the electron density map. A software program such as CNS (Brunger et al., Acta Crystallogr. D54:905-921, 1998) can be used to refine the model. The quality of fit in the comparative model can be measured by, for example, an $R_{work}$ or $R_{free}$ value. A smaller value of $R_{work}$ or $R_{free}$ generally indicates a better fit. Misalignments in the comparative model can be adjusted to provide a modified comparative model and a lower $R_{work}$ or $R_{free}$ value. The adjustments can be based on information (e.g., sequence information) relating to αVβ3 ectodomain, an inhibitor, e.g., hFN10 or knottin or a fragment or variant thereof, the previously known polypeptide and/or the previously known complex. As an example, in embodiments in which a model of a previously known complex of a polypeptide bound to a ligand is used, an adjustment can include replacing the ligand in the previously known complex with an inhibitor, e.g., hFN10 or knottin or a fragment or variant thereof. As another example, in certain embodiments, an adjustment can include replacing an amino acid in the previously known polypeptide with the amino acid in the corresponding site of αVβ3 ectodomain. When adjustments to the modified comparative model satisfy a best fit to the electron density map, the resulting model is that which is determined to describe the polypeptide or complex from which the X-ray data was derived (e.g., the αVβ3 ectodomain/inhibitor complex). Methods of such processes are disclosed, for example, in Carter and Sweet, eds., "Macromolecular Crystallography" in *Methods in Enzymology*, Vol. 277, Part B, New York: Academic Press, 1997, and articles therein, e.g., Jones and Kjeldgaard, "Electron-Density Map Interpretation," p. 173, and Kleywegt and Jones, "Model Building and Refinement Practice," p. 208.

Discussed above is a method of deriving a representation of a complex by aligning a three-dimensional model of a previously known polypeptide or a previously known complex with a newly calculated electron density map corresponding to a crystal of the complex. One adjustment that can be used in this modeling process can include replacing the compound in the representation of the previously known complex with an inhibitor, e.g., hFN10 or knottin or a fragment or variant thereof.

A machine, such as a computer, can be programmed in memory with the structural coordinates of a complex of the αVβ3 ectodomain bound to an inhibitor, e.g., hFN10 or knottin or a fragment or variant thereof, together with a program capable of generating a graphical representation of the structural coordinates on a display connected to the machine. Alternatively or additionally, a software system can be designed and/or utilized to accept and store the structural coordinates. The software system can be capable of generating a graphical representation of the structural coordinates. The software system can also be capable of accessing external databases to identify compounds (e.g., polypeptides) with similar structural features as αVβ3 ectodomain, and/or to identify one or more candidate agents with characteristics that may render the candidate agent(s) likely to interact with αVβ3 ectodomain.

A machine having a memory containing structure data or a software system containing such data can aid in the rational design or selection of integrin antagonists. For example, such a machine or software system can aid in the evaluation of the ability of an agent to associate with the αVβ3 ectodomain. As used herein, an antagonist refers to a compound that inhibits at least one activity, or has an opposite activity, of an integrin, e.g., integrin αVβ3.

The machine can produce a representation (e.g., a two dimensional representation, a three dimensional representation) of a complex of the αVβ3 ectodomain bound to an inhibitor, e.g., hFN10 or knottin or a fragment or variant thereof, or a fragment thereof. A software system, for example, can cause the machine to produce such information. The machine can include a machine-readable data storage medium including a data storage material encoded with machine-readable data. The machine-readable data can include structural coordinates of atoms of a complex of the αVβ3 ectodomain bound to an inhibitor, e.g., hFN10 or knottin or a fragment or variant thereof, or a fragment thereof. Machine-readable storage media (e.g., data storage material) include, for example, conventional computer hard drives, floppy disks, DAT tape, CD-ROM, DVD, and other magnetic, magneto-optical, optical, and other media which may be adapted for use with a machine (e.g., a computer). The machine can also have a working memory for storing instructions for processing the machine-readable data, as well as a central processing unit (CPU) coupled to the working memory and to the machine-readable data storage medium for the purpose of processing the machine-readable data into the desired three-dimensional representation. A display can be connected to the CPU so that the three-dimensional representation can be visualized by the user. Accordingly, when used with a machine programmed with instructions for using the data (e.g., a computer loaded with one or more programs of the sort described herein) the machine is capable of displaying a graphical representation (e.g., a two dimensional graphical representation, a three-dimensional graphical representation) of any of the polypeptides, polypeptide fragments, complexes, or complex fragments described herein.

A display (e.g., a computer display) can show a representation of a complex of αVβ3 ectodomain bound to an inhibitor, e.g., hFN10 or knottin or a fragment or variant thereof, or a fragment of either of these complexes. The user can inspect the representation and, using information gained from the representation, generate a model of a complex or fragment thereof that includes an agent other than the inhibitor, e.g., hFN10 or knottin or a fragment or variant thereof. The model can be generated, for example, by using the coordinates set forth herein. Optionally, the user can superimpose a three-dimensional model of a candidate agent on the representation of αVβ3 ectodomain bound to an inhibitor, e.g., hFN10 or knottin or a fragment or variant thereof. In some embodiments, the agent can be a known compound or fragment of a compound. In certain embodiments, the agent can be a previously unknown compound, or a fragment of a previously unknown compound.

It can be desirable for the agent to have a shape that complements the shape of the binding site. There can be a preferred distance, or range of distances, between atoms of the agent and atoms of the αVβ3 ectodomain binding site. Distances longer than a preferred distance may be associated with a weak interaction between the agent and inhibitor binding site (e.g., αVβ3 ectodomain inhibitor binding site). Distances shorter than a preferred distance may be associated with repulsive forces that can weaken the interaction between the agent and the polypeptide. A steric clash can occur when distances between atoms are too short. A steric clash occurs when the locations of two atoms are unreasonably close together, for example, when two atoms are separated by a distance less than the sum of their van der Waals radii. If a steric clash exists, the user can adjust the position of the agent relative to the αVβ3 ectodomain (e.g., a rigid body translation or rotation of the agent), until the steric clash is relieved. The user can adjust the conformation of the agent or of the αVβ3 ectodomain in the vicinity of the agent in order to relieve a steric clash. Steric clashes can also be removed by altering the structure of the agent, for example, by changing a "bulky group," such as an aromatic ring, to a smaller group, such as to a methyl or hydroxyl group, or by changing a rigid group to a flexible group that can accommodate a conformation that does not produce a steric clash. Electrostatic forces can also influence an interaction between an agent and a ligand-binding domain. For example, electrostatic properties can be associated with repulsive forces that can weaken the interaction between the agent and the αVβ3 ectodomain. Electrostatic repulsion can be relieved by altering the charge of the agent, e.g., by replacing a positively charged group with a neutral group.

Forces that influence binding strength between an inhibitor, e.g., hFN10 or knottin or a fragment or variant thereof, and αVβ3 ectodomain can be evaluated in the polypeptide/agent model. These can include, for example, hydrogen bonding, electrostatic forces, hydrophobic interactions, van der Waals interactions, dipole-dipole interactions, π-stacking forces, and cation-π interactions. The user can evaluate these forces visually, for example by noting a hydrogen bond donor/acceptor pair arranged with a distance and angle suitable for a hydrogen bond. Based on the evaluation, the user can alter the model to find a more favorable interaction between the αVβ3 ectodomain and the agent. Altering the model can include changing the three-dimensional structure of the polypeptide without altering its chemical structure, for example by altering the conformation of amino acid side chains or backbone dihedral angles. Altering the model can include altering the position or conformation of the agent, as described above. Altering the model can also include altering the chemical structure of the agent, for example by substituting, adding, or removing groups. For example, if a hydrogen bond donor on the αVβ3 ectodomain is located near a hydrogen bond donor on the agent, the user can replace the hydrogen bond donor on the agent with a hydrogen bond acceptor. In preferred embodiments, the potential inhibitors identified, designed or selected by a method described herein have at least an interaction, e.g., one or more of:

- an attractive interaction with Tyr122 in the βA (e.g., covalent or noncovalent, e.g., attractive, noncovalent interaction between aromatic rings (e.g., R-7n interaction); an interaction between the aromatic ring of Tyr122 and a cation (e.g., a metal or charged side chain, e.g., cation R interaction), or an interaction between the aromatic ring and exposed adjacent methylene groups (e.g., X-H-π));
- a hydrogen bond interaction with Tyr122 in the βA;
- a salt bridge interaction with Lys125 in the βA; and/or
- an interaction with the $Mn^{2+}$ at ADMIDAS through a water molecule.

Thus in some embodiments the potential inhibitors identified, designed or selected by a method described herein have, e.g., an interaction that mimics the edge-to-face interaction of the mutant Trp1496 in hFN10 with Tyr122 in the al helix of βA (see, e.g., FIG. 3*b*), and/or the hydrogen bond between Tyr122 and Glu1462 of hFN10, and/or forms a salt bridge with Lys125 of βA, and/or coordinates the $Mn^{2+}$ at ADMIDAS through a water molecule.

The relative locations of an agent and the αVβ3 ectodomain, or their conformations, can be adjusted to find an optimized binding geometry for a particular agent to the αVβ3 ectodomain. An optimized binding geometry is characterized by, for example, favorable hydrogen bond distances and angles, maximal electrostatic attractions, minimal electrostatic repulsions, the sequestration of hydrophobic moieties away from an aqueous environment, and the absence of steric clashes. The optimized geometry can have the lowest calculated energy of a family of possible geometries for an αVβ3 ectodomain/agent complex. An optimized geometry can be determined, for example, through molecular mechanics or molecular dynamics calculations.

A series of representations of complexes of αVβ3 ectodomain having different bound agents can be generated. A score can be calculated for each representation. The score can describe, for example, an expected strength of interaction between αVβ33 ectodomain and the agent. The score can reflect one of the factors described above that influence binding strength. The score can be an aggregate score that reflects more than one of the factors. The different agents can be ranked according to their scores.

Steps in the design of the agent can be carried out in an automated fashion by a machine. For example, a representation of αVβ33 ectodomain can be programmed in the machine, along with representations of candidate agents. The machine can find an optimized binding geometry for each of the candidate agents to the binding site, and calculate a score to determine which of the agents in the series is likely to interact most strongly with αVβ3 ectodomain.

A software system can be designed and/or implemented to facilitate these steps. Software systems (e.g., computer programs) used to generate representations or perform the fitting analyses include, for example: MCSS, Ludi, QUANTA, Insight II, Cerius2, CHarMM, and Modeler from Accelrys, Inc. (San Diego, CA); SYBYL, Unity, FleXX, and LEAPFROG from TRIPOS, Inc. (St. Louis, MO); AUTODOCK (Scripps Research Institute, La Jolla, CA); GRID (Oxford University, Oxford, UK); DOCK (University of California, San Francisco, CA); and Flo+ and Flo99 (Thistlesoft, Morris Township, NJ). Other useful programs include ROCS, ZAP, FRED, Vida, and Szybki from Openeye Scientific Software (Santa Fe, NM); Maestro, Macromodel, and Glide from Schrodinger, LLC (Portland, OR); MOE (Chemical Computing Group, Montreal, Quebec), Allegrow (Boston De Novo, Boston, MA), and GOLD (Jones et al., *J. Mol. Biol.* 245:43-53, 1995). The structural coordinates can also be used to visualize the three-dimensional structure of an ERalpha polypeptide using MOLSCRIPT, RASTER3D, or PYMOLE (Kraulis, *J. Appl. Crystallogr.* 24: 946-950, 1991; Bacon and Anderson, *J. Mol. Graph.* 6: 219-220, 1998; DeLano, The PyMOL Molecular Graphics System (2002) DeLano Scientific, San Carlos, CA).

The agent can, for example, be selected by screening an appropriate database, can be designed de novo by analyzing the steric configurations and charge potentials of unbound αVβ3 ectodomain in conjunction with the appropriate software systems, and/or can be designed using characteristics of known ligands of progesterone receptors or other hormone receptors. The method can be used to design or select antagonists of αVβ3 ectodomain. A software system can be designed and/or implemented to facilitate database searching, and/or agent selection and design.

Once an agent has been designed or identified, it can be obtained or synthesized and further evaluated for its effect on integrin activity. For example, the agent can be evaluated by contacting it with αVβ3 integrin and measuring the effect of the agent on polypeptide activity. A method for evaluating the agent can include an activity assay performed in vitro or in vivo. An activity assay can be a cell-based assay, for example. A crystal containing αVβ3 ectodomain bound to the identified agent can be grown and the structure determined by X-ray crystallography. A second agent can be designed or identified based on the interaction of the first agent with αVβ3 ectodomain.

Various molecular analysis and rational drug design techniques are further disclosed in, for example, U.S. Pat. Nos. 5,834,228, 5,939,528 and 5,856,116, as well as in PCT Application No. PCT/US98/16879, published as WO 99/09148. See also US20140356324.

Compounds and Polypeptides

Provided herein are compounds and polypeptides (e.g., cyclic polypeptides) which can function as integrin antagonists.

In some embodiments, a pure ligand-mimetic integrin antagonist is provided wherein the antagonist comprises the sequence RGD. Without being bound by any theory, it is believed that this sequence can stabilize the α1 helix of the βA domain in the inactive state of the integrin, thus inhibiting integrin activation.

Peptidomimetics of the RGD peptide sequence or portions of the sequence have been studied and are well-known in the art. These peptidomimetics are directed to improving the physicochemical or biological properties of the polypeptides, and include, in non-limiting examples, replacements of the amide with all carbon chains, replacement of the basic side chain of arginine with other basic moieties, and replacement of portions of the sequence with rigid non-peptide moieties. Such strategies have been used to obtain peptidomimetic structures as demonstrated by, e.g., Miyashita, M. et al. *Bioscience, Biotechnology, and Biochemistry* 1999, 63(10), p. 1684-1690; Hershkoviz et al. *Investigative Ophthamology & Visual Science* 1994, 35(5), p. 2585-2591; Pollina, E. *Journal of Undergraduate Science* 1996, 3, p. 119-126. These methods can be used to generate peptidomimetics of the peptides and polypeptides described herein.

Exemplary polypeptides that function as pure ligand-mimetic integrin antagonists include polypeptides comprising the amino acid sequence:

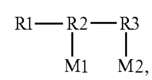

wherein

R1 is a recognition site of a Tyr 122-containing integrin;

R2 and R3 are each independently an amino acid in L or D form;

M1 and M2 are each independently absent or a side chain comprising at least one of: a branched $C_1$-$C_6$ alkyl, a heteroaryl, or an aryl, wherein the alkyl, heteroaryl, or aryl is optionally substituted with 1-3 groups consisting of: halo, $C_1$-$C_6$ alkyl, $C_2$-$C_6$ alkenyl, $C_2$-$C_6$ alkynyl, heteroaryl, aryl, heterocyclyl, and carbocyclyl;

wherein M1 and M2 are not both absent, and at least one of the bonds designated between M1 and R2, and M2 and R3, when present, is freely rotating.

In some embodiments, R1 can have a length of 3-6 amino acids (e.g., 3 amino acids, 4 amino acids, 5 amino acids). In some embodiments, R1 is selected from the group consisting of: RGD, LDV, IDA, REDV (SEQ ID NO: 45), KGD, NGR, DGR, KQAGD (SEQ ID NO: 42), DALR (SEQ ID NO: 46), DLR, RLD, L/IET, LRE, and TDE. For example, R1 can be selected from the group consisting of: RGD, LDV, KGD, KQAGD (SEQ ID NO: 42), IDA, L/IET, RLD, LRE, and TDE. In some embodiments, R1 is selected from the group consisting of: RGD, LDV, KGD, KQAGD (SEQ ID NO: 42), IDA, and L/IET. In some embodiments, R1 is selected from the group consisting of: RGD, LDV, and KGD. For example, R1 can be RGD.

In some embodiments, R2 is selected from the group consisting of: W, F, S, A, N, pG, pP, (4S)-4-hydroxy-L-proline and derivatives thereof or unnatural derivatives thereof, in L or D form. In some embodiments, $R^3$ is selected from the group consisting of: V, I, F, (4S)-4-hydroxy-L-proline, pP, pG and derivatives thereof or unnatural derivatives thereof, in L or D form.

In some embodiments, when present, M1 and M2 can be independently an electron-rich heterocyclyl or heteroaryl, such as furanyl, pyrrolyl, imidazolyl, oxazolyl, and thiophenyl. In some embodiments, when present, M1 and M2 can be independently an electron-poor heterocyclyl or heteroaryl such as pyridinyl, pyrimidinyl, and purinyl. In some embodiments, when present, M1 and M2 can be independently selected from the group consisting of indolyl, pyridyl, thiophenyl, and pyrrolyl. For example, when present, one or more of M1 and M2 can be independently indolyl.

Also provided herein are polypeptides comprising the amino acid sequence:

R*-G-D-X1-X2-X3 (SEQ ID NO: 40), wherein

R* is R or unnatural derivatives thereof, in L or D form;

X1 is any amino acid or unnatural derivatives thereof, in L or D form, with the proviso that X1 is not P;

X2 is any amino acid or unnatural derivatives thereof, in L or D form, with the proviso that X2 is not P, pP, or pG;

X3 is any amino acid, in L or D form;

and wherein the polypeptide has a length of 6 to 100 amino acids.

In some embodiments, the polypeptide does not comprise the sequence:

```
                                                    (SEQ ID NO: 20)
SDVPRDLEVVAATPTSLLISWDAPAVTVRYYRITYGETGGNSPVQEFTVPGSKSTA
TISGLKPGVDYTITVYAVTGRGDSPASSKPISINYRT;
                                                    (SEQ ID NO: 47)
GCPRPRGDNPPLTCSQDSDCLAGCVCGPNGFCG;
GCPQGRGDWAPTSCKQDSDCLAGCVCGPNGFCG   (SEQ ID NO: 41; knottin 2.5F); and
                                                    (SEQ ID NO: 26)
RGDWPC,
 |Linker|
``` wherein the linker is the moiety

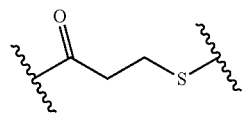 [SMILES: *SCCC(*)=O]

connecting the N-terminal end of Arg and the thiol side chain of Cys.

In some embodiments, X1 is selected from the group consisting of W, F, S, A, N, pG, and unnatural derivatives thereof, in L or D form.

In some embodiments, X2 is selected from the group consisting of V, I, N, F, (4S)-4-hydroxy-L-proline, pP, pG, and unnatural derivatives thereof, in L or D form.

In some embodiments, X1 is W or unnatural derivatives thereof, in L or D form; and X2 is N, in L or D form.

In some embodiments, X3 is P, in L or D form. For example, X3 is L-proline.

In some embodiments, the polypeptide has a length of 6 to 40 amino acids. In some embodiments, the polypeptide has a length of about 80-100 amino acids (e.g., hFN10 derivatives). In some embodiments, the polypeptide has a length of about 30-40 amino acids (e.g., knottin derivatives). In some embodiments, the polypeptide has a length of about 6 amino acids (e.g., compounds of Formula I, II, III, V, VI, VII, VIII, IX, and X).

In some embodiments, the polypeptides of SEQ ID NO: 40, can include a polypeptide based on the wild-type fibronectin (wtFN10) and a mutant high affinity form of FN10 (hFN10) as described herein. Such polypeptides can have at least 75% sequence identity to a sequence selected from the group consisting of:

```
                                                    (SEQ ID NO: 9)
SDVPRDLEVVAATPTSLLISWDAPAVTVRYYRITYGETGGNSPVQEFTV

PGSKSTATISGLKPGVDYTITVYAVTPRGDWNEGSKPISINY (SEQ ID NO: 10)
SDVPRDLEVVAATPTSLLISWDAPAVTVRYYRITYGETGGNSPVQEFTV

PGSKSTATISGLKPGVDYTITVYAVTPKGDWNEGSKPISINY (SEQ ID NO: 11)
VPRDLEVVAATPTSLLISWDAPAVTVRYYRITYGETGGNSPVQEFTVPG

SKSTATISGLKPGVDYTITVYAVTPKGDWNEGSKPISINY (SEQ ID NO: 12)
VPRDLEVVAATPTSLLISWDAPAVTVRYYRITYGETGGNSPVQEFTVPG

SKSTATISGLKPGVDYTITVYAVTPKGDWNEGGPISINY
```

-continued
```
                                                   (SEQ ID NO: 13)
VPRDLEVVAATPTSLLISWDAPAVTVRYYRITYGETGGNSPVQEFTVPG

SKSTATISGLKPGVDYTITVYAVTPRGDWNEGSKPISINY (SEQ ID NO: 55)
VPRDLEVVAATPTSLLISWDAPAVTVRYYRITYGETGGNSPVQEFTVPG

SKSTATIGLKPGVDYTITVYAVTPRGDWNEGGPISINY;

(SEQ ID NO: 29)
SDVPRDLEVVAATPTSLLISWDAPAVTVRYYRITYGETGGNSPVQEFTV

PGSKSTATISGLKPGVDYTITVYAVTPGRGDWNEGSKPISINY (SEQ ID NO: 30)
SDVPRDLEVVAATPTSLLISWDAPAVTVRYYRITYGETGGNSPVQEFTV

PGSKSTATISGLKPGVDYTITVYAVTGPGRGDWNEGSKPISINY (SEQ ID NO: 31)
SDVPRDLEVVAATPTSLLISWDAPAVTVRYYRITYGETGGNSPVQEFTV

PGSKSTATISGLKPGVDYTITVYAVTPARGDWNEGSKPISINY (SEQ ID NO: 32)
SDVPRDLEVVAATPTSLLISWDAPAVTVRYYRITYGETGGNSPVQEFTV

PGSKSTATISGLKPGVDYTITVYAVTP(HRG)GDWNEGSKPISINY.
```

In some embodiments, the polypeptide has at least 80% sequence identity (e.g., at least 90% sequence identity, at least 95% sequence identity, and at least 99% sequence identity).

In some embodiments, the polypeptide is selected from the group consisting of (SEQ ID NO: 9)
SDVPRDLEVVAATPTSLLISWDAPAVTVRYYRITYGETGGNSPVQEFTV
PGSKSTATISGLKPGVDYTITVYAVTPRGDWNEGSKPISINY (SEQ ID NO: 10)
SDVPRDLEVVAATPTSLLISWDAPAVTVRYYRITYGETGGNSPVQEFTV
PGSKSTATISGLKPGVDYTITVYAVTPKGDWNEGSKPISINY (SEQ ID NO: 11)
VPRDLEVVAATPTSLLISWDAPAVTVRYYRITYGETGGNSPVQEFTVPG
SKSTATISGLKPGVDYTITVYAVTPKGDWNEGSKPISINY (SEQ ID NO: 12)
VPRDLEVVAATPTSLLISWDAPAVTVRYYRITYGETGGNSPVQEFTVPG
SKSTATISGLKPGVDYTITVYAVTPKGDWNEGGPISINY (SEQ ID NO: 13)
VPRDLEVVAATPTSLLISWDAPAVTVRYYRITYGETGGNSPVQEFTVPG
SKSTATISGLKPGVDYTITVYAVTPRGDWNEGSKPISINY (SEQ ID NO: 55)
VPRDLEVVAATPTSLLISWDAPAVTVRYYRITYGETGGNSPVQEFTVPG
SKSTATIGLKPGVDYTITVYAVTPRGDWNEGGPISINY;

(SEQ ID NO: 29)
SDVPRDLEVVAATPTSLLISWDAPAVTVRYYRITYGETGGNSPVQEFTV
PGSKSTATISGLKPGVDYTITVYAVTPGRGDWNEGSKPISINY (SEQ ID NO: 30)
SDVPRDLEVVAATPTSLLISWDAPAVTVRYYRITYGETGGNSPVQEFTV
PGSKSTATISGLKPGVDYTITVYAVTGPGRGDWNEGSKPISINY (SEQ ID NO: 31)
SDVPRDLEVVAATPTSLLISWDAPAVTVRYYRITYGETGGNSPVQEFTV
PGSKSTATISGLKPGVDYTITVYAVTPARGDWNEGSKPISINY (SEQ ID NO: 32)
SDVPRDLEVVAATPTSLLISWDAPAVTVRYYRITYGETGGNSPVQEFTV
PGSKSTATISGLKPGVDYTITVYAVTP(HRG)GDWNEGSKPISINY.

In some embodiments, the polypeptides of SEQ ID NO: 40 include a polypeptide having at least 75% sequence identity to a sequence selected from the group consisting of:

(SEQ ID NO: 3)
G-C-P-R-P-R-G-D-W-N-E-G-T-C-S-Q-D-S-D-C-L-A-G-C-V-
C-G-P-N-G-F-C-G;

(SEQ ID NO: 50)
G-C-P-R-P-R-G-D-W-N-E-G-S-C-S-Q-D-S-D-C-L-A-G-C-V-
C-G-P-N-G-F-C-G;

(SEQ ID NO: 4)
G-C-P-R-P-R-G-D-W-N-P-L-T-C-S-Q-D-S-D-C-L-A-G-C-V-
C-G-P-N-G-F-C-G;

(SEQ ID NO: 5)
G-C-A-V-T-P-R-G-D-W-N-E-G-S-L-P-C-S-Q-D-S-D-C-L-A-
G-C-V-C-G-P-N-G-F-C-G;

(SEQ ID NO: 6)
G-C-V-R-L-H-E-S-C-L-G-Q-Q-V-P-C-C-D-P-A-A-T-C-Y-C-
Y-G-R-G-D-W-N-E-G-C-Y-C-R;

(SEQ ID NO: 7)
G-C-V-R-L-H-E-S-C-L-G-Q-Q-V-P-C-C-D-P-A-A-T-C-Y-C-
Y-G-R-G-D-W-N-L-R-C-Y-C-R;

(SEQ ID NO: 8)
G-C-V-R-L-H-E-S-C-L-G-Q-Q-V-P-C-C-D-P-A-A-T-C-Y-C-
A-V-T-P-R-G-D-W-N-E-G-S-K-P-C-Y-C-R;

(SEQ ID NO: 21)
G-C-A-V-T-P-R-G-D-W-N-E-G-S-K-P-I-S-C-S-Q-D-S-D-C-
L-A-G-C-V-C-G-P-N-G-F-C-G;

(SEQ ID NO: 22)
G-C-P-R-I-L-M-R-C-S-Q-D-S-D-C-L-A-G-C-V-C-G-P-K-S-
G-E-N-W-D-G-R-P-T-V-A-G-F-C-G;

(SEQ ID NO: 23)
G-C-P-R-G-D-W-N-E-G-S-K-P-L-S-C-S-Q-D-S-D-C-L-A-G-
C-V-C-G-P-N-G-F-C-G;

(SEQ ID NO: 24)
G-C-A-V-T-P-R-G-D-W-N-E-G-S-K-P-G-C-K-Q-D-S-D-C-L-
A-G-C-V-C-G-P-N-G-F-C-G;

(SEQ ID NO: 25)
G-C-P-R-I-L-M-R-C-K-Q-D-S-D-C-L-A-G-C-V-C-G-P-K-S-
G-E-N-W-D-G-R-P-T-V-G-F-C-G;

(SEQ ID NO. 33)
GCPRPRGDNXPLTCSQDSDCLAGCVCGPNGFCG (SEQ ID NO. 34)
GCPRPRGDN(PP)PLTCSQDSDCLAGCVCGPNGFCG (SEQ ID NO. 35)
GCPRPRGDN(XP)PLTCSQDSDCLAGCVCGPNGFCG (SEQ ID NO. 36)
GCPRPRGDN(PG)PLTCSQDSDCLAGCVCGPNGFCG;

(SEQ ID NO. 37)
GCPQGRGDWXPTSCSQDSDCLAGCVCGPNGFCG (SEQ ID NO. 38)
GCPQGRGDW(PP)PTSCSQDSDCLAGCVCGPNGFCG;
and (SEQ ID NO. 39)
GCPQGRGDW(PG)PTSCSQDSDCLAGCVCGPNGFCG, wherein X can be any amino acid or unnatural derivative thereof, in L or D form, with the proviso that X is not P.

In some embodiments, the polypeptide has at least 80% sequence identity (e.g., at least 90% sequence identity, at least 95% sequence identity, and at least 99% sequence identity).

In some embodiments, the polypeptide is selected from the group consisting of:

(SEQ ID NO: 3)
G-C-P-R-P-R-G-D-W-N-E-G-T-C-S-Q-D-S-D-C-L-A-G-C-V-
C-G-P-N-G-F-C-G;

(SEQ ID NO: 50)
G-C-P-R-P-R-G-D-W-N-E-G-S-C-S-Q-D-S-D-C-L-A-G-C-V-C-G-P-N-G-F-C-G;

(SEQ ID NO: 4)
G-C-P-R-P-R-G-D-W-N-P-L-T-C-S-Q-D-S-D-C-L-A-G-C-V-C-G-P-N-G-F-C-G;

(SEQ ID NO: 5)
G-C-A-V-T-P-R-G-D-W-N-E-G-S-L-P-C-S-Q-D-S-D-C-L-A-G-C-V-C-G-P-N-G-F-C-G;

(SEQ ID NO: 6)
G-C-V-R-L-H-E-S-C-L-G-Q-Q-V-P-C-C-D-P-A-A-T-C-Y-C-Y-G-R-G-D-W-N-E-G-C-Y-C-R;

(SEQ ID NO: 7)
G-C-V-R-L-H-E-S-C-L-G-Q-Q-V-P-C-C-D-P-A-A-T-C-Y-C-Y-G-R-G-D-W-N-L-R-C-Y-C-R;

(SEQ ID NO: 8)
G-C-V-R-L-H-E-S-C-L-G-Q-Q-V-P-C-C-D-P-A-A-T-C-Y-C-A-V-T-P-R-G-D-W-N-E-G-S-K-P-C-Y-C-R;

(SEQ ID NO: 21)
G-C-A-V-T-P-R-G-D-W-N-E-G-S-K-P-I-S-C-S-Q-D-S-D-C-L-A-G-C-V-C-G-P-N-G-F-C-G;

(SEQ ID NO: 22)
G-C-P-R-I-L-M-R-C-S-Q-D-S-D-C-L-A-G-C-V-C-G-P-K-S-G-E-N-W-D-G-R-P-T-V-A-G-F-C-G;

(SEQ ID NO: 23)
G-C-P-R-G-D-W-N-E-G-S-K-P-L-S-C-S-Q-D-S-D-C-L-A-G-C-V-C-G-P-N-G-F-C-G;

(SEQ ID NO: 24)
G-C-A-V-T-P-R-G-D-W-N-E-G-S-K-P-G-C-K-Q-D-S-D-C-L-A-G-C-V-C-G-P-N-G-F-C-G;

(SEQ ID NO: 25)
G-C-P-R-I-L-M-R-C-K-Q-D-S-D-C-L-A-G-C-V-C-G-P-K-S-G-E-N-W-D-G-R-P-T-V-G-F-C-G;

(SEQ ID NO. 33)
GCPRPRGDNXPLTCSQDSDCLAGCVCGPNGFCG (SEQ ID NO. 34)
GCPRPRGDN(PP)PLTCSQDSDCLAGCVCGPNGFCG (SEQ ID NO. 35)
GCPRPRGDN(XP)PLTCSQDSDCLAGCVCGPNGFCG (SEQ ID NO. 36)
GCPRPRGDN(PG)PLTCSQDSDCLAGCVCGPNGFCG;

(SEQ ID NO. 37)
GCPQGRGDWXPTSCSQDSDCLAGCVCGPNGFCG (SEQ ID NO. 38)
GCPQGRGDW(PP)PTSCSQDSDCLAGCVCGPNGFCG;
and (SEQ ID NO. 39)
GCPQGRGDW(PG)PTSCSQDSDCLAGCVCGPNGFCG, wherein X can be any amino acid or unnatural derivative thereof, in L or D form, with the proviso that X is not P.

In some embodiments, the polypeptides of SEQ ID NO: 40 comprises a cyclic polypeptide.

For example, a polypeptide of SEQ ID NO: 40 can include a cyclic polypeptide having at least 75% sequence identity to the sequence:

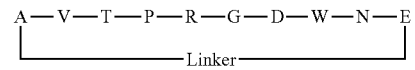
(SEQ ID NO: 1)

wherein the linker comprises two or more amino acids.

In some embodiments, the polypeptide has at least 80% sequence identity (e.g., at least 90% sequence identity, at least 95% sequence identity, and at least 99% sequence identity).

A linker as used herein can include both natural and non-natural amino acids. For example, a linker can include one or more of P, G, A, and S. In some embodiments, the linker comprises 2-13 amino acids (e.g., 2-3 amino acids, 4-6 amino acids, 2-10 amino acids, 2-6 amino acids). For example, the linker can include 3 amino acids. For example, the linker can be selected from the group consisting of: $P^D$-G-G; G-$P^D$-G; and G-G-$P^D$. In some embodiments, the linker is $P^D$-G-G.

In some embodiments, the cyclic polypeptide has the sequence:

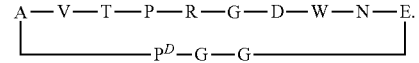
(SEQ ID NO: 2)

Also provided herein are cyclic polypeptides having at least 75% sequence identity to the sequence:

(SEQ ID NO: 27)

wherein the linker comprises two or more amino acids. In some embodiments, a cyclic polypeptide of SEQ ID NO: 40 can include a polypeptide having at least 75% sequence identity to the sequence:

(SEQ ID NO: 43)

wherein the linker comprises two or more amino acids; and

X is any amino acid or unnatural derivative thereof, in L or D form. For example, X can be selected from W, F, S, A, N, pG, pP, (4S)-4-hydroxy-L-proline and derivatives thereof or unnatural derivatives thereof, in L or D form. In some embodiments, a cyclic polypeptide of SEQ ID NO: 40 can include a polypeptide having at least 75% sequence identity to the sequence:

(SEQ ID NO: 28)

wherein the linker comprises two or more amino acids. In some embodiments, a cyclic polypeptide of SEQ ID NO: 40 can include a polypeptide having at least 75% sequence identity to the sequence:

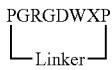
(SEQ ID NO: 44)

wherein the linker comprises two or more amino acids; and

X is any amino acid or unnatural derivative thereof, in L or D form. For example, X can be V, I, F, (4S)-4-hydroxy-L-proline, pP, pG and derivatives thereof or unnatural derivatives thereof, in L or D form.

A linker as used herein can include both natural and non-natural amino acids. For example, a linker can include one or more of P, G, A, and S. In some embodiments, the linker comprises 2-9 amino acids (e.g., 2-6 amino acids, 4-6 amino acids). For example, the linker can include 3 amino acids. For example, the linker can be selected from the group consisting of: $P^D$-G-G; G-$P^D$-G; and G-G-$P^D$. In some embodiments, the linker is $P^D$-G-G. In some embodiments, the linker comprises 2-6 amino acids.

In some embodiments, a cyclic polypeptide of SEQ ID NO: 40 can include a compound of Formula (I):

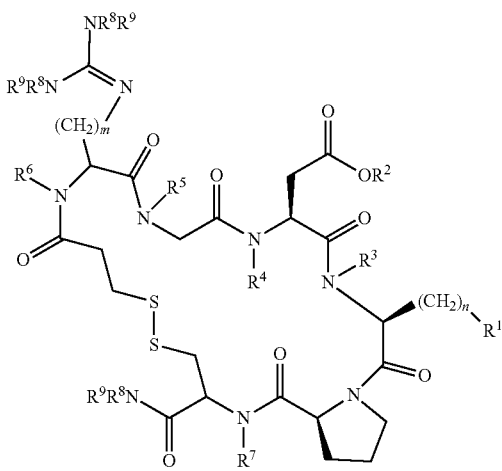
(I)

or a pharmaceutically acceptable salt thereof, wherein:

$R^1$ is selected from the group consisting of a 3-12 membered heterocyclyl and a 5-12 membered heteroaryl;

each of $R^2$, $R^3$, $R^4$, $R^5$, $R^6$, $R^7$, $R^8$, and $R^9$ is independently selected from H and ($C_1$-$C_6$)alkyl;

m is an integer from 1 to 10; and n is an integer from 1 to 6.

In some embodiments, $R^1$ is an electron-rich heterocyclyl or heteroaryl, such as furanyl, pyrrolyl, imidazolyl, oxazolyl, and thiophenyl. In some embodiments, $R^1$ is an electron-poor heterocyclyl or heteroaryl such as pyridinyl, pyrimidinyl, and purinyl. In some embodiments, $R^1$ is selected from the group consisting of indolyl, pyridyl, thiophenyl, and pyrrolyl. For example, $R^1$ can be indolyl. In some such embodiments, n is 1.

In some embodiments, $R^2$, $R^3$, $R^4$, $R^5$, $R^6$, $R^7$, $R^8$, and $R^9$ are H.

In some embodiments, m is an integer from 2 to 8. For example, m can be 4.

A non-limiting example of a compound of Formula (I) includes:

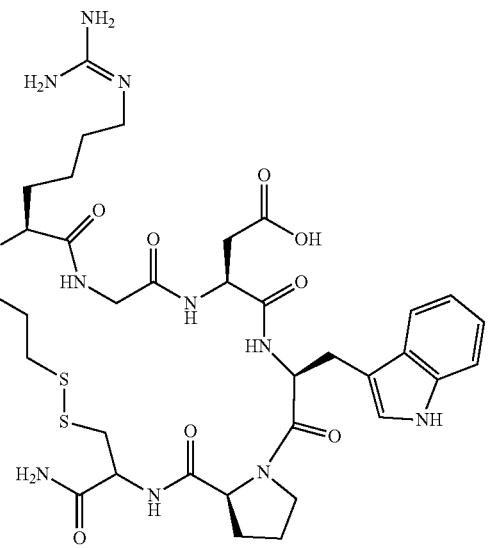

or a pharmaceutically acceptable salt thereof.

In some embodiments, a cyclic polypeptide of SEQ ID NO: 40 can include a compound of Formula (II):

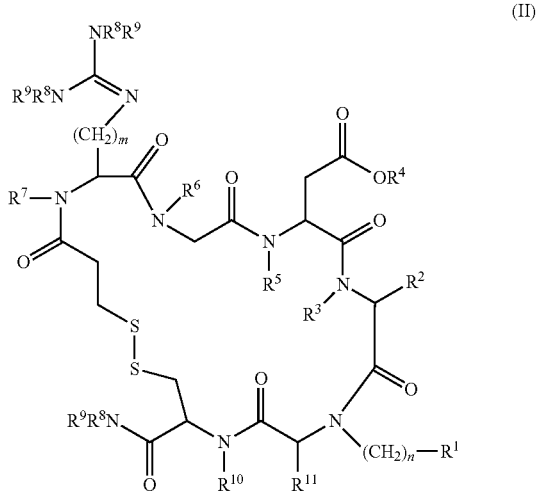
(II)

or a pharmaceutically acceptable salt thereof, wherein:

$R^1$ is selected from the group consisting of a 3-12 membered heterocyclyl and a 5-12 membered heteroaryl;

each of $R^2$, $R^3$, $R^4$, $R^5$, $R^6$, $R^7$, $R^8$, $R^9$, $R^{10}$, and $R^{11}$ is independently selected from H and ($C_1$-$C_6$)alkyl;

m is an integer from 1 to 10; and
n is an integer from 1 to 6.

In some embodiments, $R^1$ is an electron-rich heterocyclyl or heteroaryl, such as furanyl, pyrrolyl, imidazolyl, oxazolyl, and thiophenyl. In some embodiments, $R^1$ is an electron-poor heterocyclyl or heteroaryl such as pyridinyl, pyrimidinyl, and purinyl. In some embodiments, $R^1$ is selected from the group consisting of indolyl, pyridyl, thiophenyl, and pyrrolyl. For example, $R^1$ can be indolyl. In some such embodiments, n is 2.

In some embodiments, $R^3$, $R^4$, $R^5$, $R^6$, $R^7$, $R^8$, $R^9$, and $R^{10}$ are H.

In some embodiments, $R^2$ and $R^{11}$ are $CH_3$.

In some embodiments, m is an integer from 2 to 8. For example, m can be 4.

Non-limiting examples of a compound of Formula (II) include:

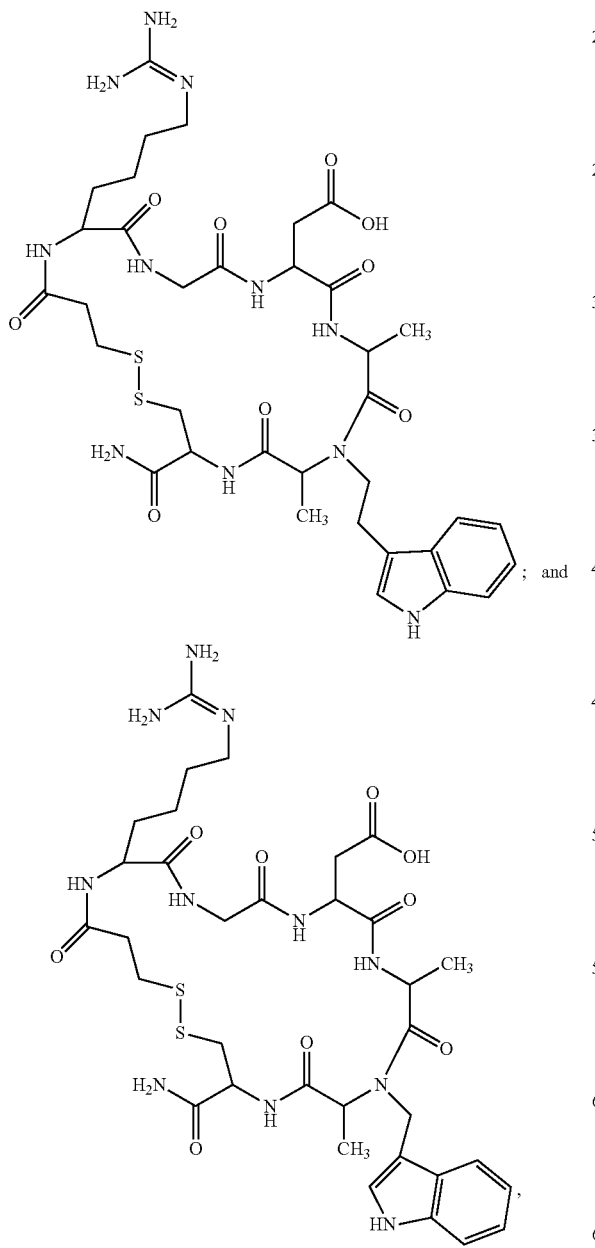

; and

, or a pharmaceutically acceptable salt thereof. For example, the compound of Formula (II) can be:

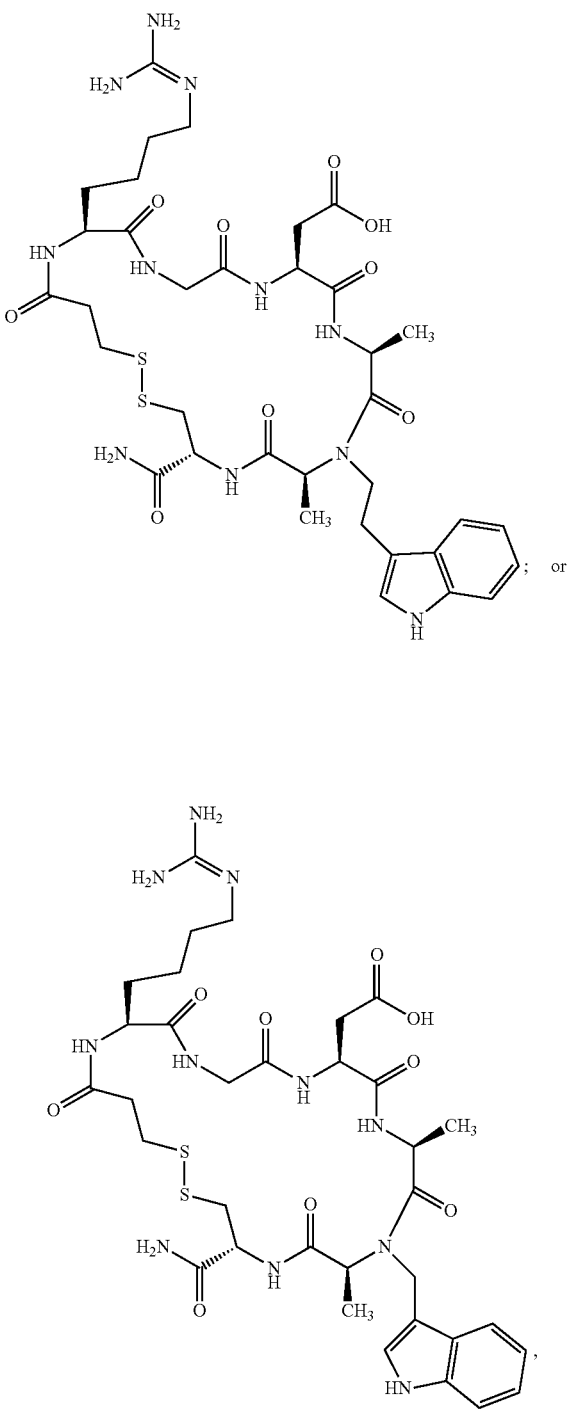

; or

, or a pharmaceutically acceptable salt thereof.

In some embodiments, a cyclic polypeptide of SEQ ID NO: 40 can include a compound of Formula (III):

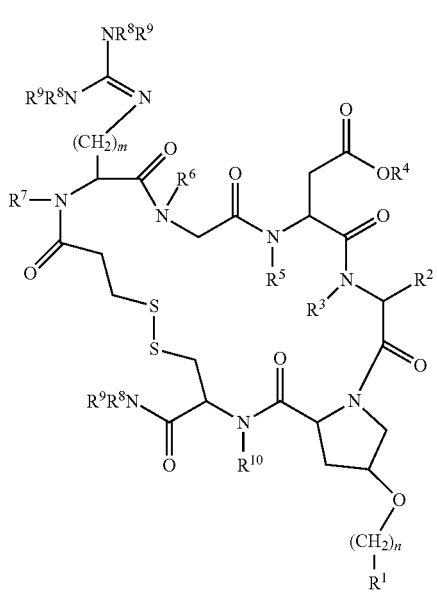

(III)

or a pharmaceutically acceptable salt thereof,
wherein:

$R^1$ is selected from the group consisting of a 3-12 membered heterocyclyl and a 5-12 membered heteroaryl;

each of $R^2$, $R^3$, $R^4$, $R^5$, $R^6$, $R^7$, $R^8$, $R^9$, and $R^{10}$ is independently selected from H and $(C_1-C_6)$alkyl;

m is an integer from 1 to 10; and n is an integer from 0 to 6.

In some embodiments, $R^1$ is an electron-rich heterocyclyl or heteroaryl, such as furanyl, pyrrolyl, imidazolyl, oxazolyl, and thiophenyl. In some embodiments, $R^1$ is an electron-poor heterocyclyl or heteroaryl such as pyridinyl, pyrimidinyl, and purinyl. In some embodiments, $R^1$ is selected from the group consisting of indolyl, pyridyl, thiophenyl, and pyrrolyl. For example, $R^1$ can be indolyl. In some such embodiments, n is 1.

In some embodiments, $R^3$, $R^4$, $R^5$, $R^6$, $R^7$, $R^8$, $R^9$, $R^{10}$ are H.

In some embodiments, $R^2$ is $CH_3$.

In some embodiments, m is an integer from 2 to 8. For example, m can be 4.

A non-limiting example of a compound of Formula (III) includes:

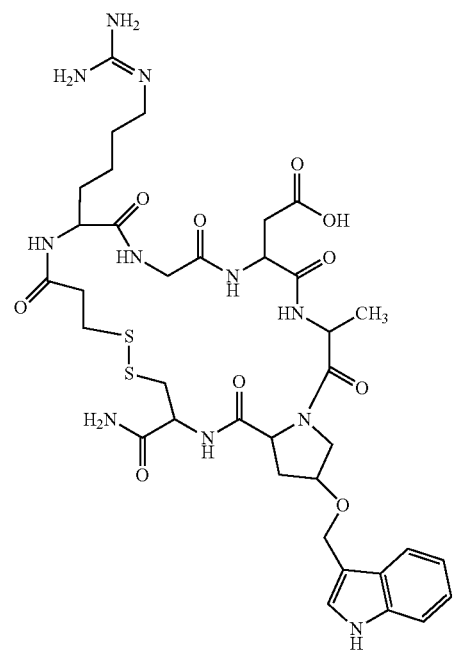 [SMILES: CC1NC(=O)C(CC(=O)O)NC(=O)CNC(=O)C(CCCCN=C(N)N)NC(=O)CCSSCC(C(N)=O)NC(=O)C2CC(OCc3c[nH]c4ccccc34)CN2C1=O]

or a pharmaceutically acceptable salt thereof. For example, the compound of Formula (III) can be:

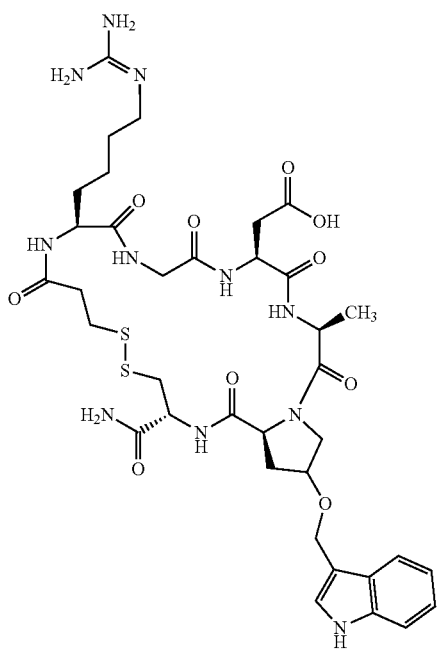

or a pharmaceutically acceptable salt thereof.

In some embodiments, a cyclic polypeptide of SEQ ID NO: 40 can include compounds of Formula (V):

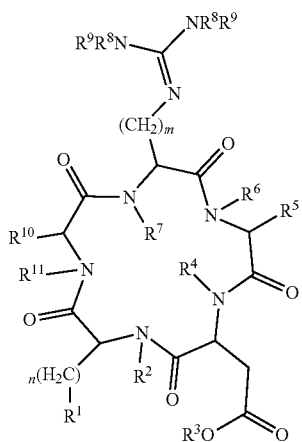

or a pharmaceutically acceptable salt thereof, wherein:

$R^1$ is selected from the group consisting of a 3-12 membered heterocyclyl and a 5-12 membered heteroaryl;

each of $R^2$, $R^3$, $R^4$, $R^5$, $R^6$, $R^7$, $R^8$, $R^9$, $R^{10}$, and $R^{11}$ is independently selected from H and $(C_1-C_6)$alkyl;

m is an integer from 1 to 10; and n is an integer from 0 to 6.

In some embodiments, $R^1$ is an electron-rich heterocyclyl or heteroaryl, such as furanyl, pyrrolyl, imidazolyl, oxazolyl, and thiophenyl. In some embodiments, $R^1$ is an electron-poor heterocyclyl or heteroaryl such as pyridinyl, pyrimidinyl, and purinyl. In some embodiments, $R^1$ is selected from the group consisting of indolyl, pyridyl, thiophenyl, and pyrrolyl. For example, $R^1$ can be indolyl. In some such embodiments, n is 1.

In some embodiments, $R^2$, $R^3$, $R^4$, $R^5$, $R^6$, $R^7$, $R^8$, $R^9$ are H.

In some embodiments, $R^{10}$ is $CH(CH_3)_2$.

In some embodiments, $R^{11}$ is $CH_3$.

In some embodiments, m is an integer from 2 to 8. For example, m can be 3.

A non-limiting example of a compound of Formula (V) includes:

or a pharmaceutically acceptable salt thereof. For example, a compound of Formula (V) can be:

or a pharmaceutically acceptable salt thereof.

In some embodiments, a cyclic polypeptide of SEQ ID NO: 40 can include compounds of Formula (VI):

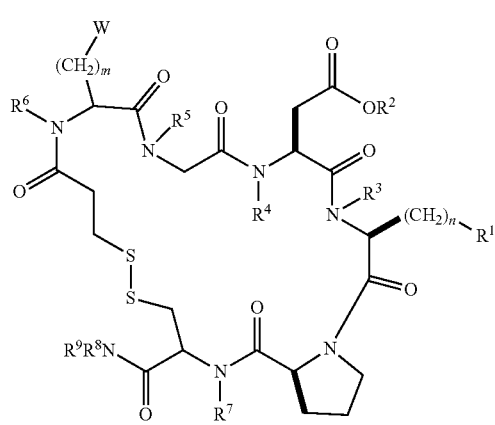

(VI)

or a pharmaceutically acceptable salt thereof, wherein:

$R^1$ is selected from the group consisting of a 3-12 membered heterocyclyl and a 5-12 membered heteroaryl;

each of $R^2$, $R^3$, $R^4$, $R^5$, $R^6$, $R^7$, $R^8$, $R^9$ and $R^{10}$ is independently selected from H and $(C_1$-$C_5)$alkyl;

W is selected from the group consisting of:

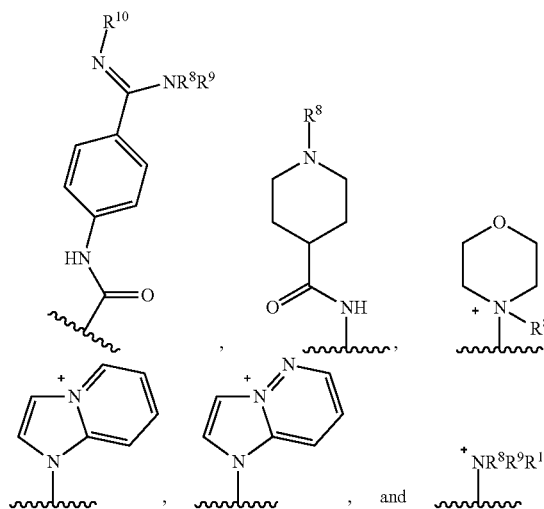

m is an integer from 1 to 10; and
n is an integer from 1 to 6.

In some embodiments, $R^1$ is an electron-rich heterocyclyl or heteroaryl, such as furanyl, pyrrolyl, imidazolyl, oxazolyl, and thiophenyl. In some embodiments, $R^1$ is an electron-poor heterocyclyl or heteroaryl such as pyridinyl, pyrimidinyl, and purinyl. In some embodiments, $R^1$ is selected from the group consisting of indolyl, pyridyl, thiophenyl, and pyrrolyl. For example, $R^1$ can be indolyl. In some such embodiments, n is 1.

In some embodiments, $R^2$, $R^3$, $R^4$, $R^5$, $R^6$, $R^7$, $R^8$, $R^9$ and $R^{10}$ are H.

In some embodiments, m is an integer from 2 to 8. For example, m can be 4.

Non-limiting examples of compounds of Formula (VI) include:

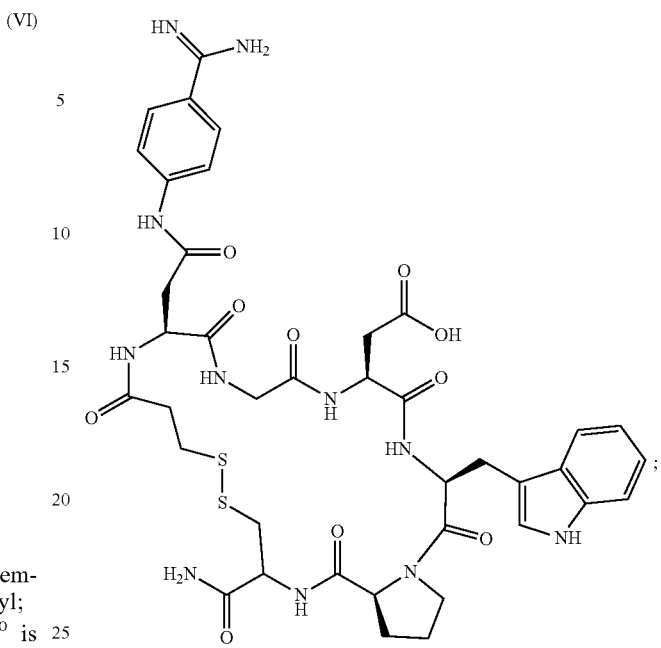

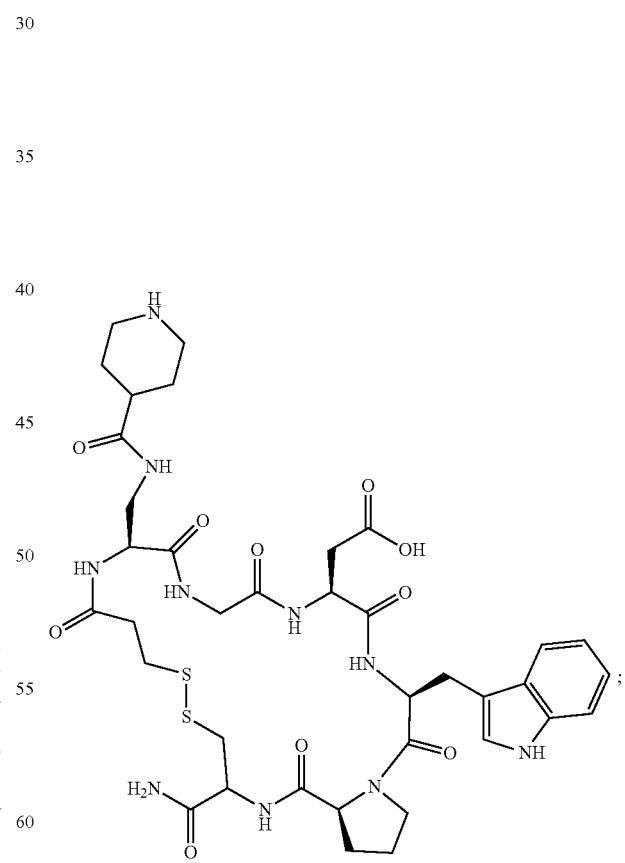

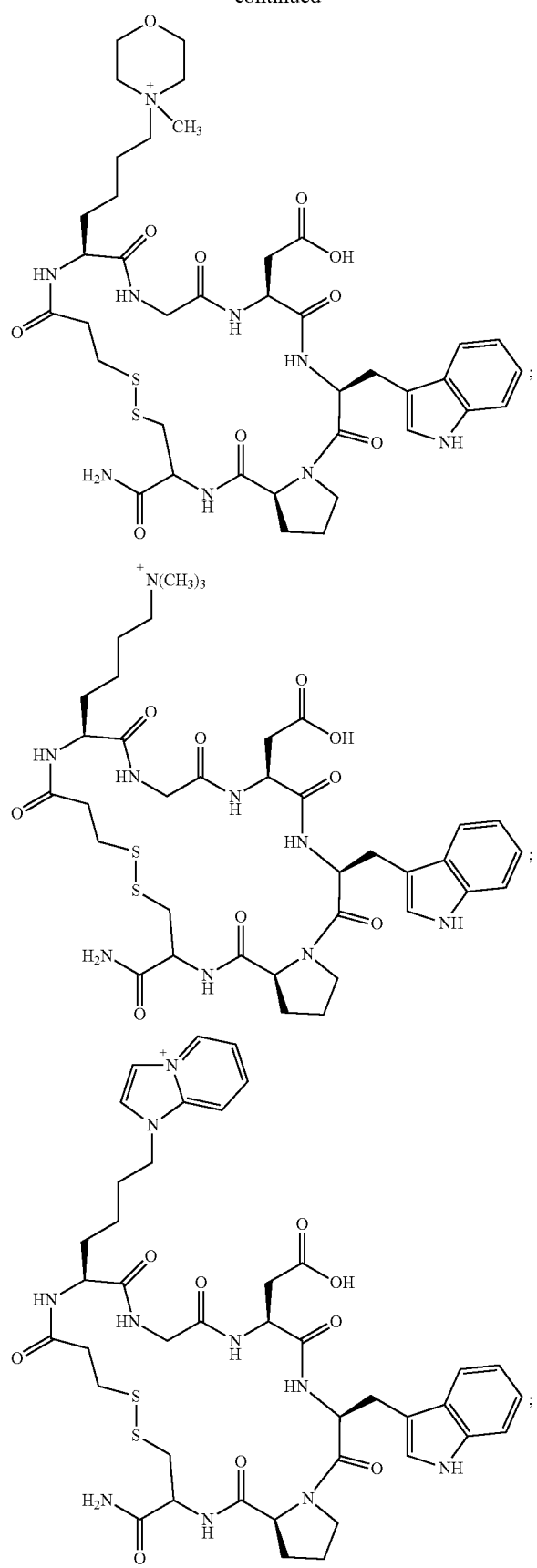

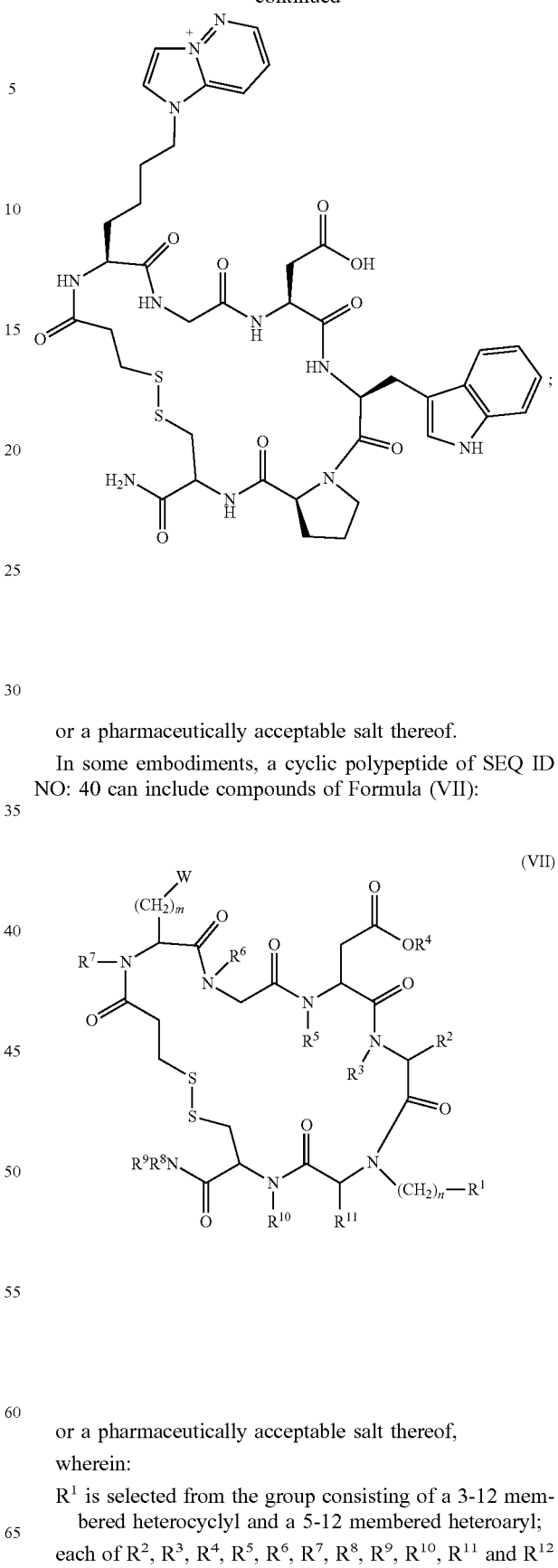

or a pharmaceutically acceptable salt thereof.

In some embodiments, a cyclic polypeptide of SEQ ID NO: 40 can include compounds of Formula (VII):

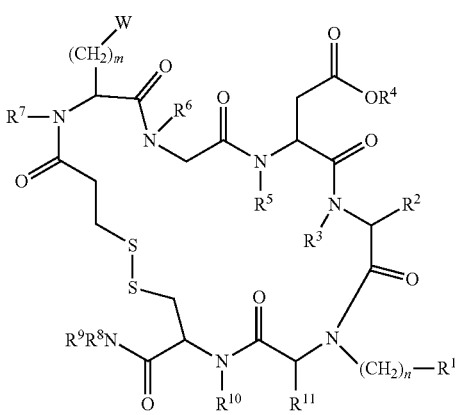

(VII)

or a pharmaceutically acceptable salt thereof,
wherein:
R¹ is selected from the group consisting of a 3-12 membered heterocyclyl and a 5-12 membered heteroaryl;
each of R², R³, R⁴, R⁵, R⁶, R⁷, R⁸, R⁹, R¹⁰, R¹¹ and R¹² is independently selected from H and (C₁-C₆)alkyl;

W is selected from the group consisting of:

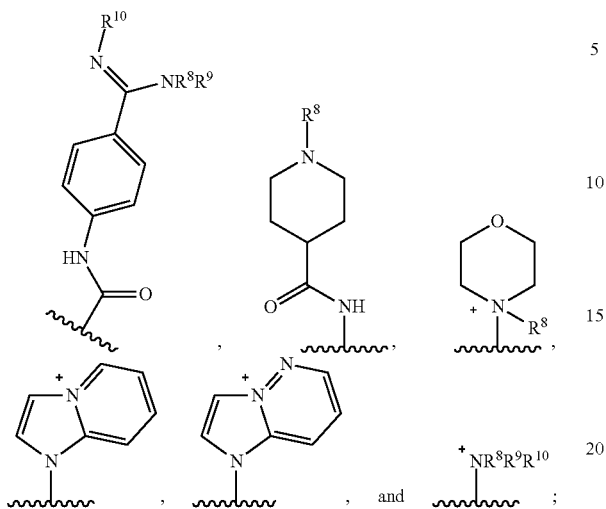

m is an integer from 1 to 10; and
n is an integer from 1 to 6.

In some embodiments, $R^1$ is an electron-rich heterocyclyl or heteroaryl, such as furanyl, pyrrolyl, imidazolyl, oxazolyl, and thiophenyl. In some embodiments, $R^1$ is an electron-poor heterocyclyl or heteroaryl such as pyridinyl, pyrimidinyl, and purinyl. In some embodiments, $R^1$ is selected from the group consisting of indolyl, pyridyl, thiophenyl, and pyrrolyl. For example, $R^1$ can be indolyl. In some such embodiments, n is 2.

In some embodiments, $R^3$, $R^4$, $R^5$, $R^6$, $R^7$, $R^8$, $R^9$, $R^{10}$, $R^{11}$ and $R^{12}$ are H.

In some embodiments, $R^2$ and $R^{11}$ are $CH_3$.

In some embodiments, m is an integer from 2 to 8. For example, m can be 4.

Non-limiting examples of compounds of Formula (VII) include:

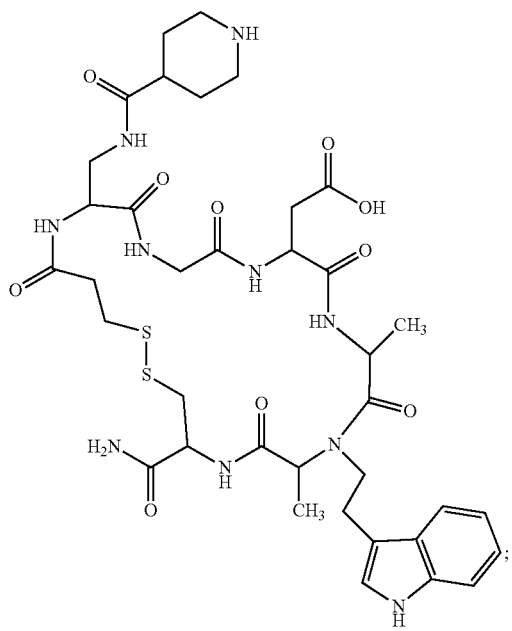

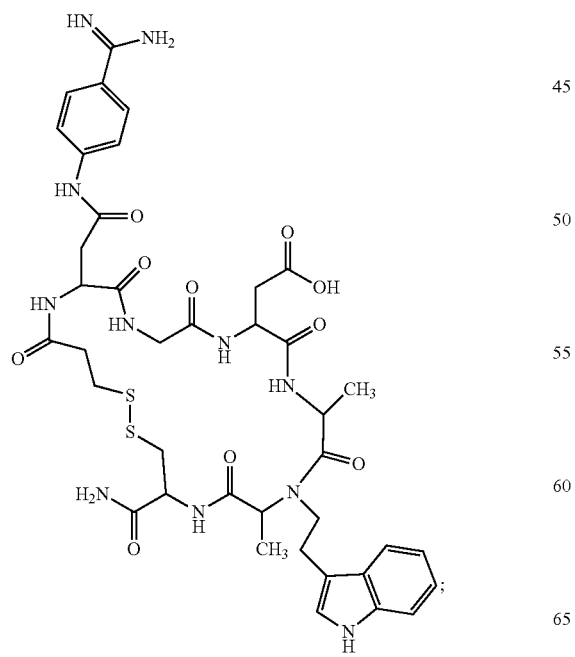

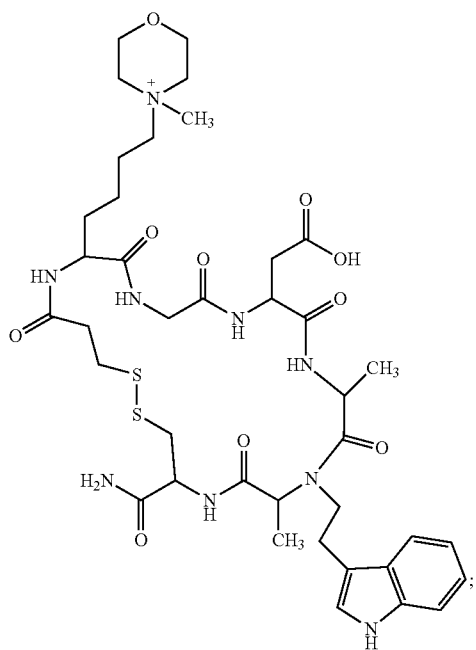

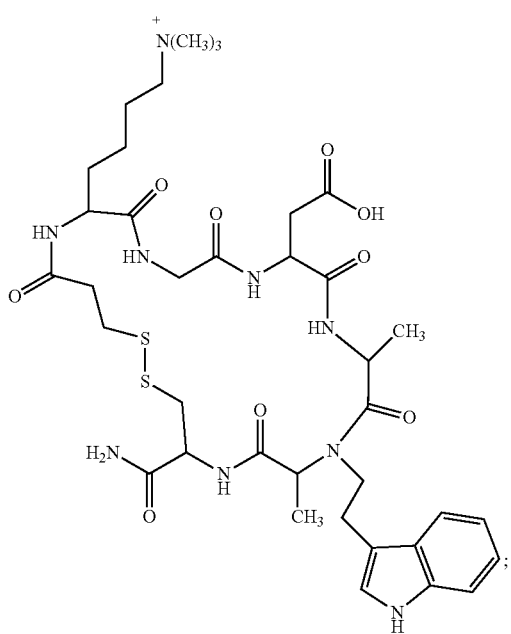
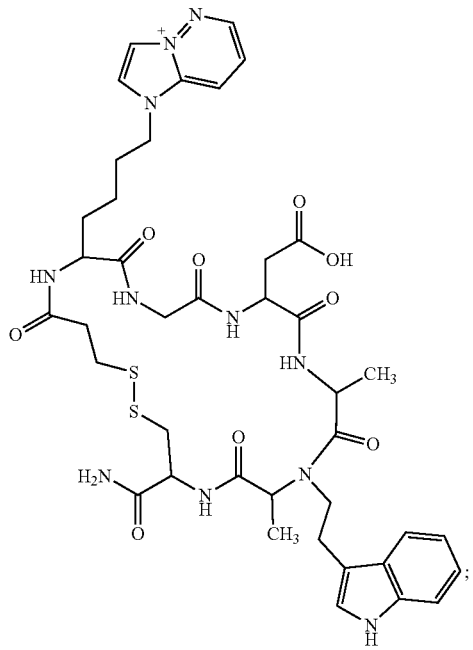
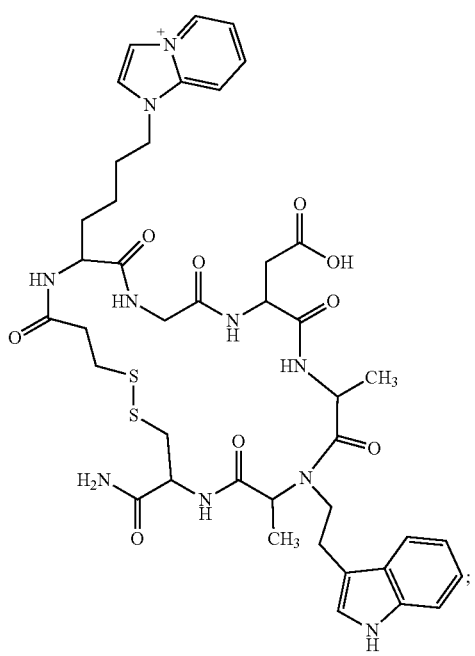
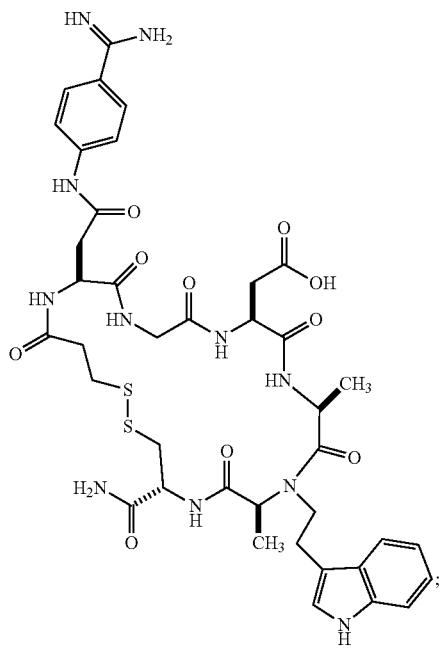
or a pharmaceutically acceptable salt thereof. For example, a compound of Formula (VII) can be:

95
-continued
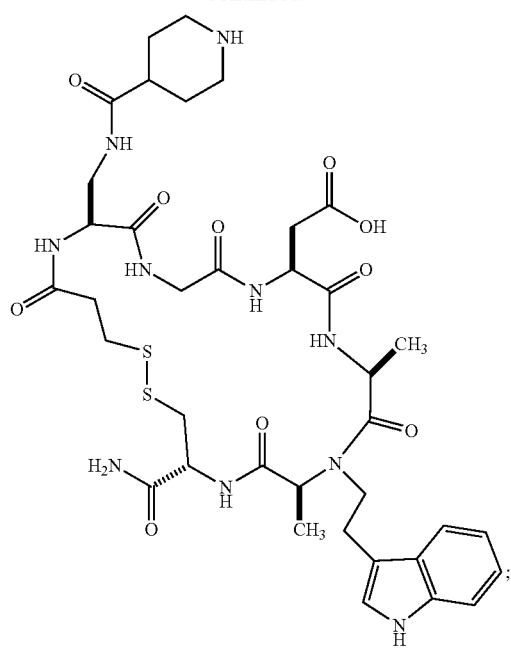
96
-continued
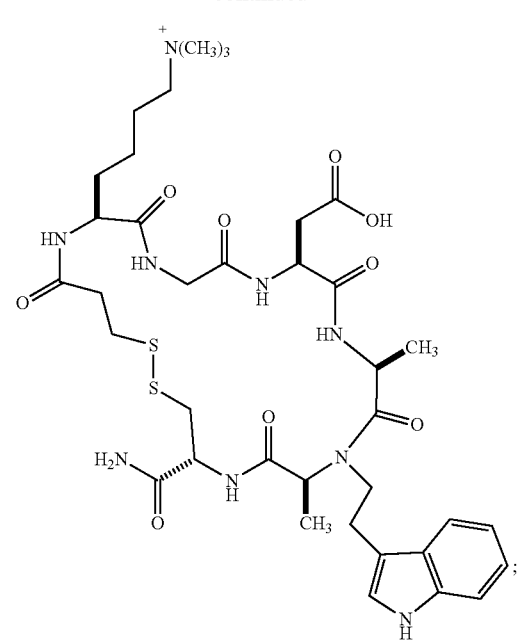
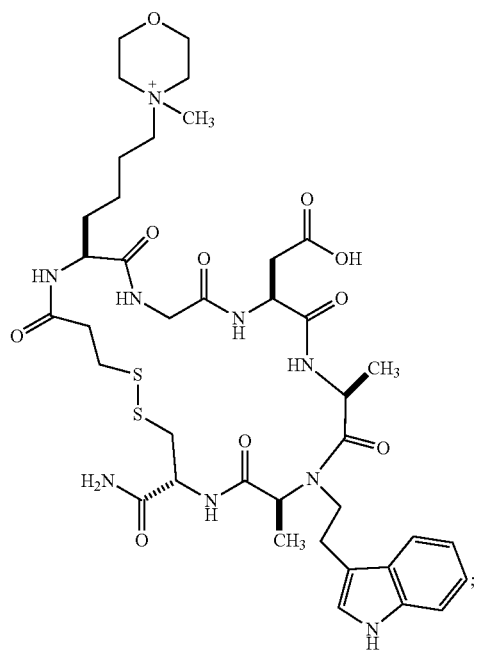
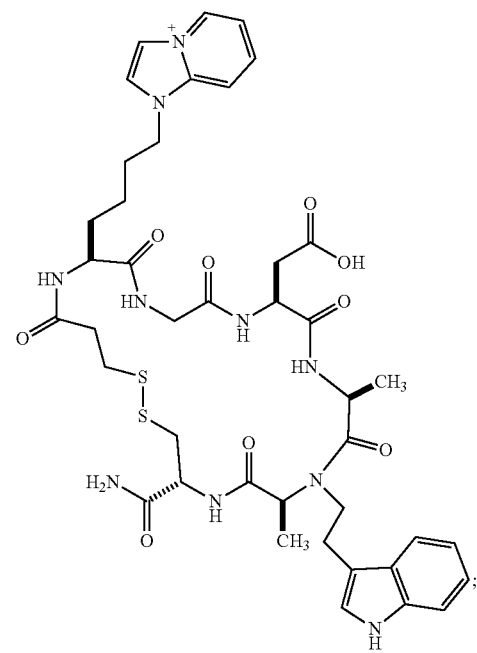

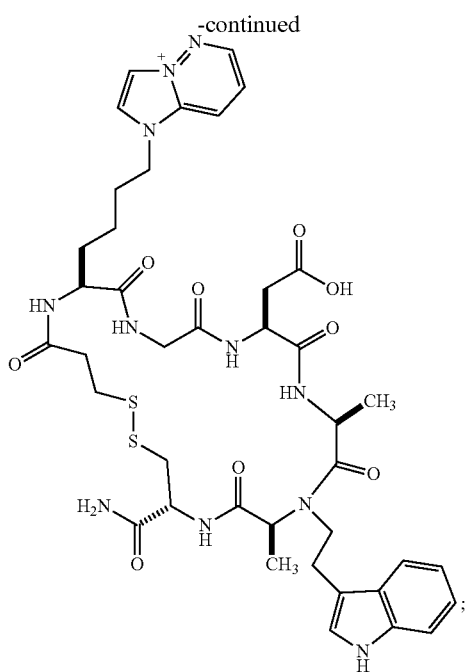

or a pharmaceutically acceptable salt thereof.

In some embodiments, a cyclic polypeptide of SEQ ID NO: 40 can include compounds of Formula (VIII):

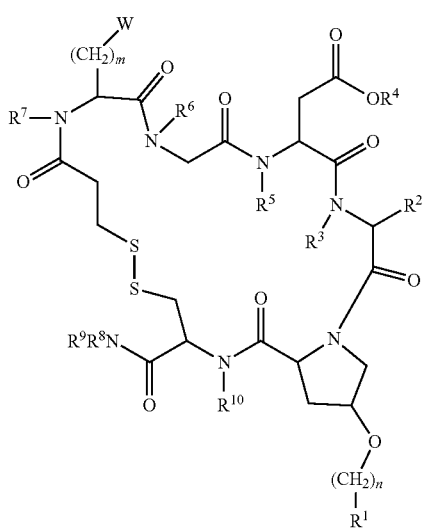

(VIII)

or a pharmaceutically acceptable salt thereof, wherein:

$R^1$ is selected from the group consisting of a 3-12 membered heterocyclyl and a 5-12 membered heteroaryl;

each of $R^2$, $R^3$, $R^4$, $R^5$, $R^6$, $R^7$, $R^8$, $R^9$, $R^{10}$ and $R^{11}$ is independently selected from H and ($C_1$-$C_6$)alkyl;

W is selected from the group consisting of:

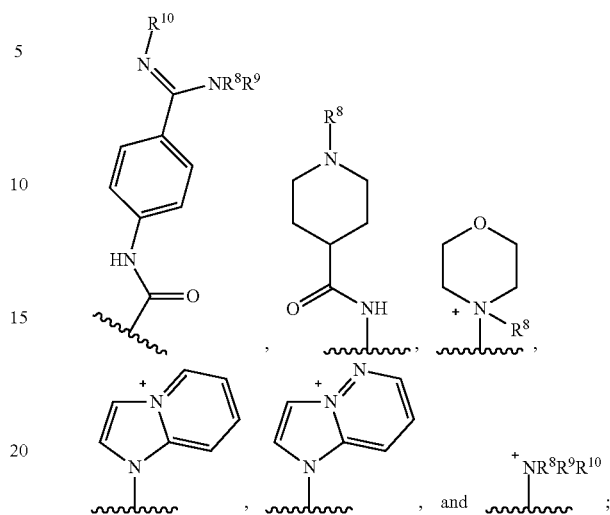

m is an integer from 1 to 10; and
n is an integer from 0 to 6.

In some embodiments, $R^1$ is an electron-rich heterocyclyl or heteroaryl, such as furanyl, pyrrolyl, imidazolyl, oxazolyl, and thiophenyl. In some embodiments, $R^1$ is an electron-poor heterocyclyl or heteroaryl such as pyridinyl, pyrimidinyl, and purinyl. In some embodiments, $R^1$ is selected from the group consisting of indolyl, pyridyl, thiophenyl, and pyrrolyl. For example, $R^1$ can be indolyl. In some such embodiments, n is 1.

In some embodiments, $R^3$, $R^4$, $R^5$, $R^6$, $R^7$, $R^8$, $R^9$, $R^{10}$, and $R^{11}$ are H.

In some embodiments, $R^2$ is $CH_3$.

In some embodiments, m is an integer from 2 to 8. For example, m can be 4.

Non-limiting examples of compounds of Formula (VIII) include:

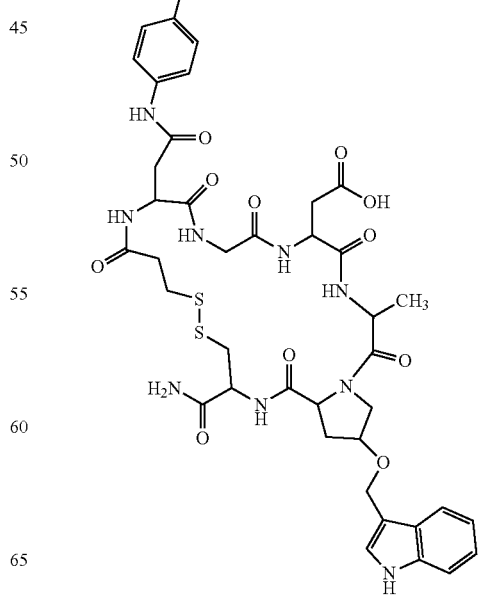

99
-continued
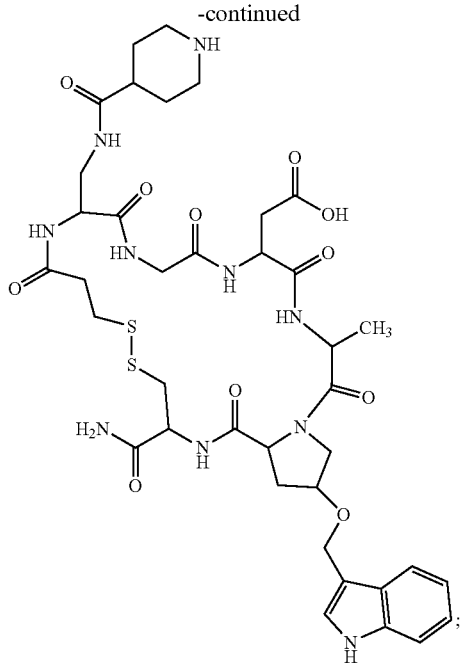
100
-continued
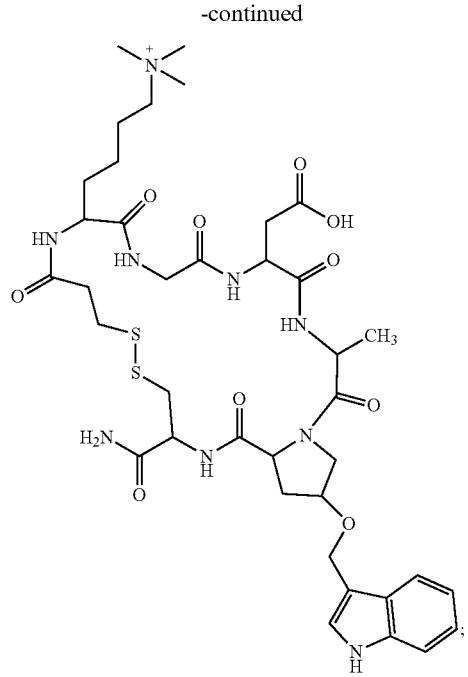
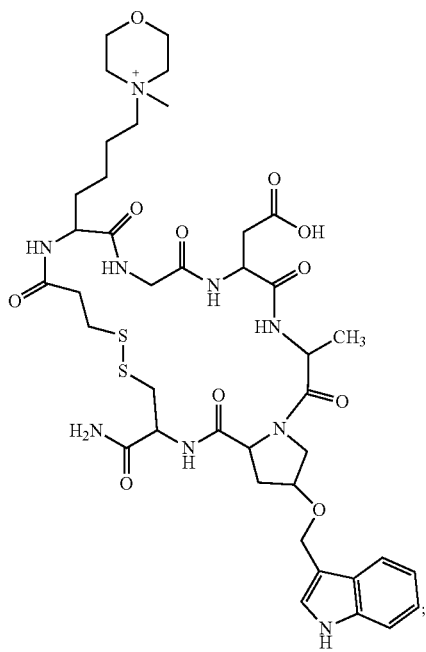
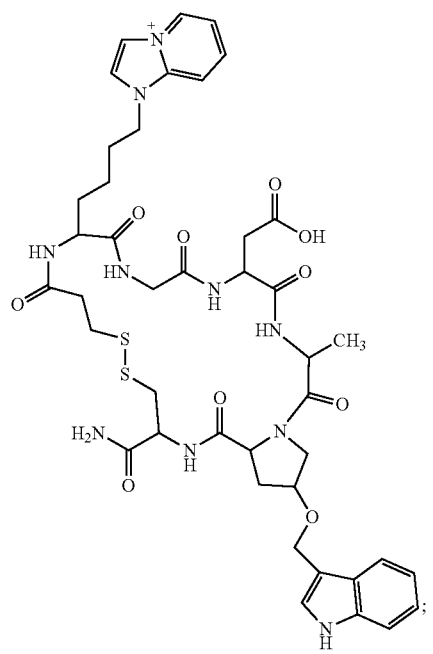

101
-continued
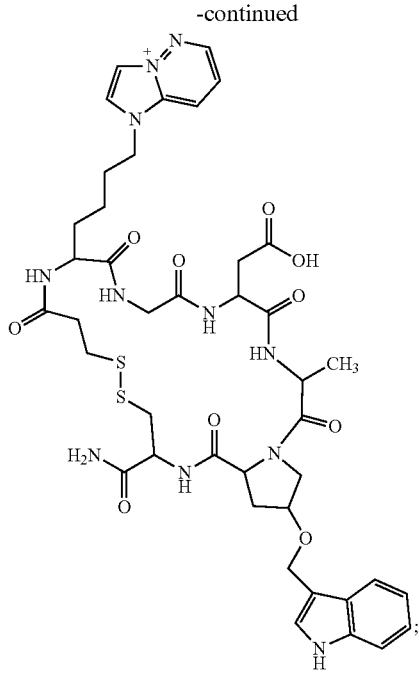
102
-continued
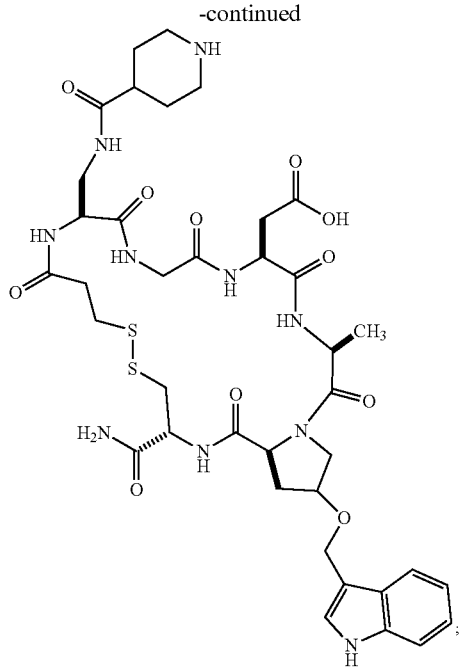
or a pharmaceutically acceptable salt thereof. For example, a compound of Formula (VIII) can be:
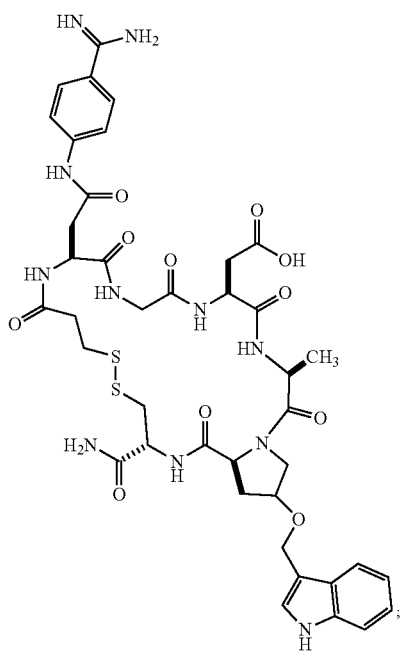
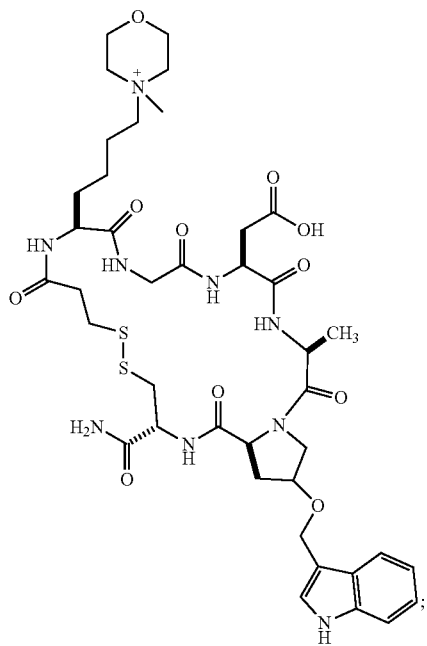

103
-continued
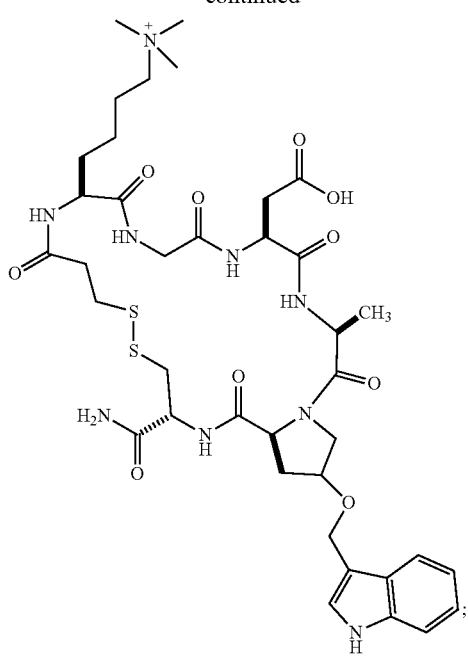
104
-continued
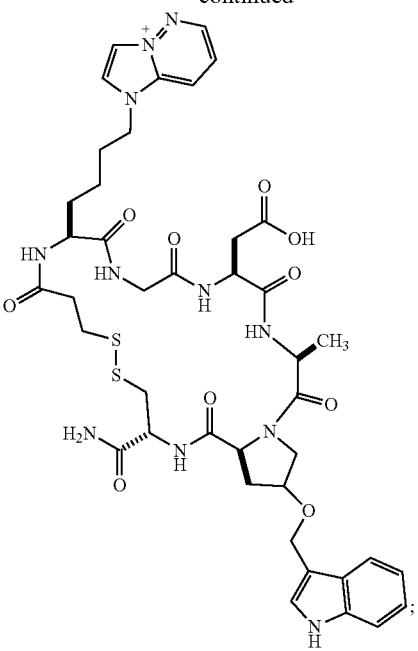
or a pharmaceutically acceptable salt thereof.
In some embodiments, a cyclic polypeptide of SEQ ID NO: 40 can include compounds of Formula (IX):
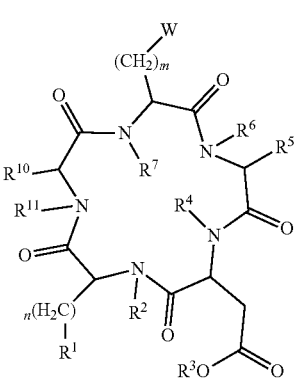
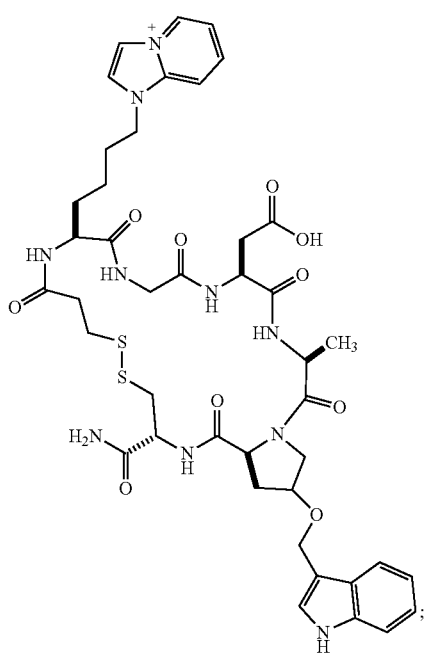
or a pharmaceutically acceptable salt thereof,
wherein:
$R^1$ is selected from the group consisting of a 3-12 membered heterocyclyl and a 5-12 membered heteroaryl;

W is selected from the group consisting of:

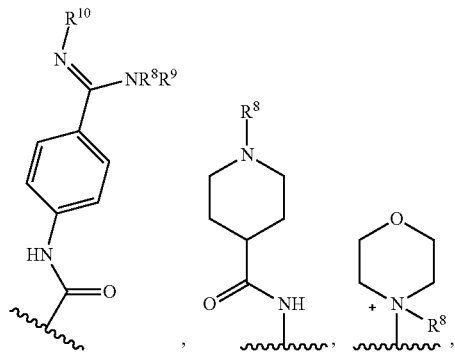

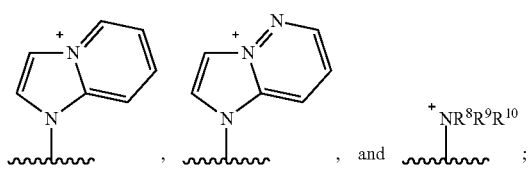

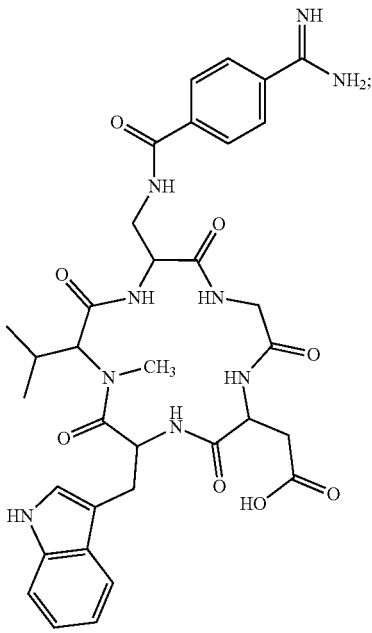

each of $R^2$, $R^3$, $R^4$, $R^5$, $R^6$, $R^7$, $R^1$, $R^9$, $R^{10}$, $R^{11}$, and $R^{12}$ is independently selected from H and $(C_1-C_6)$alkyl;

m is an integer from 1 to 10; and n is an integer from 0 to 6.

In some embodiments, $R^1$ is an electron-rich heterocyclyl or heteroaryl, such as furanyl, pyrrolyl, imidazolyl, oxazolyl, and thiophenyl. In some embodiments, $R^1$ is an electron-poor heterocyclyl or heteroaryl such as pyridinyl, pyrimidinyl, and purinyl. In some embodiments, $R^1$ is selected from the group consisting of indolyl, pyridyl, thiophenyl, and pyrrolyl. For example, $R^1$ can be indolyl. In some such embodiments, n is 1.

In some embodiments, $R^2$, $R^3$, $R^4$, $R^5$, $R^6$, $R^7$, $R^8$, $R^9$, $R^{10}$, $R^{11}$, and $R^{12}$ are H.

In some embodiments, $R^{10}$ is $CH(CH_3)_2$.

In some embodiments, $R^{11}$ is $CH_3$.

In some embodiments, m is an integer from 2 to 8. For example, m can be 3.

Non-limiting examples of compounds of Formula (IX) include:

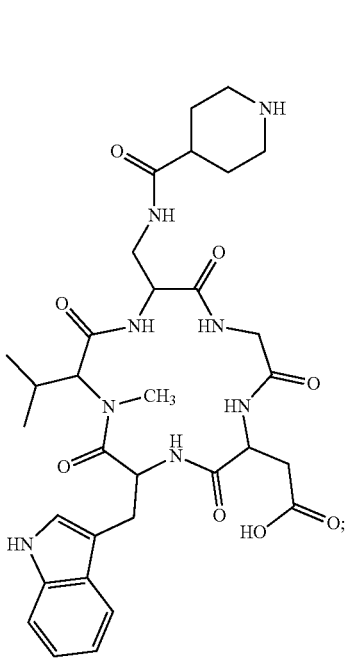

107
-continued
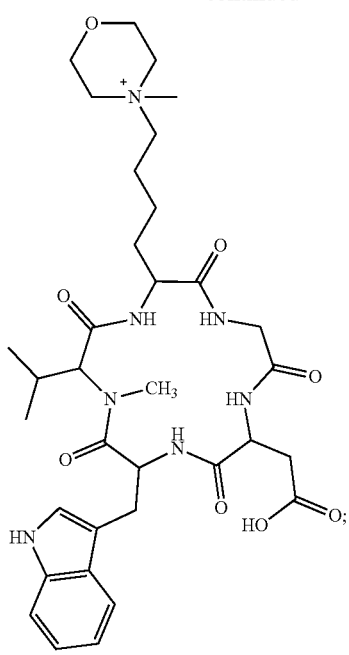
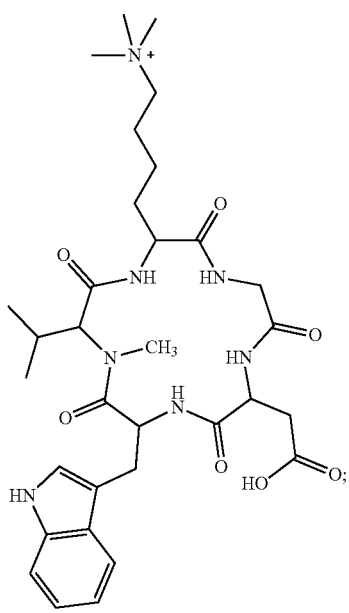
108
-continued
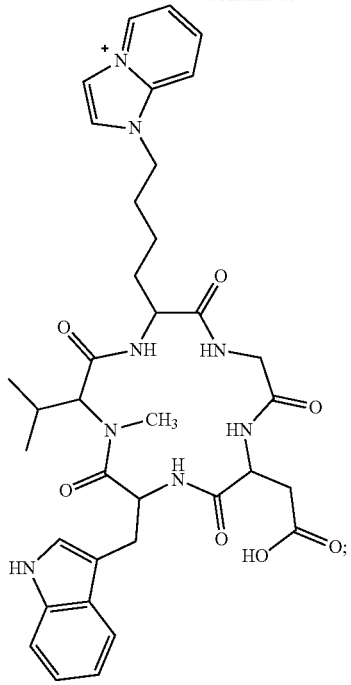
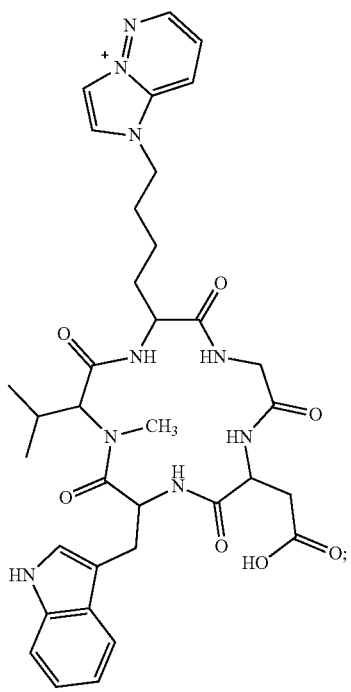
or a pharmaceutically acceptable salt thereof. For example, a compound of Formula (IX) can be:

109
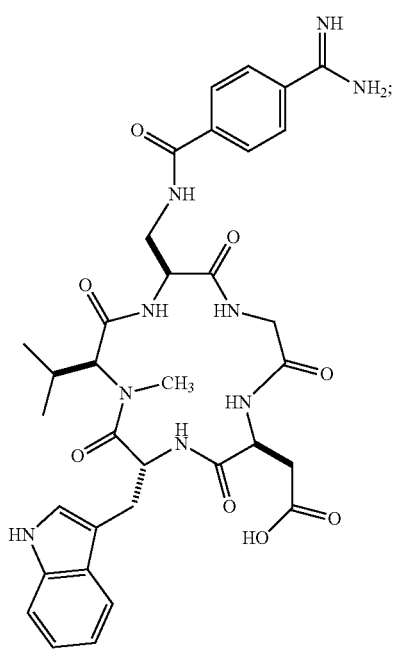
110
-continued
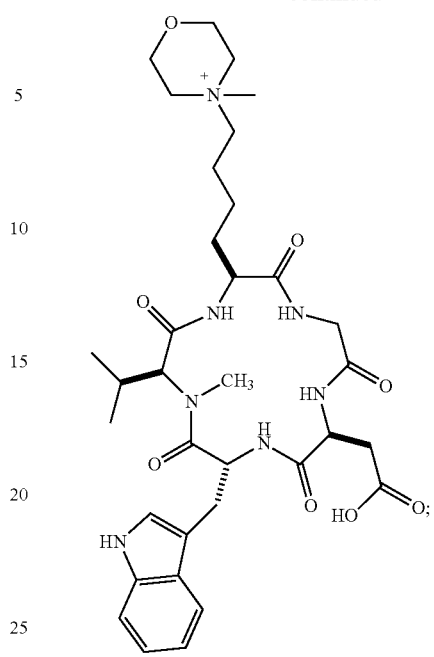
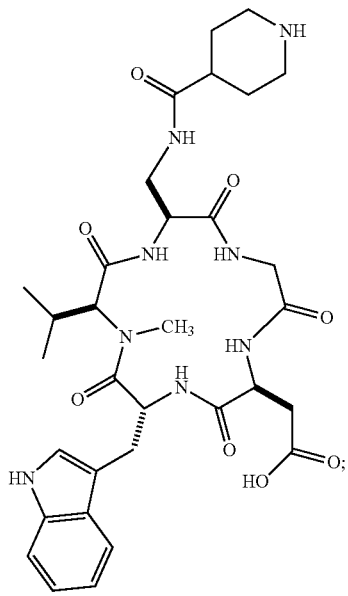
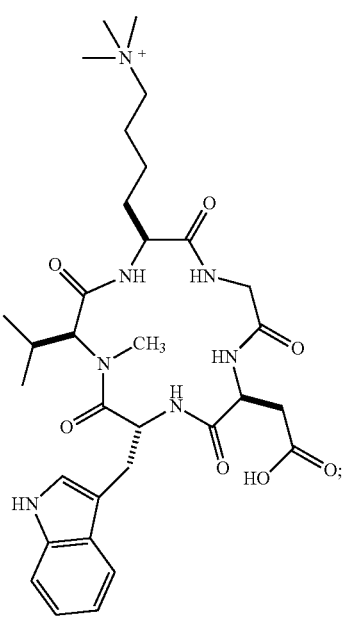

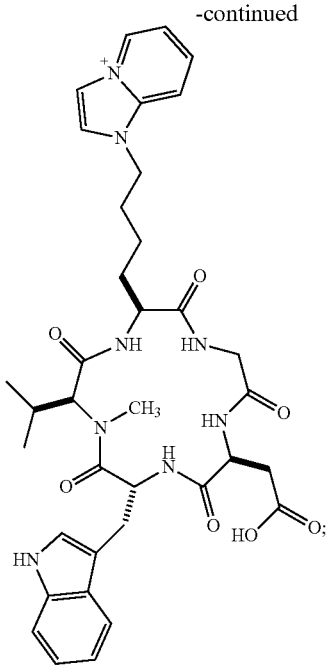
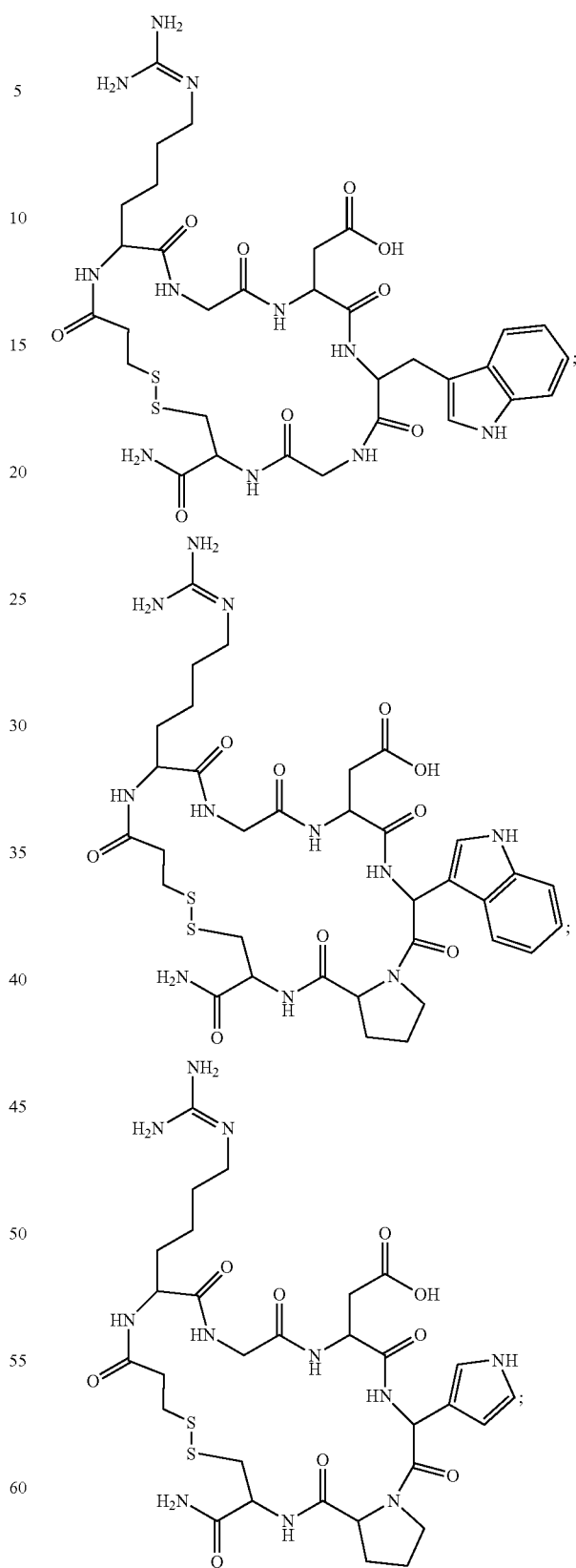
or a pharmaceutically acceptable salt thereof.
In some embodiments, a cyclic polypeptide of SEQ ID NO: 40 can include compounds that are selected from:

113
-continued
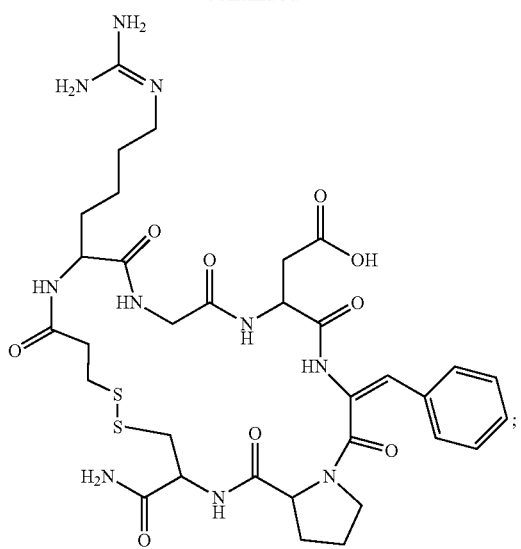
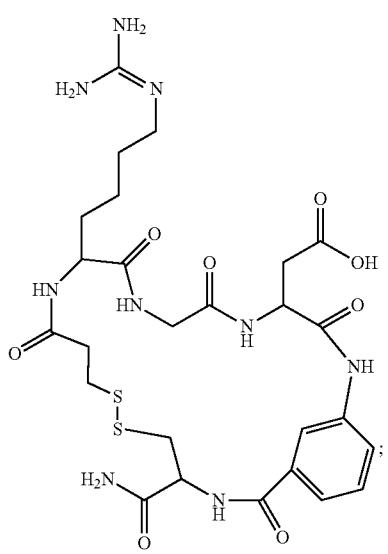
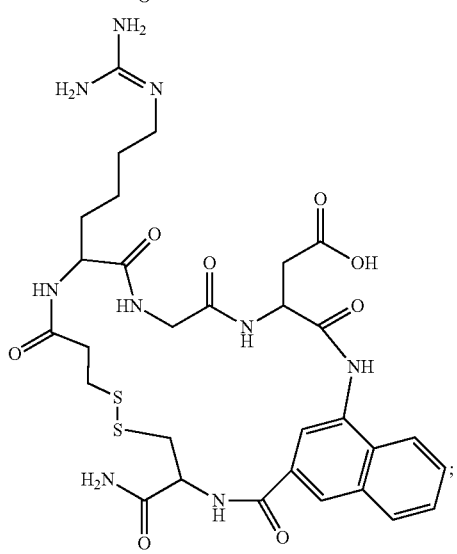
114
-continued
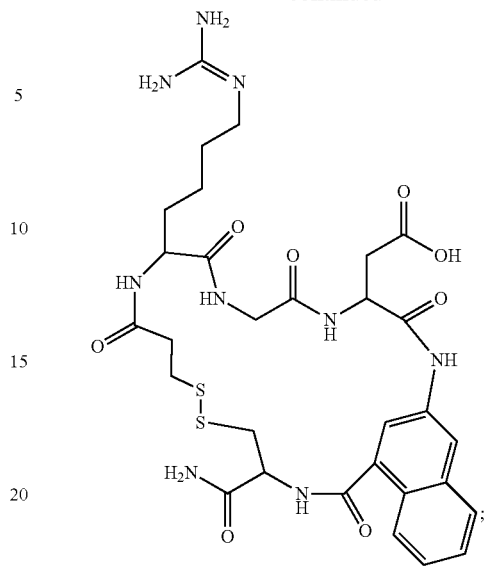
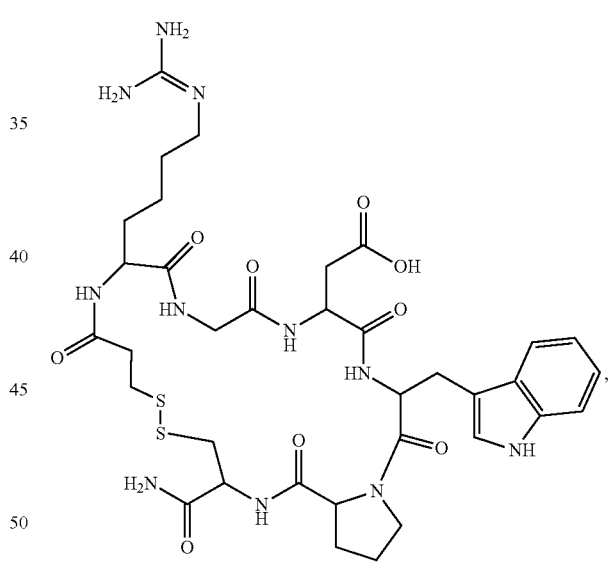
or a pharmaceutically acceptable salt thereof. For example, the compound can be selected from:

115
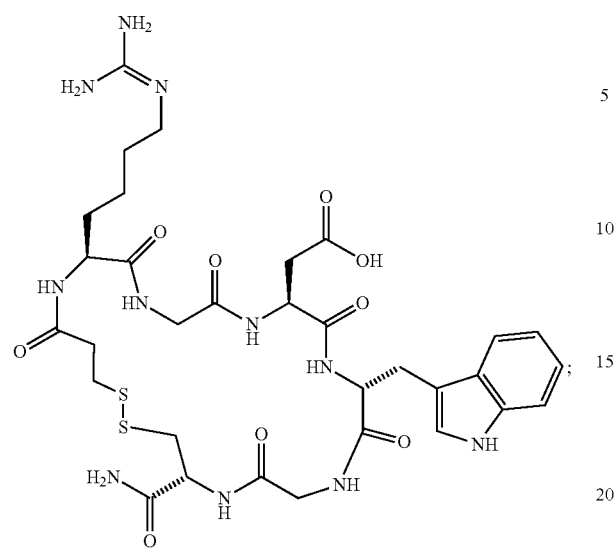
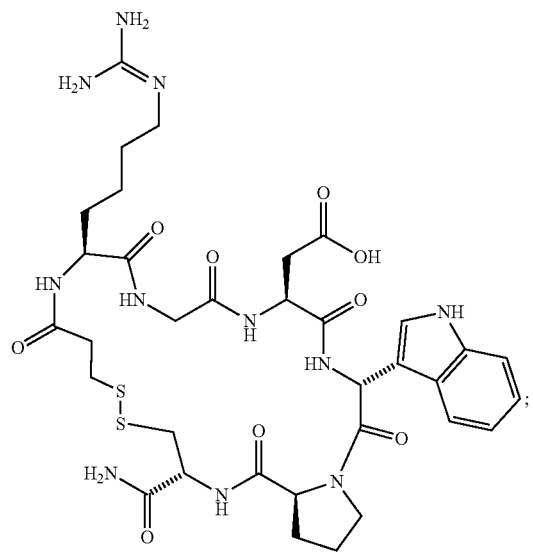
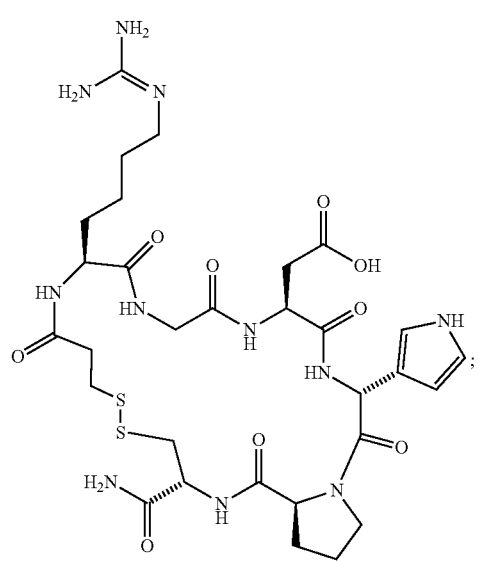
116
-continued
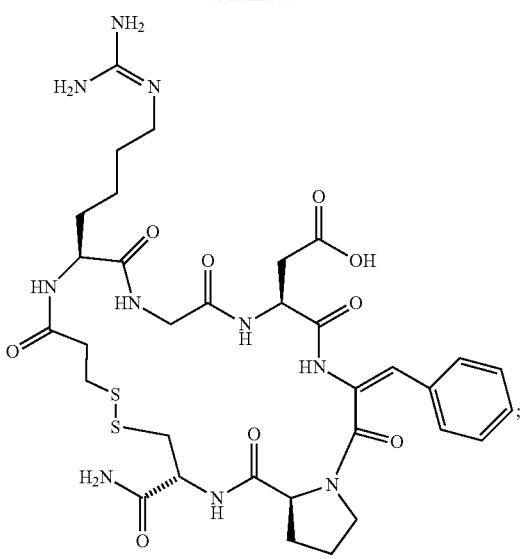
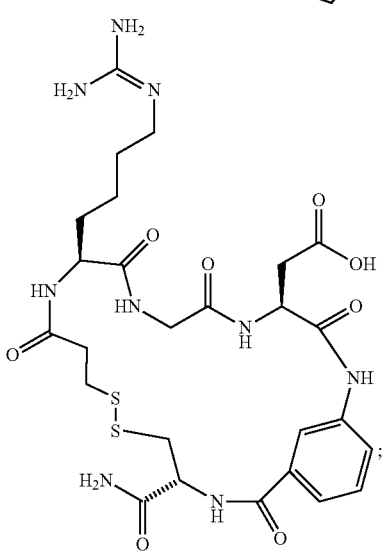
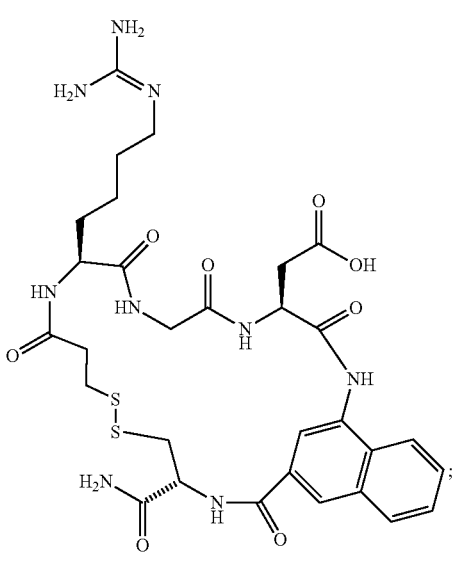

-continued

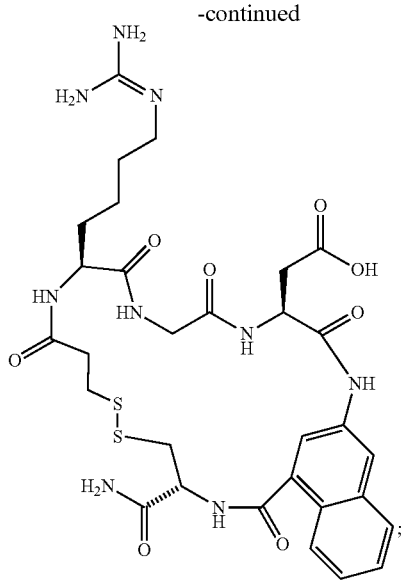

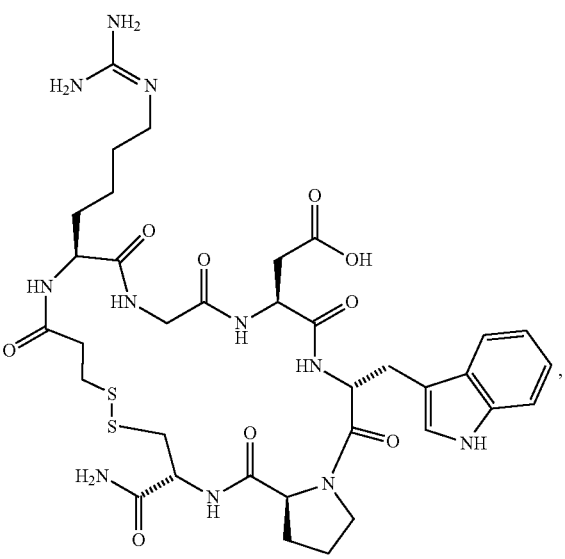

or a pharmaceutically acceptable salt thereof.

Compounds of Formula (I), (II), (III), (V), (VI), (VII), and/or (VIII) can be prepared, for example using standard peptide chemistry starting from the C-terminus. For example, a S-trytyl cysteine amide can be incorporated with homoarginine (or arginine) and D-tryptophan (see, for example, Takahashi D, Yano T, and Fukui T (2012) *Organic letters* 14: 4514-4517). Cyclization to form the disulfide bond can be carried out using iodine mediated oxidative coupling (see, for example, Kamber B et al. (1980) *Helvetica chimica acta* 63: 899-915). Finally, any protecting groups used during the synthesis can be removed using trifluoroacetic acid (TFA). In certain procedures, modified amino acids and/or non-natural derivatives thereof (e.g., N-alkylated L-alanine and O-alkylated 4-hydroxy-L-proline) can be used to prepare the compounds provided herein.

Further provided herein is a compound of Formula (IV):

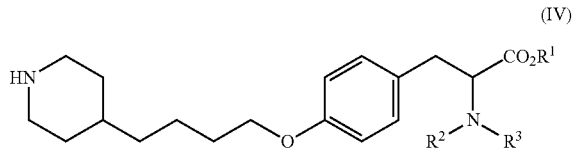

(IV)

or a pharmaceutically acceptable salt thereof,
wherein:
$R^1$ and $R^2$ are independently selected from H and ($C_1$-$C_6$)alkyl;
$R^3$ is selected from the group consisting of:

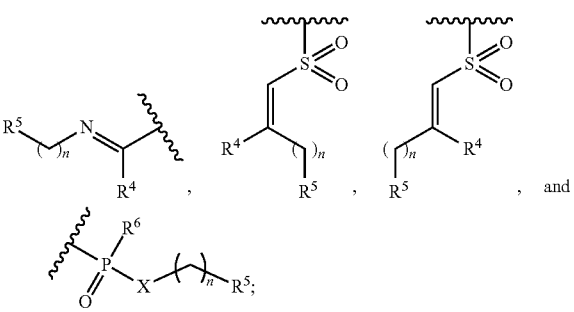

$R^4$ is selected from H and ($C_1$-$C_6$)alkyl;
$R^5$ is selected from the group consisting of a 3-12 membered heterocyclyl and a 5-12 membered heteroaryl;
$R^6$ is selected from H, ($C_1$-$C_6$)alkyl, OH, and O($C_1$-$C_6$)alkyl;
X is O or $CH_2$; and
n is an integer from 0 to 6.
In some embodiments, $R^1$ and $R^2$ are H.
In some embodiments, $R^4$ is a ($C_1$-$C_6$)alkyl.
In some embodiments, $R^5$ is an electron-rich heterocyclyl or heteroaryl, such as furanyl, pyrrolyl, imidazolyl, oxazolyl, and thiophenyl. In some embodiments, $R^5$ is an electron-poor heterocyclyl or heteroaryl such as pyridinyl, pyrimidinyl, and purinyl. In some embodiments, $R^5$ is selected from the group consisting of indolyl, pyridyl, thiophenyl, and pyrrolyl. For example, $R^5$ can be indolyl.
In some embodiments, $R^3$ is:

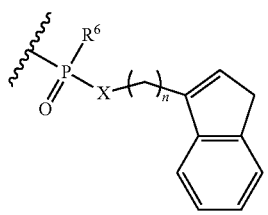

wherein $R^6$ is selected from H, ($C_1$-$C_6$)alkyl, OH, and O($C_1$-$C_6$)alkyl; X is O or $CH_2$; and
n is an integer from 0 to 6.
In some embodiments, X is O. In some embodiments, X is $CH_2$.
In some embodiments, n is an integer from 1 to 2.
In some embodiments, $R^6$ is a O($C_1$-$C_6$)alkyl. In some embodiments, $R^6$ is a ($C_1$-$C_6$)alkyl.
Non-limiting examples of a compound of Formula (IV) include:

119
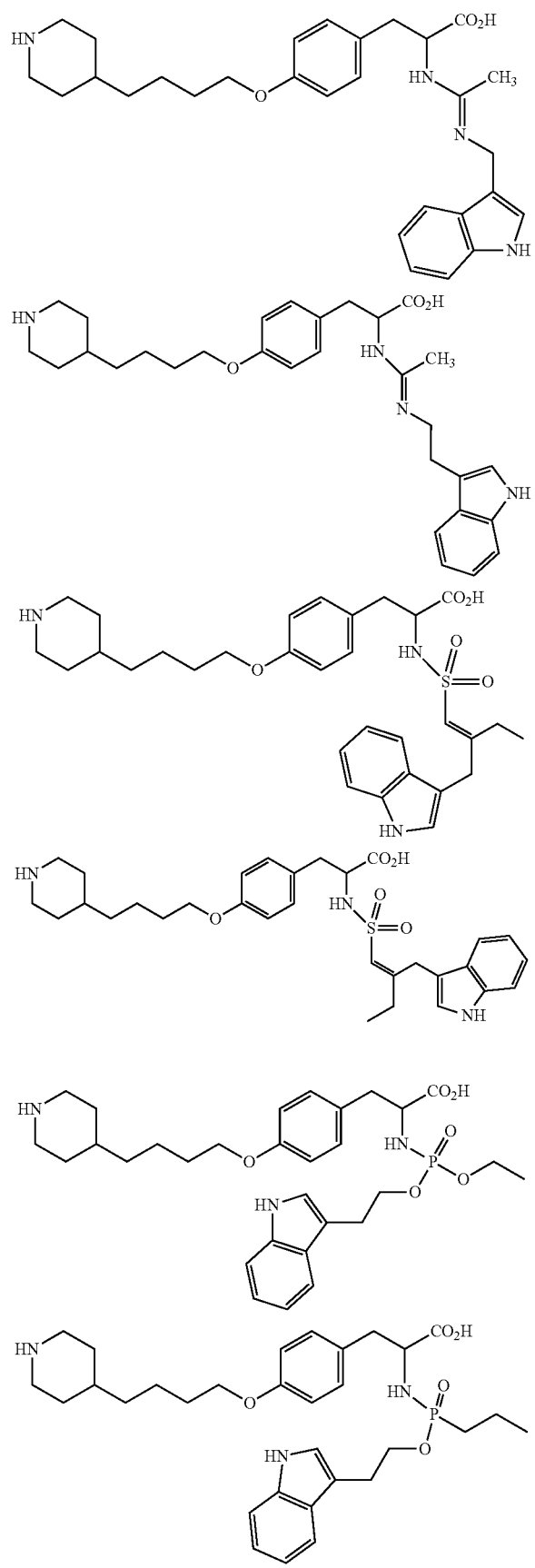
120
-continued
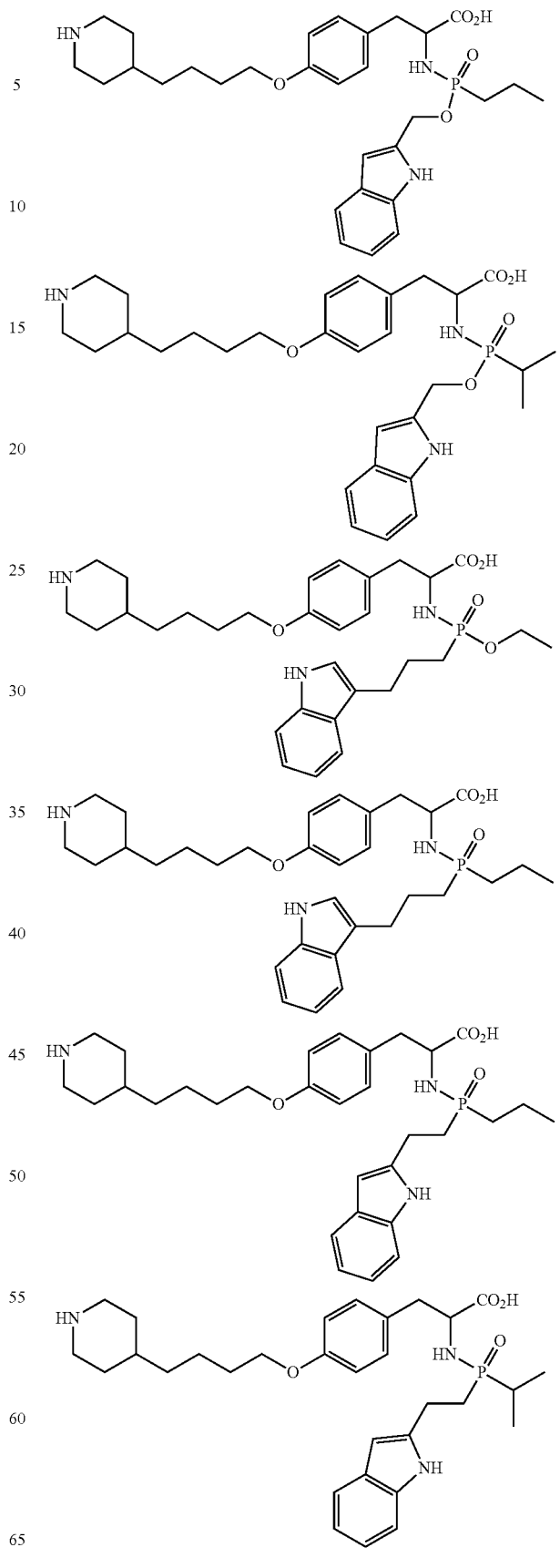

or a pharmaceutically acceptable salt thereof. For example, a compound of Formula (IV) can be a compound selected from:
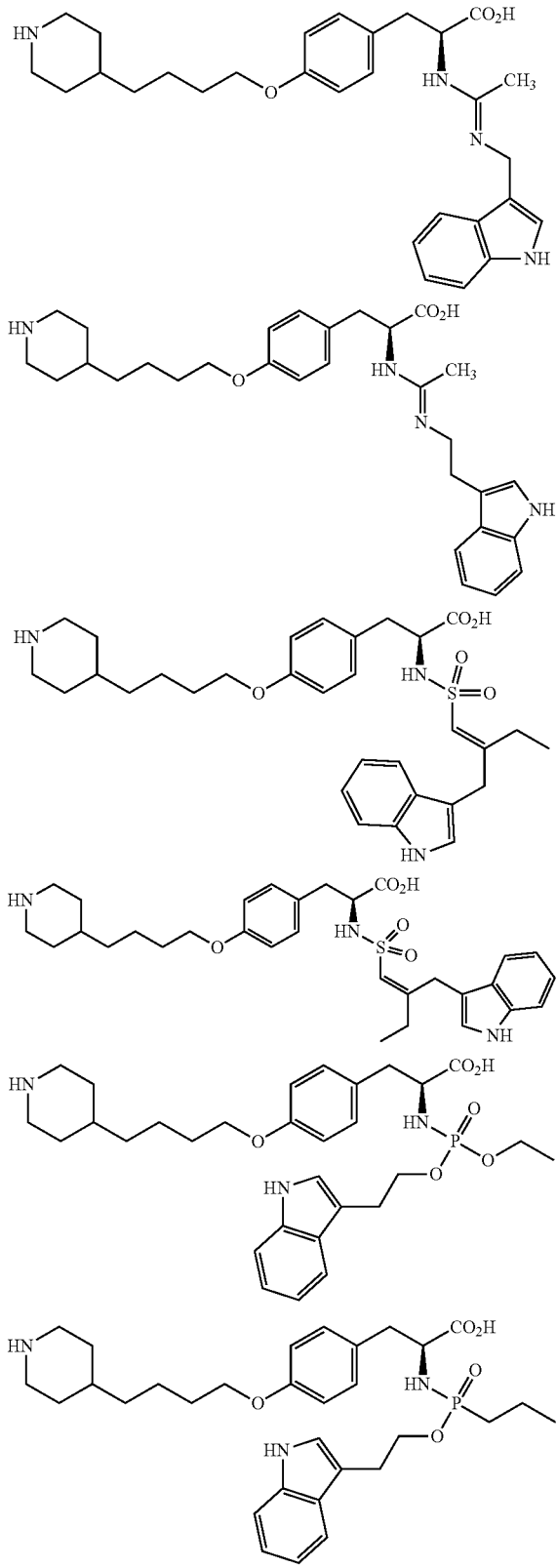
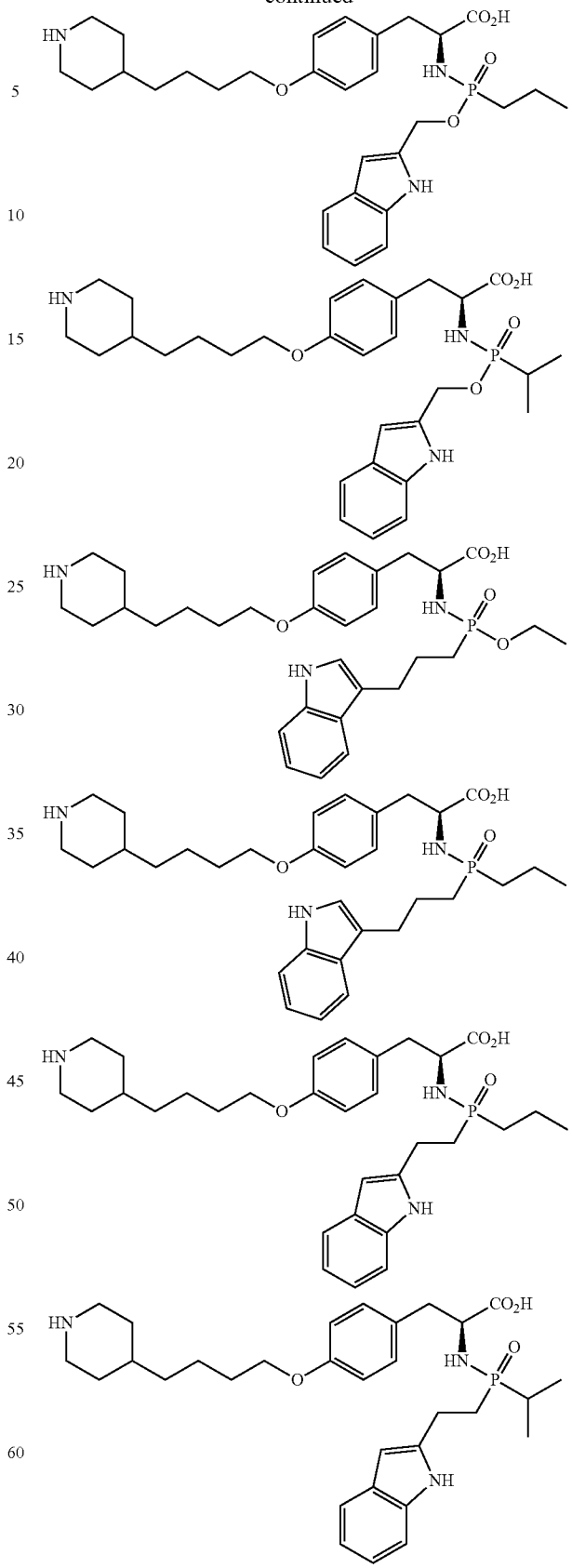
or a pharmaceutically acceptable salt thereof.

Compound of Formula (IV) can be prepared, for example, using known synthetic methods (see, for example, Chung J Y L et al. (1993) *Tetrahedron* 49: 5767-5776; Viertler M et al. (2012) *Bioorganic & Medicinal Chemistry* 20: 628-632; Zhou Y. et al. (2010) *The Journal of Organic Chemistry*). For example, compounds of Formula (IV) can be prepared as shown in Scheme 1.

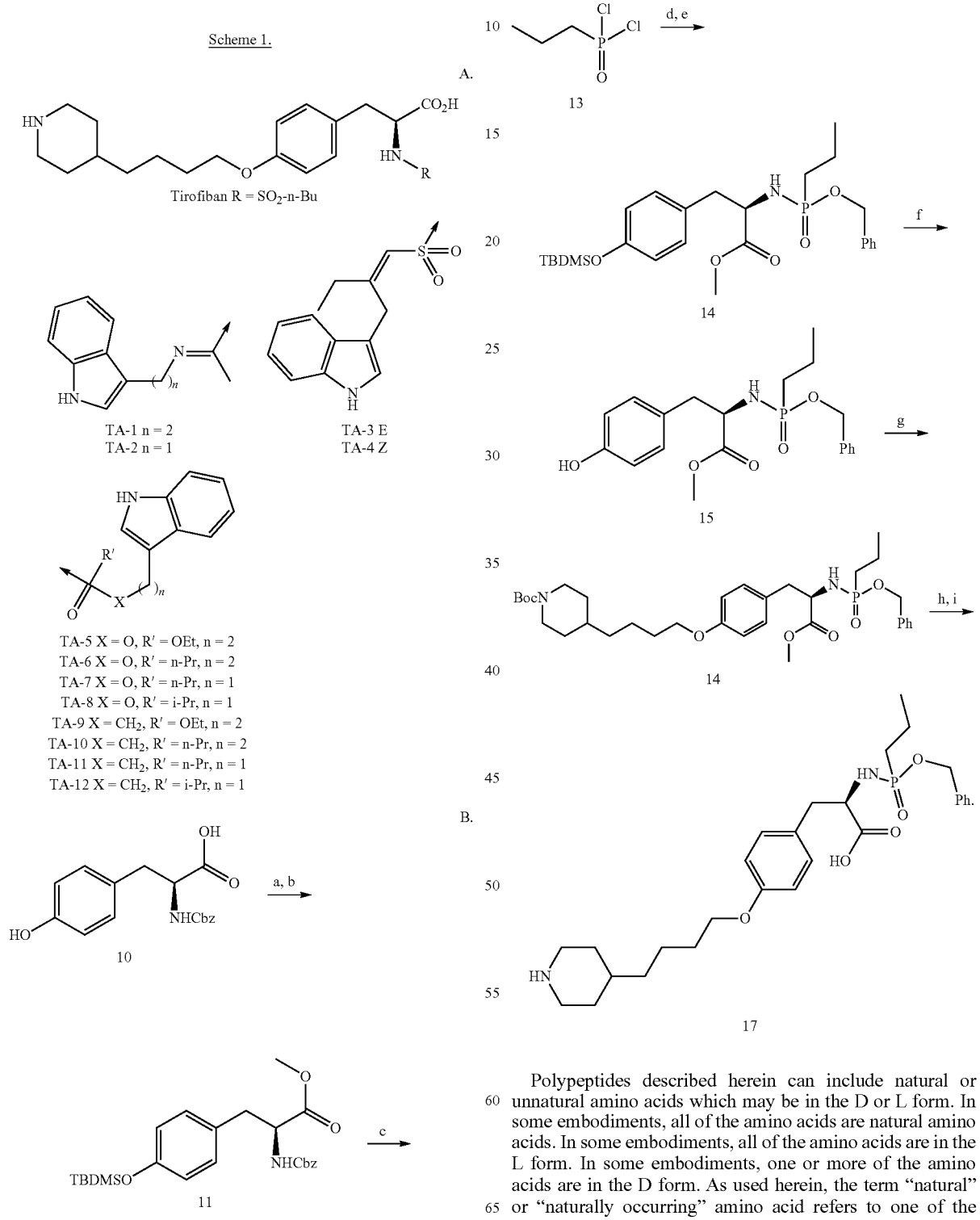

Polypeptides described herein can include natural or unnatural amino acids which may be in the D or L form. In some embodiments, all of the amino acids are natural amino acids. In some embodiments, all of the amino acids are in the L form. In some embodiments, one or more of the amino acids are in the D form. As used herein, the term "natural" or "naturally occurring" amino acid refers to one of the twenty most common occurring amino acids. Natural amino acids modified to provide a label for detection purposes (e.g., radioactive labels, optical labels, or dyes) are considered to be natural amino acids. Natural amino acids are referred to by their standard one- or three-letter abbreviations.

In some embodiments, a polypeptide provided herein comprises one or more synthetic amino acids, e.g., an amino acid non-native to a mammal (a non-natural derivative). Synthetic amino acids include β-alanine (β-Ala), N—OC-methyl-alanine (Me-Ala), aminobutyric acid (Abu), γ-aminobutyric acid (γ-Abu), aminohexanoic acid (ε-Ahx), aminoisobutyric acid (Aib), aminomethylpyrrole carboxylic acid, aminopiperidinecarboxylic acid, aminoserine (Ams), aminotetrahydropyran-4-carboxylic acid, arginine N-methoxy-N-methyl amide, β-aspartic acid (β-Asp), azetidine carboxylic acid, 3-(2-benzothiazolyl)alanine, oc-ie/t-butylglycine, 2-amino-5-ureido-n-valeric acid (citrulline, Cit), β-Cyclohexylalanine (Cha), acetamidomethyl-cysteine, diaminobutanoic acid (Dab), diaminopropionic acid (Dpr), dihydroxyphenylalanine (DOPA), dimethylthiazolidine (DMTA), γ-Glutamic acid (γ-Glu), homoserine (Hse), hydroxyproline (Hyp), isoleucine N-methoxy-N-methyl amide, methyl-isoleucine (MeIle), isonipecotic acid (Isn), methyl-leucine (MeLeu), methyl-lysine, dimethyl-lysine, trimethyl-lysine, methanoproline, methionine-sulfoxide (Met(O)), methionine-sulfone (Met(O$_2$)), norleucine (Nle), methyl-norleucine (Me-Nle), norvaline (Nva), ornithine (Orn), para-aminobenzoic acid (PABA), penicillamine (Pen), methylphenylalanine (MePhe), 4-Chlorophenylalanine (Phe(4-Cl)), 4-fluorophenylalanine (Phe(4-F)), 4-nitrophenylalanine (Phe(4-N02)), 4-cyanophenylalanine ((Phe(4-CN)), phenylglycine (Phg), piperidinylalanine, piperidinylglycine, 3,4-dehydroproline, pyrrolidinylalanine, sarcosine (Sar), selenocysteine (Sec), O-Benzyl-phosphoserine, 4-amino-3-hydroxy-6-methylheptanoic acid (Sta), 4-amino-5-cyclohexyl-3-hydroxypentanoic acid (ACHPA), 4-amino-3-hydroxy-5-phenylpentanoic acid (AHPPA), 1,2,3,4,-tetrahydro-isoquinoline-3-carboxylic acid (Tic), tetrahydropyranglycine, thienylalanine (Thi), O-benzyl-phosphotyrosine, O-Phosphotyrosine, methoxytyrosine, ethoxytyrosine, O-(bis-dimethylamino-phosphono)-tyrosine, tyrosine sulfate tetrabutylamine, methyl-valine (Me-Val), and alkylated 3-mercaptopropionic acid.

Polypeptides as provided herein can be synthesized according to standard synthesis methods. Charged groups on the polypeptides can be neutralized if desired. For example, the C-terminal carboxylate moiety can be amidated with an —NH$_2$ group, yielding a C(=O)NH$_2$ moiety. For ease of synthesis and cost considerations, in some embodiments, the polypeptides have between 10 to 100 amino acids (e.g., 10 to 80, 15 to 100, 15 to 50, 10 to 30, 20 to 80, 25 to 75, 10 to 50, 50 to 75, or 40 to 80 amino acids in length).

Polypeptides can be prepared using known methods (see, e.g., S. J. Moore et al. PNAS 2013 110(36):14598-14603; and Silverman, A. P. et al. *J. Mol. Biol.* (2009) 385, 1064-1075). Briefly, cDNA encoding c-terminal his-tagged rEETI 2.5F knottin can be synthesized and fused at the c-terminus to the Fc fragment of human IgG in a mammalian expression vector. Modified versions of WT rEETI 2.5F can be generated by site-directed mutagenesis.

Cyclic polypeptides provided herein can be prepared using known methods. For example, a convergent synthesis can be used. c-A-V-T-P-R-G-D-W-N-E-G-G-PQ (SEQ ID NO: 73) can be disconnected into a linear 13mer and then into a pentapeptide (D-W-N-E-G (SEQ ID NO: 56)), hexpapetide (A-V-T-P-R-G (SEQ ID NO: 57)) and dipeptide (G-P-D). In some embodiments, protecting groups can be used such as Fmoc-protected amines, benzyl esters, t-butyl ethers, t-butyl esters, trityl groups, Boc carbamates, and Pbf sulfonamides. Protecting groups can be removed during or at the completion of the synthesis using known methods (e.g., under acidic conditions and by hydrogenation).

Amino acids with many different protecting groups appropriate for immediate use in the solid phase synthesis of polypeptides are commercially available.

In some instances, the polypeptide of the disclosure comprises a non-native sequence (e.g., tag, label). A tag can be fused to the polypeptide sequence of the polypeptide. The tag can be fused to the N-terminus, or the C-terminus, or any combination thereof. The tag can be inserted in the polypeptide sequence (e.g., in a solvent accessible surface loop). Examples of tags can include, but are not limited to, affinity tags (e.g., myc, maltose binding protein, 6×his (SEQ ID NO: 58), metal chelating peptides such as multiple histine residues or histidine-tryptophan modules that allow purification on immobilized metals, protein A domains that allow purification on immobilized immunoglobulin, and the domain utilized in the FLAGS extension/affinity purification system), fluorescent tags (e.g., green fluorescent protein).

A tag can be a composition detectable by spectroscopic, photochemical, biochemical, immunochemical, chemical, or other physical means. For example, tags suitable for use in the present disclosure can include, biotin, digoxigenin, or haptens as well as proteins which can be made detectable, fluorescent dyes (e.g., fluorescein isothiocyanate, Texas red, rhodamine, and the like), radiolabels (e.g., $^3$H, $^{125}$I, $^{35}$S, $^{14}$C, or $^{32}$P), dyes (e.g., alexa, cy3 cy5), chemical conjugates (e.g., quantum dots), enzymes (e.g., horse radish peroxidase, alkaline phosphatase and others commonly used in an ELISA), and colorimetric labels such as colloidal gold, colored glass or plastic beads (e.g., polystyrene, polypropylene, latex, etc.).

A tag can be detected. For example, where the tag is radioactive, means for detection can include a scintillation counter or photographic film, as in autoradiography. Where the tag is a fluorescent tag, it may be detected by exciting the fluorochrome with the appropriate wavelength of light and detecting the resulting fluorescence. The fluorescence may be detected visually, by the use of electronic detectors such as charge coupled devices (CCDs) or photomultipliers and the like. Similarly, enzymatic tags may be detected by providing the appropriate substrates for the enzyme and detecting the resulting reaction product. Colorimetric or chemiluminescent tags may be detected simply by observing the color associated with the tag.

Exemplary polypeptides comprising a tag include the following wherein (His) represents a multiple of histidine residues (e.g., 4, 6, 8, or 10).

(SEQ ID NO: 15)
(His)GS-

SDVPRDLEVVAATPTSLLISWDAPAVTVRYYRITYGETGGNSPVQEFTV

PGSKSTATISGLKPGVDYTITVYAVTPKGDWNEGSKPISINY hFN10 R/K + SD deletion (hR/K-ΔSD)
(SEQ ID NO: 16)
(His)GS---

VPRDLEVVAATPTSLLISWDAPAVTVRYYRITYGETGGNSPVQEFTVPG

SKSTATISGLKPGVDYTITVYAVTPKGDWNEGSKPISINY

```
                          -continued
hFN10 R/K + ΔSD + SK deletion (hR/K-ΔSD-ΔSK)
                                              (SEQ ID NO: 17)
(His)GS---

VPRDLEVVAATPTSLLISWDAPAVTVRYYRITYGETGGNSPVQEFTVPG

SKSTATISGLKPGVDYTITVYAVTPKGDWNEG-PISINY hFN10 + SD deletion (hΔSD)
                                              (SEQ ID NO: 18)
(His)GS---

VPRDLEVVAATPTSLLISWDAPAVTVRYYRITYGETGGNSPVQEFTVPG

SKSTATISGLKPGVDYTITVYAVTPRGDWNEGSKPISINY hFN10 + ΔSD + SK deletion (hΔSD-ΔSK)
                                              (SEQ ID NO: 19)
(His)GS---

VPRDLEVVAATPTSLLISWDAPAVTVRYYRITYGETGGNSPVQEFTVPG

SKSTATISGLKPGVDYTITVYAVTPRGDWNEG-PISINY
```

Thrombin Cleavage Site

In some embodiments, a polypeptide provided herein is a polypeptide analog having a structure based on one of the polypeptides disclosed herein (the "parent polypeptide") but differs from the parent polypeptide in one or more respects. Accordingly, as appreciated by one of ordinary skill in the art the teachings of the parent polypeptide provided herein may also be applicable the peptide analogs.

In some embodiments, the polypeptide analog comprises the structure of a parent polypeptide, except that the polypeptide analog comprises one or more non-peptide bonds in place of peptide bond(s). In some embodiments, the peptide analog comprises in place of a peptide bond, an ester bond, an ether bond, a thioether bond, an amide bond, and the like. For example, the polypeptide analog can be a depsipeptide comprising an ester linkage in place of a peptide bond.

In some embodiments, the polypeptide analog comprises the structure of a parent polypeptide described herein, except that the polypeptide analog comprises one or more amino acid substitutions, e.g., one or more conservative amino acid substitutions. Conservative amino acid substitutions are known in the art, and include amino acid substitutions in which one amino acid having certain physical and/or chemical properties is exchanged for another amino acid that has the same chemical or physical properties. For instance, the conservative amino acid substitution may be an acidic amino acid substituted for another acidic amino acid (e.g., Asp or Glu), an amino acid with a nonpolar side chain substituted for another amino acid with a nonpolar side chain (e.g., Ala, Gly, Val, Ile, Leu, Met, Phe, Pro, Trp, Val, etc.), a basic amino acid substituted for another basic amino acid (Lys, Arg, etc.), an amino acid with a polar side chain substituted for another amino acid with a polar side chain (Asn, Cys, Gln, Ser, Thr, Tyr, etc.).

In some embodiments, the polypeptide analog comprises one or more non-conservative amino acid substitutions and the polypeptide analog still functions to a similar extent, the same extent, or an improved extent as the parent polypeptide.

In some embodiments, the polypeptide analog has one or more amino acid insertions or deletions, in reference to the parent polypeptide described herein. In some embodiments, the polypeptide analog comprises an insertion of one or more amino acids at the N- or C-terminus in reference to the parent polypeptide. In some embodiments, the polypeptide analog comprises a deletion of one or more amino acids at the N- or C-terminus in reference to the parent polypeptide. In these aspects, the polypeptide analog still functions to a similar extent, the same extent, or an improved extent as the parent polypeptide to inhibit integrin activity.

Pharmaceutical Compositions and Methods of Administration

The methods described herein include the manufacture and use of pharmaceutical compositions, which include compounds and/or polypeptides provided herein or identified by a method provided herein. Also included are the pharmaceutical compositions themselves.

Pharmaceutical compositions typically include a pharmaceutically acceptable carrier. As used herein the language "pharmaceutically acceptable carrier" includes saline, solvents, dispersion media, coatings, antibacterial and antifungal agents, isotonic and absorption delaying agents, and the like, compatible with pharmaceutical administration.

Pharmaceutical compositions are typically formulated to be compatible with its intended route of administration. Examples of routes of administration include parenteral, e.g., intravenous, intradermal, subcutaneous, oral (e.g., inhalation), transdermal (topical), transmucosal, and rectal administration.

Methods of formulating suitable pharmaceutical compositions are known in the art, see, e.g., *Remington: The Science and Practice of Pharmacy,* 21st ed., 2005; and the books in the series *Drugs and the Pharmaceutical Sciences: a Series of Textbooks and Monographs* (Dekker, NY). For example, solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use can include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, NJ) or phosphate buffered saline (PBS). In all cases, the composition must be sterile and should be fluid to the extent that easy syringability exists. It should be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent that delays absorption, for example, aluminum monostearate and gelatin.

Sterile injectable solutions can be prepared by incorporating a compound and/or polypeptide as provided herein in the required amount in an appropriate solvent with one or a combination of ingredients enumerated above, as required, followed by filtered sterilization. Generally, dispersions are prepared by incorporating a compound and/or polypeptide as provided herein into a sterile vehicle, which contains a basic dispersion medium and the required other ingredients from those enumerated above. In the case of sterile powders for the preparation of sterile injectable solutions, the preferred methods of preparation are vacuum drying and freeze-drying, which yield a powder of the active ingredient plus any additional desired ingredient from a previously sterile-filtered solution thereof.

Oral compositions generally include an inert diluent or an edible carrier. For the purpose of oral therapeutic administration, a compound and/or polypeptide as provided herein can be incorporated with excipients and used in the form of tablets, troches, or capsules, e.g., gelatin capsules. Oral compositions can also be prepared using a fluid carrier for use as a mouthwash. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds can be delivered in the form of an aerosol spray from a pressured container or dispenser that contains a suitable propellant, e.g., a gas such as carbon dioxide, or a nebulizer. Such methods include those described in U.S. Pat. No. 6,468,798.

Systemic administration of a compound and/or polypeptide provided herein can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, a compound and/or polypeptide as provided herein is formulated into ointments, salves, gels, or creams as generally known in the art.

The pharmaceutical compositions can also be prepared in the form of suppositories (e.g., with conventional suppository bases such as cocoa butter and other glycerides) or retention enemas for rectal delivery.

In one embodiment, the compounds and/or polypeptides provided herein are prepared with carriers that will protect the compounds and/or polypeptides provided herein against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Such formulations can be prepared using standard techniques, or obtained commercially, e.g., from Alza Corporation and Nova Pharmaceuticals, Inc. Liposomal suspensions (including liposomes targeted to selected cells with monoclonal antibodies to cellular antigens) can also be used as pharmaceutically acceptable carriers. These can be prepared according to methods known to those skilled in the art, for example, as described in U.S. Pat. No. 4,522,811.

The pharmaceutical compositions can be included in a container, pack, or dispenser together with instructions for administration.

An "effective amount" is an amount sufficient to effect beneficial or desired results. For example, a therapeutic amount is one that achieves the desired therapeutic effect. This amount can be the same or different from a prophylactically effective amount, which is an amount necessary to prevent onset of disease or disease symptoms. An effective amount can be administered in one or more administrations, applications or dosages. A therapeutically effective amount of a compound and/or polypeptide provided herein (i.e., an effective dosage) depends on the compounds and/or polypeptides selected. The compositions can be administered one from one or more times per day to one or more times per week; including once every other day. The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of the compounds and/or polypeptides provided herein can include a single treatment or a series of treatments.

Dosage, toxicity and therapeutic efficacy of the compounds and/or polypeptides provided herein can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds and/or polypeptides which exhibit high therapeutic indices are preferred. While compounds and/or polypeptides that exhibit toxic side effects may be used, care should be taken to design a delivery system that targets such compounds and/or polypeptides to the site of affected tissue in order to minimize potential damage to uninfected cells and, thereby, reduce side effects.

The data obtained from cell culture assays and animal studies can be used in formulating a range of dosage for use in humans. The dosage of such compounds and/or polypeptides lies preferably within a range of circulating concentrations that include the ED50 with little or no toxicity. The dosage may vary within this range depending upon the dosage form employed and the route of administration utilized. For any compound and/or polypeptide used herein, the therapeutically effective dose can be estimated initially from cell culture assays. A dose may be formulated in animal models to achieve a circulating plasma concentration range that includes the IC50 (i.e., the concentration of the test compound and/or polypeptide which achieves a half-maximal inhibition of symptoms) as determined in cell culture. Such information can be used to more accurately determine useful doses in humans. Levels in plasma may be measured, for example, by high performance liquid chromatography.

Methods of Treatment

Methods of using the integrin inhibiting compounds, polypeptides, and compositions described herein, or identified by a method described herein, are further provided. Integrins have been established as therapeutic targets in a number of conditions, see, e.g., Cox et al., Nature Reviews Drug Discovery 2010; 9(10):804-20 (various conditions); Maile et al., Sci Transl Med 2, 18ra11 (2010) (atherosclerosis); and Gerber et al., Nature 503:126-130 (2013) (scleroderma), among others. Thus, the disclosure provides methods for inhibiting integrin activity to treat diseases or conditions that would benefit from reduced integrin activity. In some embodiments, the compounds, polypeptides, and compositions provided herein are useful for blocking integrin function while decreasing or avoiding the side effects that can result from inadvertent activation of the receptor. Such side effects include, for example, thrombocytopenia (e.g., severe thrombocytopenia).

The present disclosure includes methods for the treatment of diseases mediated by integrin function, wherein the integrin has a conserved tyrosine in a position analogous to Tyr122 in beta3. An alignment of integrin sequences, shown in FIG. 8, demonstrated that the following integrins have a conserved Tyrosine beta3 integrins: αIIbβ3 and αVβ3 beta1 integrins: α1β1, α2β1, α3β1, α4β1, α5β1, α6β1, α7β1, α8β1 α9β1, α10β1, α11β1, αVβ1 beta2 integrins: αLβ2 (LFA-1, CD11a/CD18), αMβ2 (CD11b/CD18), αXβ2 (p150.95, CD11c/CD18) and αDβ2 (CD11 d/CD18)

beta7 integrins: α4β7 and αEβ7.

These Tyr122-containing integrins have been shown to be involved in various diseases, as shown in the following Table A:

TABLE A

| Integrin | Disease or condition |
|---|---|
| $α_{IIb}β_3$ | Thrombosis (e.g. heart attacks, stroke) |
| $α_vβ_3$ | Fibrosis (e.g., in the heart, kidney, lung and other systems), atherosclerosis, diabetes; tumor angiogenesis, melanoma |
| $α_2β_1$ | Solid tumors |
| $α_3β_1$ | Solid tumors |
| $α_4β_1$ | Multiple sclerosis, asthma, ulcerative colitis |
| $α_5β_1$ | Angiogenesis, age-related macular degeneration |
| $α_Lβ_2$ | Psoriasis (terminated), but perhaps can get a better drug |
| $α_Mβ_2$ | Ischemia-reprfusion, fibrosis |
| $α_4β_7$ | inflammatory bowel disease (ulcerative colitis) |

Thus the compositions, polypeptides, and compounds described herein can be used to treat a disease listed in Table A, and the present invention provides for these uses as well as methods of treating conditions associated with these integrins, e.g., conditions listed in Table A.

In some embodiments, the compositions, polypeptides, and compounds provided herein can be used to treat one or more disorders selected from the group consisting of: thrombosis, unstable angina, first or recurrent myocardial infarction, ischemic sudden death, diastolic dysfunction, transient ischemic attack, stroke, atherosclerosis, venous thrombosis, deep vein thrombosis, thrombophlebitis, arterial embolism, coronary and cerebral arterial thrombosis, myocardial infarction, cerebral embolisms, kidney embolisms, pulmonary embolisms, fibrosis, renal fibrosis, delayed graft function, diabetes, tumor angiogenesis, melanoma, cancer metastasis, diabetic nephropathy, diabetic retinopathy, neovascular glaucoma, restenosis, osteoporosis, multiple sclerosis, asthma, ulcerative colitis, side burns, random flaps, and macular degeneration.

In some embodiments the condition is cancer metastasis, diabetic retinopathy, neovascular glaucoma, thrombosis, restenosis, osteoporosis, or macular degeneration. The methods include administering to a patient in need of such treatment a therapeutically effective amount of a compound, polypeptide, and/or composition provided herein.

The compounds, polypeptides, and compositions provided herein are useful for the treatment (including prevention) of angiogenic disorders, comprising administering to a patient in need of such treatment a therapeutically effective amount of a compound, polypeptide, and/or composition provided herein. The term "angiogenic disorders" as used herein includes conditions involving abnormal neovascularization, such as tumor metastasis and ocular neovascularization, including, for example, diabetic retinopathy, neovascular glaucoma, age-related macular degeneration, and retinal vein occlusion.

The compounds, polypeptides, and compositions provided herein are also useful for the treatment (including prevention) of thromboembolic disorders, comprising administering to a patient in need of such treatment a therapeutically effective amount of a compound, polypeptide, and/or composition provided herein. The term "thromboembolic disorders" as used herein includes conditions involving platelet activation and aggregation, such as arterial or venous cardiovascular or cerebrovascular thromboembolic disorders, including, for example, thrombosis, unstable angina, first or recurrent myocardial infarction, ischemic sudden death, transient ischemic attack, stroke, atherosclerosis, venous thrombosis, deep vein thrombosis, thrombophlebitis, arterial embolism, coronary and cerebral arterial thrombosis, myocardial infarction, cerebral embolisms, kidney embolisms, pulmonary embolisms, or such disorders associated with diabetes. Because thrombosis play a role in stroke and heart attack, the disclosure furthermore provides a method of treating or preventing a stroke or a heart attack in a patient in need thereof. The method comprises the step of administering to the patient a compound, polypeptide, and/or composition provided herein in an amount effective to treat or prevent stroke or heart attack.

The compounds, polypeptides, and/or compositions provided herein may also be useful for the treatment or prevention of other diseases which involve cell adhesion processes, including, but not limited to, inflammation, bone degradation, restenosis, rheumatoid arthritis, asthma, allergies, adult respiratory distress syndrome, graft versus host disease, organ transplantation rejection, septic shock, psoriasis, eczema, contact dermatitis, osteoporosis, osteoarthritis, atherosclerosis, inflammatory bowel disease and other autoimmune diseases. The compounds, polypeptides, and/or compositions provided herein may also be useful for wound healing.

A method of inhibiting integrin activity (e.g., integrin binding and activation) on a cell is also provided herein, the method comprising contacting the cell with an effective amount of a compound, polypeptide, and/or composition provided herein. The method of inhibiting integrin activity on a cell may be performed by contacting the cell with a compound, polypeptide, and/or composition provided herein, in vitro, thereby inducing inhibition of integrin activity of a cell in vitro. Uses of such an in vitro method of inhibiting integrin activity include, but are not limited to use in a screening assay (for example, wherein a compound, polypeptide, and/or composition provided herein is used as a positive control or standard compared to compounds of unknown activity or potency in inhibiting integrin activity).

The compounds, polypeptides, and/or compositions provided herein may also be used in ex vivo applications to prevent cellular adhesion in biological samples.

The method of inhibiting integrin activity (e.g., integrin binding and activation) on a cell may be performed, for example, by contacting a cell with a compound, polypeptide, and/or composition provided herein, in vivo, thereby inhibiting integrin activity in a patient in vivo. The contacting is achieved by causing a compound, polypeptide, and/or composition provided herein, to be present in the patient in an amount effective to achieve inhibition of integrin activity. This may be achieved, for example, by administering an effective amount of a compound, polypeptide, and/or composition provided herein to a patient. Uses of such an in vivo method of inhibiting integrin activity include, but are not limited to use in methods of treating a disease or condition, wherein inhibiting integrin activity is beneficial.

The compounds, polypeptides, and/or compositions provided herein can also be administered in combination with one or more additional therapeutic agents selected from: anti-coagulant or coagulation inhibitory agents, such as heparin, sodium crystalline clathrate or warfarin; anti-platelet or platelet inhibitory agents, such as aspirin, piroxicam, or ticlopidine; thrombin inhibitors such as boropeptides, hirudin or argatroban; or thrombolytic or fibrinolytic agents, such as plasminogen activators, anistreplase, urokinase, or streptokinase.

The compounds, polypeptides, and/or compositions provided herein can be administered in combination with one or more of the foregoing additional therapeutic agents, thereby to reduce the doses of each drug required to achieve the desired therapeutic effect. Thus, the combination treatment provided herein may permit the use of lower doses of each component, with reduced adverse, toxic effects of each component. A lower dosage can minimize the potential of side effects of the compounds, thereby providing an increased margin of safety relative to the margin of safety for each component when used as a single agent. Such combination therapies may be employed to achieve synergistic or additive therapeutic effects for the treatment of thromboembolic or other disorders.

By "administered in combination" or "combination therapy" it is meant that the compounds, polypeptides, and/or compositions provided herein and one or more additional therapeutic agents are administered concurrently to the patient being treated. When administered in combination each component may be administered at the same time or sequentially in any order at different points in time. Thus, each component may be administered separately but sufficiently closely in time so as to provide the desired therapeutic effect.

EXAMPLES

The invention is further described in the following examples, which do not limit the scope of the invention described in the claims.

General Methods.

Reagents and Antibodies. Restriction and modification enzymes were obtained from New England Biolabs Inc. (Beverly, MA). Cell culture reagents were purchased from Invitrogen Corp (San Diego, CA) or Fisher Scientific (Hampton, NH). Human plasma fibronectin was obtained from Sigma-Aldrich (St Louis, MO). The non-inhibitory mouse monoclonal antibody (mAb) AP3 (American Type Culture Collection, ATCC) detects the β3-subunit in all conformations. Mouse mAb AP5 detects the N-terminal sequence in the PSI domain (residues 1-6 of the β3-subunit) only in high-affinity/ligand-bound states. Mouse mAbs LIBS-1 recognizes a neoepitope distinct from that of AP5, and mouse mAbs LIBS-6 binds the C-terminal and membrane proximal βTD (residues 602-690). The Fab fragment of AP5 was prepared by papain digestion followed by anion exchange and size-exclusion chromatography. The function-blocking and heterodimer-specific mAb LM609 to αVβ3 was from Millipore (Danvers, MA) and APC-labeled goat anti-mouse Fc-specific antibody was from Jackson ImmunoResearch (West Grove, PA).

Plasmids, mutagenesis, protein expression and purification. Human αVβ3 ectodomain was expressed in insect cells and purified as described (Mehta, R. J. et al. *Biochem J* 330 (Pt 2), 861-869 (1998)). The activating N339/S mutation in the β3 subunit was generated as described (Cheng, M. et al. *The Journal of Biological Chemistry* 282, 18225-18232 (2007)). Expression plasmids encoding wild-type human N-terminally His-tagged FN10 (S1417-T1509) were generated by PCR from a plasmid containing human FN7-10 (Leahy, D. J., Aukhil, I. & Erickson, H. P. Cell 84, 155-164 (1996)). Plasmid encoding His-tagged high affinity FN10 (hFN10) was PCR-generated by replacing cDNA encoding the loop sequence $^{1492}$GRGDSPAS (SEQ ID NO: 59) in wtFN10 with $^{1492}$PRGDWNEG (SEQ ID NO: 60). RGD-loop substitutions 1496W/S and TPRGDWNE (SEQ ID NO: 61) to IARGDWND (SEQ ID NO: 62) (substituted residues underlined) in hFN10 to produce hFN10W/S and hFN10/B, respectively, were generated using PCR-based mutagenesis with the Quick-change kit (Agilent Technologies), cloned into bacterial expression plasmid pET11a and verified by DNA sequencing. The double mutation N266/Q (in αV Propeller) plus N339/S (in βA domain), and Y122/A mutation were generated by PCR in pcDNA3 expression plasmids and confirmed by DNA sequencing. FN10 forms were expressed in bacteria and purified by affinity chromatography on nickel columns followed by gel filtration. Thrombin-cleaved FN10 was further purified by gel filtration. Protein purity was confirmed by SDS PAGE.

Cell lines, cell culture and transfection. The human erythroleukemia cell line K562 stably expressing recombinant αVβ3 (K562-αVβ3) and the human melanoma cell line M21, which constitutively expresses αVβ3, have been previously described (Xiong, J. P. et al. The *Journal of Cell Biology* 186, 589-600 (2009); and Mitjans, F. et al. *J Cell Sci* 108 (Pt 8), 2825-2838 (1995)). Cells were maintained in Iscove's modified Dulbecco's medium (K562-αVβ3) or RPMI1640 (M21), supplemented with 10% fetal calf serum, 2 mM L-glutamine, penicillin and streptomycin, plus G418 (0.5-1.0 mg/ml) in cultured K562-αVβ3. HEK293T (ATCC) were transiently co-transfected with pcDNA3 plasmids encoding full-length WT αVβ3, αVβ3(Y122/A), αVβ3 (N339/S), or αV(N266/Q)β3(N339/S) using Lipofectamine 2000 reagent (Invitrogen) according to the manufacturer's protocol.

Fluorescent labeling of FN10 and mAbs. FN10, and mAbs AP5 (Fab) and AP3 (IgG) were labeled respectively with N-hydroxy succinimidyl esters of Fluor 488 (Alexa488) and Alexa647, (Invitrogen) according to the manufacturer's instructions. Excess dye was removed using Centri-Spin size-exclusion microcentrifuge columns (Princeton Separations, Adelphia, NJ). The final FN10, AP5 and AP3 concentrations and dye to protein molar ratios (F/P) were determined spectrophotometrically, giving F/P molar ratios of 1.2 (for FN10) and 3 (for AP5 and AP3).

Ligand binding and flow cytometry. In cellular and biochemical assays where calcium, magnesium or manganese ions were used, they were each at final concentrations of 1 mM. Cells stably (K562) or transiently (HEK293T) expressing WT or mutant forms of αVβ3 were preincubated (30 min; 0° C.) in the dark with Alexa647-conjugated AP3 (10 μg/ml), washed in Hepes-buffered saline (20 mM Hepes, 150 mM NaCl, pH 7.4) containing BSA (0.1% w/v; washing buffer, WB), incubated in 10 mM EDTA in WB (5 min; 25° C.), then washed three times in WB. $1\times10^6$ cells were suspended in 100 μl WB containing $CaCl_2$ plus $MgCl_2$ or $MnCl_2$ (10 min; 37° C.), then incubated with Alexa488-labeled wt- or hFN10 (each at 3-10 μg/ml) (30 min; 25° C.) in the dark, washed in the respective metal ion-containing buffer, resuspended, fixed in 4% paraformaldehyde and analyzed using FACSCalibur or BD-LSRII flow cytometers (BD Biosciences). Binding of soluble FN10 to $\alpha V\beta 3^+$ cells was expressed as mean fluorescence intensity (MFI), as determined using the CellQuest software (BD). Binding of soluble FN10 to HEK293T was normalized by dividing its MFI by the MFI of Alexa647-conjugated AP3 to the same cells and multiplying by 100. Mean and SD from independent experiments were calculated, and compared using Student's t test.

LIBS epitope expression. K562-αVβ3 cells, transiently transfected HEK293T or αVβ3 M21 cells ($0.5\times10^6$ in 100 μl WB) were incubated in the absence or presence of unlabeled soluble FN10 (5 μg) in $Ca^{2+}/Mg^{2+}$ or in $Mn^{2+}$ (30 min; at 25° C.). Alexa647-labeled AP5 Fab (plus Alexa488-labeled AP3, when HEK293T cells were used), unlabeled anti-LIBS-1 (all to 10 μg/ml) or LIBS-6 ascites (to 1:50 dilution) were added, and the cells incubated for an additional 30 min before washing. APC-labeled goat anti-mouse Fc-specific antibody was added to anti-LIBS-1- or anti-LIBS-6-bound M21 cells, cells were incubated for an additional 30 min at 4° C. then washed, resuspended, fixed in 4% paraformaldehyde and analyzed by flow cytometry. LIBS epitope expression was measured and expressed as MFI (in case of K562-αVβ3 or M21 cells) and normalized (in case of HEK293T cells) by dividing its MFI by the MFI for Alexa488-labeled AP3, and multiplied by 100.

Hydrodynamic shift assay for locked integrin. αVβ3 ectodomain was incubated alone or with FN10 (at 2:1 FN10/integrin molar ratio) in 145 mM NaCl and 25 mM Tris-HCl, pH 7.4 (TBS) containing $Ca^{2+}$, $Ca^{2+}/Mg^{2+}$ or $Mn^{2+}$ (20° C.; 1.5 h). Aliquots were taken and chromatographed at room temperature at this time point on a precalibrated Superdex S-200 GL column equilibrated buffer with the same metal ion composition used during the incubation, and Stokes radii were derived as described previously (Xiong, J. P. et al. The Journal of Cell Biology 186, 589-600 (2009)). The elution profiles resolved by molecular sieve chromatography were monitored in-line by UV adsorption at 280 nm. Unliganded±FN10-treated αVβ3 species were resolved as single discrete symmetrical peaks. Excess FN10 served as an internal standard. Identity of resolved peaks was formally confirmed by SDS-PAGE.

Cell adhesion assays. wtFN10, hFN10 or full-length FN (each at a 100 μg/ml in PBS) were adsorbed to demarcated areas in Maxisorp Nunc Omni Tray plates (Sigma-Aldrich, St Louis, MO) overnight at 25° C. The various FN-coated surfaces were washed with PBS, and blocked with bovine serum albumin (5% w/v in PBS; 1 h; 25° C.). K562-αVβ3 cells ($5\times10^4$) were added (in TBS; 1 mM $Mn^{2+}$), in the absence or presence of LM609 mAb (10 μg/ml, added 15 min prior to plating). Cells were incubated (2 h; 37° C.), washed three times in warm TBS and fixed with 4% formaldehyde (in PBS; 25° C.; 10 min). Images were captured using an inverted phase microscope (Zeiss Axiovert 40CFL) fitted with a powershot G12 Cannon Camera. ImageJ 1.48a software (National Institutes of Health, USA) was used to quantify cell spreading of 300-400 random selected cells. Spread cells were clearly distinguishable from round, refringent non-spread cells. Representative phase contrast images were collected using Zeiss Axiovert 35 inverted microscope using a CCD camera and Spot software (Diagnostics Instruments). Adhesion of transiently transfected HEK293 expressing equivalent amounts of αVβ3(N339/S) or αV(N266/Q)β3(N339/S) was done by adding cells ($3\times10^4$) in TBS containing $Ca^{2+}/Mg^{2+}$ and 0.1% BSA (w/v) to FN-coated surfaces (45 min; 25° C.). Non-adherent cells were removed by washing and adherent cells fixed (2% paraformaldehyde; 30 min; 25° C.), stained (0.1% Crystal Violet; 30 min; 25° C.), washed with water, air dried and then solubilized (1% SDS). Relative cell attachment was estimated by absorbance of the lysates at 540 nm measured using a SpectraMax M2E microplate reader (Molecular Devices, Sunnyvale, CA).

Crystallography, structure determination, and refinement. αVβ3 ectodomain was crystallized at 4° C. by vapor diffusion using the hanging drop method as previously described (Xiong, J. P. et al. Crystal structure of the complete integrin alphaVbeta3 ectodomain plus an alpha/beta transmembrane fragment. The Journal of cell biology 186, 589-600 (2009)). hFN10, wtFN10 or hFN10/B (at 1.5 mM) were soaked into αVβ3 crystals in the crystallization well solution containing 2 mM $Mn^{2+}$ for 2-3 weeks. Crystals were harvested in 12% PEG 3500 (polyethylene glycol, molecular weight 3500), in 100 mM sodium acetate, pH 4.5, 800 mM NaCl plus 2 mM $Mn^{2+}$ and FN10 (at 1.5 mM), cryoprotected by addition of glycerol in 2% increments up to 24% final concentration, and then flash-frozen in liquid nitrogen. Diffraction data from cryocooled crystals were collected on the ID19 beamline fitted with a CCD detector at the APS Facility (Chicago, IL). Data were indexed, integrated and scaled with HKL2000 program (Otwinowski and Minor, Methods Enzymol. 276, 307-326 (1997)) for αVβ3-hFN10, αVβ3-hFN10B, and with iMosflm (Bettye et al., Acta Crystallogr D Biol Crystallogr 67, 271-281 (2011)) for αVβ3-wtFN10, using the same $R_{free}$ set imported from pdb id 3ije structure factors. Phases were determined by molecular replacement using PHASER (McCoy et al., Journal of applied crystallography 40, 658-674 (2007)), with structures of unliganded αVβ3 ectodomain (pdb id 3ije) and FN10 domain (pdb id 1fnf) used as search models. The resulting models were refined with 1.8.4 version of Phenix 11 (Adams et al., Acta Crystallogr D Biol Crystallogr 66, 213-221(2010)) using simulated annealing, TLS, positional and individual temperature-factor refinement, and default restrains. Several cycles of refinement and model building using Coot (Emsley et al., Acta Crystallogr D Biol Crystallogr 60, 2126-2132 (2004)) were applied to refine the complex structures of αVβ3-hFN10, αVβ3-wtFN10 and αVβ3-hFN10/B (Table 1), with automatic optimization of X-ray and stereochemistry/ADP, and additional Ramachandran restrains in last cycles. Ramachandran statistics were as follows: αVβ3-hFN10 structure, 89% in most favored regions, 10.47% in additional allowed regions and 0.53% outliers; αVβ3-wtFN10 structure, 89% in most favored regions, 10.18% in additional allowed regions and 0.82% outliers; αVβ3-hFN10/B structure, 91% in most favored regions, 0.56% in additional allowed regions and 0.56% outliers. σA weighted Fo-Fc omit maps were generated by removing the FN10 ligand from the final complex models using phenix.maps. All structural illustrations were prepared with the Chimera software (Petterson et al., J Comput Chem 25, 1605-1612 (2004)).

Example 1. Crystallography, Structure Determination, and Refinement

αVβ3 ectodomain was crystallized at 4° C. by vapor diffusion using the hanging drop method as previously described (Xiong, J. P. et al. *The Journal of Cell Biology* 186, 589-600 (2009)). hFN10, wtFN10 or hFN10/B (at 1.5 mM) were soaked into αVβ3 crystals in the crystallization well solution containing 2 mM Mn²⁺ for 2-3 weeks.

The α$_v$ ectodomain sequence from the α$_v$ β$_3$-wtFN10 crystal structure (underlined, not visible in structure; gray, not included in ectodomain construct [TM+cytoplasmic tail]) (SEQ ID NO: 63):

```
  1   FNLDVDSPAEYSGPEGSYFGFAVDFFVPSASSRMFLLVGAPKANTTQPGIVEGGQVLKCD    60
 61   WSSTRRCQPIEFDATGNRDYAKDDPLEFKSHQWFGASVRSKQDKILACAPLYHWRTEMKQ   120
121   EREPVGTCFLQDGTKTVEYAPCRSQDIDADGQGFCQGGFSIDFTKADRVLLGGPGSFYWQ   180
181   GQLISDQVAEIVSKYDPNVYSIKYNNQLATRTAQAIFDDSYLGYSVAVGDFNGDGIDDFV   240
241   SGVPRAARTLGMVYIYDGKNMSSLYNFTGEQMAAYFGFSVAATDINGDDYADVFIGAPLF   300
301   MDRGSDGKLQEVGQVSVSLQRASGDFQTTKLNGFEVFARFGSAIAPLGDLDQDGFNDIAI   360
361   AAPYGGEDKKGIVYIFNGRSTGLNAVPSQILEGQWAARSMPPSFGYSMKGATDIDKNGYP   420
421   DLIVGAFGVDRAILYRARPVITVNAGLEVYPSILNQDNKTCSLPGTALKVSCFNVRFCLK   480
481   ADGKGVLPRKLNFQVELLLDKLKQKGAIRRALFLYSRSPSHSKNMTISRGGLMQCEELIA   540
541   YLRDESEFRDKLTPITIFMEYRLDYRTAADTTGLQPILNQFTPANISRQAHILLDCGEDN   600
601   VCKPKLEVSVDSDQKKIYIGDDNPLTLIVKAQNQGEGAYEAELIVSIPLQADFIGVVRNN   660
661   EALARLSCAFKTENQTRQVVCDLGNPMKAGTQLLAGLRFSVHQQSEMDTSVKFDLQIQSS   720
721   NLFDKVSPVVSHKVDLAVLAAVEIRGVSSPDHIFLPIPNWEHKENPETEEDVGPVVQHIY   780
781   ELRNNGPSSFSKAMLHLQWPYKYNNNTLLYILHYDIDGPMNCTSDMEINPLRIKISSLQT   840
841   TEKNDTVAGQGERDHLITKRDLALSEGDIHTLGCGVAQCLKIVCQVGRLDRGKSAILYVK   900
901   SLLWTETFMNKENQNHSYSLKSSASFNVIEFPYKNLPIEDITNSTLVTTNVTWGIQPAPM   960
961   PVPVWVIILAVLAGLLLLAVLVFVMYRMGFFKRVRPPQEEQEREQLQPHENGEGNSET   1018
```

β$_3$ ectodomain sequence from the α$_v$ β$_3$-wtFN10 crystal structure (underlined, not visible in structure; gray not included in ectodomain construct [TM+cytoplasmic tail]):

```
  1   GPNICTTRGVSSCQQCLAVSPMCAWCSDEALPLGSPRCDLKENLLKDNCAPESIEFPVSE    60
 61   ARVLEDRPLSDKGSGDSSQVTQVSPQRIALRLRPDDSKNFSIQVRQVEDYPVDIYYLMDL   120
121   SYSMKDDLWSIQNLGTKLATQMRKLTSNLRIGFGAFVDKPVSPYMYISPPEALENPCYDM   180
181   KTTCLPMFGYKHVLTLTDQVTRFNEEVKKQSVSRNRDAPEGGFDAIMQATVCDEKIGWRN   240
241   DASHLLVFTTDAKTHIALDGRLAGIVQPNDGQCHVGSDNHYSASTTMDYPSLGLMTEKLS   300
301   QKNINLIFAVTENVVNLYQNYSELIPGTTVGVLSMDSSNVLQLIVDAYGKIRSKVELEVR   360
361   DLPEELSLSFNATCLNNEVIPGLKSCMGLKIGDTVSFSIEAKVRGCPQEKEKSFTIKPVG   420
421   FKDSLIVQVTFDCDCACQAQAEPNSHRCNNGNGTFECGVCRCGPGWLGSQCECSEEDYRP   480
481   SQQDECSPREGQPVCSQRGECLCGQCVCHSSDFGKITGKYECDDFSCVRYKGEMCSGHG   540
541   QCSCGDCLCDSDWTGYYCNCTTRTDTCMSSNGLLCSGRGKCECGSCVCIQPGSYGDTCEK   600
601   CPTCPDACTFKKECVECKKFDREPYMTENTCNRYCRDEIESVKELKDTGKDAVNCTYKNE   660
661   DDCVVRFQYYEDSSGKSILYVVEEPECPKGPDILVVLLSVMGAILLIGLAALLIWKLLIT   720
721   IHDRKEFAKFEEERARAKWDTANNPLYKEATSTFTNITYRGT                    762
```

α_v ectodomain sequence from the α_v β3-hFN10 crystal structure (underlined not visible in structure; gray not included in ectodomain construct [TM+cytoplasmic tail]) (SEQ ID NO: 65)

| | | |
|---|---|---|
| 1 | FNLDVDSPAEYSGPEGSYFGFAVDFFVPSASSRMFLLVGAPKANTTQPGIVEGGQVLKCD | 60 |
| 61 | WSSTRRCQPIEFDATGNRDYAKDDPLEFKSHQWFGASVRSKQDKILACAPLYHWRTEMKQ | 120 |
| 121 | EREPVGTCFLQDGTKTVEYAPCRSQDIDADGQGFCQGGFSIDFTKADRVLLGGPGSFYWQ | 180 |
| 181 | GQLISDQVAEIVSKYDPNVYSIKYNNQLATRTAQAIFDDSYLGYSVAVGDFNGDGIDDFV | 240 |
| 241 | SGVPRAARTLGMVYIYDGKNMSSLYNFTGEQMAAYFGFSVAATDINGDDYADVFIGAPLF | 300 |
| 301 | MDRGSDGKLQEVGQVSVSLQRASGDFQTTKLNGFEVFARFGSAIAPLGDLDQDGFNDIAI | 360 |
| 361 | AAPYGGEDKKGIVYIFNGRSTGLNAVPSQILEGQWAARSMPPSFGYSMKGATDIDKNGYP | 420 |
| 421 | DLIVGAFGVDRAILYRARPVITVNAGLEVYPSILNQDNKTCSLPGTALKVSCFNVRFCLK | 480 |
| 481 | ADGKGVLPRKLNFQVELLLDKLKQKGAIRRALFLYSRSPSHSKNMTISRGGLMQCEELIA | 540 |
| 541 | YLRDESEFRDKLTPITIFMEYRLDYRTAADTTGLQPILNQFTPANISRQAHILLDCGEDN | 600 |
| 601 | VCKPKLEVSVDSDQKKIYIGDDNPLTLIVKAQNQGEGAYEAELIVSIPLQADFIGVVRNN | 660 |
| 661 | EALARLSCAFKTENQTRQVVCDLGNPMKAGTQLLAGLRFSVHQQSEMDTSVKFDLQIQSS | 720 |
| 721 | NLFDKVSPVVSHKVDLAVLAAVEIRGVSSPDHIFLPIPNWEHKENPETEEDVGPVVQHIY | 780 |
| 781 | ELRNNGPSSFSKAMLHLQWPYKYNNNTLLYILHYDIDGPMNCTSDMEINPLRIKI<u>SSLQT</u> | 840 |
| 841 | <u>TEKNDTVAGQGERDHLITKRDLALSEGDIHTLGCGVAQCLKIVCQVGRLDRGKSAILYVK</u> | 900 |
| 901 | <u>SLLWTETFMNKENQNHSYSLKSSASFNVIEFPYKNLPIEDITNSTLVTTNVTWGIQ</u>PAPM | 960 |
| 961 | PVPVWVIILAVLAGLLLLAVLVFVMYRMGFFKVRPPQEEQEREQLQPHENGEGNSET | 1018 |

β_3 ectodomain sequence from the α_v β_3-hFN10 crystal structure (underlined not visible in structure; gray not included in ectodomain construct [TM+cytoplasmic tail]) (SEQ ID NO: 66)

| | | |
|---|---|---|
| 1 | GPNICTTRGVSSCQQCLAVSPMCAWCSDEALPLGSPRCDLKENLLKDNCAPESIEFPVSE | 60 |
| 61 | ARVLEDRPLSDKGSGDSSQVTQVSPQRIALRLRPDDSKNFSIQVRQVEDYPVDIYYLMDL | 120 |
| 121 | SYSMKDDLWSIQNLGTKLATQMRKLTSNLRIGFGAFVDKPVSPYMYISPPEALENPCYDM | 180 |
| 181 | KTTCLPMFGYKHVLTLTDQVTRFNEEVKKQSVSRNRDAPEGGFDAIMQATVCDEKIGWRN | 240 |
| 241 | DASHLLVFTTDAKTHIALDGRLAGIVQPNDGQCHVGSDNHYSASTTMDYPSLGLMTEKLS | 300 |
| 301 | QKNINLIFAVTENVVNLYQNYSELIPGTTVGVLSMDSSNVLQLIVDAYGKIRSKVELEVR | 360 |
| 361 | DLPEELSLSFNATCLNNEVIPGLKSCMGLKIGDTVSFSIEAKVRGCPQEKEKSFTIKPVG | 420 |
| 421 | FKDSLIVQVTFDCDCACQAQAEPNSHRCNNGNGTFECGVCRCGPGWLGSQCECSEEDYRP | 480 |
| 481 | SQQDECSPREGQPVCSQRGECLCGQCVCHSSDFGKITGKYCECDDFSCVRYKGEMCSGHG | 540 |
| 541 | QCSCGDCLCDSDWTGYYCNCTTRTDTCMSSNGLLCSGRGKCECGSCVCIQPGSYGDTCEK | 600 |
| 601 | CPTCPDACTFKKECVECKKFDREPYMTENTCNRYCRDEIESVKELKDTGKDAVNCTYKNE | 660 |
| 661 | DDCVVRFQYYEDSSGKSILYVVEEPECPKGPDILVVLLSVMGAILLIGLAALLIWKLLIT | 720 |
| 721 | IHDRKEFAKFEEERARAKWDTANNPLYKEATSTFTNITYRGT | 762 |

The sequences for the hFN10, wtFN10 or hFN10/B polypeptides were as follows: wtFN10:

```
wtFN10:
                                    (SEQ ID NO: 20)
SDVPRDLEVVAATPTSLLISWDAPAVTVRYYRITYGETGGNSPVQEFTV

PGSKSTATISGLKPGVDYTITVYAVTGRGDSPASSKPISINYRT
```

```
              -continued
hFN10:
                                    (SEQ ID NO: 9)
SDVPRDLEVVAATPTSLLISWDAPAVTVRYYRITYGETGGNSPVQEFTV

PGSKSTATISGLKPGVDYTITVYAVTPRGDWNEGSKPISINY hFN10/B:
                                    (SEQ ID NO: 67)
SDVPRDLEVVAATPTSLLISWDAPAVTVRYYRITYGETGGNSPVQEFTV

PGSKSTATISGLKPGVDYTITVYAVIARGDWNDGSKPISINY
```

Crystals were harvested in 12% PEG 3500 (polyethylene glycol, molecular weight 3500), in 100 mM sodium acetate, pH 4.5, 800 mM NaCl plus 2 mM $Mn^{2+}$ and FN10 (at 1.5 mM), cryoprotected by addition of glycerol in 2% increments up to 24% final concentration, and then flash-frozen in liquid nitrogen. Diffraction data from cryocooled crystals were collected on the ID19 beamline fitted with a CCD detector at the APS Facility (Chicago, IL). All data were indexed, integrated and scaled with HKL2000 program. Phases were determined by molecular replacement using PHASER, with structures of unliganded αVβ3 ectodomain (pdb id 3ije) and FN10 domain (pdb id 1fnf) used as search models. αVβ3-hFN10, αVβ3-wtFN10 and αVβ3-hFN10/B datasets were refined using 1.8.4 version of Phenix to resolutions of 3.10, 3.32 and 3.17 A°. All structural illustrations were prepared with the Chimera software. The data collection and refinement statistics are shown in Table 1.

TABLE 1

| Data collection and refinement statistics (molecular replacement) | | | |
|---|---|---|---|
| | $α_vβ_3$-hFN10 | $α_vβ_3$-wtFN10 | $α_vβ_3$-hFN10/B |
| Data collection | | | |
| Space group | P3221 | P3221 | P3221 |
| Cell dimensions | | | |
| a, b, c (A) | 129.8, 129.8, 307.6 | 129.7, 129.7, 305.8 | 130.0, 130.0, 308.2 |
| α, β, γ (°) | 90, 90, 120 | 90, 90, 120 | 90, 90, 120 |
| Resolution (Å)[a] | 50-3.1 (3.21-3.1) | 75.49-3.32 (3.5-3.32) | 50-3.17 (3.28-3.17) |
| $R_{sym}$[a] | 7.9 (79.7) | 10.9 (67.2) | 10.4 (89.4) |
| I/σ[a] | 27.1 (2.3) | 13.9 (3.3) | 12.6 (2.2) |
| Completeness (%)[a] | 99.9 (100) | 88.0 (88.0) | 99.7 (99.7) |
| Redundancy[a] | 6.1 (6.1) | 6.2 (6.4) | 5.3 (5.1) |
| Refinement | | | |
| Resolution (Å) | 49.3-3.1 | 42.5-3.32 | 49.4-3.18 |
| No. reflections | 55, 243 | 39, 536 | 51, 260 |
| $R_{work}/R_{free}$ | 20.5/25.5 | 21.1/25.8 | 20.5/23.9 |
| Number of atoms | 13, 501 | 13, 626 | 13, 000 |
| Protein | 12, 794 | 12, 922 | 12, 922 |
| Ligand/Ion | | | |
| FN10 | 690 | 694 | 65 |
| $Mn^{2+}$ | 8 | 8 | 8 |
| Water | 9 | 2 | 5 |
| B factors | | | |
| All atoms (Å$^2$) | 116.7 | 102.8 | 75.8 |
| Protein | 114.2 | 98.5 | 75.7 |
| Ligand/Ion | | | |
| FN10 | 163.2 | 181.8 | 83.7 |
| $Mn^{2+}$ | 135.9 | 102.9 | 80.5 |
| Water | 95.2 | 67.7 | 54.8 |
| r.m.s. deviations | | | |
| Bond lengths (Å) | 0.004 | 0.003 | 0.005 |
| Bond angles ( ) | 0.89 | 0.9 | 0.98 |

[a]Values in parenthesis are for highest-resolution shell. One crystal was used for each dataset.

The coordinates are given in Tables 2-5, which are submitted herewith in .txt format.

| Table | Crystal |
|---|---|
| Table 2 | avb3 complex with high affinity FN10 |
| Table 3 | avb3 complex with wild type FN10 (for baseline) |
| Table 4 | allbb3 complex with eptifibatide |
| Table 5 | aVb3 complex with modified eptifibatide |
| | (changes lysine in RGD to arg and changed L-Trp to D-Trp) |

In the modular matrix protein fibronectin (FN), the wild-type 12 kDa 10th type-III domain is thought to be both necessary and sufficient for binding to αVβ33. The studies described herein compared the integrin binding properties of wtFN10 to those of a high affinity form (hFN10) selected for strong αVβ3 binding from a FN10 phage display library, where five residues N- and C-terminal to the RGD motif were randomized (see, e.g., Richards, J. et al. *Journal of*

*Molecular Biology* 326, 1475-1488, (2003)). In hFN10, the sequence $^{1492}$PRGDWNEG (SEQ ID NO: 60) replaces $^{1492}$GRGDSPAS (SEQ ID NO: 59) of wtFN10. Interestingly, KGDWN (SEQ ID NO: 68) is the core sequence of the disintegrin barbourin (on which the drug eptifibatide was based (see, e.g., Scarborough, R. M. *American Heart Journal* 138, 1093-1104 (1999)); the R-to-K substitution mediates barbourin specificity to platelet αIIbβ3 over αVβ3 (see. e.g., Xiao, T. et al. *Nature* 432, 59-67 (2004)).

Binding of fluoresceinated fluid-phase wtFN10 to wild-type αVβ3 (stably expressed in K562 cells (K562-αVβ3) was a low background in 1 mM concentrations of the physiological cations $Ca^{2+}$ and $Mg^{2+}$ ($Ca^{2+}/Mg^{2+}$)) was increased 10-fold by the integrin activator $Mn^{2+}$ (FIG. 1a), and 6-fold by an N339/S mutation in the βA domain (known to activate αVβ3 in vitro and in vivo) (FIG. 1b). By contrast, strong binding, 6-fold background, of fluoresceinated hFN10 to K562-αVβ3 occurred in $Ca^{2+}/Mg^{2+}$, and increased almost an addition 1.5 fold in $Mn^{2+}$ (FIG. 1a). Binding of hFN10 was similar both to wild type (WT) αVβ3 and to active αVβ3(N339/S) expressed on HEK293T cells (FIG. 1b). Surprisingly, while $Mn^{2+}$-driven binding of wtFN10 to WTαVβ3 induced expression of LIBS epitopes for mAbs AP5, LIBS-1 and LIBS-6, binding of hFN10 did not (FIG. 1c). This effect was observed whether αVβ3 was expressed artificially (on K562 cells) or constitutively (on melanoma M21 cells). In addition, the AP5 LIBS was not induced by binding of hFN10 to αVβ3(N339/S) (FIG. 1d). Global effects of binding were assessed by comparing the hydrodynamic radii of αVβ3-hFN10 and αVβ3-wtFN10 complexes using molecular sieve chromatography. The hydrodynamic radii differed significantly (FIG. 1e): wtFN10 increased the Stokes' radius (Rs) of αVβ3 in $Mn^{2+}$ to 6.6 nm, compared to the Rs in $Mn^{2+}$ alone (6.3 nm). But hFN10 had little effect on the Rs of αVβ3 in $Mn^{2+}$ (6.3 nm) or $Ca^{2+}/Mg^{2+}$ (6.0 nm vs. 5.9 nm without hFN10). There was extensive spreading of K562-αVβ3 cells on full-length FN or wtFN10, but little spreading occurred on hFN10 (FIG. 1f-h). Thus, several approaches showed that binding of hFN10 did not induce those structural rearrangements in αVβ3 usually accompanying outside-in signaling. These data suggested that hFN10 acts as a pure antagonist of αVβ3, without partial agonism.

To elucidate the structural basis for these effects, wtFN10 or hFN10 were soaked into preformed αVβ3 ectodomain crystals in 2 mM $MnCl_2$, and the crystal structures of αVβ3-wtFN10 and αVβ3-hFN10 were determined (FIG. 2, Table 1). Macromolecular-ligated αVβ3 was genuflected, with an additional electron density (ED) of FN10 at the integrin head (FIG. 2a,b). However, the orientation of FN10 relative to the βA domain changed considerably between the two complexes, which differed by a ~60° rotation around the RGD-loop (FIG. 2, inset). The RGD motif of wtFN10 and hFN10 bound αVβ3 identically and as cilengitide (see, e.g., Xiong, J. P. et al. *Science* 296, 151-155, (2002)): RGD inserted into the crevice between the Propeller and βA domains, and contacted both. But wtFN10 made additional contacts with the Propeller involving mannose 2271 (MAN2271) of the glycan at N266 (FIG. 3a), contributing to the ~40% increase in the size of the αVβ3/wtFN10 interface when compared with that of αVβ3/cilengitide. Glycosylation at N266 was abolished by an N266/Q mutation in αVβ3(N339/S). Adhesion of HEK293 cells expressing the doubly mutated integrin αV(N266/Q)β3(N339/S) to immobilized full-length FN was reduced by 56% vs. αVβ3(N339/S) (p=0.003, n=3) in $Ca^{2+}/Mg^{2+}$ buffer (FIG. 3a, inset). N266 is conserved in α5β1, where an equivalent mutation produced a similar anti-adhesive effect (see e.g., Nagae, M. et al. *The Journal of Cell Biology* 197, 131-140, (2012); and Sato, Y. et al. *The Journal of Biological Chemistry* 284, 11873-11881, (2009)).

By contrast to wtFN10, hFN10 did not contact MAN2271. It interacted more extensively with the βA domain, which may account for its different orientation on αVβ3 and the coordination patterns of $Mn^{2+}$ at MIDAS and ADMIDAS (FIG. 3b). hFN10-βA contacts centered on a π-π edge-to-face interaction of FN10-Trp1496 with Tyr122 from the al helix (FIG. 3b and inset), which sterically blocked the inward movement of al helix towards MIDAS observed in wtFN10-αVβ3 (FIG. 3c). Thus, hFN10-bound βA took the conformation of the unliganded inactive integrin (FIG. 3d). Replacing Trp1496 in hFN10 with a serine to produce hFN10W/S or substituting Tyr122 with alanine to produce αVβ3(Y122/A) converted hFN10 into a partial agonist, as reported by binding of mAb AP5 to cellular αVβ3 (FIG. 3e). These findings support the role of the inward movement of helix al in ligand-induced outside-in integrin signaling. In αVβ3-hFN10, αVβ3 also displayed other features of the inactive state, which were absent from αVβ3-wtFN10. These included electrostatic interactions between αV and β3 subunits and within the β3 subunit, suggesting that in the hFN10-bound form, αVβ3 was at or close to an inactive state that would not transduce outside-in signals, despite overt ligand occupancy.

The core RGDWN (SEQ ID NO: 69) sequence in hFN10 matches that in the αIIbβ3 partial agonist barbourin. Superposition of the R/KGD-containing loops in hFN10, barbourin (pdb id 1q7j) and eptifibatide (pdb id 2vdn) showed that the tryptophan side-chains of barbourin and eptifibatide point towards the center of their R/KGD loops (FIG. 4a), and away from the critical Tyr122 side chain, thus permitting the activating inward movement of the al helix seen in βA-bound eptifibatide. The three loop residues flanking the RGDWN (SEQ ID NO: 69) sequence from hFN10 (TPRGDWNE) (SEQ ID NO: 61) were mutated to match barbourin (IAKGDWND) (SEQ ID NO: 70), and this hFN10/B domain was purified. The crystal structure of the αVβ3-hFN10/B complex showed that the RGD-containing loop was visible in the Fo-Fc omit map but the rest of hFN10/B domain was not, likely reflecting flexibility at the new N- and C-termini of the RGD-containing loop. It was clear, however, that the main-chain structure of this loop changed to position the Cα and Cβ of Trp1496 in the αVβ3-hFN10/B complex to match barbourin and eptifibatide (FIG. 4b). The Trp1496 side-chain of hFN10/B repositioned to no longer face the Tyr122 side-chain of the al helix, which let Tyr122 move freely inwards, as in the eptifibatide-bound integrin structure, with metal coordination at MIDAS and LIMBS returning to those found in αVβ3-wtFN10 (FIG. 4c). In agreement, it was found that binding of both hFN10/B and wtFN10 to cellular αVβ3 induced similar expression of AP5 LIBS (FIG. 4d). Thus, altering side-chain orientation of Trp1496 by design or by selection of its local environment dramatically affected those tertiary/quaternary changes known to be induced by binding of RGD-based ligands. It may be possible to replicate this effect, for example, in a cyclized form of the RGD-containing loop of hFN10, or by changing the orientation of Trp side-chain in from the L- to the D isomer, for example, in a modified eptifibatide. The critical 3 Å-Tyr122 is conserved in both α5β1 and β2 integrins, which like αVβ3 are drug targets. Our surprising results clearly suggest a path to a structure-based drug design of a new generation of ligand-mimetic integrin inhibitors that can act as pure antagonists.

Example 2. Generation, Expression and Testing of Mutated Forms of Knottin Based on the hFN10 RGD-Containing Loop cDNA encoding c-terminal his-tagged rEETI 2.5F knottin (Moore et al., PNAS 2013) was synthesized and fused at the c-terminus to the Fc fragment of human IgG in a mammalian expression vector. Modified versions of WT rEETI 2.5F were generated by site-directed mutagenesis.

```
                                                     (SEQ ID NO. 21)
G-C-P-R-P-R-G-D-N-P-P-L-T-C-S-Q-D-S-D-C-L-A-G-C-V-

C-G-P-N-G-F-C-G (WT 2.5F)
                                                     (SEQ ID NO. 3)
G-C-P-R-P-R-G-D-W-N-E-G-T-C-S-Q-D-S-D-C-L-A-G-C-V-

C-G-P-N-G-F-C-G (M);
                                                     (SEQ ID NO: 50)
G-C-P-R-P-R-G-D-W-N-E-G-S-C-S-Q-D-S-D-C-L-A-G-C-V-

C-G-P-N-G-F-C-G;
                                                     (SEQ ID NO. 4)
G-C-P-R-P-R-G-D-W-N-P-L-T-C-S-Q-D-S-D-C-L-A-G-C-V-

C-G-P-N-G-F-C-G (M1)
```

The wild type and modified versions were transiently expressed in HEK293 cells grown in 3% FBS. Culture supernatant contained equivalent amounts of the respective fusion proteins (verified by ELISA) and of the correct size (using western blotting with anti-his tag antibody). Binding of each to K562 cells expressing recombinant αVβ3 (K562-αVβ3) was examined using FACS as described in the methods section of the above-referenced paper, except that the unlabeled bound knottin was detected by adding fluoresceinated anti-human Fc mAb. M1 bound better than M but binding was significantly less than that of WT to cellular αVβ3 (FIG. 6A) in physiologic concentrations of $Ca^{2+}$ and $Mg^{2+}$ (1 mM of each). WT 2.5F knottin acted as a partial agonist (i.e. it induced binding of LIBS mAb AP5). In contrast, binding of M1 induced minimal AP5 expression (FIG. 6B). This reduction cannot be explained by the reduced binding of M1 per se, suggesting that the introduced change reduced/reversed partial agonism.

Example 3. Design and Structural Characterization of Eptifibatide Derivatives

Based on the hypothesis that introduction of a π-π interaction with Y122 will generate pure synthetic antagonists, Eptifibatide is modified in several ways. First, the tryptophan residue in Eptifibatide, which is directed away from Y122 in its co-crystal structure, is inverted (FIG. 7A). Based on modeling studies, incorporation of a D-tryptophan (e.g. E-1) would place the indole proximal to Y122, allowing for the desired π-π interaction. Smaller electron-rich heterocycles, such as pyrrole and thiophene, which would be less sterically demanding, are also investigated.

A second approach is to transpose the indole ring to backbone amide of an alanine that will replace the proline residue (e.g. E-2). The rationale for this change is the proximity of this amide to Y122. Although a two-carbon linker is shown connecting the indole to the amide, other tether lengths are examined. If removal of the proline is not tolerated, then this residue is replaced with a 4-hydroxy-L-proline (either cis or trans) that incorporates a tethered indole to the hydroxyl group (e.g. E-3). Again, this would position the indole close to Y122.

All Eptifibatide derivatives are synthesized using standard peptide chemistry from the C-terminus starting with S-trytyl cysteine amide followed by incorporation of homoarginine (or arginine) and D-tryptophan (Takahashi et al, Organic letters 14: 4514-4517, 2012). Cyclization to form the disulfide bond will be carried out using iodine mediated oxidative coupling (Kamber et al, Helvetica chimica acta 63: 899-915, 1980). Finally the protecting groups will be removed using TFA. Modified amino acids, e.g. N-alkylated L-alanine and O-alkylated 4-hydroxy-L-proline, are used to generate E-2 and E-3.

Example 4. Design and Structural Characterization of Tirofiban Derivatives

Tirofiban is a small molecule partial agonist that has been crystalized with αIIbβ3 head segment (2vdm.pdb). An analysis of this structure revealed that the molecule makes several key interactions with the protein, including an ionic interaction between the carboxylate and the $Mg^{2+}$ (2.4 Å), two water mediated H-bonds with the ether (2.9 Å and 3.5 Å) and a salt bridge between the piperidine nitrogen and D224 (3.1 Å). In addition, the sulfonamide NH forms a H-bond with the backbone carbonyl of N215 (2.8 Å) and one of the oxygen atoms of the sulfonamide forms a H-bond with the guanidine NH of R214 (3.1 Å). The sulfonamide portion of the molecule is most proximal to Y122. Therefore, to design derivatives that maintain the H-bonding network of the sulfonamide, various mimetics were selected for introduction of an indole (or similar heterocycle) (FIG. 7B). For example, the sulfonamide was replaced with an amidine (TA-1 and TA-2) or phosphate (TA-5), or an E- or Z-α,β-unsaturated sulfonamide (TA-3 and TA-4). Each of these structures would also preserve similar H-bonding capabilities as the parent compound. In each case, the energy minimized structures positioned the indole in a relative conformation that would allow its interaction with Y122 when bound to the receptor. Each structure was then docked in the protein using Glide, and the overall fit assessed by docking scores, internal ligand strains and overlap with bound Tirofiban. Based on this analysis, TA-6 had a good overlap with Tirofiban and maintained all of the critical interactions (FIG. 7C). Interestingly, the n-Pr group overlapped with the n-Bu of Tirofiban, while the OEt group of TA-5 did not, likely due to its hydrophilicity. Consequently, TA-6 placed the indole proximal to Y122. Based on these results, two additional compounds were designed (TA-7 and TA-8), which shortened the tether to the indole and increased steric bulk on phosphorous to further improve π-π interaction. TA-6, -7 and -8 will be prepared in a straightforward manner. The amino acid portions are generated using published methodology (Chung et al, (1993) Tetrahedron 49: 5767-5776) and phosphonamide moiety introduced using reported procedures (Viertler et al., Bioorganic & Medicinal Chemistry 20:628-632, 2012; Zhou et al. The Journal of organic chemistry 75:7924-7, 2010)).

Example 5. Design and Structural Characterization of hFN10 Derivatives

A wild type hFN10 sequence is as follows:

(SEQ ID NO: 71)
(His)GS-
SDVPRDLEVVAATPTSLLISWDAPAVIVRYYRITYGEIGGNSPVQEFTV
PGSKSTATISGLKPGVDYTITVYAVTP<u>RGDW</u>NEGSKPISINY

This hFN10 sequence was altered to enable it to bind $\alpha_{IIb}\beta_3$, as follows; each peptide included a thrombin cleavage site:

hFN10 R/K (hR/K)-
(SEQ ID NO: 15)
(His)GS-
SDVPRDLEVVAATPTSLLISWDAPAVTVRYYRITYGETGGNSPVQEFTVP
GSKSTATISGLKPGVDYTITVYAVTP<u>KGDW</u>NEGSKPISINY hFN10 R/K (hR/K + ΔSDV + ΔSK = G)
(SEQ ID NO: 72)
(His)GS-
SDVPRDLEVVAATPTSLLISWDAPAVIVRYYRITYGEIGGNSPVQEFTVP
GSKSTATISGLKPGVDYTITVYAVTP<u>KGDW</u>NEGGPISINY hFN10 R/K + SD deletion (hR/K-ΔSD)
(SEQ ID NO: 16)
(His)GS---
VPRDLEVVAATPTSLLISWDAPAVIVRYYRITYGEIGGNSPVQEFTVPGS
KSTATISGLKPGVDYTITVYAVTP<u>KGDW</u>NEGSKPISINY hFN10 R/K + ΔSD + SK deletion (hR/K-ΔSD-ΔSK)
(SEQ ID NO: 17)
(His)GS---
VPRDLEVVAATPTSLLISWDAPAVIVRYYRITYGEIGGNSPVQEFTVPGS
KSTATISGLKPGVDYTITVYAVTP<u>KGDW</u>NEGPISINY The following controls were used to make sure the deletions did not impair hFN10 binding to $\alpha_v\beta_3$:

hFN10 + SD deletion (hΔSD)
(SEQ ID NO: 18)
(His)GS---
VPRDLEVVAATPTSLLISWDAPAVTVRYYRITYGETGGNSPVQEFTVPG
SKSTATISGLKPGVDYTITVYAVTP<u>RGDW</u>NEGSKPISINY hFN10 + ΔSD + SK deletion (hΔSD-ΔSK)
(SEQ ID NO: 19)
(His)GS---
VPRDLEVVAATPTSLLISWDAPAVTVRYYRITYGETGGNSPVQEFTVPG
SKSTATISGLKPGVDYTITVYAVTP<u>RGDW</u>NEG-PISINY These compounds can be screened, e.g., in a phage display assay, e.g., wherein residues N- and C-terminal to the RGDW (SEQ ID NO: 54) or RGDWN (SEQ ID NO: 69) motif are randomized (see, e.g., Richards, J. et al. Journal of Molecular Biology 326, 1475-1488, (2003)), to identify inhibitors of other integrins.

Example 6. Modification of hFN10 to Increase Binding to αIIbβ3

Various modifications to hFN10 were made to extend the reach of the Arg1493 sidechain to engage the a-subunits propeller domain and convert hFN10 into a pure antagonist of the αIIbβ3 integrin.

First, a glycine was inserted after proline 1492 of hFN10 by site-directed mutagenesis to generate hFN10-G (FIG. 9A)(SDVPRDLEVVAATPTSLLISWDAPAVTVRYYRI-TYGETGGNSPVQEFTVPGS KSTATIS-GLKPGVDYTITVYAVTPGRGDWNEGSKPISINY (hFN10-G) (SEQ ID NO: 29)). Molecular dynamic simulations (MDS) was performed as follows. All atom simulations of αV Propeller domain and 17E6 Fab were performed with the program NAMD, using CHARMM27 force field (Phillips et al. (2005) Journal of computational chemistry 26, 1781-1802; Mehrbod et al. (2013) Biophysical journal 105, 1304-1315; Mehrbod, M., and Mofrad, M. R. (2013) PLoS computational biology 9, e1002948). The temperature and pressure of the system were held constant at 310K and 1 atm, respectively, using the Langevin's piston and Hoover's method, as successfully used previously for modeling integrins (Phillips et al. (2005) Journal of computational chemistry 26, 1781-1802; Mehrbod et al. (2013) Biophysical journal 105, 1304-1315; Mehrbod, M., and Mofrad, M. R. (2013) PLoS computational biology 9, e1002948; Chen et al. (2011) PLoS computational biology 7, e1001086). The time step was taken as 2 femtoseconds (fs). The cutoff distance for non-bonded interactions was 1.2 nm and the Particle Mesh Ewald (PME) method was used for electrostatic force calculations (Phillips et al. (2005) Journal of computational chemistry 26, 1781-1802). Hydrogen atom bond length was constrained using SHAKE (Krautler et al. (2001) Journal of computational chemistry 22, 501-508). All systems were minimized, at 20,000 steps, and equilibrated for 40 nanoseconds (ns).

Interactions were simulated using the crystal structure of αVβ3 headpiece (Propeller+βA domains) in complex with the respective (hFN10, knottin, eptifibatide). Mutations were made in the ligand structure using the software Swiss-Pdb Viewer 4.1.0 (Guex, N., and Peitsch, M. C. (1997) Electrophoresis 18, 2714-2723). The integrin and ligand molecules were shifted by ~1 Å from their original bound state to compare the effects of the mutations. Each of the three systems was solvated in a water box of 188×127×139 Å in size and ionized with 150 mM NaCl to represent the solvent.

The association constant ($k_a$) of integrin-ligand interaction was calculated according to equation 1:

$$k_a = e^{\frac{-\Delta G}{k_B T}} \quad \text{(Eq. 1)}$$

where ΔG, kB, and T are the free energy of association per mole, Boltzmann constant, and temperature, respectively. Gibbs free energy was calculated according to equation 2:

$$G = U + PV - TS \quad \text{(Eq. 2)}$$

where U, P, V, S and T are the interaction energy, pressure, volume, entropy, and temperature (at 310K), respectively. Interaction energy was computed as the sum of the electrostatic and van der Waals energies. The ratio of $k_a$ for mutant to that of wild-type structure was derived according to equation 3:

$$\frac{k_{a-mu}}{k_{a-wt}} \cong \frac{e^{\frac{-\Delta U_{mu}+T\cdot\Delta S_{mu}}{k_B T}}}{e^{\frac{-\Delta U_{wt}+T\cdot\Delta S_{wt}}{k_B T}}} \cong e^{\frac{-\Delta U_{mu}+\Delta U_{wt}}{k_B T}} \quad \text{(Eq. 3)}$$

See also Rui et al., J Biol Chem. 2014 Aug. 15; 289(33): 23256-63 and Mahalingam et al., J Biol Chem. 2014 May 16; 289(20):13801-9.

The MDS predicted that hFN10-G has lower energy of interaction with αIIbβ3 when compared with hFN10/αIIbβ3 energy of interaction. Expressed fluorescein-tagged hFN10-G showed some binding to preactivated cellular αIIbβ3 (activation was achieved by an N339 to S mutation, αIIbβ3$^{N/S}$). The degree of binding was lower that of hFN10 to αVβ3, as predicted by MDS. Nevertheless, binding was specific in that hFN10-G did not bind cellular preactivated αVβ3 (αVβ3N/S) (FIG. 9C).

To further increase affinity of hFN10-G to αIIbβ3, a second mutant sequence was prepared by inserting a glycine before proline 1492 of hFN10-G by site-directed mutagenesis to generate hFN10-GPG (FIG. 10) (SDVPRDLEVVAATPTSLLI SWDAPAVTVRYYRITY-GETGGNSPVQEFTVPGSKSTATIS-GLKPGVDYTITVYAV TGPGRGDWNEGSKPISINY (hFN10-GPG) (SEQ ID NO: 30). MDS predicted that hFN10-GPG has equivalent energy of interaction with αIIbβ3 (80±12) as hFN10 has with αVβ3 (83±21), and that Trp1496 interacts with Tyr122 of the integrin although this interaction is weaker (2.6±1.0) that in hFN10/αVβ3 (4.4±1.1) (FIG. 10).

Example 7. Crystal Structure of αVβ3 Bound to the Partial Agonist Knottin 2.5F and Modifications to Produce a Pure Antagonist A 37-amino acid cysteine-knot peptide, knottin 2.5F, was cloned based on its published sequence (Kimura et al, *Cancer Res* 2009; 69: 2435-42). It was then expressed as a knottin 2.5F-Fc fusion protein in HEK293 T cells, and shown to act as a partial agonist of integrin αVβ3. Using chemically synthesized knottin 2.5F, its crystal structure was determined in complex with αVβ3.

The crystal structure of αVβ3-2.5F was determined at 3-3.1 Å resolution as follows: αVβ33 ectodomain was crystallized at 4° C. by vapor diffusion using the hanging drop method as previously described (Xiong, J. P. et al. The Journal of Cell Biology 186, 589-600 (2009)). The purified modified knottin 2.5F peptides (Moore et al, 2013, PNAS, 110:14598-603) were soaked into αVβ3 crystals in the crystallization well solution containing 2 mM Mn$^{2+}$ for 2-3 weeks. Crystals were harvested in 12% PEG 3500 (polyethylene glycol, molecular weight 3500) in 100 mM sodium acetate, pH 4.5, 800 mM NaCl plus 2 mM Mn$^{2+}$ and FN10 (at 1.5 mM), cryoprotected by addition of glycerol in 2% increments up to 24% final concentration, and then flash-frozen in liquid nitrogen. Diffraction data from cryocooled crystals were collected on the ID19 beamline fitted with a CCD detector at the APS Facility (Chicago, IL). Data were indexed, integrated and scaled with HKL2000 program (Otwinowski and Minor, Methods Enzymol. 276, 307-326 (1997)) for αVβ33-2.5F and αVβ3-2.5D using the same Rfree set imported from pdb id 4MMX.pdb structure factors. Phases were determined by molecular replacement using PHASER (McCoy et al., Journal of Applied Crystallography 40, 658-674 (2007)), with structures of liganded αVβ3 ectodomain (pdb id 4MMX) and NMR structure of unmodified knottin used as search models. The resulting models were refined with 1.8.4 version of Phenix 11 11 (Adams et al., Acta Crystallogr D Biol Crystallogr 66, 213-221(2010)) using simulated annealing, TLS, positional and individual temperature-factor refinement, and default restrains. Several cycles of refinement and model building using Coot (Emsley et al., Acta Crystallogr D Biol Crystallogr 60, 2126-2132 (2004)) were applied to refine the complex structures, with automatic optimization of X-ray and stereochemistry/ADP, and additional Ramachandran restrains in last cycles.

TABLE 8

Data collection and refinement statistics (molecular replacement)

| | αvβ3/knottin2.5f |
|---|---|
| Data collection | |
| Space group | P3221 P3221 |
| Cell dimensions | |
| a, b, c (Å) | 129.8, 129.8, 305.2 |
| α, β, γ (°) | 90, 90, 120 |
| Resolution (Å) | 50-3.0* |
| R$_{sym}$ or R$_{merge}$ | 13.7 (100)# |
| I/σI | 14.7 (1.6) |
| Completeness (%) | 100 (99.9) |
| Redundancy | 7.3 (7.0) |
| Refinement | |
| Resolution (Å) | 44.5-3.1 |
| No. reflections | 60, 231 |
| R$_{work}$/R$_{free}$ | 22.3/27.7 |
| No. atoms | 13, 155 |
| Protein | 13, 144 |
| Ligand/ion | 8 |
| Water | 3 |
| B factors | |
| Protein | 123.9 |
| Integrin | 123.2 |
| FN10 | 165.5 |
| Bond lengths (Å) | 0.006 |
| Bond angles (°) | 1.3 |

*1 crystal.
Values in parentheses are for highest-resolution shell.

The coordinates of the αVβ3-2.5F crystal are given in Table 6, which is submitted herewith in .txt format.

Analysis of the structures showed that the RGD containing loop of knottin 2.5F bound to the integrin, but simultaneously activated the integrin as reflected by inward movement of the al helix (reported by movement of Tyr122 (brown in original), compared to the position of Tyr122 in inactive αVβ3 complexed with hFN10 (gray residues in original) (FIG. 11). Trp1496 of hFN10 was replaced by Proline-10 (P10) in the RGDNP sequence (SEQ ID NO: 86) of bound knottin 2.5F. Since knottin 2.5F also binds integrins αVβ5 and 051 (Moore et al, 2013, *PNAS,* 110:14598-603), it is expected to also act as a partial agonist in these receptors.

Several approaches can be used to convert knottin 2.5F based on the knottin 2.5F/αVβ3 crystal structure, where Proline 10 (P10) faces Tyr122 but does not block its movement (FIG. 12A). Placing a bulky residue at the 10$^{th}$ position is expected to convert knottin 2.5F into a pure antagonist. Models have been generated where P10 is replaced with Trp (FIG. 12B), or the unnatural amino acids phenylproline (pP) (FIG. 12C) and phenylglycine (pG) (FIG. 12D).

Wild type and P/W substituted forms of knottin 2.5F were expressed as Fe fusion proteins in mammalian cells and their abilities to bind cellular αVβ3 and to express the LIBS mAb AP5 were compared. αVβ3-K562 (1×10⁶) cells were suspended in 100 µl of culture supernatant containing equivalent amounts (based on ELISA) of WT knottin 2.5F-Fc fusion protein, knottin 2.5F (P/W)-Fc, WT knottin 2.5D-Fc, or knottin 2.5F (A/W)-Fc or medium alone and incubated for 30 min; 25° C., washed in 400 µl buffer and fluoresceinated anti-FC-specific antibody added for an additional 30 min at 4° C. Cells were washed, resuspended, fixed in 4% paraformaldehyde, and analyzed using FACSCalibur or BD-LSRII flow cytometers (BD Biosciences). Binding of soluble knottin dimers to αVβ3-K562 cells was expressed as mean fluorescence intensity (MFI), as determined using FlowJo software. K562-αVβ3 cells were incubated in medium, unlabeled hFN10 (5 µg) or 100 µl of culture supernatant containing various knottin-Fc preps (30 min; at 25° C.). Alexa647-labeled mAb AP5 Fab (10 µg/ml) was added, and cells incubated for an additional 30 min before washing. APC-labeled goat anti-mouse Fc-specific antibody was added to anti-LIBS-1- or anti-LIBS-6-bound M21 cells for an additional 30 min at 4° C. Cells were then washed, resuspended, fixed in 4% paraformaldehyde and analyzed by flow cytometry. AP5 epitope expression was measured and expressed as MFI.

It has been shown that binding of wild type and P/W knottin 2.5F to cellular αVβ3 is equivalent (FIG. 13). However, bound P/W suppressed AP5 expression vs. wild-type knottin 2.5F, suggesting that the mutant acts as a pure antagonist.

Example 8. Crystal Structure of βVβ3 Bound to the Partial Agonist Knottin 2.5D and Modifications to Produce a Pure Antagonist Using chemically synthesized knottin 2.5D, its crystal structure in complex with αVβ3 (αVβ3-2.5D) was determined at 3-3.1A as described above in Example 7.

TABLE 9

Data collection and refinement statistics (molecular replacement)

| | αvβ3/knottin2.5d |
|---|---|
| Data collection | |
| Space group | P3221 |
| Cell dimensions | |
| a, b, c (Å) | 129.7, 129.7, 305.9 |
| α, β, γ (°) | 90, 90, 120 |
| Resolution (Å) | 49.2-3.0 |
| $R_{sym}$ or $R_{merge}$ | 15.3 (100) |
| I/σI | 9.6 (1.0) |
| Completeness (%) | 99.8 (99.9) |
| Redundancy | 4.7 (3.6) |
| Refinement | |
| Resolution (Å) | 49.2-3.0 |
| No. reflections | 60, 166 |
| $R_{work}/R_{free}$ | 24.4/27.9 |
| No. atoms | 13, 135 |
| Protein | 13, 125 |
| Ligand/ion | 8 |
| Water | 2 |
| B factors | |
| Protein | 124.2 |
| Integrin | 122.9 |
| FN10 | 210.81 |

TABLE 9-continued

Data collection and refinement statistics (molecular replacement)

| | αvβ3/knottin2.5d |
|---|---|
| Bond lengths (Å) | 0.005 |
| Bond angles (°) | 1.1 |

*1 crystal.
Values in parentheses are for highest-resolution shell.

The coordinates of the αVβ3-2.5D crystal are given in Table 7, which is submitted herewith in .txt format.

The RGD containing loop of knottin 2.5D bound to the integrin, but simultaneously activated it as reflected by inward movement of the al helix (reported by movement of Tyr122 (green in original), compared to the position of Tyr122 in inactive αVβ3 complexed with hFN10 (residues shown as gray in original) (FIG. 14). Trp1496 of hFN10 was replaced here by Alanine-10 (A10) in the RGDWA (SEQ ID NO: 87) sequence.

Note that although knottin 2.5D has the same basic motif (RGDW) (SEQ ID NO: 54) as hFN10, the Trp points inwards (as in Barbourin and eptifibatide), with the next residue (A10) now facing Y122. Again, as A10 lacks a bulky sidechain, it did not prevent the inward movement of Tyr122, accounting for its integrin-activating property.

Figure 12:
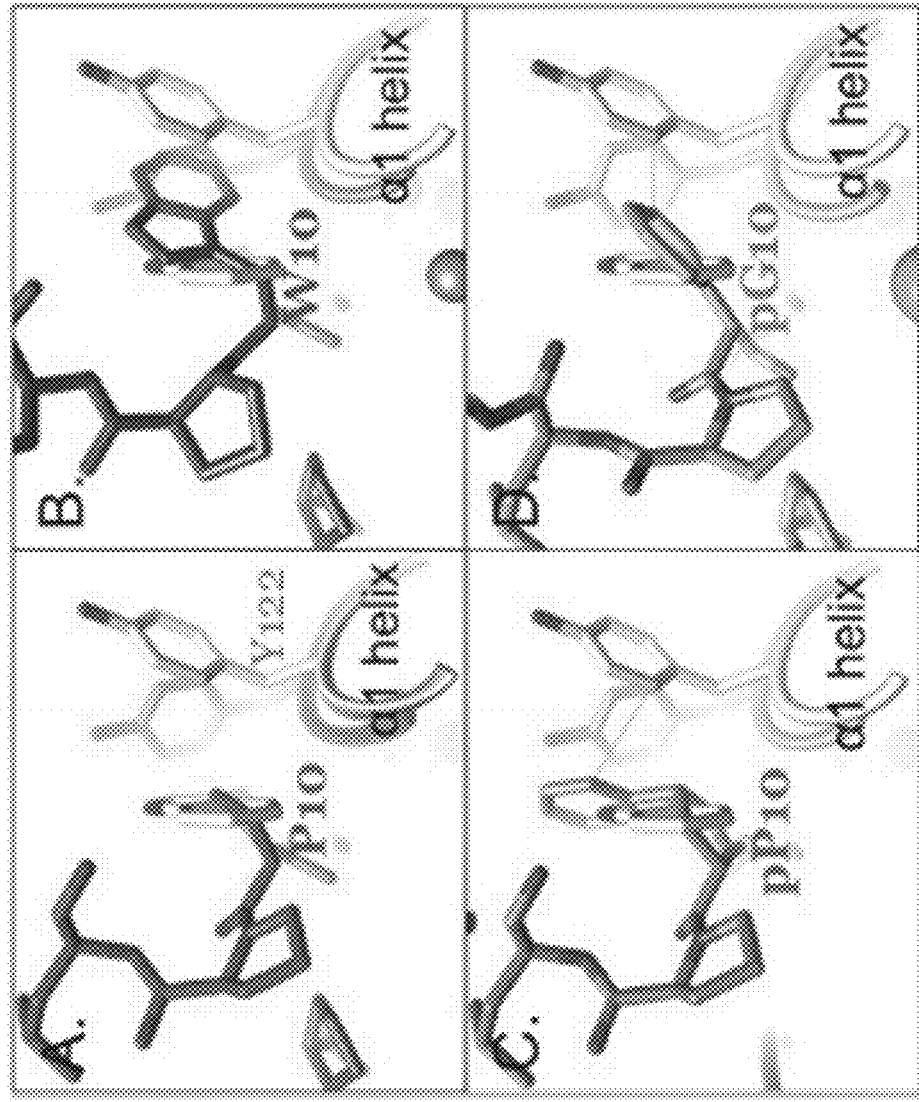

Structure models of knottin 2.5D complexed to the integrin as in FIG. 12, where A10 was replaced with a Trp (A/W), a phenylproline (A/pP) or a phenylglycine (pG) were generated.

Wild type and A/W substituted forms of knottin 2.5D were expressed as Fc fusion proteins in mammalian cells and their abilities to bind cellular αVβ3 and to express the AP5 epitope were compared (FIG. 15). αVβ3-K562 (1×10⁶) cells were suspended in 100 µl of culture supernatant containing equivalent amounts (based on ELISA) of WT knottin 2.5F-Fc fusion protein, knottin 2.5F (P/W)-Fc, WT knottin 2.5D-Fc, or knottin 2.5F (A/W)-Fc or medium alone and incubated for 30 min; 25° C., washed in 400 µl buffer and fluoresceinated anti-FC-specific antibody added for an additional 30 min at 4° C. Cells were washed, resuspended, fixed in 4% paraformaldehyde, and analyzed using FACSCalibur or BD-LSRII flow cytometers (BD Biosciences). Binding of soluble knottin dimers to αVβ3-K562 cells was expressed as mean fluorescence intensity (MFI), as determined using FlowJo software. K562-αVβ3 cells were incubated in medium, unlabeled hFN10 (5 µg) or 100 µl of culture supernatant containing various knottin-Fc preps (30 min; at 25° C.). Alexa647-labeled mAb AP5 Fab (10 µg/ml) was added, and cells incubated for an additional 30 min before washing. APC-labeled goat anti-mouse Fc-specific antibody was added to anti-LIBS-1- or anti-LIBS-6-bound M21 cells for an additional 30 min at 4° C. Cells were then washed, resuspended, fixed in 4% paraformaldehyde and analyzed by flow cytometry. AP5 epitope expression was measured and expressed as MFI.

Slightly reduced binding of wild type and A/W knottin 2.5D to cellular αVβ3 compared to wild type was observed. Bound A/W suppressed AP5 expression vs. wild-type knottin 2.5D, as expected of a pure antagonist.

Example 9. Synthesis of a Modified Eptifibatide
A modified eptifibatide was prepared as shown in Scheme 2
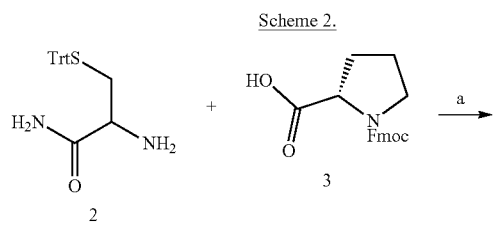
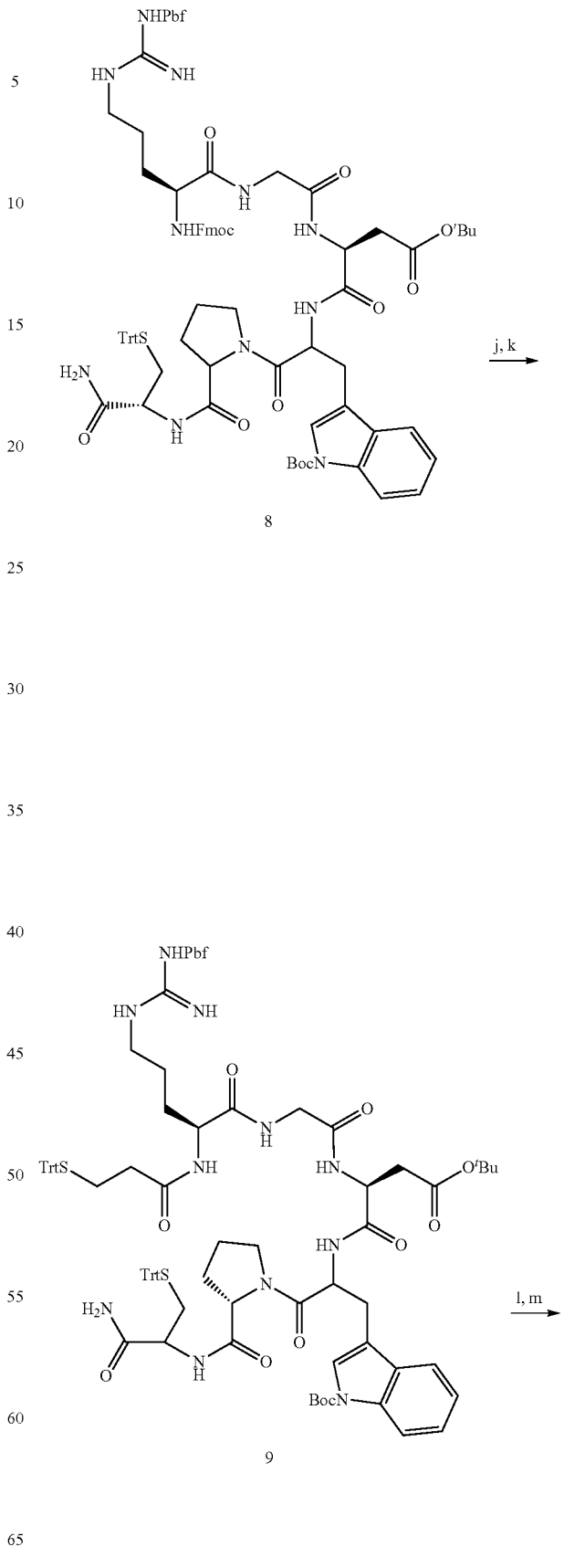

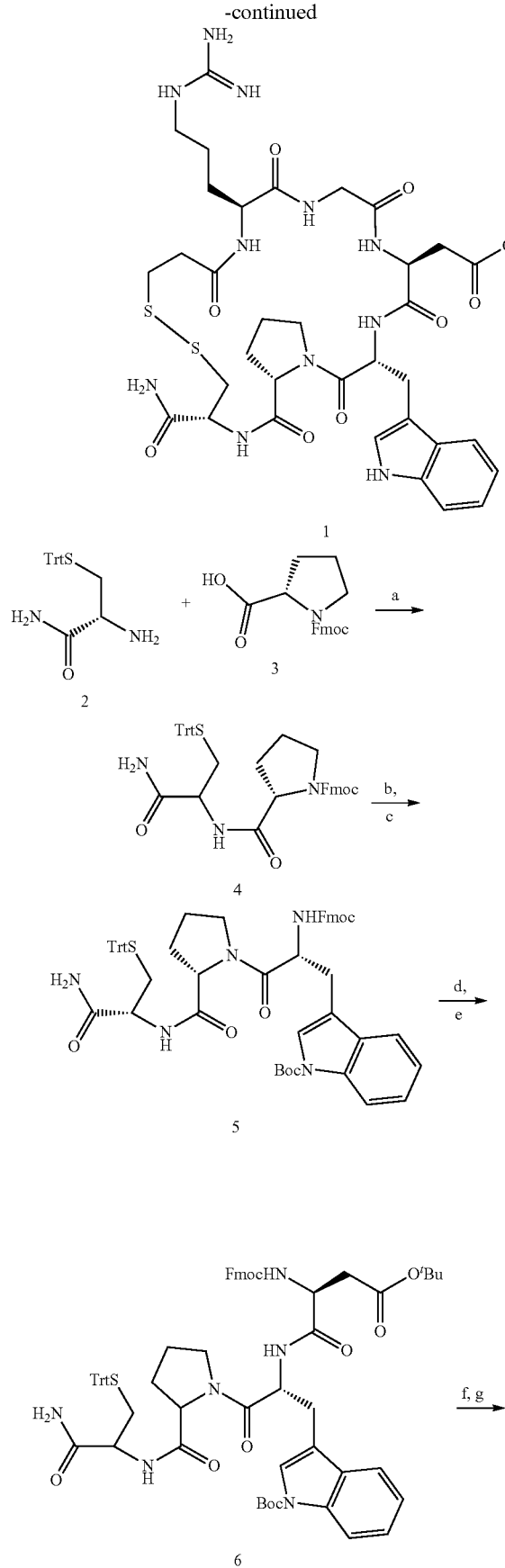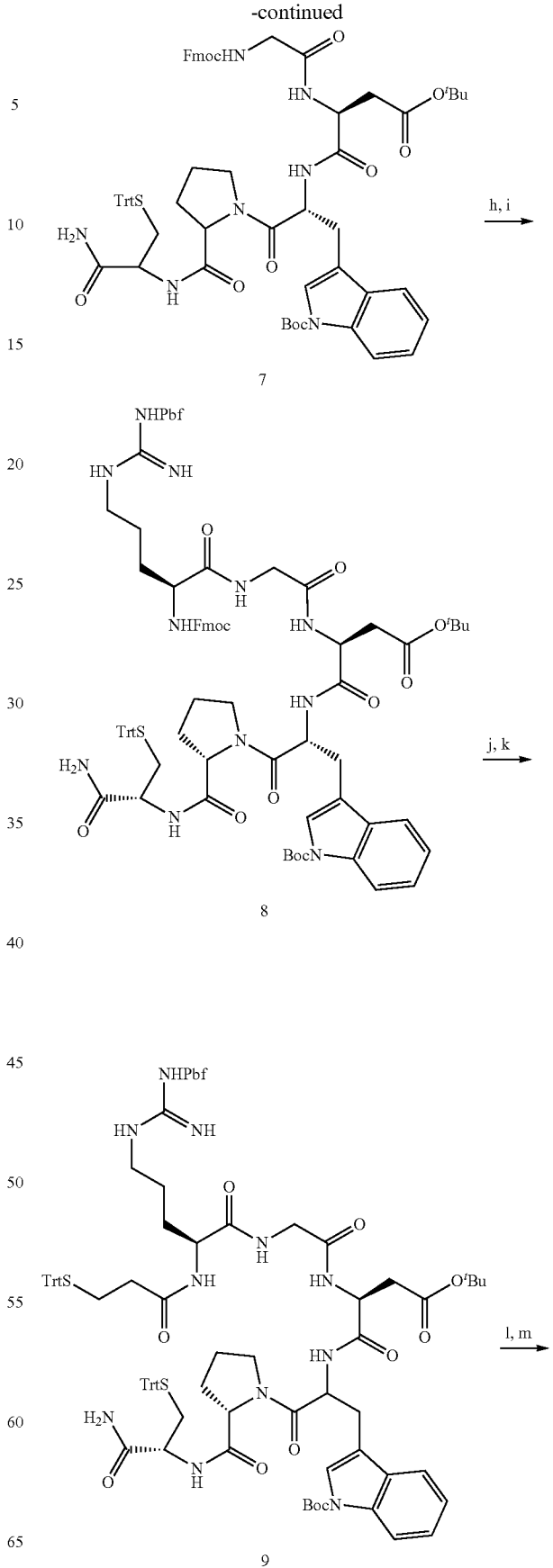

-continued

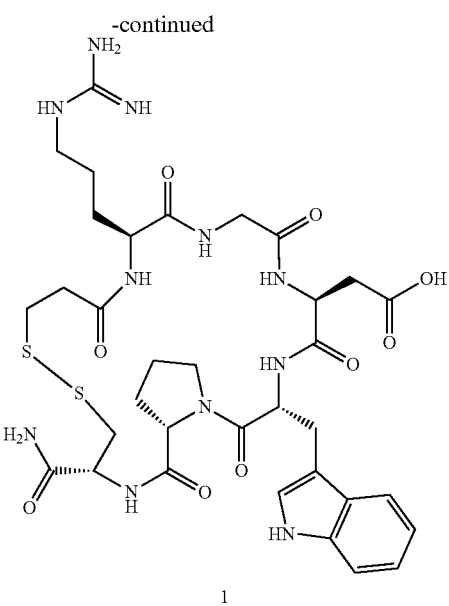

1 a) EDC, Hot, DMF, 98%;
b) piperidine, DMF, 97%;
c) Fmoc-D-Trp(Boc)-OH, EDC, HOAt, DMF, 95%;
d) piperidine, DMF, 96%;
e) Fmoc-L-Asp(tBu)-OH, EDC, HOAt, DMF, 98%;
f) piperidine, DMF, 96%;
g) Fmoc-Gly-OH, EDC, HOAt, DMF, 95%;
h) piperidine, 86%;
i) Fmoc-L-Arg(Pbf)-OH, EDC, HOAt, DMF, 91%;
j) piperidine, DMF, 89%;
k) 3-(Tritylthio)propionic acid, EDC, HOAt, DMF, 97%;
l) I$_2$, DCM/MeOH, 42%;
m) TFA, 78%.

Briefly, protected cysteine amide 2 was coupled to Fmoc-proline 3 to give 4, which was de-protected and coupled to a diprotected R-tryptophan derivative to give 5. Several additional Fmoc-de-protection/coupling sequences were performed, including use of the t-butyl ester of aspartic acid and a Pbf-protected arginine derivative, to give 8. Next 3-(tritylthio) propionic acid was installed to give 9, and de-protective cyclization to form the disulfide was induced in presence of iodine (Kambes et al, *Helv Chem Acta,* 1980, 63: 899-915) followed by removal of the remaining three acid-sensitive protecting groups in the presence of TFA. All intermediates were purified by normal-phase silica gel chromatography, except the final product, which was purified by reverse-phase chromatography followed by lyophilization to give an amorphous white powder that was characterized by $^1$H NMR and LC/MS, and demonstrated aqueous solubility characteristics similar to eptifibatide.

Figure 16A:
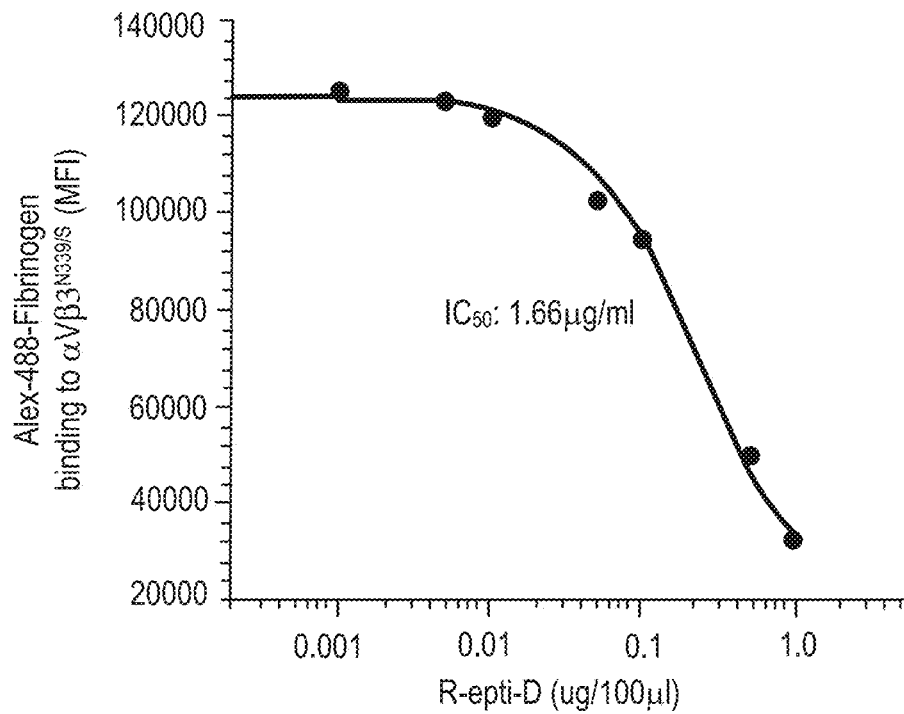
Figure 16B:
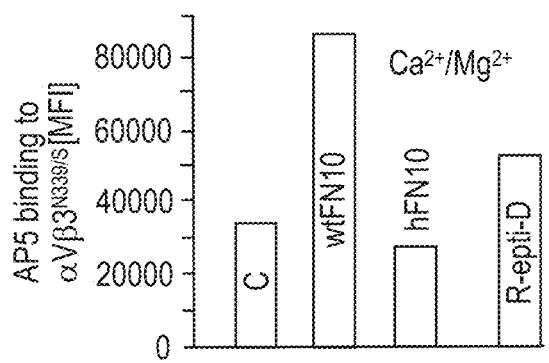
Figure 16C:
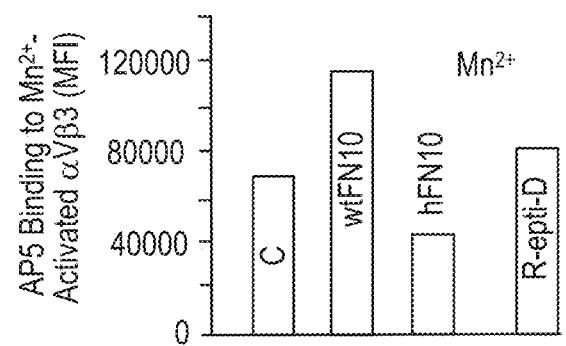

Example 10. Binding Properties of R-Epti-D and Crystal Structure of R-Epti-D/αVβ3 Complex While regular eptifibatide does not bind αVβ3, R-epti-D showed low affinity binding (IC50=1.7 µg/ml, ~2 µM) to constitutively active αVβ3N/S expressed on HEK293 cells (FIG. 16A). In a preliminary study, bound R-epti-D reduced AP5 LIBS expression on αVβ3$^N$/S or on Mn$^{2+}$-activated αVβ3, but to a lesser degree than that seen in the presence of hFN10 (FIG. 16B, C), suggesting that it may act as a weak but pure antagonist.

Figure 16D:
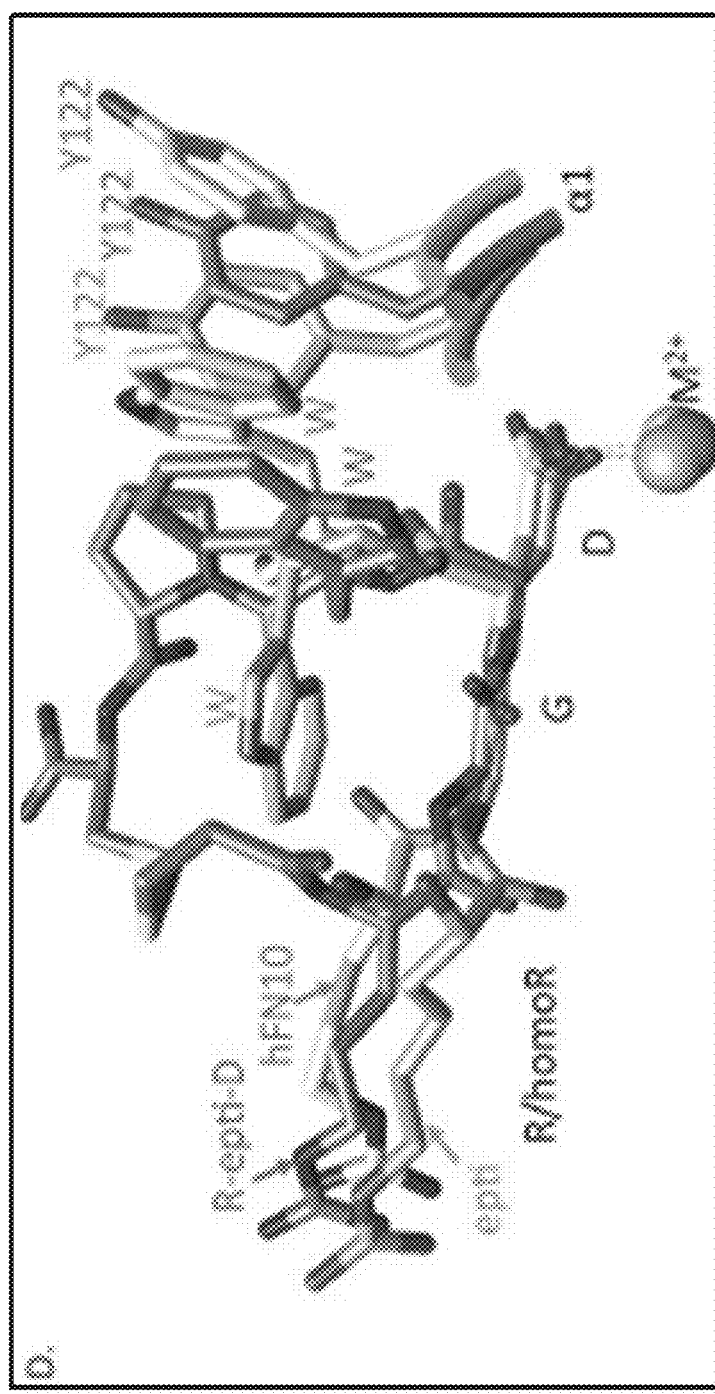

The crystal structure of the R-epti-D/αVβ3 complex was determined (FIG. 16D). It revealed the expected switch in the Trp side chain from the L to D position, which now pointed outwards towards the βA domain, but retarded the inward movement of Tyr122 only partially (FIG. 16D), explaining the partial suppression of LIBS expression seen experimentally. The low affinity R-epti-D/αVβ3 interaction was verified in molecular dynamics simulations.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A polypeptide consisting of the sequence (SEQ ID NO: 9)
SDVPRDLEVVAATPTSLLISWDAPAVTVRYYRITYGETGGNSPVQEFTVP
GSKSTATISGLKPGVDYTITVYAVTPRGDWNEGSKPISINY.

2. A pharmaceutical composition comprising a pharmaceutically acceptable carrier and the polypeptide according to claim 1.

3. A method of inhibiting integrin binding and activation on a cell, comprising contacting the cell with a therapeutically effective amount of the polypeptide of claim 1.

4. A method of treating one or more disorders selected from the group consisting of thrombosis, unstable angina, ischemic sudden death, diastolic dysfunction, transient ischemic attack, stroke, atherosclerosis, thrombophlebitis, arterial embolism, myocardial infarction, cerebral embolisms, kidney embolisms, pulmonary embolism, fibrosis, renal fibrosis, delayed graft function, diabetes, tumor angiogenesis, melanoma, cancer metastasis, diabetic nephropathy, diabetic retinopathy, neovascular glaucoma, restenosis, osteoporosis, multiple sclerosis, asthma, ulcerative colitis, random flaps, and macular degeneration, wherein the method comprises administering to a patient in need thereof a therapeutically effective amount of the polypeptide of claim 1.

5. The method of claim 4, wherein the thrombosis is selected from the group consisting of venous thrombosis, deep vein thrombosis, coronary arterial thrombosis, and cerebral arterial thrombosis.

6. The method of claim 4, wherein the myocardial infarction is selected from the group consisting of a first myocardial infarction and recurrent myocardial infarction.

7. A polypeptide consisting of the sequence (SEQ ID NO: 13)
VPRDLEVVAATPTSLLISWDAPAVTVRYYRITYGETGGNSPVQEFTVPGS
KSTATISGLKPGVDYTITVYAVTPRGDWNEGSKPISINY.

8. A pharmaceutical composition comprising a pharmaceutically acceptable carrier and the polypeptide of claim 7.

9. A method of inhibiting integrin binding and activation on a cell, comprising contacting the cell with a therapeutically effective amount of the polypeptide of claim 7.

10. A method of treating one or more disorders selected from the group consisting of thrombosis, unstable angina, ischemic sudden death, diastolic dysfunction, transient ischemic attack, stroke, atherosclerosis, thrombophlebitis, arterial embolism, myocardial infarction, cerebral embolisms, kidney embolisms, pulmonary embolism, fibrosis, renal fibrosis, delayed graft function, diabetes, tumor angiogenesis, melanoma, cancer metastasis, diabetic nephropathy, diabetic retinopathy, neovascular glaucoma, restenosis, osteoporosis, multiple sclerosis, asthma, ulcerative colitis, random flaps, and macular degeneration, wherein the method comprises administering to a patient in need thereof a therapeutically effective amount of the polypeptide of claim 7.

11. The method of claim 10, wherein the thrombosis is selected from the group consisting of venous thrombosis, deep vein thrombosis, coronary arterial thrombosis, and cerebral arterial thrombosis.

12. The method of claim 10, wherein the myocardial infarction is selected from the group consisting of a first myocardial infarction and recurrent myocardial infarction.

\* \* \* \* \*

SEQUENCE LISTING

```
<160> NUMBER OF SEQ ID NOS: 87

<210> SEQ ID NO 1
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Ala Val Thr Pro Arg Gly Asp Trp Asn Glu
1               5                   10

<210> SEQ ID NO 2
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(13)
```

```
<223> OTHER INFORMATION: Cyclic peptide
<220> FEATURE:
<221> NAME/KEY: MOD_RES
<222> LOCATION: (13)..(13)
<223> OTHER INFORMATION: D-Pro

<400> SEQUENCE: 2

Ala Val Thr Pro Arg Gly Asp Trp Asn Glu Gly Gly Pro
1               5                   10

<210> SEQ ID NO 3
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Gly Cys Pro Arg Pro Arg Gly Asp Trp Asn Glu Gly Thr Cys Ser Gln
1               5                   10                  15

Asp Ser Asp Cys Leu Ala Gly Cys Val Cys Gly Pro Asn Gly Phe Cys
            20                  25                  30

Gly

<210> SEQ ID NO 4
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Gly Cys Pro Arg Pro Arg Gly Asp Trp Asn Pro Leu Thr Cys Ser Gln
1               5                   10                  15

Asp Ser Asp Cys Leu Ala Gly Cys Val Cys Gly Pro Asn Gly Phe Cys
            20                  25                  30

Gly

<210> SEQ ID NO 5
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Gly Cys Ala Val Thr Pro Arg Gly Asp Trp Asn Glu Gly Ser Leu Pro
1               5                   10                  15

Cys Ser Gln Asp Ser Asp Cys Leu Ala Gly Cys Val Cys Gly Pro Asn
            20                  25                  30

Gly Phe Cys Gly
        35

<210> SEQ ID NO 6
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6
```

Gly Cys Val Arg Leu His Glu Ser Cys Leu Gly Gln Gln Val Pro Cys
1               5                   10                  15

Cys Asp Pro Ala Ala Thr Cys Tyr Cys Tyr Gly Arg Gly Asp Trp Asn
                20                  25                  30

Glu Gly Cys Tyr Cys Arg
            35

<210> SEQ ID NO 7
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Gly Cys Val Arg Leu His Glu Ser Cys Leu Gly Gln Gln Val Pro Cys
1               5                   10                  15

Cys Asp Pro Ala Ala Thr Cys Tyr Cys Tyr Gly Arg Gly Asp Trp Asn
                20                  25                  30

Leu Arg Cys Tyr Cys Arg
            35

<210> SEQ ID NO 8
<211> LENGTH: 43
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Gly Cys Val Arg Leu His Glu Ser Cys Leu Gly Gln Gln Val Pro Cys
1               5                   10                  15

Cys Asp Pro Ala Ala Thr Cys Tyr Cys Ala Val Thr Pro Arg Gly Asp
                20                  25                  30

Trp Asn Glu Gly Ser Lys Pro Cys Tyr Cys Arg
            35                  40

<210> SEQ ID NO 9
<211> LENGTH: 91
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Ser Asp Val Pro Arg Asp Leu Glu Val Val Ala Ala Thr Pro Thr Ser
1               5                   10                  15

Leu Leu Ile Ser Trp Asp Ala Pro Ala Val Thr Val Arg Tyr Tyr Arg
                20                  25                  30

Ile Thr Tyr Gly Glu Thr Gly Gly Asn Ser Pro Val Gln Glu Phe Thr
            35                  40                  45

Val Pro Gly Ser Lys Ser Thr Ala Thr Ile Ser Gly Leu Lys Pro Gly
    50                  55                  60

Val Asp Tyr Thr Ile Thr Val Tyr Ala Val Thr Pro Arg Gly Asp Trp
65                  70                  75                  80

Asn Glu Gly Ser Lys Pro Ile Ser Ile Asn Tyr
                85                  90

<210> SEQ ID NO 10
<211> LENGTH: 91
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Ser Asp Val Pro Arg Asp Leu Glu Val Val Ala Ala Thr Pro Thr Ser
1               5                   10                  15

Leu Leu Ile Ser Trp Asp Ala Pro Ala Val Thr Val Arg Tyr Tyr Arg
            20                  25                  30

Ile Thr Tyr Gly Glu Thr Gly Gly Asn Ser Pro Val Gln Glu Phe Thr
        35                  40                  45

Val Pro Gly Ser Lys Ser Thr Ala Thr Ile Ser Gly Leu Lys Pro Gly
    50                  55                  60

Val Asp Tyr Thr Ile Thr Val Tyr Ala Val Thr Pro Lys Gly Asp Trp
65                  70                  75                  80

Asn Glu Gly Ser Lys Pro Ile Ser Ile Asn Tyr
                85                  90

<210> SEQ ID NO 11
<211> LENGTH: 89
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Val Pro Arg Asp Leu Glu Val Val Ala Ala Thr Pro Thr Ser Leu Leu
1               5                   10                  15

Ile Ser Trp Asp Ala Pro Ala Val Thr Val Arg Tyr Tyr Arg Ile Thr
            20                  25                  30

Tyr Gly Glu Thr Gly Gly Asn Ser Pro Val Gln Glu Phe Thr Val Pro
        35                  40                  45

Gly Ser Lys Ser Thr Ala Thr Ile Ser Gly Leu Lys Pro Gly Val Asp
    50                  55                  60

Tyr Thr Ile Thr Val Tyr Ala Val Thr Pro Lys Gly Asp Trp Asn Glu
65                  70                  75                  80

Gly Ser Lys Pro Ile Ser Ile Asn Tyr
                85

<210> SEQ ID NO 12
<211> LENGTH: 88
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Val Pro Arg Asp Leu Glu Val Val Ala Ala Thr Pro Thr Ser Leu Leu
1               5                   10                  15

Ile Ser Trp Asp Ala Pro Ala Val Thr Val Arg Tyr Tyr Arg Ile Thr
            20                  25                  30

Tyr Gly Glu Thr Gly Gly Asn Ser Pro Val Gln Glu Phe Thr Val Pro
        35                  40                  45

Gly Ser Lys Ser Thr Ala Thr Ile Ser Gly Leu Lys Pro Gly Val Asp

```
                  50                  55                  60

Tyr Thr Ile Thr Val Tyr Ala Val Thr Pro Lys Gly Asp Trp Asn Glu
 65                  70                  75                  80

Gly Gly Pro Ile Ser Ile Asn Tyr
                 85
```

<210> SEQ ID NO 13
<211> LENGTH: 89
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

```
Val Pro Arg Asp Leu Glu Val Val Ala Ala Thr Pro Thr Ser Leu Leu
 1               5                  10                  15

Ile Ser Trp Asp Ala Pro Ala Val Thr Val Arg Tyr Tyr Arg Ile Thr
                 20                  25                  30

Tyr Gly Glu Thr Gly Gly Asn Ser Pro Val Gln Glu Phe Thr Val Pro
             35                  40                  45

Gly Ser Lys Ser Thr Ala Thr Ile Ser Gly Leu Lys Pro Gly Val Asp
 50                  55                  60

Tyr Thr Ile Thr Val Tyr Ala Val Thr Pro Arg Gly Asp Trp Asn Glu
 65                  70                  75                  80

Gly Ser Lys Pro Ile Ser Ile Asn Tyr
                 85
```

<210> SEQ ID NO 14
<211> LENGTH: 88
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

```
Val Pro Arg Asp Leu Glu Val Val Ala Ala Thr Pro Thr Ser Leu Leu
 1               5                  10                  15

Ile Ser Trp Asp Ala Pro Ala Val Thr Val Arg Tyr Tyr Arg Ile Thr
                 20                  25                  30

Tyr Gly Glu Thr Gly Gly Asn Ser Pro Val Gln Glu Phe Thr Val Pro
             35                  40                  45

Gly Ser Lys Ser Thr Ala Thr Ile Ser Gly Leu Lys Pro Gly Val Asp
 50                  55                  60

Tyr Thr Ile Thr Val Tyr Ala Val Thr Pro Arg Gly Asp Trp Asn Glu
 65                  70                  75                  80

Gly Gly Pro Ile Ser Ile Asn Tyr
                 85
```

<210> SEQ ID NO 15
<211> LENGTH: 103
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: misc_feature
<222> LOCATION: (1)..(10)
<223> OTHER INFORMATION: This region may encompass 4, 6, 8, or 10
      residues, wherein some positions may be absent

<400> SEQUENCE: 15

His His His His His His His His His Gly Ser Ser Asp Val Pro
1               5                   10                  15

Arg Asp Leu Glu Val Val Ala Ala Thr Pro Thr Ser Leu Leu Ile Ser
            20                  25                  30

Trp Asp Ala Pro Ala Val Thr Val Arg Tyr Tyr Arg Ile Thr Tyr Gly
        35                  40                  45

Glu Thr Gly Gly Asn Ser Pro Val Gln Glu Phe Thr Val Pro Gly Ser
50                  55                  60

Lys Ser Thr Ala Thr Ile Ser Gly Leu Lys Pro Gly Val Asp Tyr Thr
65                  70                  75                  80

Ile Thr Val Tyr Ala Val Thr Pro Lys Gly Asp Trp Asn Glu Gly Ser
                85                  90                  95

Lys Pro Ile Ser Ile Asn Tyr
            100

<210> SEQ ID NO 16
<211> LENGTH: 101
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: misc_feature
<222> LOCATION: (1)..(10)
<223> OTHER INFORMATION: This region may encompass 4, 6, 8, or 10
      residues, wherein some positions may be absent

<400> SEQUENCE: 16

His His His His His His His His His Gly Ser Val Pro Arg Asp
1               5                   10                  15

Leu Glu Val Val Ala Ala Thr Pro Thr Ser Leu Leu Ile Ser Trp Asp
            20                  25                  30

Ala Pro Ala Val Thr Val Arg Tyr Tyr Arg Ile Thr Tyr Gly Glu Thr
        35                  40                  45

Gly Gly Asn Ser Pro Val Gln Glu Phe Thr Val Pro Gly Ser Lys Ser
    50                  55                  60

Thr Ala Thr Ile Ser Gly Leu Lys Pro Gly Val Asp Tyr Thr Ile Thr
65                  70                  75                  80

Val Tyr Ala Val Thr Pro Lys Gly Asp Trp Asn Glu Gly Ser Lys Pro
                85                  90                  95

Ile Ser Ile Asn Tyr
            100

<210> SEQ ID NO 17
<211> LENGTH: 99
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: misc_feature
<222> LOCATION: (1)..(10)
<223> OTHER INFORMATION: This region may encompass 4, 6, 8, or 10
      residues, wherein some positions may be absent

<400> SEQUENCE: 17

His His His His His His His His His Gly Ser Val Pro Arg Asp
1               5                   10                  15

Leu Glu Val Val Ala Ala Thr Pro Thr Ser Leu Leu Ile Ser Trp Asp
            20                  25                  30

Ala Pro Ala Val Thr Val Arg Tyr Tyr Arg Ile Thr Tyr Gly Glu Thr
            35                  40                  45

Gly Gly Asn Ser Pro Val Gln Glu Phe Thr Val Pro Gly Ser Lys Ser
50                      55                  60

Thr Ala Thr Ile Ser Gly Leu Lys Pro Gly Val Asp Tyr Thr Ile Thr
65                  70                  75                  80

Val Tyr Ala Val Thr Pro Lys Gly Asp Trp Asn Glu Gly Pro Ile Ser
                85                  90                  95

Ile Asn Tyr

<210> SEQ ID NO 18
<211> LENGTH: 101
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: misc_feature
<222> LOCATION: (1)..(10)
<223> OTHER INFORMATION: This region may encompass 4, 6, 8, or 10
      residues, wherein some positions may be absent

<400> SEQUENCE: 18

His His His His His His His His His Gly Ser Val Pro Arg Asp
1               5                   10                  15

Leu Glu Val Val Ala Ala Thr Pro Thr Ser Leu Leu Ile Ser Trp Asp
            20                  25                  30

Ala Pro Ala Val Thr Val Arg Tyr Tyr Arg Ile Thr Tyr Gly Glu Thr
            35                  40                  45

Gly Gly Asn Ser Pro Val Gln Glu Phe Thr Val Pro Gly Ser Lys Ser
50                      55                  60

Thr Ala Thr Ile Ser Gly Leu Lys Pro Gly Val Asp Tyr Thr Ile Thr
65                  70                  75                  80

Val Tyr Ala Val Thr Pro Arg Gly Asp Trp Asn Glu Gly Ser Lys Pro
                85                  90                  95

Ile Ser Ile Asn Tyr
            100

<210> SEQ ID NO 19
<211> LENGTH: 99
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: misc_feature
<222> LOCATION: (1)..(10)
<223> OTHER INFORMATION: This region may encompass 4, 6, 8, or 10
      residues, wherein some positions may be absent

<400> SEQUENCE: 19

His His His His His His His His His Gly Ser Val Pro Arg Asp
1               5                   10                  15

Leu Glu Val Val Ala Ala Thr Pro Thr Ser Leu Leu Ile Ser Trp Asp
            20                  25                  30

Ala Pro Ala Val Thr Val Arg Tyr Tyr Arg Ile Thr Tyr Gly Glu Thr
            35                  40                  45

```
Gly Gly Asn Ser Pro Val Gln Glu Phe Thr Val Pro Gly Ser Lys Ser
        50                  55                  60

Thr Ala Thr Ile Ser Gly Leu Lys Pro Gly Val Asp Tyr Thr Ile Thr
 65                  70                  75                  80

Val Tyr Ala Val Thr Pro Arg Gly Asp Trp Asn Glu Gly Pro Ile Ser
                 85                  90                  95

Ile Asn Tyr

<210> SEQ ID NO 20
<211> LENGTH: 93
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Ser Asp Val Pro Arg Asp Leu Glu Val Val Ala Ala Thr Pro Thr Ser
  1               5                  10                  15

Leu Leu Ile Ser Trp Asp Ala Pro Ala Val Thr Val Arg Tyr Tyr Arg
                 20                  25                  30

Ile Thr Tyr Gly Glu Thr Gly Gly Asn Ser Pro Val Gln Glu Phe Thr
                 35                  40                  45

Val Pro Gly Ser Lys Ser Thr Ala Thr Ile Ser Gly Leu Lys Pro Gly
 50                  55                  60

Val Asp Tyr Thr Ile Thr Val Tyr Ala Val Thr Gly Arg Gly Asp Ser
 65                  70                  75                  80

Pro Ala Ser Ser Lys Pro Ile Ser Ile Asn Tyr Arg Thr
                 85                  90

<210> SEQ ID NO 21
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Gly Cys Ala Val Thr Pro Arg Gly Asp Trp Asn Glu Gly Ser Lys Pro
  1               5                  10                  15

Ile Ser Cys Ser Gln Asp Ser Asp Cys Leu Ala Gly Cys Val Cys Gly
                 20                  25                  30

Pro Asn Gly Phe Cys Gly
                 35

<210> SEQ ID NO 22
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

Gly Cys Pro Arg Ile Leu Met Arg Cys Ser Gln Asp Ser Asp Cys Leu
  1               5                  10                  15

Ala Gly Cys Val Cys Gly Pro Lys Ser Gly Glu Asn Trp Asp Gly Arg
                 20                  25                  30

Pro Thr Val Ala Gly Phe Cys Gly
```

35          40

<210> SEQ ID NO 23
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

Gly Cys Pro Arg Gly Asp Trp Asn Glu Gly Ser Lys Pro Leu Ser Cys
1               5                   10                  15

Ser Gln Asp Ser Asp Cys Leu Ala Gly Cys Val Cys Gly Pro Asn Gly
            20                  25                  30

Phe Cys Gly
        35

<210> SEQ ID NO 24
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

Gly Cys Ala Val Thr Pro Arg Gly Asp Trp Asn Glu Gly Ser Lys Pro
1               5                   10                  15

Gly Cys Lys Gln Asp Ser Asp Cys Leu Ala Gly Cys Val Cys Gly Pro
            20                  25                  30

Asn Gly Phe Cys Gly
        35

<210> SEQ ID NO 25
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

Gly Cys Pro Arg Ile Leu Met Arg Cys Lys Gln Asp Ser Asp Cys Leu
1               5                   10                  15

Ala Gly Cys Val Cys Gly Pro Lys Ser Gly Glu Asn Trp Asp Gly Arg
            20                  25                  30

Pro Thr Val Gly Phe Cys Gly
        35

<210> SEQ ID NO 26
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Arg Gly Asp Trp Pro Cys
1               5

<210> SEQ ID NO 27
<211> LENGTH: 7

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Pro Arg Pro Arg Gly Asp Asn
1               5

<210> SEQ ID NO 28
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Pro Gln Gly Arg Gly Asp Trp
1               5

<210> SEQ ID NO 29
<211> LENGTH: 92
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29

Ser Asp Val Pro Arg Asp Leu Glu Val Val Ala Ala Thr Pro Thr Ser
1               5                   10                  15

Leu Leu Ile Ser Trp Asp Ala Pro Ala Val Thr Val Arg Tyr Tyr Arg
            20                  25                  30

Ile Thr Tyr Gly Glu Thr Gly Gly Asn Ser Pro Val Gln Glu Phe Thr
        35                  40                  45

Val Pro Gly Ser Lys Ser Thr Ala Thr Ile Ser Gly Leu Lys Pro Gly
    50                  55                  60

Val Asp Tyr Thr Ile Thr Val Tyr Ala Val Thr Pro Gly Arg Gly Asp
65                  70                  75                  80

Trp Asn Glu Gly Ser Lys Pro Ile Ser Ile Asn Tyr
                85                  90

<210> SEQ ID NO 30
<211> LENGTH: 93
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30

Ser Asp Val Pro Arg Asp Leu Glu Val Val Ala Ala Thr Pro Thr Ser
1               5                   10                  15

Leu Leu Ile Ser Trp Asp Ala Pro Ala Val Thr Val Arg Tyr Tyr Arg
            20                  25                  30

Ile Thr Tyr Gly Glu Thr Gly Gly Asn Ser Pro Val Gln Glu Phe Thr
        35                  40                  45

Val Pro Gly Ser Lys Ser Thr Ala Thr Ile Ser Gly Leu Lys Pro Gly
    50                  55                  60

Val Asp Tyr Thr Ile Thr Val Tyr Ala Val Thr Gly Pro Gly Arg Gly
65                  70                  75                  80
```

```
Asp Trp Asn Glu Gly Ser Lys Pro Ile Ser Ile Asn Tyr
            85                  90

<210> SEQ ID NO 31
<211> LENGTH: 92
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 31

Ser Asp Val Pro Arg Asp Leu Glu Val Val Ala Ala Thr Pro Thr Ser
1               5                   10                  15

Leu Leu Ile Ser Trp Asp Ala Pro Ala Val Thr Val Arg Tyr Tyr Arg
            20                  25                  30

Ile Thr Tyr Gly Glu Thr Gly Gly Asn Ser Pro Val Gln Glu Phe Thr
        35                  40                  45

Val Pro Gly Ser Lys Ser Thr Ala Thr Ile Ser Gly Leu Lys Pro Gly
    50                  55                  60

Val Asp Tyr Thr Ile Thr Val Tyr Ala Val Thr Pro Ala Arg Gly Asp
65                  70                  75                  80

Trp Asn Glu Gly Ser Lys Pro Ile Ser Ile Asn Tyr
                85                  90

<210> SEQ ID NO 32
<211> LENGTH: 93
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32

Ser Asp Val Pro Arg Asp Leu Glu Val Val Ala Ala Thr Pro Thr Ser
1               5                   10                  15

Leu Leu Ile Ser Trp Asp Ala Pro Ala Val Thr Val Arg Tyr Tyr Arg
            20                  25                  30

Ile Thr Tyr Gly Glu Thr Gly Gly Asn Ser Pro Val Gln Glu Phe Thr
        35                  40                  45

Val Pro Gly Ser Lys Ser Thr Ala Thr Ile Ser Gly Leu Lys Pro Gly
    50                  55                  60

Val Asp Tyr Thr Ile Thr Val Tyr Ala Val Thr Pro His Arg Gly Gly
65                  70                  75                  80

Asp Trp Asn Glu Gly Ser Lys Pro Ile Ser Ile Asn Tyr
                85                  90

<210> SEQ ID NO 33
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (10)..(10)
<223> OTHER INFORMATION: Any amino acid or unnatural derivative thereof,
      in L or D form, except Pro

<400> SEQUENCE: 33

Gly Cys Pro Arg Pro Arg Gly Asp Asn Xaa Pro Leu Thr Cys Ser Gln
```

```
1               5                   10                  15
Asp Ser Asp Cys Leu Ala Gly Cys Val Cys Gly Pro Asn Gly Phe Cys
            20                  25                  30

Gly

<210> SEQ ID NO 34
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 34

Gly Cys Pro Arg Pro Arg Gly Asp Asn Pro Pro Leu Thr Cys Ser
1               5                   10                  15

Gln Asp Ser Asp Cys Leu Ala Gly Cys Val Cys Gly Pro Asn Gly Phe
            20                  25                  30

Cys Gly

<210> SEQ ID NO 35
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (10)..(10)
<223> OTHER INFORMATION: Any amino acid or unnatural derivative thereof,
      in L or D form, except Pro

<400> SEQUENCE: 35

Gly Cys Pro Arg Pro Arg Gly Asp Asn Xaa Pro Pro Leu Thr Cys Ser
1               5                   10                  15

Gln Asp Ser Asp Cys Leu Ala Gly Cys Val Cys Gly Pro Asn Gly Phe
            20                  25                  30

Cys Gly

<210> SEQ ID NO 36
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36

Gly Cys Pro Arg Pro Arg Gly Asp Asn Pro Gly Pro Leu Thr Cys Ser
1               5                   10                  15

Gln Asp Ser Asp Cys Leu Ala Gly Cys Val Cys Gly Pro Asn Gly Phe
            20                  25                  30

Cys Gly

<210> SEQ ID NO 37
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
```

```
<222> LOCATION: (10)..(10)
<223> OTHER INFORMATION: Any amino acid or unnatural derivative thereof,
      in L or D form, except Pro

<400> SEQUENCE: 37

Gly Cys Pro Gln Gly Arg Gly Asp Trp Xaa Pro Thr Ser Cys Ser Gln
1               5                   10                  15

Asp Ser Asp Cys Leu Ala Gly Cys Val Cys Gly Pro Asn Gly Phe Cys
            20                  25                  30

Gly

<210> SEQ ID NO 38
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 38

Gly Cys Pro Gln Gly Arg Gly Asp Trp Pro Pro Thr Ser Cys Ser
1               5                   10                  15

Gln Asp Ser Asp Cys Leu Ala Gly Cys Val Cys Gly Pro Asn Gly Phe
            20                  25                  30

Cys Gly

<210> SEQ ID NO 39
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 39

Gly Cys Pro Gln Gly Arg Gly Asp Trp Pro Gly Pro Thr Ser Cys Ser
1               5                   10                  15

Gln Asp Ser Asp Cys Leu Ala Gly Cys Val Cys Gly Pro Asn Gly Phe
            20                  25                  30

Cys Gly

<210> SEQ ID NO 40
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Arg or unnatural derivatives thereof, in L or D
      form
<220> FEATURE:
<221> NAME/KEY: MOD_RES
<222> LOCATION: (4)..(4)
<223> OTHER INFORMATION: Any amino acid or unnatural derivatives
      thereof, in L or D form, except Pro
<220> FEATURE:
<221> NAME/KEY: MOD_RES
<222> LOCATION: (5)..(5)
<223> OTHER INFORMATION: Any amino acid or unnatural derivatives
      thereof, in L or D form, except Pro, pPro or pGly
<220> FEATURE:
<221> NAME/KEY: MOD_RES
<222> LOCATION: (6)..(6)
<223> OTHER INFORMATION: Any amino acid, in L or D form
```

```
<220> FEATURE:
<223> OTHER INFORMATION: See specification as filed for detailed
      description of substitutions and preferred embodiments

<400> SEQUENCE: 40

Xaa Gly Asp Xaa Xaa Xaa
1               5

<210> SEQ ID NO 41
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 41

Gly Cys Pro Gln Gly Arg Gly Asp Trp Ala Pro Thr Ser Cys Lys Gln
1               5                   10                  15

Asp Ser Asp Cys Leu Ala Gly Cys Val Cys Gly Pro Asn Gly Phe Cys
            20                  25                  30

Gly

<210> SEQ ID NO 42
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Lys Gln Ala Gly Asp
1               5

<210> SEQ ID NO 43
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Any amino acid or unnatural derivative thereof,
      in L or D form
<220> FEATURE:
<223> OTHER INFORMATION: See specification as filed for detailed
      description of substitutions and preferred embodiments

<400> SEQUENCE: 43

Pro Arg Gly Asp Asn Xaa Pro
1               5

<210> SEQ ID NO 44
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: Any amino acid or unnatural derivative thereof,
      in L or D form
<220> FEATURE:
<223> OTHER INFORMATION: See specification as filed for detailed
``` description of substitutions and preferred embodiments

<400> SEQUENCE: 44

Pro Gly Arg Gly Asp Trp Xaa Pro
1               5

<210> SEQ ID NO 45
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Arg Glu Asp Val
1

<210> SEQ ID NO 46
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Asp Ala Leu Arg
1

<210> SEQ ID NO 47
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 47

Gly Cys Pro Arg Pro Arg Gly Asp Asn Pro Pro Leu Thr Cys Ser Gln
1               5                   10                  15

Asp Ser Asp Cys Leu Ala Gly Cys Val Cys Gly Pro Asn Gly Phe Cys
            20                  25                  30

Gly

<210> SEQ ID NO 48
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 48

Gly Cys Pro Gln Gly Arg Gly Asp Trp Ala Pro Thr Ser Cys Ser Gln
1               5                   10                  15

Asp Ser Asp Cys Leu Ala Gly Cys Val Cys Gly Pro Asn Gly Phe Cys
            20                  25                  30

Gly

<210> SEQ ID NO 49
<211> LENGTH: 87
<212> TYPE: PRT
<213> ORGANISM: Artificial Sequence
<220> FEATURE:

```
<223> OTHER INFORMATION: Description of Artificial Sequence: Synthetic
      polypeptide

<400> SEQUENCE: 49

Val Pro Arg Asp Leu Glu Val Ala Ala Thr Pro Thr Ser Leu Leu
1               5                   10                  15

Ile Ser Trp Asp Ala Pro Ala Val Thr Val Arg Tyr Tyr Arg Ile Thr
            20                  25                  30

Tyr Gly Glu Thr Gly Gly Asn Ser Pro Val Gln Glu Phe Thr Val Pro
        35                  40                  45

Gly Ser Lys Ser Thr Ala Thr Ile Ser Gly Leu Lys Pro Gly Val Asp
    50                  55                  60

Tyr Thr Ile Thr Val Tyr Ala Val Thr Pro Lys Gly Asp Trp Asn Glu
65                  70                  75                  80

Gly Pro Ile Ser Ile Asn Tyr
                85

<210> SEQ ID NO 50
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 50

Gly Cys Pro Arg Pro Arg Gly Asp Trp Asn Glu Gly Ser Cys Ser Gln
1               5                   10                  15

Asp Ser Asp Cys Leu Ala Gly Cys Val Cys Gly Pro Asn Gly Phe Cys
            20                  25                  30

Gly

<210> SEQ ID NO 51
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Arg or Lys

<400> SEQUENCE: 51

Xaa Gly Asp Trp Asn
1               5

<210> SEQ ID NO 52
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Pro Arg Gly Asp Trp Asn
1               5

<210> SEQ ID NO 53
<211> LENGTH: 7
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 53

Pro Gly Arg Gly Asp Trp Asn
1               5

<210> SEQ ID NO 54
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Arg Gly Asp Trp
1

<210> SEQ ID NO 55
<211> LENGTH: 87
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 55

Val Pro Arg Asp Leu Glu Val Ala Ala Thr Pro Thr Ser Leu Leu
1               5                  10                  15

Ile Ser Trp Asp Ala Pro Ala Val Thr Val Arg Tyr Tyr Arg Ile Thr
                20                  25                  30

Tyr Gly Glu Thr Gly Gly Asn Ser Pro Val Gln Glu Phe Thr Val Pro
            35                  40                  45

Gly Ser Lys Ser Thr Ala Thr Ile Gly Leu Lys Pro Gly Val Asp Tyr
        50                  55                  60

Thr Ile Thr Val Tyr Ala Val Thr Pro Arg Gly Asp Trp Asn Glu Gly
65                  70                  75                  80

Gly Pro Ile Ser Ile Asn Tyr
                85

<210> SEQ ID NO 56
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Asp Trp Asn Glu Gly
1               5

<210> SEQ ID NO 57
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Ala Val Thr Pro Arg Gly
1               5
```

<210> SEQ ID NO 58
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 58

His His His His His His
1               5

<210> SEQ ID NO 59
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Gly Arg Gly Asp Ser Pro Ala Ser
1               5

<210> SEQ ID NO 60
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Pro Arg Gly Asp Trp Asn Glu Gly
1               5

<210> SEQ ID NO 61
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Thr Pro Arg Gly Asp Trp Asn Glu
1               5

<210> SEQ ID NO 62
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Ile Ala Arg Gly Asp Trp Asn Asp
1               5

<210> SEQ ID NO 63
<211> LENGTH: 1018
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 63

Phe Asn Leu Asp Val Asp Ser Pro Ala Glu Tyr Ser Gly Pro Glu Gly
1               5                   10                  15

Ser Tyr Phe Gly Phe Ala Val Asp Phe Phe Val Pro Ser Ala Ser Ser
            20                  25                  30

Arg Met Phe Leu Leu Val Gly Ala Pro Lys Ala Asn Thr Thr Gln Pro
        35                  40                  45

Gly Ile Val Glu Gly Gly Gln Val Leu Lys Cys Asp Trp Ser Ser Thr
    50                  55                  60

Arg Arg Cys Gln Pro Ile Glu Phe Asp Ala Thr Gly Asn Arg Asp Tyr
65              70                  75                  80

Ala Lys Asp Asp Pro Leu Glu Phe Lys Ser His Gln Trp Phe Gly Ala
                85                  90                  95

Ser Val Arg Ser Lys Gln Asp Lys Ile Leu Ala Cys Ala Pro Leu Tyr
            100                 105                 110

His Trp Arg Thr Glu Met Lys Gln Glu Arg Glu Pro Val Gly Thr Cys
        115                 120                 125

Phe Leu Gln Asp Gly Thr Lys Thr Val Glu Tyr Ala Pro Cys Arg Ser
130                 135                 140

Gln Asp Ile Asp Ala Asp Gly Gln Gly Phe Cys Gln Gly Gly Phe Ser
145                 150                 155                 160

Ile Asp Phe Thr Lys Ala Asp Arg Val Leu Leu Gly Gly Pro Gly Ser
                165                 170                 175

Phe Tyr Trp Gln Gly Gln Leu Ile Ser Asp Gln Val Ala Glu Ile Val
            180                 185                 190

Ser Lys Tyr Asp Pro Asn Val Tyr Ser Ile Lys Tyr Asn Asn Gln Leu
        195                 200                 205

Ala Thr Arg Thr Ala Gln Ala Ile Phe Asp Asp Ser Tyr Leu Gly Tyr
    210                 215                 220

Ser Val Ala Val Gly Asp Phe Asn Gly Asp Gly Ile Asp Asp Phe Val
225                 230                 235                 240

Ser Gly Val Pro Arg Ala Ala Arg Thr Leu Gly Met Val Tyr Ile Tyr
                245                 250                 255

Asp Gly Lys Asn Met Ser Ser Leu Tyr Asn Phe Thr Gly Glu Gln Met
            260                 265                 270

Ala Ala Tyr Phe Gly Phe Ser Val Ala Ala Thr Asp Ile Asn Gly Asp
        275                 280                 285

Asp Tyr Ala Asp Val Phe Ile Gly Ala Pro Leu Phe Met Asp Arg Gly
    290                 295                 300

Ser Asp Gly Lys Leu Gln Glu Val Gly Gln Val Ser Val Ser Leu Gln
305                 310                 315                 320

Arg Ala Ser Gly Asp Phe Gln Thr Thr Lys Leu Asn Gly Phe Glu Val
                325                 330                 335

Phe Ala Arg Phe Gly Ser Ala Ile Ala Pro Leu Gly Asp Leu Asp Gln
            340                 345                 350

Asp Gly Phe Asn Asp Ile Ala Ile Ala Ala Pro Tyr Gly Gly Glu Asp
        355                 360                 365

Lys Lys Gly Ile Val Tyr Ile Phe Asn Gly Arg Ser Thr Gly Leu Asn
    370                 375                 380

Ala Val Pro Ser Gln Ile Leu Glu Gly Gln Trp Ala Ala Arg Ser Met
385                 390                 395                 400

Pro Pro Ser Phe Gly Tyr Ser Met Lys Gly Ala Thr Asp Ile Asp Lys

```
            405                 410                 415
Asn Gly Tyr Pro Asp Leu Ile Val Gly Ala Phe Gly Val Asp Arg Ala
            420                 425                 430

Ile Leu Tyr Arg Ala Arg Pro Val Ile Thr Val Asn Ala Gly Leu Glu
            435                 440                 445

Val Tyr Pro Ser Ile Leu Asn Gln Asp Asn Lys Thr Cys Ser Leu Pro
    450                 455                 460

Gly Thr Ala Leu Lys Val Ser Cys Phe Asn Val Arg Phe Cys Leu Lys
465                 470                 475                 480

Ala Asp Gly Lys Gly Val Leu Pro Arg Lys Leu Asn Phe Gln Val Glu
            485                 490                 495

Leu Leu Leu Asp Lys Leu Lys Gln Lys Gly Ala Ile Arg Arg Ala Leu
            500                 505                 510

Phe Leu Tyr Ser Arg Ser Pro Ser His Ser Lys Asn Met Thr Ile Ser
            515                 520                 525

Arg Gly Gly Leu Met Gln Cys Glu Glu Leu Ile Ala Tyr Leu Arg Asp
            530                 535                 540

Glu Ser Glu Phe Arg Asp Lys Leu Thr Pro Ile Thr Ile Phe Met Glu
545                 550                 555                 560

Tyr Arg Leu Asp Tyr Arg Thr Ala Ala Asp Thr Thr Gly Leu Gln Pro
                565                 570                 575

Ile Leu Asn Gln Phe Thr Pro Ala Asn Ile Ser Arg Gln Ala His Ile
            580                 585                 590

Leu Leu Asp Cys Gly Glu Asp Asn Val Cys Lys Pro Lys Leu Glu Val
            595                 600                 605

Ser Val Asp Ser Asp Gln Lys Lys Ile Tyr Ile Gly Asp Asp Asn Pro
    610                 615                 620

Leu Thr Leu Ile Val Lys Ala Gln Asn Gln Gly Glu Gly Ala Tyr Glu
625                 630                 635                 640

Ala Glu Leu Ile Val Ser Ile Pro Leu Gln Ala Asp Phe Ile Gly Val
                645                 650                 655

Val Arg Asn Asn Glu Ala Leu Ala Arg Leu Ser Cys Ala Phe Lys Thr
            660                 665                 670

Glu Asn Gln Thr Arg Gln Val Cys Asp Leu Gly Asn Pro Met Lys
            675                 680                 685

Ala Gly Thr Gln Leu Leu Ala Gly Leu Arg Phe Ser Val His Gln Gln
            690                 695                 700

Ser Glu Met Asp Thr Ser Val Lys Phe Asp Leu Gln Ile Gln Ser Ser
705                 710                 715                 720

Asn Leu Phe Asp Lys Val Ser Pro Val Val Ser His Lys Val Asp Leu
                725                 730                 735

Ala Val Leu Ala Ala Val Glu Ile Arg Gly Val Ser Ser Pro Asp His
            740                 745                 750

Ile Phe Leu Pro Ile Pro Asn Trp Glu His Lys Glu Asn Pro Glu Thr
            755                 760                 765

Glu Glu Asp Val Gly Pro Val Val Gln His Ile Tyr Glu Leu Arg Asn
            770                 775                 780

Asn Gly Pro Ser Ser Phe Ser Lys Ala Met Leu His Leu Gln Trp Pro
785                 790                 795                 800

Tyr Lys Tyr Asn Asn Asn Thr Leu Leu Tyr Ile Leu His Tyr Asp Ile
                805                 810                 815

Asp Gly Pro Met Asn Cys Thr Ser Asp Met Glu Ile Asn Pro Leu Arg
            820                 825                 830
```

```
Ile Lys Ile Ser Ser Leu Gln Thr Thr Glu Lys Asn Asp Thr Val Ala
        835                 840                 845

Gly Gln Gly Glu Arg Asp His Leu Ile Thr Lys Arg Asp Leu Ala Leu
    850                 855                 860

Ser Glu Gly Asp Ile His Thr Leu Gly Cys Gly Val Ala Gln Cys Leu
865                 870                 875                 880

Lys Ile Val Cys Gln Val Gly Arg Leu Asp Arg Gly Lys Ser Ala Ile
                885                 890                 895

Leu Tyr Val Lys Ser Leu Leu Trp Thr Glu Thr Phe Met Asn Lys Glu
                900                 905                 910

Asn Gln Asn His Ser Tyr Ser Leu Lys Ser Ser Ala Ser Phe Asn Val
                915                 920                 925

Ile Glu Phe Pro Tyr Lys Asn Leu Pro Ile Glu Asp Ile Thr Asn Ser
                930                 935                 940

Thr Leu Val Thr Thr Asn Val Thr Trp Gly Ile Gln Pro Ala Pro Met
945                 950                 955                 960

Pro Val Pro Val Trp Val Ile Ile Leu Ala Val Leu Ala Gly Leu Leu
                965                 970                 975

Leu Leu Ala Val Leu Val Phe Val Met Tyr Arg Met Gly Phe Phe Lys
                980                 985                 990

Arg Val Arg Pro Pro Gln Glu Glu  Gln Glu Arg Glu Gln  Leu Gln Pro
                995                  1000                 1005

His Glu  Asn Gly Glu Gly Asn  Ser Glu Thr
    1010                 1015

<210> SEQ ID NO 64
<211> LENGTH: 762
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 64

Gly Pro Asn Ile Cys Thr Thr Arg Gly Val Ser Ser Cys Gln Gln Cys
1               5                   10                  15

Leu Ala Val Ser Pro Met Cys Ala Trp Cys Ser Asp Glu Ala Leu Pro
                20                  25                  30

Leu Gly Ser Pro Arg Cys Asp Leu Lys Glu Asn Leu Leu Lys Asp Asn
            35                  40                  45

Cys Ala Pro Glu Ser Ile Glu Phe Pro Val Ser Glu Ala Arg Val Leu
    50                  55                  60

Glu Asp Arg Pro Leu Ser Asp Lys Gly Ser Gly Asp Ser Ser Gln Val
65                  70                  75                  80

Thr Gln Val Ser Pro Gln Arg Ile Ala Leu Arg Leu Arg Pro Asp Asp
                85                  90                  95

Ser Lys Asn Phe Ser Ile Gln Val Arg Gln Val Glu Asp Tyr Pro Val
                100                 105                 110

Asp Ile Tyr Tyr Leu Met Asp Leu Ser Tyr Ser Met Lys Asp Asp Leu
            115                 120                 125

Trp Ser Ile Gln Asn Leu Gly Thr Lys Leu Ala Thr Gln Met Arg Lys
    130                 135                 140

Leu Thr Ser Asn Leu Arg Ile Gly Phe Gly Ala Phe Val Asp Lys Pro
145                 150                 155                 160

Val Ser Pro Tyr Met Tyr Ile Ser Pro Pro Glu Ala Leu Glu Asn Pro
```

```
            165                 170                 175
Cys Tyr Asp Met Lys Thr Thr Cys Leu Pro Met Phe Gly Tyr Lys His
            180                 185                 190

Val Leu Thr Leu Thr Asp Gln Val Thr Arg Phe Asn Glu Glu Val Lys
            195                 200                 205

Lys Gln Ser Val Ser Arg Asn Arg Asp Ala Pro Glu Gly Gly Phe Asp
            210                 215                 220

Ala Ile Met Gln Ala Thr Val Cys Asp Glu Lys Ile Gly Trp Arg Asn
225                 230                 235                 240

Asp Ala Ser His Leu Leu Val Phe Thr Asp Ala Lys Thr His Ile
            245                 250                 255

Ala Leu Asp Gly Arg Leu Ala Gly Ile Val Gln Pro Asn Asp Gly Gln
            260                 265                 270

Cys His Val Gly Ser Asp Asn His Tyr Ser Ala Ser Thr Thr Met Asp
            275                 280                 285

Tyr Pro Ser Leu Gly Leu Met Thr Glu Lys Leu Ser Gln Lys Asn Ile
            290                 295                 300

Asn Leu Ile Phe Ala Val Thr Glu Asn Val Val Asn Leu Tyr Gln Asn
305                 310                 315                 320

Tyr Ser Glu Leu Ile Pro Gly Thr Thr Val Gly Val Leu Ser Met Asp
            325                 330                 335

Ser Ser Asn Val Leu Gln Leu Ile Val Asp Ala Tyr Gly Lys Ile Arg
            340                 345                 350

Ser Lys Val Glu Leu Glu Val Arg Asp Leu Pro Glu Glu Leu Ser Leu
            355                 360                 365

Ser Phe Asn Ala Thr Cys Leu Asn Asn Glu Val Ile Pro Gly Leu Lys
            370                 375                 380

Ser Cys Met Gly Leu Lys Ile Gly Asp Thr Val Ser Phe Ser Ile Glu
385                 390                 395                 400

Ala Lys Val Arg Gly Cys Pro Gln Glu Lys Glu Lys Ser Phe Thr Ile
            405                 410                 415

Lys Pro Val Gly Phe Lys Asp Ser Leu Ile Val Gln Val Thr Phe Asp
            420                 425                 430

Cys Asp Cys Ala Cys Gln Ala Gln Ala Glu Pro Asn Ser His Arg Cys
            435                 440                 445

Asn Asn Gly Asn Gly Thr Phe Glu Cys Gly Val Cys Arg Cys Gly Pro
450                 455                 460

Gly Trp Leu Gly Ser Gln Cys Glu Cys Ser Glu Glu Asp Tyr Arg Pro
465                 470                 475                 480

Ser Gln Gln Asp Glu Cys Ser Pro Arg Glu Gly Gln Pro Val Cys Ser
            485                 490                 495

Gln Arg Gly Glu Cys Leu Cys Gly Gln Cys Val Cys His Ser Ser Asp
            500                 505                 510

Phe Gly Lys Ile Thr Gly Lys Tyr Cys Glu Cys Asp Asp Phe Ser Cys
            515                 520                 525

Val Arg Tyr Lys Gly Glu Met Cys Ser Gly His Gly Gln Cys Ser Cys
            530                 535                 540

Gly Asp Cys Leu Cys Asp Ser Asp Trp Thr Gly Tyr Tyr Cys Asn Cys
545                 550                 555                 560

Thr Thr Arg Thr Asp Thr Cys Met Ser Asn Gly Leu Leu Cys Ser
            565                 570                 575

Gly Arg Gly Lys Cys Glu Cys Gly Ser Cys Val Cys Ile Gln Pro Gly
            580                 585                 590
```

```
Ser Tyr Gly Asp Thr Cys Glu Lys Cys Pro Thr Cys Pro Asp Ala Cys
        595                 600                 605

Thr Phe Lys Lys Glu Cys Val Glu Cys Lys Lys Phe Asp Arg Glu Pro
    610                 615                 620

Tyr Met Thr Glu Asn Thr Cys Asn Arg Tyr Cys Arg Asp Glu Ile Glu
625                 630                 635                 640

Ser Val Lys Glu Leu Lys Asp Thr Gly Lys Asp Ala Val Asn Cys Thr
            645                 650                 655

Tyr Lys Asn Glu Asp Asp Cys Val Val Arg Phe Gln Tyr Tyr Glu Asp
            660                 665                 670

Ser Ser Gly Lys Ser Ile Leu Tyr Val Val Glu Glu Pro Glu Cys Pro
            675                 680                 685

Lys Gly Pro Asp Ile Leu Val Val Leu Leu Ser Val Met Gly Ala Ile
            690                 695                 700

Leu Leu Ile Gly Leu Ala Ala Leu Leu Ile Trp Lys Leu Leu Ile Thr
705                 710                 715                 720

Ile His Asp Arg Lys Glu Phe Ala Lys Phe Glu Glu Arg Ala Arg
                725                 730                 735

Ala Lys Trp Asp Thr Ala Asn Asn Pro Leu Tyr Lys Glu Ala Thr Ser
            740                 745                 750

Thr Phe Thr Asn Ile Thr Tyr Arg Gly Thr
            755                 760
```

<210> SEQ ID NO 65
<211> LENGTH: 1018
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 65

```
Phe Asn Leu Asp Val Asp Ser Pro Ala Glu Tyr Ser Gly Pro Glu Gly
1               5                   10                  15

Ser Tyr Phe Gly Phe Ala Val Asp Phe Phe Val Pro Ser Ala Ser Ser
            20                  25                  30

Arg Met Phe Leu Leu Val Gly Ala Pro Lys Ala Asn Thr Thr Gln Pro
            35                  40                  45

Gly Ile Val Glu Gly Gly Gln Val Leu Lys Cys Asp Trp Ser Ser Thr
    50                  55                  60

Arg Arg Cys Gln Pro Ile Glu Phe Asp Ala Thr Gly Asn Arg Asp Tyr
65                  70                  75                  80

Ala Lys Asp Asp Pro Leu Glu Phe Lys Ser His Gln Trp Phe Gly Ala
                85                  90                  95

Ser Val Arg Ser Lys Gln Asp Lys Ile Leu Ala Cys Ala Pro Leu Tyr
            100                 105                 110

His Trp Arg Thr Glu Met Lys Gln Glu Arg Glu Pro Val Gly Thr Cys
            115                 120                 125

Phe Leu Gln Asp Gly Thr Lys Thr Val Glu Tyr Ala Pro Cys Arg Ser
    130                 135                 140

Gln Asp Ile Asp Ala Asp Gly Gln Gly Phe Cys Gln Gly Gly Phe Ser
145                 150                 155                 160

Ile Asp Phe Thr Lys Ala Asp Arg Val Leu Leu Gly Gly Pro Gly Ser
                165                 170                 175

Phe Tyr Trp Gln Gly Gln Leu Ile Ser Asp Gln Val Ala Glu Ile Val
```

-continued

```
                180                 185                 190
Ser Lys Tyr Asp Pro Asn Val Tyr Ser Ile Lys Tyr Asn Asn Gln Leu
            195                 200                 205

Ala Thr Arg Thr Ala Gln Ala Ile Phe Asp Asp Ser Tyr Leu Gly Tyr
            210                 215                 220

Ser Val Ala Val Gly Asp Phe Asn Gly Asp Gly Ile Asp Asp Phe Val
225                 230                 235                 240

Ser Gly Val Pro Arg Ala Ala Arg Thr Leu Gly Met Val Tyr Ile Tyr
            245                 250                 255

Asp Gly Lys Asn Met Ser Ser Leu Tyr Asn Phe Thr Gly Glu Gln Met
            260                 265                 270

Ala Ala Tyr Phe Gly Phe Ser Val Ala Ala Thr Asp Ile Asn Gly Asp
            275                 280                 285

Asp Tyr Ala Asp Val Phe Ile Gly Ala Pro Leu Phe Met Asp Arg Gly
            290                 295                 300

Ser Asp Gly Lys Leu Gln Glu Val Gly Gln Val Ser Val Ser Leu Gln
305                 310                 315                 320

Arg Ala Ser Gly Asp Phe Gln Thr Thr Lys Leu Asn Gly Phe Glu Val
                325                 330                 335

Phe Ala Arg Phe Gly Ser Ala Ile Ala Pro Leu Gly Asp Leu Asp Gln
            340                 345                 350

Asp Gly Phe Asn Asp Ile Ala Ile Ala Ala Pro Tyr Gly Gly Glu Asp
            355                 360                 365

Lys Lys Gly Ile Val Tyr Ile Phe Asn Gly Arg Ser Thr Gly Leu Asn
            370                 375                 380

Ala Val Pro Ser Gln Ile Leu Glu Gly Gln Trp Ala Ala Arg Ser Met
385                 390                 395                 400

Pro Pro Ser Phe Gly Tyr Ser Met Lys Gly Ala Thr Asp Ile Asp Lys
                405                 410                 415

Asn Gly Tyr Pro Asp Leu Ile Val Gly Ala Phe Gly Val Asp Arg Ala
            420                 425                 430

Ile Leu Tyr Arg Ala Arg Pro Val Ile Thr Val Asn Ala Gly Leu Glu
            435                 440                 445

Val Tyr Pro Ser Ile Leu Asn Gln Asp Asn Lys Thr Cys Ser Leu Pro
450                 455                 460

Gly Thr Ala Leu Lys Val Ser Cys Phe Asn Val Arg Phe Cys Leu Lys
465                 470                 475                 480

Ala Asp Gly Lys Gly Val Leu Pro Arg Lys Leu Asn Phe Gln Val Glu
            485                 490                 495

Leu Leu Leu Asp Lys Leu Lys Gln Lys Gly Ala Ile Arg Arg Ala Leu
            500                 505                 510

Phe Leu Tyr Ser Arg Ser Pro Ser His Ser Lys Asn Met Thr Ile Ser
            515                 520                 525

Arg Gly Gly Leu Met Gln Cys Glu Glu Leu Ile Ala Tyr Leu Arg Asp
            530                 535                 540

Glu Ser Glu Phe Arg Asp Lys Leu Thr Pro Ile Thr Ile Phe Met Glu
545                 550                 555                 560

Tyr Arg Leu Asp Tyr Arg Thr Ala Ala Asp Thr Thr Gly Leu Gln Pro
                565                 570                 575

Ile Leu Asn Gln Phe Thr Pro Ala Asn Ile Ser Arg Gln Ala His Ile
            580                 585                 590

Leu Leu Asp Cys Gly Glu Asp Asn Val Cys Lys Pro Lys Leu Glu Val
            595                 600                 605
```

```
Ser Val Asp Ser Asp Gln Lys Lys Ile Tyr Ile Gly Asp Asn Pro
    610             615                 620
Leu Thr Leu Ile Val Lys Ala Gln Asn Gln Gly Glu Gly Ala Tyr Glu
625                 630                 635                 640
Ala Glu Leu Ile Val Ser Ile Pro Leu Gln Ala Asp Phe Ile Gly Val
                645                 650                 655
Val Arg Asn Asn Glu Ala Leu Ala Arg Leu Ser Cys Ala Phe Lys Thr
            660                 665                 670
Glu Asn Gln Thr Arg Gln Val Val Cys Asp Leu Gly Asn Pro Met Lys
        675                 680                 685
Ala Gly Thr Gln Leu Leu Ala Gly Leu Arg Phe Ser Val His Gln Gln
690                 695                 700
Ser Glu Met Asp Thr Ser Val Lys Phe Asp Leu Gln Ile Gln Ser Ser
705                 710                 715                 720
Asn Leu Phe Asp Lys Val Ser Pro Val Ser His Lys Val Asp Leu
                725                 730                 735
Ala Val Leu Ala Ala Val Glu Ile Arg Gly Val Ser Ser Pro Asp His
            740                 745                 750
Ile Phe Leu Pro Ile Pro Asn Trp Glu His Lys Glu Asn Pro Glu Thr
            755                 760                 765
Glu Glu Asp Val Gly Pro Val Val Gln His Ile Tyr Glu Leu Arg Asn
770                 775                 780
Asn Gly Pro Ser Ser Phe Ser Lys Ala Met Leu His Leu Gln Trp Pro
785                 790                 795                 800
Tyr Lys Tyr Asn Asn Asn Thr Leu Leu Tyr Ile Leu His Tyr Asp Ile
                805                 810                 815
Asp Gly Pro Met Asn Cys Thr Ser Asp Met Glu Ile Asn Pro Leu Arg
            820                 825                 830
Ile Lys Ile Ser Ser Leu Gln Thr Thr Glu Lys Asn Asp Thr Val Ala
            835                 840                 845
Gly Gln Gly Glu Arg Asp His Leu Ile Thr Lys Arg Asp Leu Ala Leu
850                 855                 860
Ser Glu Gly Asp Ile His Thr Leu Gly Cys Gly Val Ala Gln Cys Leu
865                 870                 875                 880
Lys Ile Val Cys Gln Val Gly Arg Leu Asp Arg Gly Lys Ser Ala Ile
                885                 890                 895
Leu Tyr Val Lys Ser Leu Leu Trp Thr Glu Thr Phe Met Asn Lys Glu
            900                 905                 910
Asn Gln Asn His Ser Tyr Ser Leu Lys Ser Ser Ala Ser Phe Asn Val
        915                 920                 925
Ile Glu Phe Pro Tyr Lys Asn Leu Pro Ile Glu Asp Ile Thr Asn Ser
    930                 935                 940
Thr Leu Val Thr Thr Asn Val Thr Trp Gly Ile Gln Pro Ala Pro Met
945                 950                 955                 960
Pro Val Pro Val Trp Val Ile Leu Ala Val Leu Ala Gly Leu Leu
                965                 970                 975
Leu Leu Ala Val Leu Val Phe Val Met Tyr Arg Met Gly Phe Phe Lys
            980                 985                 990
Arg Val Arg Pro Pro Gln Glu Glu  Gln Glu Arg Glu Gln Leu Gln Pro
            995                 1000                1005
His Glu  Asn Gly Glu Gly Asn  Ser Glu Thr
    1010                1015
```

```
<210> SEQ ID NO 66
<211> LENGTH: 762
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 66
```

Gly Pro Asn Ile Cys Thr Thr Arg Gly Val Ser Ser Cys Gln Gln Cys
1               5                   10                  15

Leu Ala Val Ser Pro Met Cys Ala Trp Cys Ser Asp Glu Ala Leu Pro
            20                  25                  30

Leu Gly Ser Pro Arg Cys Asp Leu Lys Glu Asn Leu Leu Lys Asp Asn
        35                  40                  45

Cys Ala Pro Glu Ser Ile Glu Phe Pro Val Ser Glu Ala Arg Val Leu
    50                  55                  60

Glu Asp Arg Pro Leu Ser Asp Lys Gly Ser Gly Asp Ser Ser Gln Val
65                  70                  75                  80

Thr Gln Val Ser Pro Gln Arg Ile Ala Leu Arg Leu Arg Pro Asp Asp
                85                  90                  95

Ser Lys Asn Phe Ser Ile Gln Val Arg Gln Val Glu Asp Tyr Pro Val
            100                 105                 110

Asp Ile Tyr Tyr Leu Met Asp Leu Ser Tyr Ser Met Lys Asp Asp Leu
        115                 120                 125

Trp Ser Ile Gln Asn Leu Gly Thr Lys Leu Ala Thr Gln Met Arg Lys
130                 135                 140

Leu Thr Ser Asn Leu Arg Ile Gly Phe Gly Ala Phe Val Asp Lys Pro
145                 150                 155                 160

Val Ser Pro Tyr Met Tyr Ile Ser Pro Pro Glu Ala Leu Glu Asn Pro
                165                 170                 175

Cys Tyr Asp Met Lys Thr Thr Cys Leu Pro Met Phe Gly Tyr Lys His
            180                 185                 190

Val Leu Thr Leu Thr Asp Gln Val Thr Arg Phe Asn Glu Glu Val Lys
        195                 200                 205

Lys Gln Ser Val Ser Arg Asn Arg Asp Ala Pro Glu Gly Gly Phe Asp
    210                 215                 220

Ala Ile Met Gln Ala Thr Val Cys Asp Glu Lys Ile Gly Trp Arg Asn
225                 230                 235                 240

Asp Ala Ser His Leu Leu Val Phe Thr Thr Asp Ala Lys Thr His Ile
                245                 250                 255

Ala Leu Asp Gly Arg Leu Ala Gly Ile Val Gln Pro Asn Asp Gly Gln
            260                 265                 270

Cys His Val Gly Ser Asp Asn His Tyr Ser Ala Ser Thr Thr Met Asp
        275                 280                 285

Tyr Pro Ser Leu Gly Leu Met Thr Glu Lys Leu Ser Gln Lys Asn Ile
    290                 295                 300

Asn Leu Ile Phe Ala Val Thr Glu Asn Val Val Asn Leu Tyr Gln Asn
305                 310                 315                 320

Tyr Ser Glu Leu Ile Pro Gly Thr Thr Val Gly Val Leu Ser Met Asp
                325                 330                 335

Ser Ser Asn Val Leu Gln Leu Ile Val Asp Ala Tyr Gly Lys Ile Arg
            340                 345                 350

Ser Lys Val Glu Leu Glu Val Arg Asp Leu Pro Glu Glu Leu Ser Leu
        355                 360                 365

-continued

Ser Phe Asn Ala Thr Cys Leu Asn Asn Glu Val Ile Pro Gly Leu Lys
    370                 375                 380
Ser Cys Met Gly Leu Lys Ile Gly Asp Thr Val Ser Phe Ser Ile Glu
385                 390                 395                 400
Ala Lys Val Arg Gly Cys Pro Gln Glu Lys Glu Lys Ser Phe Thr Ile
                405                 410                 415
Lys Pro Val Gly Phe Lys Asp Ser Leu Ile Val Gln Val Thr Phe Asp
                420                 425                 430
Cys Asp Cys Ala Cys Gln Ala Gln Ala Glu Pro Asn Ser His Arg Cys
            435                 440                 445
Asn Asn Gly Asn Gly Thr Phe Glu Cys Gly Val Cys Arg Cys Gly Pro
450                 455                 460
Gly Trp Leu Gly Ser Gln Cys Glu Cys Ser Glu Glu Asp Tyr Arg Pro
465                 470                 475                 480
Ser Gln Gln Asp Glu Cys Ser Pro Arg Glu Gly Gln Pro Val Cys Ser
                485                 490                 495
Gln Arg Gly Glu Cys Leu Cys Gly Gln Cys Val Cys His Ser Ser Asp
                500                 505                 510
Phe Gly Lys Ile Thr Gly Lys Tyr Cys Glu Cys Asp Asp Phe Ser Cys
                515                 520                 525
Val Arg Tyr Lys Gly Glu Met Cys Ser Gly His Gly Gln Cys Ser Cys
530                 535                 540
Gly Asp Cys Leu Cys Asp Ser Asp Trp Thr Gly Tyr Tyr Cys Asn Cys
545                 550                 555                 560
Thr Thr Arg Thr Asp Thr Cys Met Ser Ser Asn Gly Leu Leu Cys Ser
                565                 570                 575
Gly Arg Gly Lys Cys Glu Cys Gly Ser Cys Val Cys Ile Gln Pro Gly
                580                 585                 590
Ser Tyr Gly Asp Thr Cys Glu Lys Cys Pro Thr Cys Pro Asp Ala Cys
                595                 600                 605
Thr Phe Lys Lys Glu Cys Val Glu Cys Lys Lys Phe Asp Arg Glu Pro
                610                 615                 620
Tyr Met Thr Glu Asn Thr Cys Asn Arg Tyr Cys Arg Asp Glu Ile Glu
625                 630                 635                 640
Ser Val Lys Glu Leu Lys Asp Thr Gly Lys Asp Ala Val Asn Cys Thr
                645                 650                 655
Tyr Lys Asn Glu Asp Asp Cys Val Val Arg Phe Gln Tyr Tyr Glu Asp
                660                 665                 670
Ser Ser Gly Lys Ser Ile Leu Tyr Val Val Glu Glu Pro Glu Cys Pro
                675                 680                 685
Lys Gly Pro Asp Ile Leu Val Val Leu Leu Ser Val Met Gly Ala Ile
690                 695                 700
Leu Leu Ile Gly Leu Ala Ala Leu Leu Ile Trp Lys Leu Leu Ile Thr
705                 710                 715                 720
Ile His Asp Arg Lys Glu Phe Ala Lys Phe Glu Glu Glu Arg Ala Arg
                725                 730                 735
Ala Lys Trp Asp Thr Ala Asn Asn Pro Leu Tyr Lys Glu Ala Thr Ser
                740                 745                 750
Thr Phe Thr Asn Ile Thr Tyr Arg Gly Thr
                755                 760

<210> SEQ ID NO 67
<211> LENGTH: 91

<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 67

Ser Asp Val Pro Arg Asp Leu Glu Val Val Ala Ala Thr Pro Thr Ser
1               5                   10                  15

Leu Leu Ile Ser Trp Asp Ala Pro Ala Val Thr Val Arg Tyr Tyr Arg
            20                  25                  30

Ile Thr Tyr Gly Glu Thr Gly Gly Asn Ser Pro Val Gln Glu Phe Thr
        35                  40                  45

Val Pro Gly Ser Lys Ser Thr Ala Thr Ile Ser Gly Leu Lys Pro Gly
    50                  55                  60

Val Asp Tyr Thr Ile Thr Val Tyr Ala Val Ile Ala Arg Gly Asp Trp
65                  70                  75                  80

Asn Asp Gly Ser Lys Pro Ile Ser Ile Asn Tyr
                85                  90

<210> SEQ ID NO 68
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Lys Gly Asp Trp Asn
1               5

<210> SEQ ID NO 69
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Arg Gly Asp Trp Asn
1               5

<210> SEQ ID NO 70
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Ile Ala Lys Gly Asp Trp Asn Asp
1               5

<210> SEQ ID NO 71
<211> LENGTH: 103
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: misc_feature
<222> LOCATION: (1)..(10)

```
<223> OTHER INFORMATION: This region may encompass 4, 6, 8, or 10
      residues, wherein some positions may be absent

<400> SEQUENCE: 71

His His His His His His His His His Gly Ser Ser Asp Val Pro
1               5                   10                  15

Arg Asp Leu Glu Val Val Ala Ala Thr Pro Thr Ser Leu Leu Ile Ser
                20                  25                  30

Trp Asp Ala Pro Ala Val Thr Val Arg Tyr Tyr Arg Ile Thr Tyr Gly
                35                  40                  45

Glu Thr Gly Gly Asn Ser Pro Val Gln Glu Phe Thr Val Pro Gly Ser
            50                  55                  60

Lys Ser Thr Ala Thr Ile Ser Gly Leu Lys Pro Gly Val Asp Tyr Thr
65                  70                  75                  80

Ile Thr Val Tyr Ala Val Thr Pro Arg Gly Asp Trp Asn Glu Gly Ser
                85                  90                  95

Lys Pro Ile Ser Ile Asn Tyr
                100

<210> SEQ ID NO 72
<211> LENGTH: 102
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: misc_feature
<222> LOCATION: (1)..(10)
<223> OTHER INFORMATION: This region may encompass 4, 6, 8, or 10
      residues, wherein some positions may be absent

<400> SEQUENCE: 72

His His His His His His His His His Gly Ser Ser Asp Val Pro
1               5                   10                  15

Arg Asp Leu Glu Val Val Ala Ala Thr Pro Thr Ser Leu Leu Ile Ser
                20                  25                  30

Trp Asp Ala Pro Ala Val Thr Val Arg Tyr Tyr Arg Ile Thr Tyr Gly
                35                  40                  45

Glu Thr Gly Gly Asn Ser Pro Val Gln Glu Phe Thr Val Pro Gly Ser
            50                  55                  60

Lys Ser Thr Ala Thr Ile Ser Gly Leu Lys Pro Gly Val Asp Tyr Thr
65                  70                  75                  80

Ile Thr Val Tyr Ala Val Thr Pro Lys Gly Asp Trp Asn Glu Gly Gly
                85                  90                  95

Pro Ile Ser Ile Asn Tyr
                100

<210> SEQ ID NO 73
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (14)..(14)
<223> OTHER INFORMATION: D-Pro

<400> SEQUENCE: 73

Cys Ala Val Thr Pro Arg Gly Asp Trp Asn Glu Gly Gly Pro
```

-continued

```
1               5                   10

<210> SEQ ID NO 74
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Ala Val Thr Pro Arg Gly Asp Trp Asn Glu Gly
1               5                   10

<210> SEQ ID NO 75
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: D-Pro

<400> SEQUENCE: 75

Gly Pro Ala Val Thr Pro Arg Gly Asp Trp Asn Glu Gly
1               5                   10

<210> SEQ ID NO 76
<211> LENGTH: 240
<212> TYPE: PRT
<213> ORGANISM: Homo sapiens

<400> SEQUENCE: 76

Tyr Pro Val Asp Ile Tyr Tyr Leu Met Asp Leu Ser Tyr Ser Met Lys
1               5                   10                  15

Asp Asp Leu Trp Ser Ile Gln Asn Leu Gly Thr Lys Leu Ala Thr Gln
            20                  25                  30

Met Arg Lys Leu Thr Ser Asn Leu Arg Ile Gly Phe Gly Ala Phe Val
        35                  40                  45

Asp Lys Pro Val Ser Pro Tyr Met Tyr Ile Ser Pro Pro Glu Ala Leu
    50                  55                  60

Glu Asn Pro Cys Tyr Asp Met Lys Thr Thr Cys Leu Pro Met Phe Gly
65                  70                  75                  80

Tyr Lys His Val Leu Thr Leu Thr Asp Gln Val Thr Arg Phe Asn Glu
                85                  90                  95

Glu Val Lys Lys Gln Ser Val Ser Arg Asn Arg Asp Ala Pro Glu Gly
            100                 105                 110

Gly Phe Asp Ala Ile Met Gln Ala Thr Val Cys Asp Glu Lys Ile Gly
        115                 120                 125

Trp Arg Asn Asp Ala Ser His Leu Leu Val Phe Thr Thr Thr His Ile
    130                 135                 140

Ala Leu Asp Gly Arg Leu Ala Gly Ile Val Gln Pro Asn Asp Gly Gln
145                 150                 155                 160

Cys His Val Gly Ser Asp Asn His Tyr Ser Ala Ser Thr Thr Met Asp
                165                 170                 175

Tyr Pro Ser Leu Gly Leu Met Thr Glu Lys Leu Ser Gln Lys Asn Ile
            180                 185                 190

Asn Leu Ile Phe Ala Val Thr Glu Asn Val Val Asn Leu Tyr Gln Asn
```

```
                    195                 200                 205
Tyr Ser Glu Leu Ile Pro Gly Thr Thr Val Gly Val Leu Ser Met Asp
210                 215                 220

Ser Ser Asn Val Leu Gln Leu Ile Val Asp Ala Tyr Gly Lys Ile Arg
225                 230                 235                 240

<210> SEQ ID NO 77
<211> LENGTH: 238
<212> TYPE: PRT
<213> ORGANISM: Homo sapiens

<400> SEQUENCE: 77

Tyr Pro Ile Asp Leu Tyr Tyr Leu Met Asp Leu Ser Tyr Ser Met Lys
1               5                   10                  15

Asp Asp Leu Glu Asn Val Lys Ser Leu Gly Thr Asp Leu Met Asn Glu
                20                  25                  30

Met Arg Arg Ile Thr Ser Asp Phe Arg Ile Gly Phe Gly Ser Phe Val
            35                  40                  45

Glu Lys Thr Val Met Pro Tyr Ile Ser Thr Thr Pro Ala Lys Leu Arg
        50                  55                  60

Asn Pro Cys Thr Ser Glu Gln Asn Cys Thr Thr Pro Phe Ser Tyr Lys
65                  70                  75                  80

Asn Val Leu Ser Leu Thr Asn Lys Gly Glu Val Phe Asn Glu Leu Val
                85                  90                  95

Gly Lys Gln Arg Ile Ser Gly Asn Leu Asp Ser Pro Glu Gly Gly Phe
            100                 105                 110

Asp Ala Ile Met Gln Val Ala Val Cys Gly Ser Leu Ile Gly Trp Arg
        115                 120                 125

Asn Val Thr Arg Leu Leu Val Phe Ser Thr Asp Ala Gly Phe His Phe
130                 135                 140

Ala Gly Asp Gly Lys Leu Gly Gly Ile Val Leu Pro Asn Asp Gly Gln
145                 150                 155                 160

Cys His Leu Glu Asn Asn Met Tyr Thr Met Ser His Tyr Tyr Asp Tyr
                165                 170                 175

Pro Ser Ile Ala His Leu Val Gln Lys Leu Ser Glu Asn Asn Ile Gln
            180                 185                 190

Thr Ile Phe Ala Val Thr Glu Glu Phe Gln Pro Val Tyr Lys Glu Leu
        195                 200                 205

Lys Asn Leu Ile Pro Lys Ser Ala Val Gly Thr Leu Ser Ala Asn Ser
    210                 215                 220

Ser Asn Val Ile Gln Leu Ile Ile Asp Ala Tyr Asn Ser Leu
225                 230                 235

<210> SEQ ID NO 78
<211> LENGTH: 239
<212> TYPE: PRT
<213> ORGANISM: Homo sapiens

<400> SEQUENCE: 78

Tyr Pro Ile Asp Leu Tyr Tyr Leu Met Asp Leu Ser Tyr Ser Met Leu
1               5                   10                  15

Asp Asp Leu Arg Asn Val Lys Lys Leu Gly Gly Asp Leu Leu Arg Ala
                20                  25                  30

Leu Asn Glu Ile Thr Glu Ser Gly Arg Ile Gly Phe Gly Ser Phe Val
            35                  40                  45

Asp Lys Thr Val Leu Pro Phe Val Asn Thr His Pro Asp Lys Leu Arg
```

-continued

```
                    50                  55                  60
Asn Pro Cys Pro Asn Lys Glu Lys Glu Cys Gln Pro Pro Phe Ala Phe
 65                  70                  75                  80

Arg His Val Leu Lys Leu Thr Asn Asn Ser Asn Gln Phe Gln Thr Glu
                     85                  90                  95

Val Gly Lys Gln Leu Ile Ser Gly Asn Leu Asp Ala Pro Glu Gly Gly
                100                 105                 110

Leu Asp Ala Met Met Gln Val Ala Ala Cys Pro Glu Glu Ile Gly Trp
            115                 120                 125

Arg Asn Val Thr Arg Leu Leu Val Phe Ala Thr Asp Asp Gly Phe His
        130                 135                 140

Phe Ala Gly Asp Gly Lys Leu Gly Ala Ile Leu Thr Pro Asn Asp Gly
145                 150                 155                 160

Arg Cys His Leu Glu Asp Asn Leu Tyr Lys Arg Ser Asn Glu Phe Asp
                165                 170                 175

Tyr Pro Ser Val Gly Gln Leu Ala His Lys Leu Ala Glu Asn Asn Ile
            180                 185                 190

Gln Pro Ile Phe Ala Val Thr Ser Arg Met Val Lys Thr Tyr Glu Lys
        195                 200                 205

Leu Thr Glu Ile Ile Pro Lys Ser Ala Val Gly Glu Leu Ser Glu Asp
    210                 215                 220

Ser Ser Asn Val Val His Leu Ile Lys Asn Ala Tyr Asn Lys Leu
225                 230                 235
```

<210> SEQ ID NO 79
<211> LENGTH: 240
<212> TYPE: PRT
<213> ORGANISM: Homo sapiens

<400> SEQUENCE: 79

```
Tyr Pro Val Asp Leu Tyr Tyr Leu Met Asp Leu Ser Tyr Ser Met Lys
 1               5                  10                  15

Asp Asp Leu Glu Arg Val Arg Gln Leu Gly His Ala Leu Leu Val Arg
                 20                  25                  30

Leu Gln Glu Val Thr His Ser Val Arg Ile Gly Phe Gly Ser Phe Val
             35                  40                  45

Asp Lys Thr Val Leu Pro Phe Val Ser Thr Val Pro Ser Lys Leu Arg
         50                  55                  60

His Pro Cys Pro Thr Arg Leu Glu Arg Cys Gln Ser Pro Phe Ser Phe
 65                  70                  75                  80

His His Val Leu Ser Leu Thr Gly Asp Ala Gln Ala Phe Glu Arg Glu
                     85                  90                  95

Val Gly Arg Gln Ser Val Ser Gly Asn Leu Asp Ser Pro Glu Gly Gly
                100                 105                 110

Phe Asp Ala Ile Leu Gln Ala Ala Leu Cys Gln Glu Gln Ile Gly Trp
            115                 120                 125

Arg Asn Val Ser Arg Leu Leu Val Phe Thr Ser Asp Asp Thr Phe His
        130                 135                 140

Thr Ala Gly Asp Gly Lys Leu Gly Gly Ile Phe Met Pro Ser Asp Gly
145                 150                 155                 160

His Cys His Leu Asp Ser Asn Gly Leu Tyr Ser Arg Ser Thr Glu Phe
                165                 170                 175

Asp Tyr Pro Ser Val Gly Gln Val Ala Gln Ala Leu Ser Ala Ala Asn
            180                 185                 190
```

Ile Gln Pro Ile Phe Ala Val Thr Ser Ala Ala Leu Pro Val Tyr Gln
                195                 200                 205

Glu Leu Ser Lys Leu Ile Pro Lys Ser Ala Val Gly Glu Leu Ser Glu
            210                 215                 220

Asp Ser Ser Asn Val Val Gln Leu Ile Met Asp Ala Tyr Asn Ser Leu
225                 230                 235                 240

<210> SEQ ID NO 80
<211> LENGTH: 240
<212> TYPE: PRT
<213> ORGANISM: Homo sapiens

<400> SEQUENCE: 80

Tyr Pro Val Asp Leu Tyr Tyr Leu Val Asp Val Ser Ala Ser Met His
1               5                   10                  15

Asn Asn Ile Glu Lys Leu Asn Ser Val Gly Asn Asp Leu Ser Arg Lys
            20                  25                  30

Met Ala Phe Phe Ser Arg Asp Phe Arg Leu Gly Phe Gly Ser Tyr Val
        35                  40                  45

Asp Lys Thr Val Ser Pro Tyr Ile Ser Ile His Pro Glu Arg Ile His
    50                  55                  60

Asn Gln Cys Ser Asp Tyr Asn Leu Asp Cys Met Pro Pro His Gly Tyr
65                  70                  75                  80

Ile His Val Leu Ser Leu Thr Glu Asn Ile Thr Glu Phe Glu Lys Ala
                85                  90                  95

Val His Arg Gln Lys Ile Ser Gly Asn Ile Asp Thr Pro Glu Gly Gly
            100                 105                 110

Phe Asp Ala Met Leu Gln Ala Ala Val Cys Glu Ser His Ile Gly Trp
        115                 120                 125

Arg Lys Glu Ala Lys Arg Leu Leu Leu Val Met Thr Asp Gln Thr Ser
    130                 135                 140

His Leu Ala Leu Asp Ser Lys Leu Ala Gly Ile Val Val Pro Asn Asp
145                 150                 155                 160

Gly Asn Cys His Leu Lys Asn Asn Val Tyr Val Lys Ser Thr Thr Met
                165                 170                 175

Glu His Pro Ser Leu Gly Gln Leu Ser Glu Lys Leu Ile Asp Asn Asn
            180                 185                 190

Ile Asn Val Ile Phe Ala Val Gln Gly Lys Gln Phe His Trp Tyr Lys
        195                 200                 205

Asp Leu Leu Pro Leu Leu Pro Gly Thr Ile Ala Gly Glu Ile Glu Ser
    210                 215                 220

Lys Ala Ala Asn Leu Asn Asn Leu Val Val Glu Ala Tyr Gln Lys Leu
225                 230                 235                 240

<210> SEQ ID NO 81
<211> LENGTH: 242
<212> TYPE: PRT
<213> ORGANISM: Homo sapiens

<400> SEQUENCE: 81

Tyr Pro Val Asp Leu Tyr Tyr Leu Met Asp Leu Ser Ala Ser Met Asp
1               5                   10                  15

Asp Asp Leu Asn Thr Ile Lys Glu Leu Gly Ser Arg Leu Ser Lys Glu
            20                  25                  30

Met Ser Lys Leu Thr Ser Asn Phe Arg Leu Gly Phe Gly Ser Phe Val
        35                  40                  45

Glu Lys Pro Val Ser Pro Phe Val Lys Thr Thr Pro Glu Glu Ile Ala
50                  55                  60

Asn Pro Cys Ser Ser Ile Pro Tyr Phe Cys Leu Pro Thr Phe Gly Phe
65                  70                  75                  80

Lys His Ile Leu Pro Leu Thr Asn Asp Ala Glu Arg Phe Asn Glu Ile
                85                  90                  95

Val Lys Asn Gln Lys Ile Ser Ala Asn Ile Asp Thr Pro Glu Gly Gly
                100                 105                 110

Phe Asp Ala Ile Met Gln Ala Ala Val Cys Lys Glu Lys Ile Gly Trp
                115                 120                 125

Arg Asn Asp Ser Leu His Leu Leu Val Phe Val Ser Asp Ala Asp Ser
130                 135                 140

His Phe Gly Met Asp Ser Lys Leu Ala Gly Ile Val Ile Pro Asn Asp
145                 150                 155                 160

Gly Leu Cys His Leu Asp Ser Lys Asn Glu Tyr Ser Met Ser Thr Val
                165                 170                 175

Leu Glu Tyr Pro Thr Ile Gly Gln Leu Ile Asp Lys Leu Val Gln Asn
                180                 185                 190

Asn Val Leu Leu Ile Phe Ala Val Thr Gln Glu Gln Val His Leu Tyr
    195                 200                 205

Glu Asn Tyr Ala Lys Leu Ile Pro Gly Ala Thr Val Gly Leu Leu Gln
210                 215                 220

Lys Asp Ser Gly Asn Ile Leu Gln Leu Ile Ile Ser Ala Tyr Glu Glu
225                 230                 235                 240

Leu Arg

<210> SEQ ID NO 82
<211> LENGTH: 212
<212> TYPE: PRT
<213> ORGANISM: Homo sapiens

<400> SEQUENCE: 82

Tyr Pro Val Asp Leu Tyr Tyr Leu Met Asp Leu Ser Leu Ser Met Lys
1               5                   10                  15

Asp Asp Leu Asp Asn Ile Arg Ser Leu Gly Thr Lys Leu Ala Glu Glu
                20                  25                  30

Met Arg Lys Leu Thr Ser Asn Phe Arg Leu Gly Phe Gly Ser Phe Val
            35                  40                  45

Asp Lys Asp Ile Ser Pro Phe Ser Tyr Thr Ala Pro Arg Tyr Gln Thr
        50                  55                  60

Asn Pro Cys Ile Gly Tyr Lys Leu Phe Pro Asn Cys Val Pro Ser Phe
65                  70                  75                  80

Gly Phe Arg His Leu Leu Pro Leu Thr Asp Arg Val Asp Ser Phe Asn
                85                  90                  95

Glu Glu Val Arg Lys Gln Arg Val Ser Arg Asn Arg Asp Ala Pro Glu
                100                 105                 110

Gly Gly Phe Asp Ala Val Leu Gln Ala Ala Val Cys Lys Glu Lys Ile
                115                 120                 125

Gly Trp Arg Lys Asp Ala Leu His Leu Leu Val Phe Thr Thr Asp Asp
130                 135                 140

Val Pro His Ile Ala Leu Asp Gly Lys Leu Gly Gly Leu Val Gln Pro
145                 150                 155                 160

His Asp Gly Gln Cys His Leu Asn Glu Ala Asn Glu Tyr Thr Ala Ser
                165                 170                 175

```
Asn Gln Met Asp Tyr Pro Ser Leu Ala Leu Leu Gly Glu Lys Leu Ala
            180                 185                 190

Glu Asn Asn Ile Asn Leu Ile Phe Ala Val Thr Lys Asn His Tyr Met
        195                 200                 205

Leu Tyr Lys Asn
        210

<210> SEQ ID NO 83
<211> LENGTH: 239
<212> TYPE: PRT
<213> ORGANISM: Homo sapiens

<400> SEQUENCE: 83

Pro Val Asp Leu Tyr Ile Leu Met Asp Phe Ser Asn Ser Met Ser Asp
1               5                   10                  15

Asp Leu Asp Asn Leu Lys Lys Met Gly Gln Asn Leu Ala Arg Val Leu
            20                  25                  30

Ser Gln Leu Thr Ser Asp Tyr Thr Ile Gly Phe Gly Lys Phe Val Asp
        35                  40                  45

Lys Val Ser Val Pro Gln Thr Asp Met Arg Pro Glu Lys Leu Lys Glu
    50                  55                  60

Pro Trp Pro Asn Ser Asp Pro Pro Phe Ser Phe Lys Asn Val Ile Ser
65                  70                  75                  80

Leu Thr Glu Asp Val Asp Glu Phe Arg Asn Lys Leu Gln Gly Glu Arg
                85                  90                  95

Ile Ser Gly Asn Leu Asp Ala Pro Glu Gly Gly Phe Asp Ala Ile Leu
            100                 105                 110

Gln Thr Ala Val Cys Thr Arg Asp Ile Gly Trp Arg Pro Asp Ser Thr
        115                 120                 125

His Leu Leu Val Phe Ser Thr Glu Ser Ala Phe His Tyr Glu Ala Asp
    130                 135                 140

Gly Ala Asn Val Leu Ala Gly Ile Met Ser Arg Asn Asp Glu Arg Cys
145                 150                 155                 160

His Leu Asp Thr Thr Gly Thr Tyr Thr Gln Tyr Arg Thr Gln Asp Tyr
                165                 170                 175

Pro Ser Val Pro Thr Leu Val Arg Leu Leu Ala Lys His Asn Ile Ile
            180                 185                 190

Pro Ile Phe Ala Val Thr Asn Tyr Ser Tyr Ser Tyr Tyr Glu Lys Leu
        195                 200                 205

His Thr Tyr Phe Pro Val Ser Ser Leu Gly Val Leu Gln Glu Asp Ser
    210                 215                 220

Ser Asn Ile Val Glu Leu Leu Glu Glu Ala Phe Asn Arg Ile Arg
225                 230                 235

<210> SEQ ID NO 84
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

Gly Pro Gly Arg Gly Asp Trp Asn
1               5

<210> SEQ ID NO 85
<211> LENGTH: 7
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 85

Pro Ala Arg Gly Asp Trp Asn
1               5

<210> SEQ ID NO 86
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86

Arg Gly Asp Asn Pro
1               5

<210> SEQ ID NO 87
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 87

Arg Gly Asp Trp Ala
1               5
```